United States Patent [19]

Bock et al.

[11] Patent Number: 5,225,528
[45] Date of Patent: Jul. 6, 1993

[54] CYCLIC HEXAPEPTIDE OXYTOCIN ANTAGONISTS

[75] Inventors: Mark G. Bock, Hatfield; Roger M. Freidinger, Lansdale, both of Pa.; Roger D. Tung, Cambridge, Mass.; Daniel F. Veber, Ambler; Peter D. Williams, Harleysville, both of Pa.

[73] Assignee: Merck & Co., Inc., Rahway, N.J.

[21] Appl. No.: 628,986

[22] Filed: Dec. 17, 1990

[51] Int. Cl.$^5$ .............. C07D 487/14; A61K 37/02
[52] U.S. Cl. ...................... 530/321; 530/315; 540/455; 540/460
[58] Field of Search .............. 540/460, 455; 530/315, 530/321

[56] References Cited

U.S. PATENT DOCUMENTS

| | | | |
|---|---|---|---|
| 3,296,243 | 1/1967 | Hartmann et al. | 530/315 |
| 3,318,864 | 11/1967 | Boissonnas et al. | 530/315 |
| 3,691,147 | 9/1972 | Manning et al. | 530/320 |
| 4,237,119 | 12/1980 | Barth et al. | 530/315 |
| 4,367,225 | 1/1983 | Manning et al. | 530/315 |
| 4,402,942 | 9/1983 | Melin et al. | 530/315 |
| 4,504,469 | 3/1980 | Melin et al. | 530/315 |
| 4,551,445 | 11/1985 | Manning et al. | 530/321 |
| 4,599,324 | 7/1986 | Ali et al. | 530/315 |
| 4,658,015 | 4/1987 | Callahan et al. | 530/315 |
| 4,684,621 | 8/1987 | Callahan et al. | 530/329 |
| 4,684,622 | 8/1987 | Ali et al. | 530/315 |

FOREIGN PATENT DOCUMENTS

| | | | |
|---|---|---|---|
| 514812 | 9/1976 | U.S.S.R. | 530/321 |
| 2078755 | 1/1982 | United Kingdom | 530/315 |
| WO87/02676 | 5/1987 | World Int. Prop. O. | 530/315 |

*Primary Examiner*—Robert T. Bond
*Attorney, Agent, or Firm*—Frank P. Grassler; C. M. Caruso

[57] ABSTRACT

Disclosed are cyclic hexapeptides of the formula:

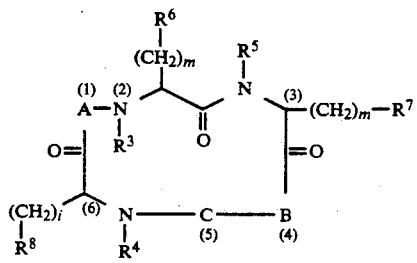

These compounds are antagonists of oxytocin and are useful in the treatment of preterm labor and dysmenorrhea, and for stoppage of labor prepatory to Caesarian delivery. Also disclosed are pharmaceutical compositions containing the compounds of formula I and methods of preparing these compounds.

5 Claims, No Drawings

CYCLIC HEXAPEPTIDE OXYTOCIN ANTAGONISTS

This is a continuation of application Ser. No. 07/486,030, filed Feb. 27, 1990, now abandoned.

BACKGROUND OF THE INVENTION

This invention pertains to the field of obstetrics. In this field, one of the most important problems is the management of preterm labor. A significant number of the pregnancies progressing past 20 weeks of gestation experience premature labor and delivery which is a leading cause of neonatal morbidity and mortality.

It has recently been proposed that a selective oxytocin antagonist would be the ideal tocolytic agent. In the last few years, evidence has accumulated to suggest strongly that oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part by a well-documented increase in the number of oxytocin receptors in this tissue. This 'up-regulation' of oxytocin receptors and enhanced uterine sensitivity appears to be due to trophic effects of rising plasma levels of estrogen towards term. By blocking both the direct (contractile) and indirect (enhanced prostaglandin synthesis) effects of oxytocin on the uterus, a selective oxytocin antagonist would likely be more efficacious for treating preterm labor than current regimens. In addition, since oxytocin at term has major effects only on the uterus, such a compound would be expected to have few, if any, side effects.

The compounds of the present invention may also be useful for the treatment of dysmenorrhea. This condition is characterized by cyclic pain associated with menses during ovulatory cycles. The pain is though to result from uterine contractions and ischemia, probably mediated by the effect of prostaglandins produced in the secretory endometrium. By blocking both the direct and indirect effects of oxytocin on the uterus, a selective oxytocin antagonist may be more efficacious for treating dysmenorrhea than current regimens.

An additional use for the present invention is for the stoppage of the labor prepatory to Caesarian delivery.

The development of oxytocin antagonists has been restricted to structural analogs closely related to oxytocin and arginine vasopressin. See D. J. Pettibone, et. al. Endocrinology, (1989) 125 (1), 217–222; see also EP 327,744, published Aug. 16, 1989. Consequently, these compounds have shown little selectivity for oxytocin versus vasopressin. Another common problem of known oxytocin antagonists is that they frequently display partial agonist activity.

It was, therefore, a purpose of this invention to identify substances which more effectively antagonize the function of oxytocin in disease states in animals, preferably mammals, especially in humans. It was another purpose of this invention to prepare novel compounds which more selectively inhibit oxytocin. It was still another purpose of this invention to develop a method of antagonizing the functions of oxytocin in disease states in mammals. It is also a purpose of this invention to develop a method of preventing or treating oxytocin related disorders, particularly preterm labor and dysmenorrhea.

SUMMARY OF THE INVENTION

It has now been found that compounds of Formula I are antagonists of oxytocin and bind to the oxytocin receptor. Compounds of the present invention have novel structures which display enhanced potency and exhibit greater specificity for oxytocin versus vasopressin. In addition the compounds of the present invention contain N-alkyl amino acid residues, as well as D-amino acids and therefore are less likely to be metabolized in vivo and will display a longer duration of action and/or greater solubility for formulation in comparison to prior compounds. These compounds are useful in the treatment and prevention of oxytocin-related disorders of animals, preferably mammals and especially humans. These disorders are primarily preterm labor and dysmenorrhea. The compounds would also find usefulness for stoppage of labor prepatory to Caesarian delivery.

DETAILED DESCRIPTION OF THE INVENTION

The present invention provides novel cyclic hexapeptides of the formula:

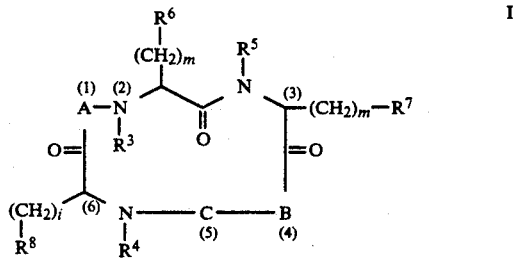

wherein:

A is glycine, N-methylglycine, alanine, N-methyl alanine, serine,

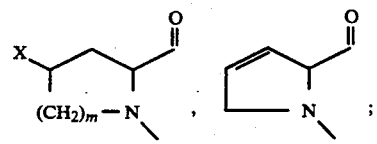

with the proviso that if X=NH$_2$ or OH, then m≠zero o.

B is

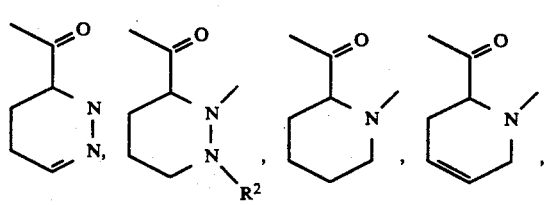

-continued

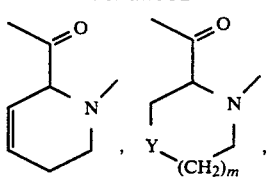

alanine, N-methylalanine, proline, serine, threonine, trans-4-hydroxyproline, cis-4-hydroxyproline, asparagine, aspartic acid, glutamic acid, glutamine, lysine, arginine, histidine, ornithine, cyclohexylalanine, ornithine-δ-tert-butyloxycarbonyl;

C is

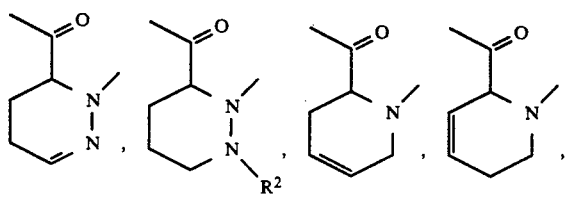

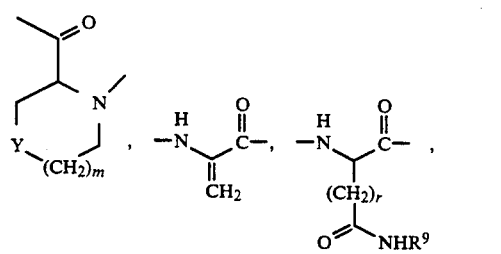

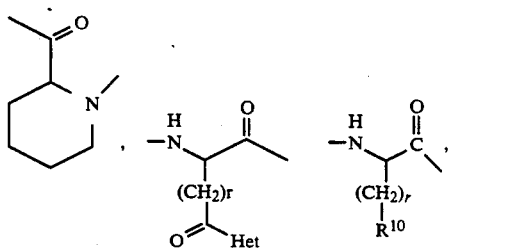

alanine, N-methylalanine, proline, threonine, trans-4-hydroxyproline, cis-4-hydroxyproline, histidine, cyclohexylalanine, ornithine-δ-tert-butyloxycarbonyl wherein Het is an unsubstituted or mono- or disubstituted 5- or 6-membered heterocyclic ring where the one or two heteroatoms are independently selected from the group consisting of N, O, S or quaternized N, and the substituent(s) is (are) independently selected from the group consisting of hydroxyl, C1-C6-alkyl, CF3, C1-C4-alkoxy, halo, amino, mono- or di-C1-C4-alkylamino, guanidyl, CO2H, CO2-C1-C4-alkyl;

$R^1$ is hydrogen glycyl, trifluoromethylsulfonyl, methanesulfonyl, acetyl, benzyl;

$R^2$ is hydrogen, methyl, carboxymethyl, benzyloxycarbonyl;

$R^3$, $R^4$ and $R^5$ are the same or different and are independently selected from the group consisting of: hydrogen, methyl, ethyl, propyl, allyl, dihydroxypropyl, carboxymethyl;

$R^6$ is hydrogen, phenyl, styryl, aminopropyl, 2-pyridyl, 3-pyridyl, 4-pyridyl, 4-aminophenyl, 4-imidazolyl, 3-indolyl 2-benzothienyl, 3-benzothienyl, mono or disubstituted phenyl where the substituent(s) is (are) independently chosen from the group consisting of: $C_1$-$C_4$-alkyl, fluoro, chloro, bromo, iodo, $C_1$-$C_4$-alkoxy, hydroxyl, benzyloxy, phenyl, phenoxy, amino, mono- or di-$C_1$-$C_4$-alkylamino, nitro, cyano, aminomethyl, mono- or di-$C_1$-$C_4$-alkylaminomethyl, or methylenedioxy; 1-naphthyl, 2-naphthyl, substituted 1- or 2-naphthyl where the substituent(s) is (are) selected from the group consisting of: fluoro, chloro, bromo, iodo, $C_1$-$C_4$-alkyl, hydroxyl, $C_1$-$C_4$-alkoxy, benzyloxy, phenyl, phenoxy, nitro, or cyano; substituted 3-indolyl where the substituent when connected to carbon is selected from the group consisting of: $C_1$-$C_4$-alkyl, $C_1$-$C_4$-alkoxy, fluoro, chloro, bromo, iodo, hydroxyl, cyano, nitro, and when connected to nitrogen the substituent is selected from the group consisting of: formyl, acetyl, benzoyl, benzyl, or $C_1$-$C_4$ alkyl;

$R^7$ is hydrogen, 2-propyl, 2-butyl, methyl, ethyl, cyclohexyl, cyclopentyl, phenyl, 4-benzyloxyphenyl, 4-hydroxyphenyl, 4-tert-butyloxy-carbonyloxyphenyl, 4-tert-butyloxyphenyl, 1-benzyloxyethyl, 1-tert-butyloxyethyl, 1-hydroxyethyl, hydroxmethyl;

$R^8$ is hydrogen, hydroxyl, sulfhydryl, 3-indolyl, 4-imidazolyl, phenyl, naphthyl, aminopropyl, N-(benzyloxycarbonyl)aminopropyl, N-(2-chlorobenzyloxycarbonyl)aminopropyl, guanidylethyl, guanidylpropyl, 2-pyridyl, 3-pyridyl, 4-pyridyl, 1-methyl-4-imidazolyl, 1-benzyloxymethylimidazolyl, 1-methyl-5-imidazolyl, (1,3-dimethyl-5-imidazolyl)$^+$Z$^-$, —S-benzyl,

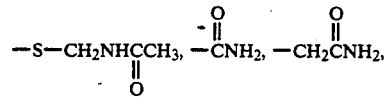

—CO2R$^9$, —CH2CO2R$^9$; mono- or disubstituted phenyl where the substituent(s) is are selected from the group consisting of: $C_1$-$C_4$ alkyl, hydroxyl, $C_1$-$C_4$-alkoxy, benzyloxy, nitro, amino, mono- or di- $C_1$-$C_4$-alkylamino, 1-pyrrolidinyl, cyano, aminomethyl, mono- or di-$C_1$-$C_4$-alkylamino, (N,N-dimethylglycl)amino, fluoro, chloro, bromo, iodo, 2-(4-morpholinyl)ethoxy;

$R^9$ is hydrogen, $(CH_2)_q NH_2$,

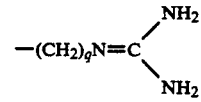

—(CH2)$_q$—NH(C1-C5alkyl), —(CH2)$_q$—N(C1-C5alkyl)2, —(CH2)$_q$-Het,

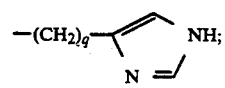

$R^{10}$ is amino, NH-t-butyloxycarbonyl, NH-benzyloxycarbonyl, NH-9-fluorenylmethyloxycarbonyl, NH(C1-C5)alkyl, N(C1-C5alkyl)2, N$^+$(C1-C5alkyl)3 Z$^-$, guanidyl, NH-1-methylquinuclidinium-3- carbonyl Z⁻, Het (where Het is defined as 1-pyrrolidinyl, 1-piperidinyl, 4-morpholinyl, 2-, 3-, and 4-pyridyl, 1-piperazinyl, 4-(C₁–C₅-alkyl)-1-piperazinyl,

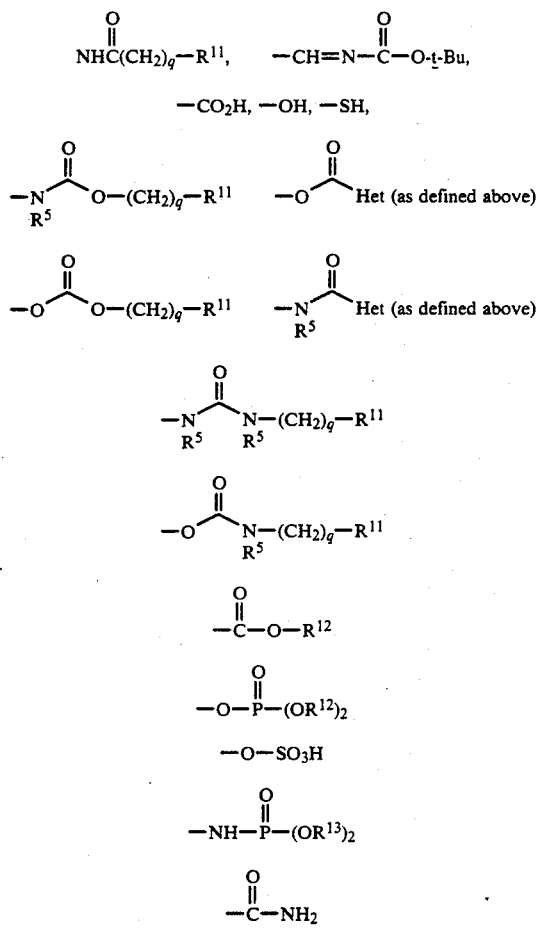

$R^{11}$ is carboxyl, amino, (C₁–C₅)alkylamino, di(C₁–C₅)alkylamino, tri(C₁–C₅)alkylamino Z⁻, guanidyl;
$R^{12}$ is hydrogen, (C₁–C₅)alkyl, benzyl, phenyl
$R^{13}$ is (C₁–C₅)alkyl, benzyl, phenyl
Y is CH₂, NR²S, SO, SO₂,

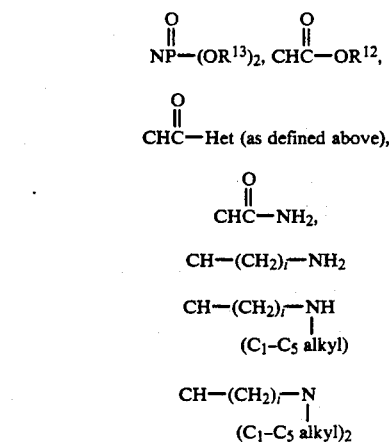

CH—(CH₂)ᵢ-Het (as defined above)
Z is chloride, bromide, sulfate, sulfamate, phosphate, nitrate, and the like; acetate, propionate, succinate, glycolate, stearate, lactate, malate, tartrate, citrate, ascorbate, pamoate, maleate, hydroxymaleate, phenyl acetate, glutamate, benzoate, salicylate, sulfanilate, 2-acetoxybenzoate, fumarate, toluenesulfonate, methanesulfonate, trifluoromethanesulfonate, ethane disulfonate, oxalate, isethionate, and the like;
i is 1 or 2;
m is 0, 1, or 2;
q is 2 or 3;
r is 1 to 5;
with the proviso that C and B cannot be simultaneously

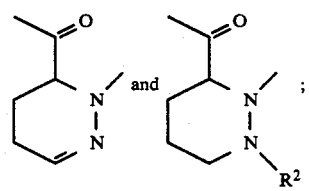

and the pharmaceutically acceptable salts thereof.
Preferred compounds of Formula I are those wherein:
A is glycine, alanine, N-methylalanine, serine,

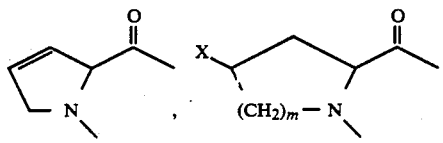

with the proviso that is X=NH₂ or OH, then m=0;
B is

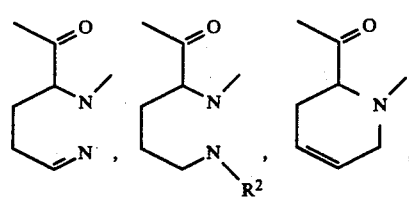

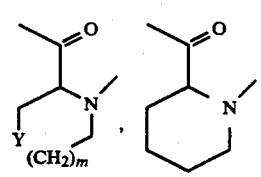

alanine, N-methylamine, proline, serine, trans-4-hydroxyproline, cis-4-hydroxyproline, asparagine, glutamine, histidine, ornithine, cyclohexylalanine, ornithine-δ-tert-butyloxycarbonyl;
C is

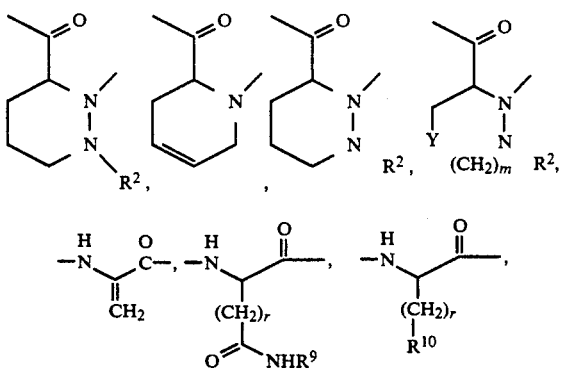

alanine, N-methylalanine, proline, serine, threonine, trans-4-hydroxyproline, cis-4-hydroxyproline, histidine, cyclohexylalanine, ornithine-δ-tert-butyloxycarbonyl;

$R^1$ is hydrogen, N-benzyloxycarbonylglycyl, methanesulfonyl, acetyl, benzyl;

$R^2$ is hydrogen, benzyloxycarbonyl;

$R^3$, $R^4$ and $R^5$ are the same or different and are independently selected from the group consisting of hydrogen, methyl, allyl;

$R^6$ is hydrogen, phenyl, 3-pyridyl, 4-imidazolyl, 3-indolyl, monosubstituted phenyl where the substituent is chosen from the group consisting of: hydroxyl, benzyloxy, methoxy, ethyloxy; 1-naphthyl, 2-naphthyl; substituted 3-indolyl where the substituent when connected to nitrogen is methyl and when connected to carbon is selected from the group consisting of methyl, methoxy, fluoro;

$R^7$ is hydrogen, 2-propyl, 2-butyl, cyclohexyl, phenyl, 4-benzyloxyphenyl, 4-hydroxyphenyl;

$R^8$ is hydrogen, hydroxyl, 3-indolyl, 4-imidazolyl, phenyl, aminopropyl, N-(benzyloxycarbonyl)aminopropyl, N-(2-chlorobenzyloxycarbonyl)aminopropyl, 3-pyridyl, 1-methyl-4-imidazolyl, 1-benzyloxymethyl-4-imidazolyl, 1-methyl-5-imidazolyl, $(1,3\text{-dimethyl-5-imidazolyl})^+ Z^-$,

—S-benzyl,

—$CO_2R^9$, monosubstituted phenyl where the substituent is selected from the group consisting of hydroxyl, benzyloxy, nitro, amino, (N,N-dimethylglycyl)amino, 2-(4-morpholinyl)ethoxy;

$R^9$ is hydrogen, $(CH_2)q\ NH_2$,

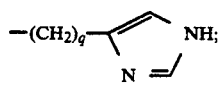

$R^{10}$ is amino, guanidyl, NH-t-butyloxycarbonyl, NH-benzyloxycarbonyl, NH-(1-methylquinuclidinium-3-carbonyl)$^+Z^-$, —CH=N—t-butyloxycarbonyl, —$CO_2R^{12}$;

$R^{12}$ is hydrogen, t-butyl;
$R^{13}$ is benzyl;
X is hydrogen, $NHR^1$, $OR^1$;
Y is $CH_2$, $NR^2$,

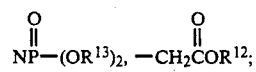

Z is chloride, citrate, maleate, trifluoromethanesulfonate, acetate;
i is 1 or 2;
m is 0, 1, or 2;
q is 2 or 3;
and the pharmaceutically accepted salts thereof.

More preferred compounds of Formula I are those wherein:

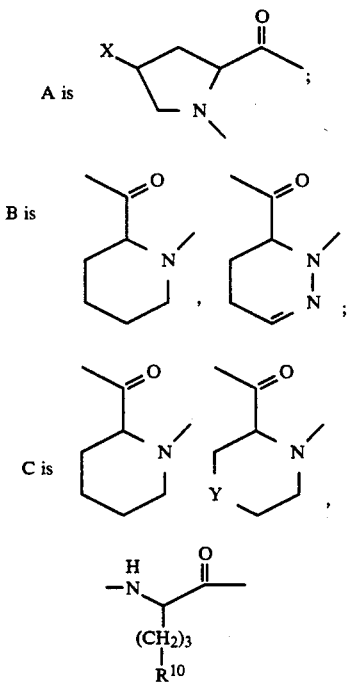

$R^2$ is hydrogen;
$R^3$ and $R^5$ are hydrogen
$R^4$ is methyl
$R^6$ is phenyl, 3-indolyl, 2-naphthyl;
$R^7$ is 2-butyl;
$R^8$ is 4-imidazolyl, phenyl;
$R^{10}$ is amino, guanidyl;
X is hydrogen;
Y is $NR^2$;

and the pharmaceutically acceptable salts thereof.

As used herein, the definition of each expression, e.g. m, q, etc., when it occurs more than once in any structure, is intended to be independent of its definitions elsewhere in the same structure.

All possible stereoisomers of the compounds of Formula I are included within the present invention. Configurations of the various amino acid residues, either naturally occuring or non-naturally ocurring, can be either D or L. Preferably, the amino acid configuration is L for position 1, D for position 2, L for position 3, D for position 4, L for position 5 and D for position 6.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods from the compounds of Formula I which contain a basic or acidic moiety. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

The ability of the compounds of Formula I to antagonize oxytocin makes these compounds useful as pharmaceutical agents for mammals, especially for humans, for the treatment and prevention of disorders wherein oxytocin may be involved. Examples of such disorders include preterm labor and especially dysmenorrhea. These compounds may also find usefulness for stoppage of labor prepatory to Caesarian delivery. Because of the known relationship of vasopressin to oxytocin, the compounds of the present invention are also useful as vasopressin antagonists. They are useful in the treatment or prevention of disease states involving vasopressin disorders.

The compounds of Formula I may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal and subcutaneous.

For oral use of an antagonist of oxytocin according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of oxytocin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.10 mg/kg to about 10 mg/kg of body weight administered in single or divided doses. In some cases, however, it may be necessary to use dosages outside these limits.

The compounds of Formula I are prepared according to the following schemes.

Reaction Schemes
SCHEME I

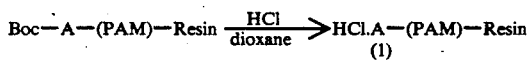

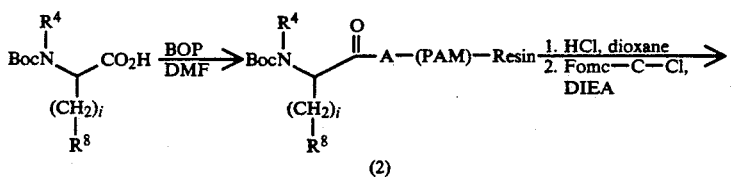

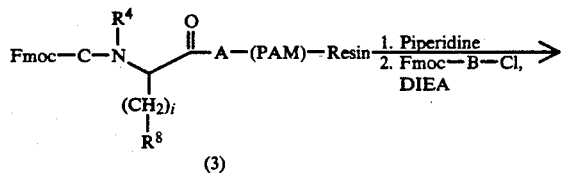

-continued
Reaction Schemes
SCHEME I
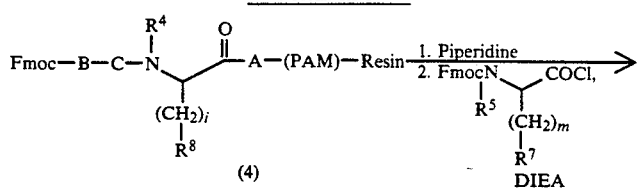
(4)
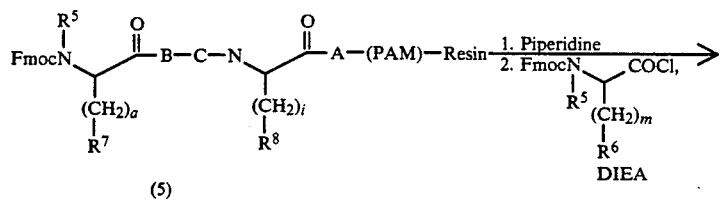
(5)
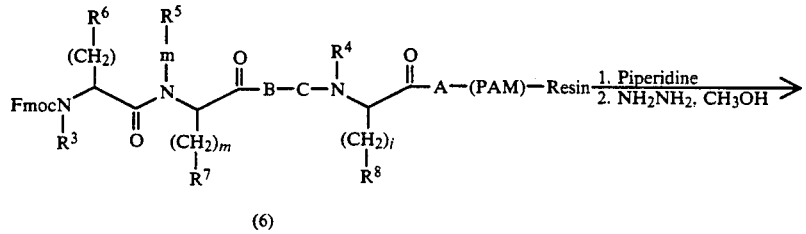
(6)
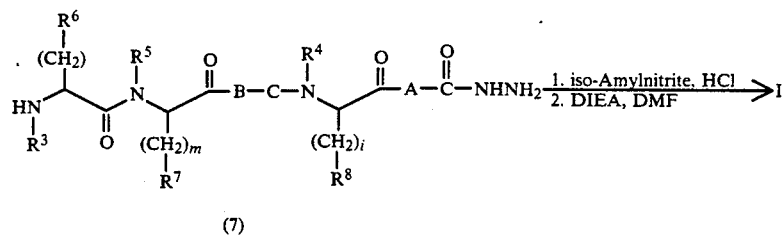
(7)
SCHEME II
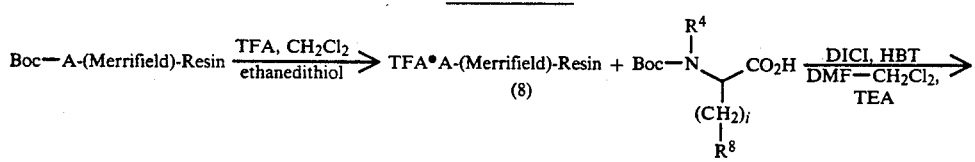
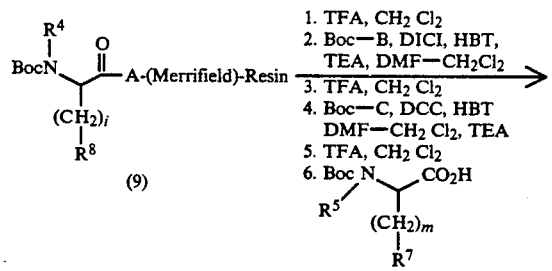
(9)
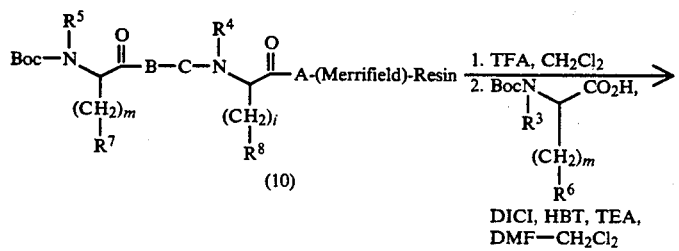
(10)

13
5,225,528
14
-continued
SCHEME II
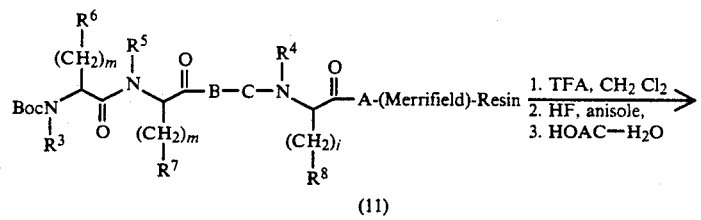
(11)
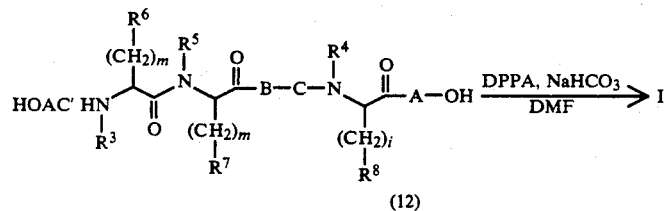
(12)
Scheme IIa
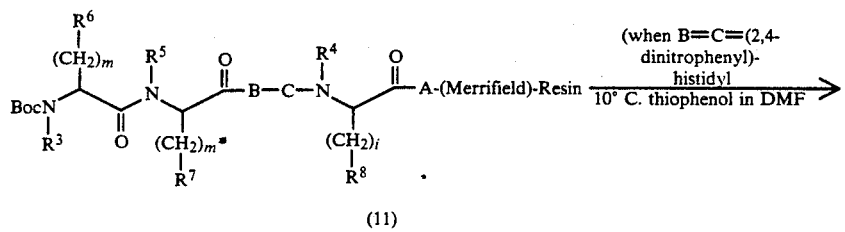
(11)
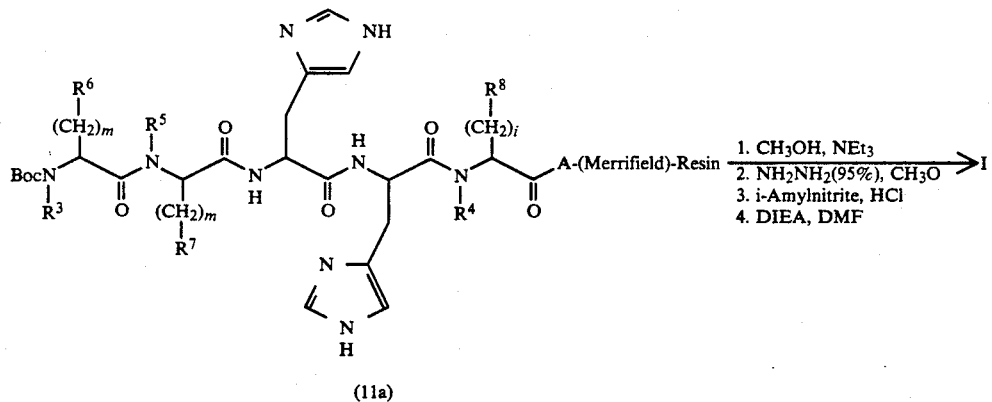
(11a)
SCHEME III
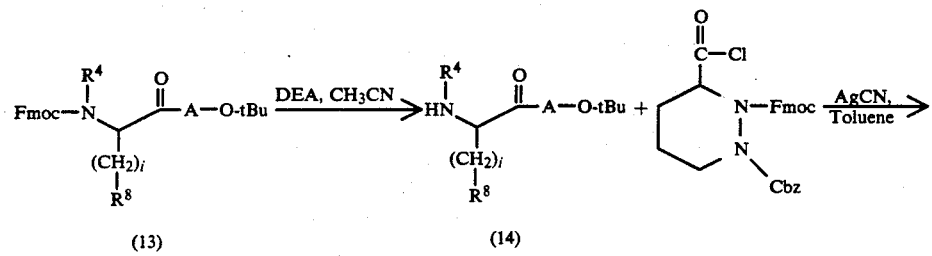
(13) (14)

5,225,528
SCHEME III
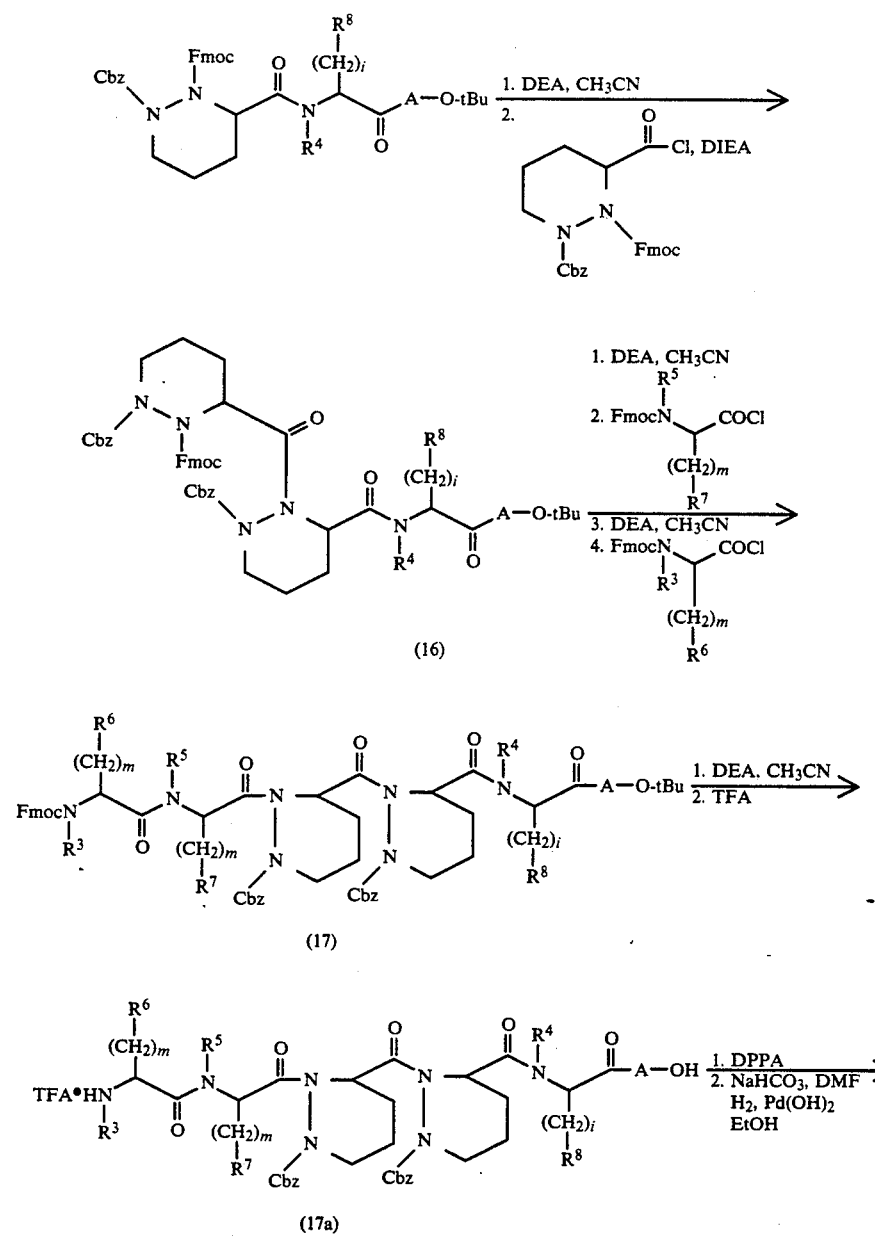
SCHEME IV
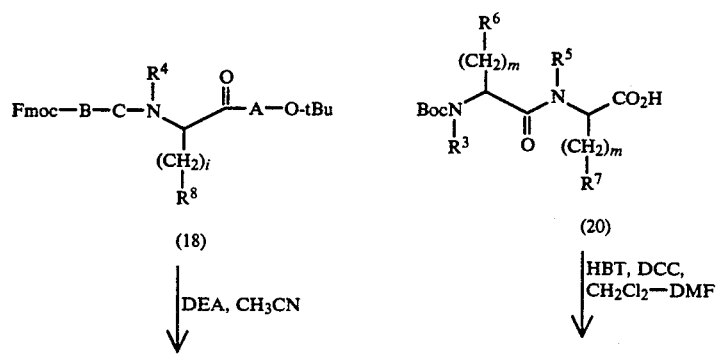

SCHEME IV
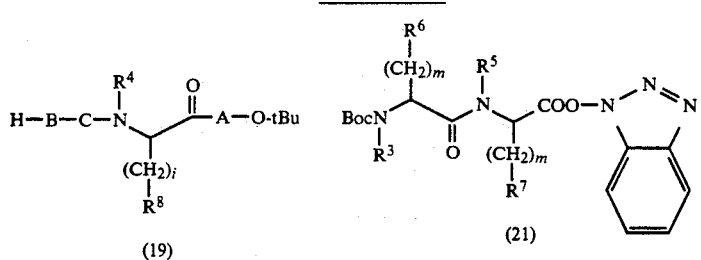
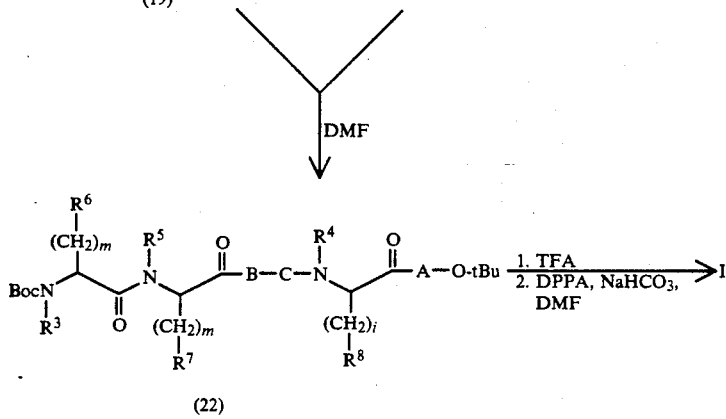
SCHEME V
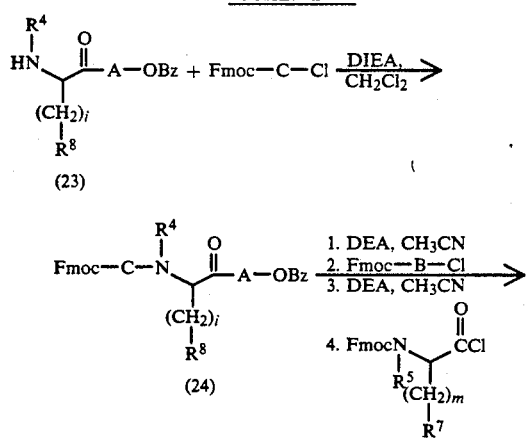
-continued SCHEME V
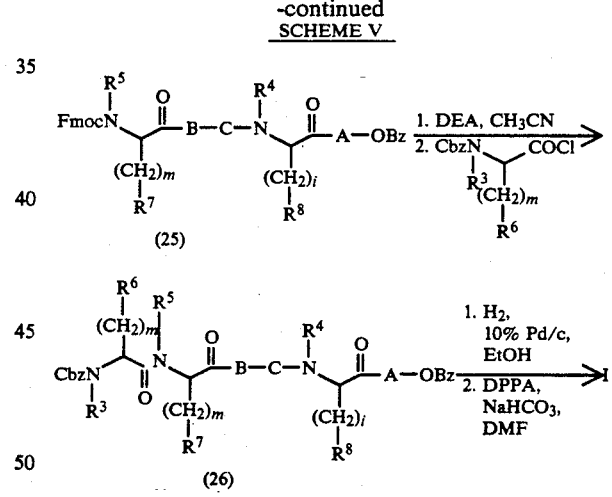
SCHEME 6
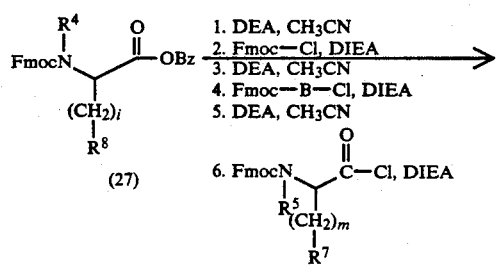

SCHEME 6
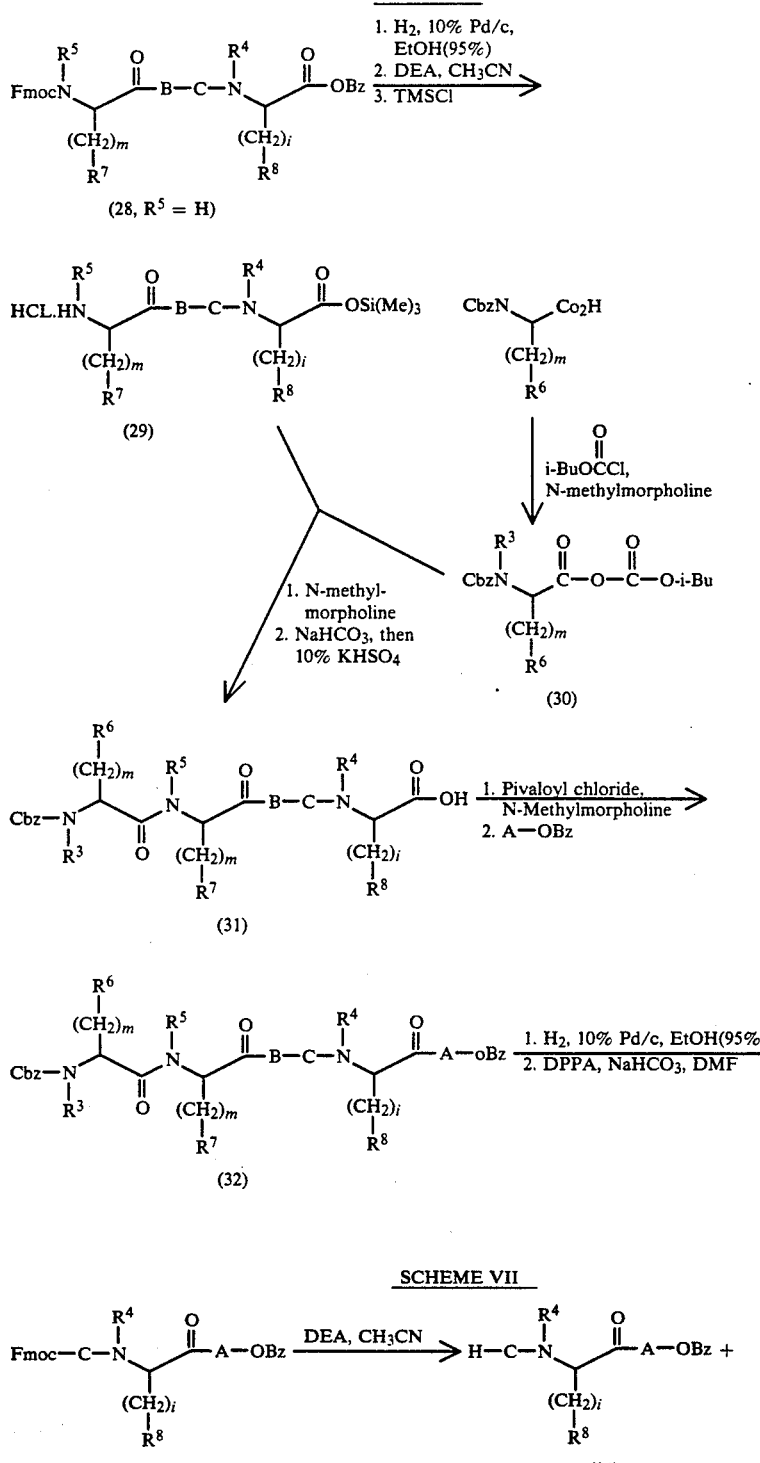
SCHEME VII
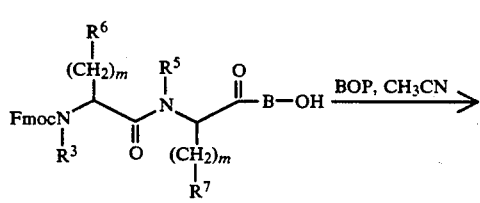

-continued
SCHEME VII
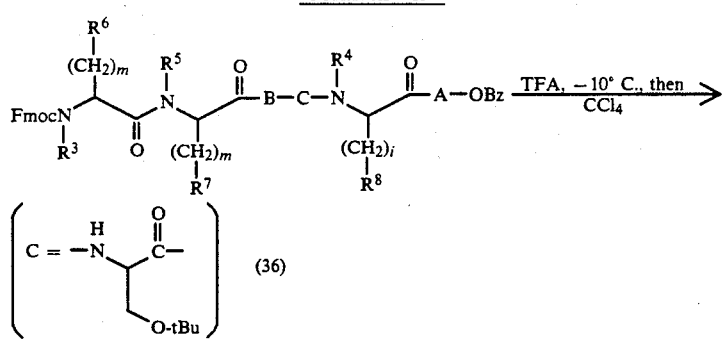
(36)
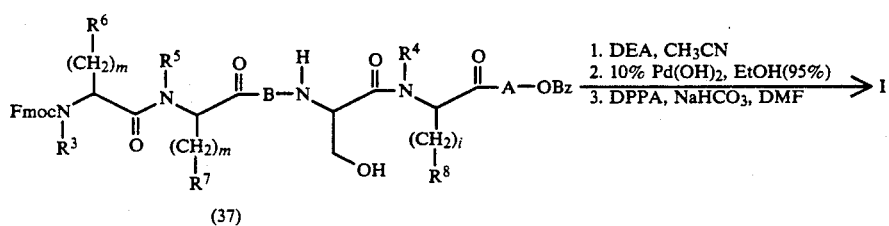
(37)
SCHEME VIII
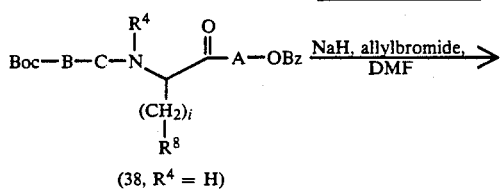
(38, R⁴ = H)
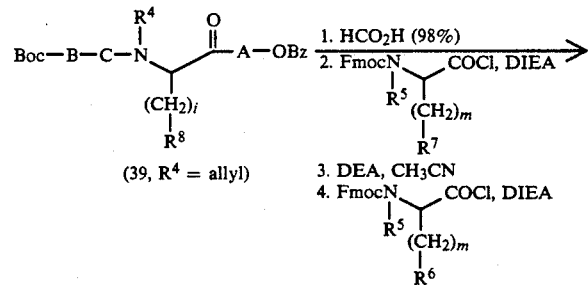
(39, R⁴ = allyl)
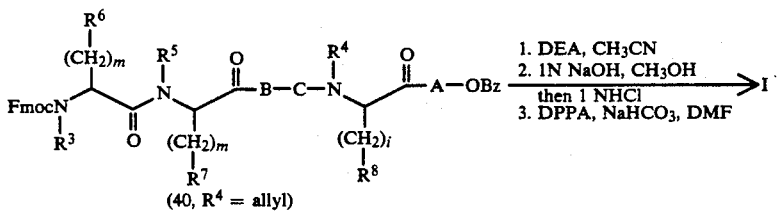
(40, R⁴ = allyl)
SCHEME IX
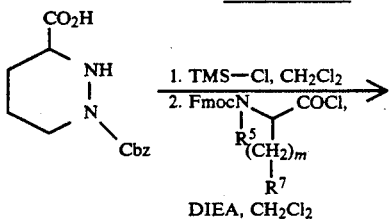
-continued
SCHEME IX
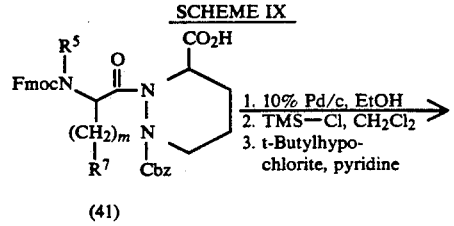
(41)

23
-continued
SCHEME IX
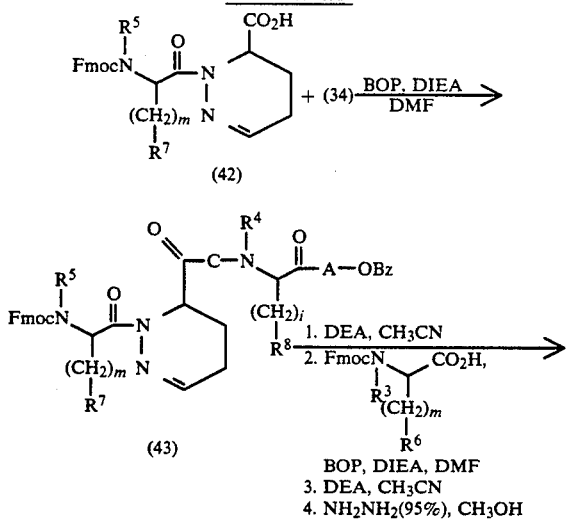
24
-continued
SCHEME IX
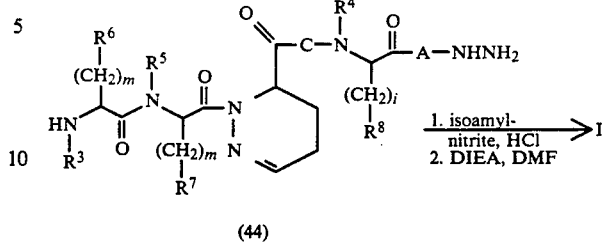
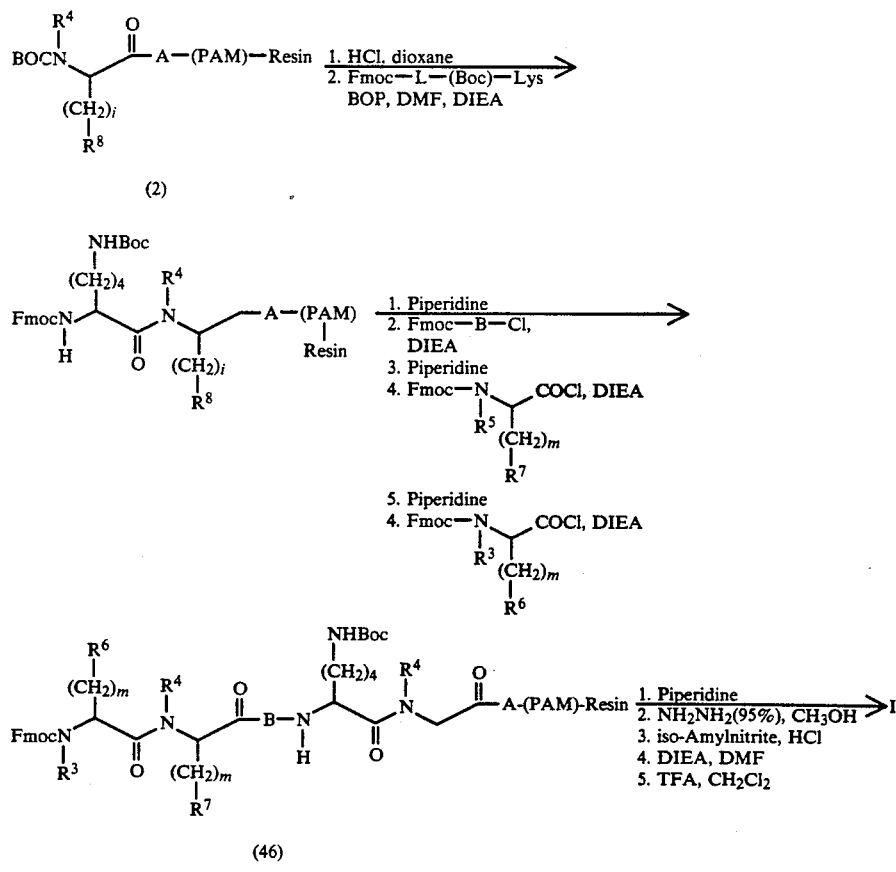

SCHEME XI
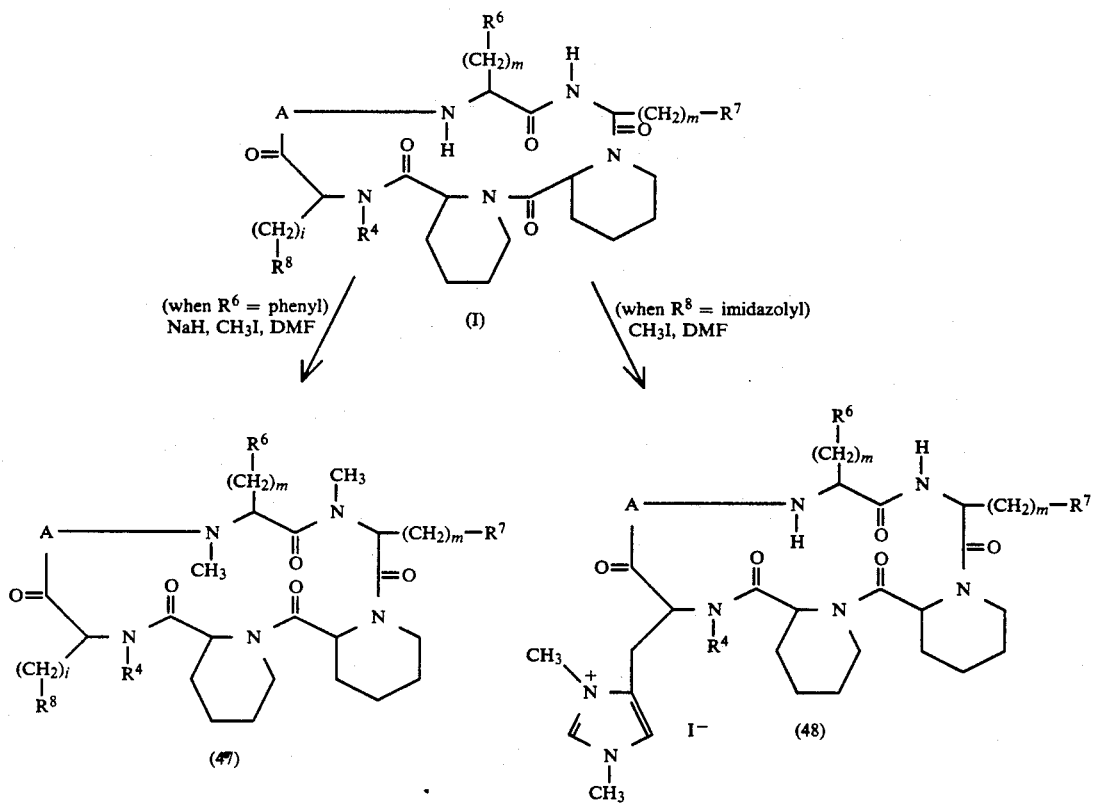
SCHEME XII
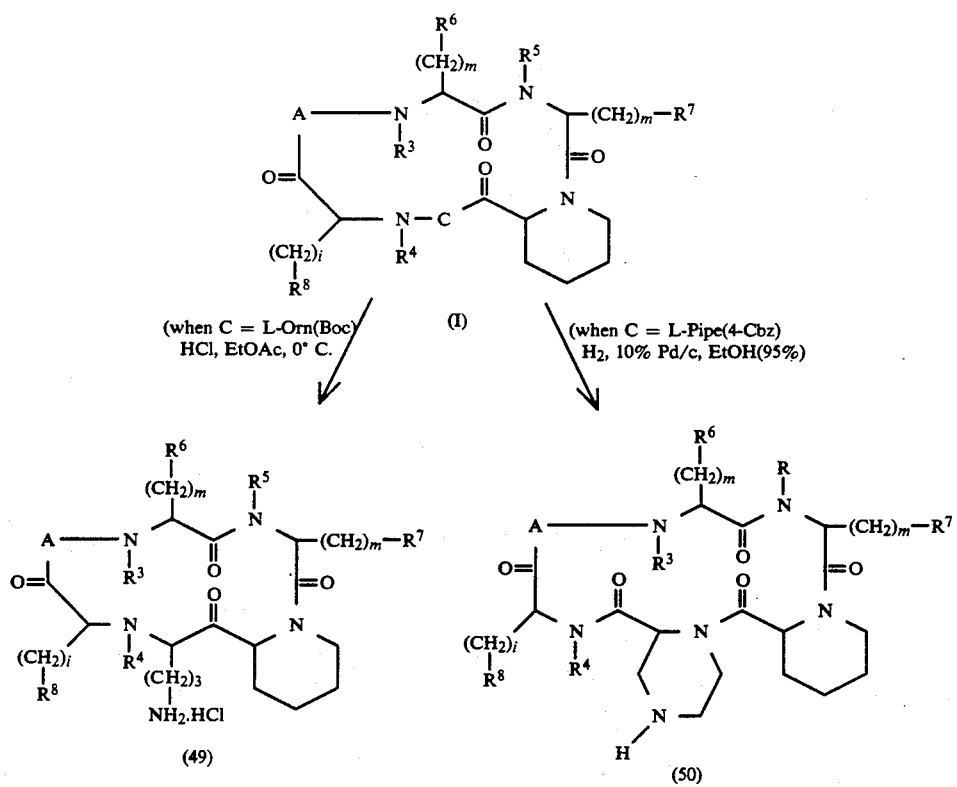

SCHEME XIII
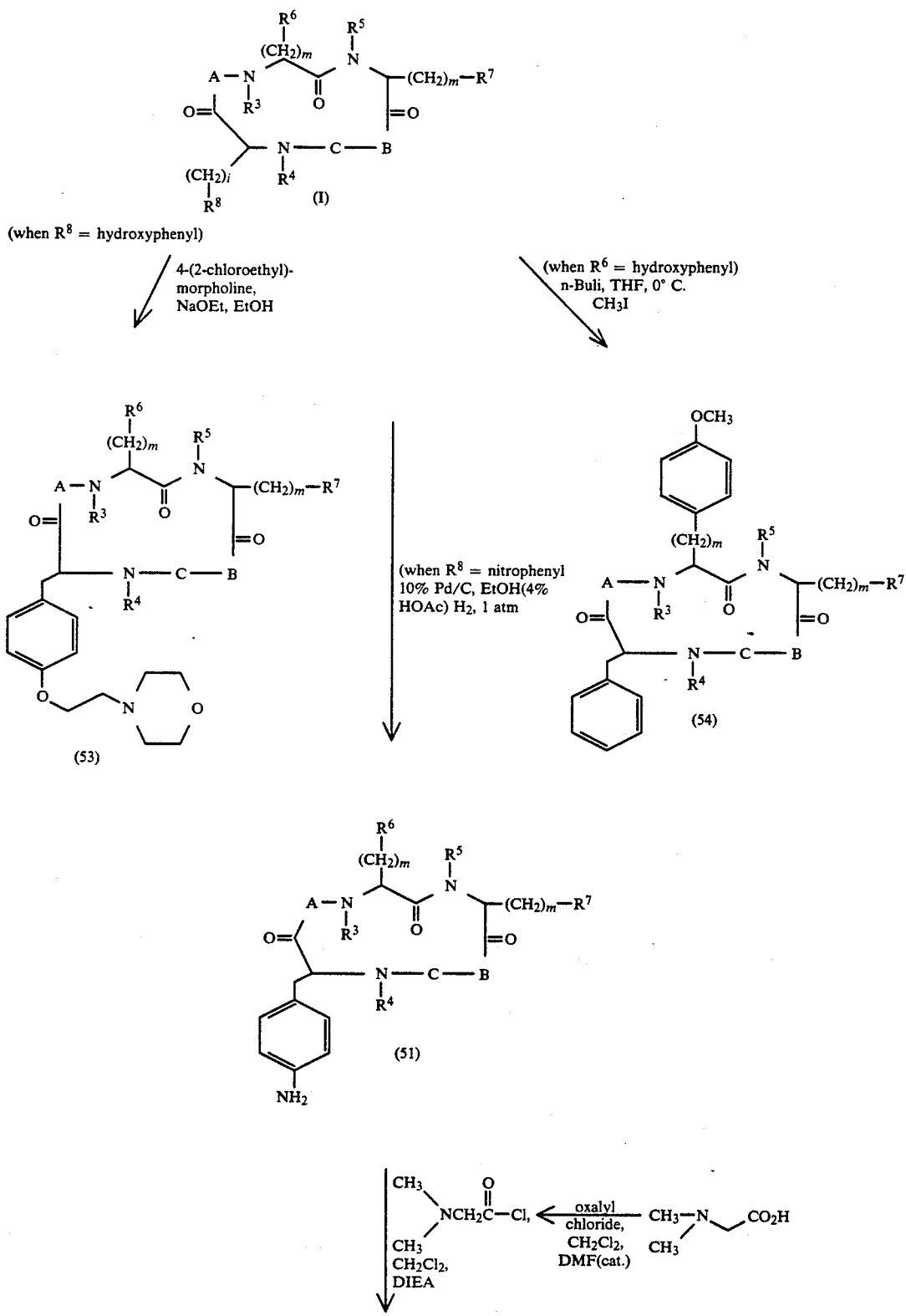

-continued
SCHEME XIII
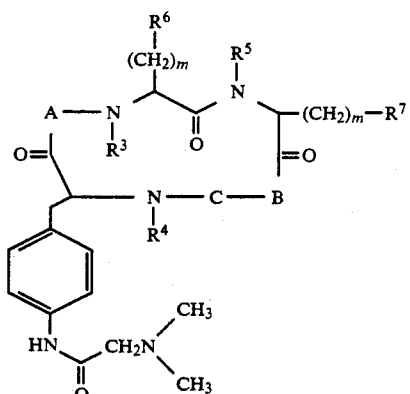
(52)
SCHEME XIV
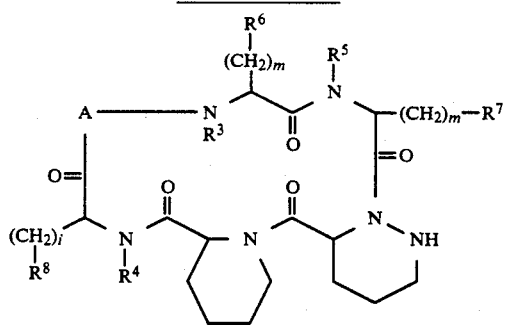
(53)
↓ t-BuOCl, pyridine, 0° C.
-continued
SCHEME XIV
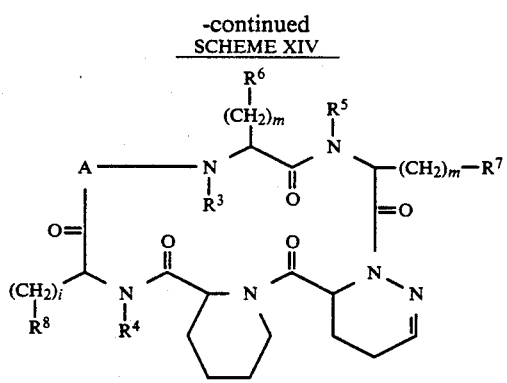
(54)
SCHEME XV
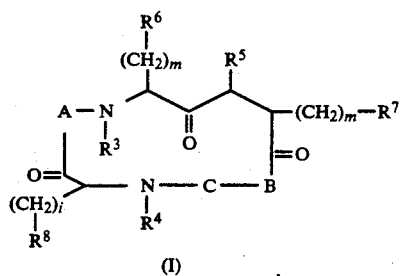
(I)
(when C = seryl)
triphenylphosphine,
phthalimide,
diethylazodicarboxylate, THF
(when C = aspartyl)
NH₄OH, EDC,
CH₂Cl₂
(when C = ornithyl)
3,5-dimethylpyrazole-1-carboxamidine nitrate, DMF -continued
SCHEME XV
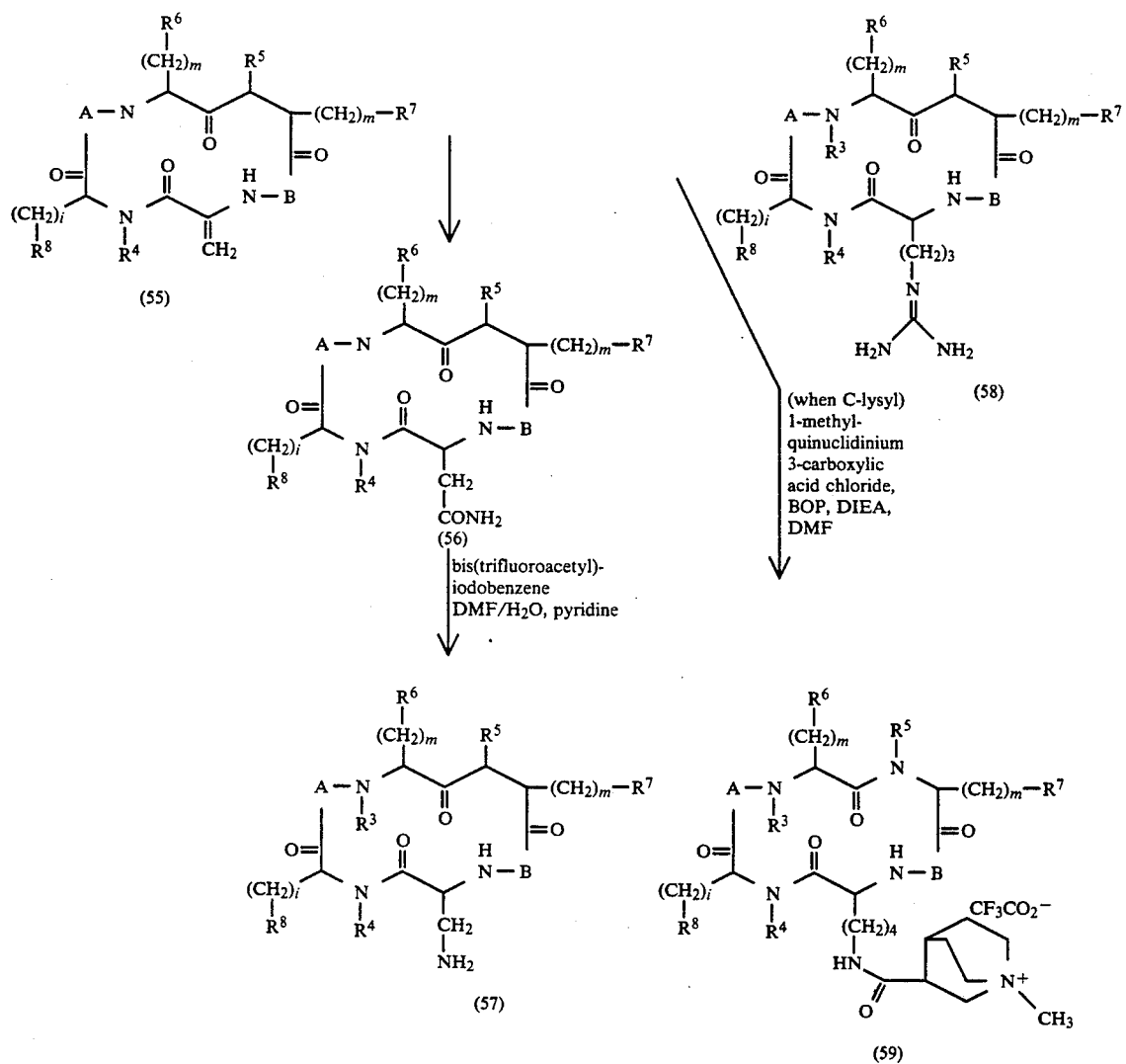
SCHEME XVI
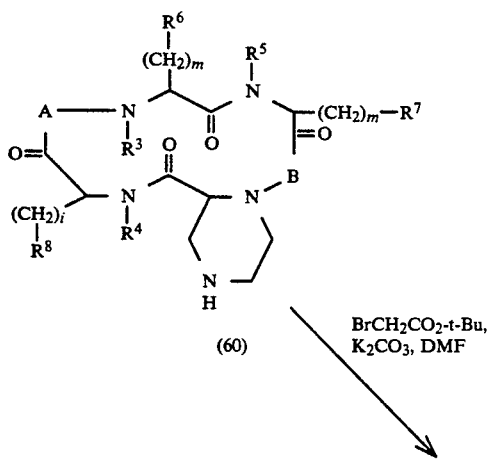

SCHEME XVI -continued

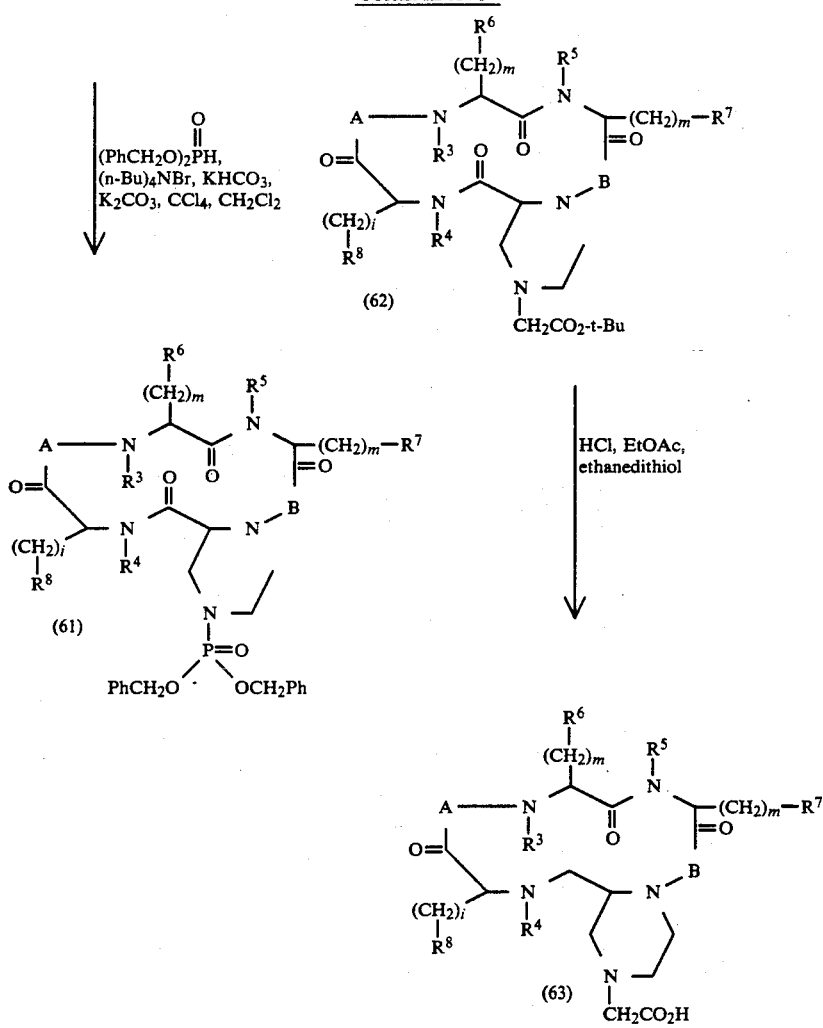

General Scheme

One preferred procedure for preparing the desired cyclic hexapeptides involves the stepwise synthesis of the linear hexapeptides on a solid phase resin support. The Boc protected C-terminal amino acid is bound covalently to an insoluble polymeric support as a carboxylic acid ester. One such resin is the PAM [4-(oxymethyl)phenyl acetamidomethyl polystyrene-co-divinyl benzene)] resin. The resin bound amino acid is deprotected for example with HCl in dioxane to give (1) and to it is coupled the second Boc protected amino acid using a coupling reagent like BOP. The second amino acid (2) is deprotected and in order to minimize diketopiperazine formation, the corresponding salt is treated at 5° C. with an Fmoc amino acid chloride, followed by the addition of base to pH 8. The Fmoc group on the third amino acid (3) is removed for example with 20% piperidine in DMF. The subsequent amino acids can then be coupled at ambient temperature. After the linear, resin bound hexapeptide (6) has been prepared, the N-terminal protecting group is removed and the peptide is then cleaved from the resin for example by treatment with 1:1 methanol/hydrazine. Cyclization of the resulting linear hexapeptide (7) is accomplished for example by formation of the corresponding acyl azide and treatment of such under high dilution with base to yield the crude cyclic hexapeptide I.

After removing the solvent under reduced pressure, product is obtained in pure form using one or more of the purification methods listed under General Procedures.

A number of the novel inhibitory peptides of the present invention can also be prepared by using the automated solid phase synthesis technique. The syntheses are carried out in a sequential manner on chloromethylated resin (Merrifield resin).

The amino acid selected to be the C-terminal amino acid of the linear peptide is converted to its amino protected derivative. After the amino protecting group is removed for example with TFA, to give (8), the amino protected derivative of the next amino acid in the sequence is added along with a coupling agent, such as diisopropylcarbodiimide. The amino reactant may also be employed in the form of a carboxyl-activated amino acid such as an amino acid chloride. Deprotection and addition of successive amino acids is performed until the desired linear peptide is formed.

The selection of protecting groups is, in part, dictated by the particular coupling conditions, by the amino acid components and by the sequence of these components. Amino-protecting groups ordinarily employed include those which are well known in the art, for example, urethane protecting substituents such as Cbz, Boc, Fmoc, and the like. It is preferred to utilize Boc for protecting the α-amino group of the amino acid undergoing reaction at the carboxyl end of said amino acid. The Boc protecting group is readily removed following such coupling reactions and prior to the subsequent step by the relatively mild action of acids such as trifluoroacetic acid or hydrogen chloride in ethyl acetate.

After the peptide (11a) has been formed on the solid phase resin, it may be removed from the resin by a variety of methods which are well known in the art. For example the peptide may be cleaved from the resin with hydrazine, by ammonia in methanol, or by methanol containing a suitable base such as triethylamine or by liquid hydrogen fluoride.

Following the removal of the linear peptide, preferably a hexapeptide, from the solid phase resin it is subjected to cyclization utilizing protocols well known in the art. For example, the carboxy terminus of the said peptide is converted to the acyl azide and the resultant species is cyclized under slightly alkaline conditions in a suitable solvent such as DMF. Alternatively, the linear peptide (12) in its unprotected amino acid form is treated with DPPA and sodium bicarbonate in a suitable solvent such as DMF.

The desired cyclic hexapeptides may also be assembled stepwise in solution. Thus, the suitably protected carboxy terminus (13) is first deprotected (14) and coupled to the appropriately protected amino acid activated as its acid chloride derivative. This coupling can be carried out employing reagents like silver cyanide in toluene to afford (15). Deprotection of the amino terminus with diethylamine, for the case of Fmoc removal and iteration of this cycle with the requisite amino acids yields the fully assembled and protected linear sequence (17). Deprotection and cyclization employing reagents common in the art, for example, diphenylphosphoryl azide, yields the title compound.

An alternative strategy for the assembly of the cyclic hexapeptides of this invention is to combine fragments of the linear sequence containing more than one amino acid. For example, the tetrapeptide (18) corresponding to positions 1, 4, 5, and 6 in the title compound I, is prepared in the standard fashion and deprotected. Then it is combined with a dipeptide (20) which is activated as its HBT ester (21) prior to reaction to give the linear hexapeptide (22). Cyclization according to the usual protocol affords the title compound I.

The solution phase assembly of the cyclic hexapeptides of this invention can be modified according to the choice of amino-terminus protection and carboxy-terminus activation. Thus, the benzyl ester of the dipeptide (23) can be elaborated by sequential coupling utilizing protected amino acid chlorides to give the pentapeptide (25). The Cbz protected linear hexapeptide (26) is then obtained by deprotection followed by acylation of the amino terminus of (25). In this way, the protecting groups on both amino and carboxy termini can be removed simultaneously, preferably via hydrogenation in the presence of a catalyst.

Another approach involving the solution phase assembly of the cyclic hexapeptides of this invention involves the assembly of the tetrapeptide (28). The amino acids of the latter compound correspond to those in positions 6, 5, 4, and 3 of structure I. Both the amino and carboxy termini are deprotected employing standard conditions and the carboxy terminus is then reprotected as its trimethylsilyl ester (29). The latter compound is then elaborated at its amino terminus by combining it with the position 2 amino acid, activated as its mixed anhydride (30). Standard workup then affords the pentapeptide (31) which is poised for elaboration at the carboxy terminus employing mixed anhydride technology, preferably the anhydride derived from pivaloyl chloride. This yields the fully protected linear hexapeptide (32) in which the protecting groups on both amino and carboxy termini can be removed simultaneously, preferably via hydrogenation in the presence of a catalyst. Cyclization in the standard manner, preferably with DPPA, affords I.

Another approach involving the solution phase assembly of the cyclic hexapeptides of this invention involves the assembly of two tripeptide fragments. Thus the tripeptide (34), containing the amino acids which correspond to those in positions 1, 2, and 3 in I, is coupled with the tripeptide (35), containing the amino acids which correspond to those in positions 4, 5, and 6 in I. The reagent of choice is BOP. The side chain protecting group in the linear hexapeptide (36) can then be selectively cleaved prior to deprotection of the amino and carboxy termini in (37), which followed by cyclization with DPPA gives I.

The peptide backbone of the cyclic hexapeptides of this invention can be modified. One approach is to selectively alkylate a fragment of the linear sequence of the cyclic hexapeptide. For example, the tetrapeptide (38), assembled in the standard fashion, can be alkylated in DMF in the presence of sodium hydride and employing electrophiles such as allyl bromide. The corresponding alkylated tetrapeptide (39) is then elaborated to the fully protected linear hexapeptide (40) employing standard solution phase synthesis protocol.

Selected sidechains of the amino acids comprising the cyclic hexapeptides of this invention can be modified. One approach is to selectively oxidize a fragment of the cyclic hexapeptide prior to its incorporation into the linear sequence. For example, the Cbz group of the dipeptide (41) can be selectively cleaved via hydrogenation in the presence of a palladium catalyst. The carboxy terminus of the resulting dipeptide is then protected as its trimethylsilyl ester and the whole is oxidized with t-butylhypochlorite in the presence of pyridine resulting in the formation of (42). The latter compound is then fragment coupled in solution with the tripeptide (34) to give the pentapeptide (43). Further elaboration at the amino terminus gives the linear hexapeptide (44) which is cyclized utilizing the standard azide method to give I.

Selected sidechains of the amino acids comprising the cyclic hexapeptides of this invention can be additionally modified. Another approach is to selectively carry out synthetic manipulations on the cyclic hexapeptide after it has been assembled. Employing solid phase methodology, the dipeptide (2) bound to a PAM resin is deprotected and then reacted with a protected amino acid to give the resin bound tripeptide (45). Further elaboration following this same protocol affords the fully protected linear hexapeptide (46). Deprotection at the amino terminus, followed by reaction with hydrazine yields the corresponding acyl hydrazide. This latter compound is converted to the acyl azide and cyclized in the standard fashion. The side chain of the amino acid corresponding to position 5 of I is then reacted with trifluoroacetic acid to afford the title compound.

The peptide backbone as well as the amino acid side chains of the cyclic hexapeptides of this invention can be chemically derivatized selectively depending on the choice of the reaction conditions. Thus, an alkyl group, like methyl can be introduced on the amide nitrogens of the amino acids corresponding to positions 2 and 3 in I by treating the compounds of the general formula I with a base such as sodium hydride in a suitable solvent, such as DMF, followed by the addition of an alkyl halide, like methyl iodide. Alternatively, the amide nitrogens in compounds of the general formula I are unreactive toward electrophilic reagents, like alkyl halides, in the absence of a base. However, if an amino acid side chain in compounds of the general formula I contains a nucleophilic moiety, as for example an imidazole ring, then treatment with an alkyl halide will result in reaction at this center to give products like the quartenary salt (48).

Compounds of the present invention I which contain a carbamate moiety can be further modified. If the carbamate is acid sensitive, as for example the tert-butyloxycarbonyl group, then it can be removed in the standard fashion with an acid such as hydrogen chloride, in a suitable solvent, such as ethyl acetate to give products like (49). Cleavage of a benzyloxycarbonyl group is carried out in a manner similarly well known in the art, as for example via hydrogenation with a palladium catalyst to yield products like (50).

The amino acid side chains of compounds of the present invention can be further reacted in a chemoselective manner thereby modifying the physicochemical and/or pharmacological profile of the compounds of the general formula I. Thus, the amino acid side chains of the residues corresponding to positions 2 and 6 in I can be alkylated, for example, with 4-(2-chloroethyl)-morpholine to give (53) or methyl iodide to afford (54). The amino acid side chain of the residue corresponding to position 2 in I can be reduced catalytically with hydrogen to yield (51). Compounds of the general formula (51) can then be acylated, as for example with the acid chloride of N,N-dimethyl glycine, to give (52).

The amino acid side chain of the residue corresponding to position 4 in I can be chemoselectively oxidized with a suitable reagent, preferably tert-butyl hypochlorite in the presence of pyridine to give (54).

The amino acid side chain of the residue corresponding to position 5 in I can be additionally modified. When C in I is serine, treatment with triphenylphosphine, phthalimide, and diethylazodicarboxylate yields (55). When C in I is aspartic acid, reaction with ammonia, preferably ammonium hydroxide, in the presence of a dehydrating agent like EDC, yields (56). Subjection of compounds of the general formula (56) to Hoffman rearrangement conditions, preferably with bis(trifluoroacetyl)iodobenzene, gives (57). If C in I is lysine, acylation with acid chlorides, preferably with 1-methylquinuclidinium-3-carboxylic acid chloride in the presence of BOP and diisopropylethylamine, affords (59). If C in I is ornithine, guanilation of the primary amino group can be effected, preferably with 3,5-dimethyl-pyrazole-1-carboxamidine nitrate to give (58). If the position 5 residue in I is piperazine-2-carboxylic acid, reaction of (60) with dibenzylphosphite under phase transfer conditions selectively converts compounds of the latter general structure to (61). Alternatively, alkylation of (60) with tert-butylbromoacetate in the presence of a base, preferably potassium carbonate, yields (62). Treatment of (62) with an anhydrous acid, preferably hydrogen chloride gas, in a suitable solvent and in the presence of a carbonium ion scavenger like ethanedithiol, affords (63).

Preparation of the novel inhibitory peptides of the present invention is illustrated in the following examples. The examples are not intended to be any limitation of the present invention.

In the following description several abbreviated designations are used for the amino acid components, certain preferred protecting groups, reagents and solvents. The meanings of such abbreviated designations are given below in Table 1.

TABLE 1

| Abbreviated Designation | |
|---|---|
| | Amino Acid |
| Ala | D or L-alanine |
| (N$^\alpha$-Me)Ala | D or L-(N-methyl)alanine |
| Arg | D or L-arginine |
| Cys | D or L-cystine |
| ChGly | D or L-cyclohexylglycine |
| Gly | glycine |
| His | D or L-histidine |
| (N$^\alpha$-Me)His | D or L-(N-methyl)histidine |
| Hyp | cis or trans-4-hydroxy proline |
| Ile | D or L-isoleucine |
| (N$^\alpha$-Me)Ile | L-(N-methyl)isoleucine |
| Leu | D or L-leucine |
| Lys | D or L-lysine |
| Met | D or L-methionine |
| $\alpha$-NAL | D-3-(1-naphthyl)alanine |
| $\beta$-NAL | D-3-(2-naphthyl)alanine |
| Nle | D or L-norleucine |
| Orn | D or L-ornithine |
| Phe | D or L-phenylalanine |
| (N$^\alpha$-Me)Phe | D-(N-methyl)phenylalanine |
| (pNO$_2$)Phe | D-(4-nitro)phenylalanine |
| Phg | D or L-phenylglycine |
| Pip | D or L-pipecolic acid |
| Pipe | D or L-piperazine-2-carboxylic acid |
| Piz | D or L-piperazic acid |
| $\Delta$-Piz | D or L-dehydropiperazic acid |
| Pro | D or L-proline |
| 3-(Pyr)Ala | D,L-3(3-pyridyl)alanine |
| Ser | D or L-serine |
| Sar | sarcosine (N-methylglycine) |
| Thr | D or L-threonine |
| Trp | D or L-tryptophan |
| Tyr | D or L-tyrosine |
| Tyr(OEt) | D or L-(O-ethyl)tyrosine |
| Val | D or L-valine |
| | Protecting Group |
| Acm | Acetaminomethyl |
| Boc | tert-butyloxycarbonyl |
| Bom | Benzyloxymethyl |
| Bzl | Benzyl |
| Cbz | Benzyloxycarbonyl |
| 2Cl-Cbz | 2-Chlorobenzyloxycarbonyl |
| Dnp | 2,4-dinitrophenyl |
| Fmoc | Fluorenylmethyloxycarbonyl |
| OMe | Methyl ester |
| Tos | p-Toluenesulfonyl |
| | Condensing Agents |
| BOP | Benzotriazol-1-yloxytris-(dimethylamino)phosphonium hexafluorophosphate |
| DCC | Dicyclohexylcarbodiimide |
| DICI | Diisopropylcarbodiimide |
| DPPA | Diphenylphosphorylazide |
| EDC | 1-ethyl-3-(3-dimethylamino-propyl)carbodiimide |
| | Reagents and Solvents |
| AcOH | Acetic acid |
| DMF | N,N-dimethylformamide |
| DIEA | Diisopropylethylamine |
| Fmoc-Cl | 9-Fluorenylmethyloxy-carbonylchloride |

TABLE 1-continued

| Abbreviated Designation | |
|---|---|
| HBT | 1-Hydroxybenzotriazole |
| HF | Hydrofluoric acid |
| Pyr | Pyridine |
| TEA | Triethylamine |
| TFA | Trifluoroacetic acid |
| THF | Tetrahydrofuran |

GENERAL PROCEDURES

Coupling Techniques

Procedure 1
(Acid chloride/AgCN)

1a) Formation of Fmoc amino acid chlorides: Fmoc-L-($N^\delta$-Cbz)-piperazic acid chloride. A solution of 535 mg (1.1 mmol) of Fmoc-L-($N^\delta$-Cbz)-Piz in 10 mL of methylene chloride was cooled in ice/water and treated with 0.19 mL (2.2 mmol) of oxalyl chloride followed by 0.01 mL (0.13 mmol) of DMF. The mixture was stirred for 1.5 hours, then concentrated to yield the acid chloride as a foam.

1b) Fmoc-L-($N^\delta$-Cbz-piperazic acyl D-phenylalanyl-L-proline tert-butyl ester. To the above acid chloride was added a solution of H-D-Phe-L-Pro-O-$^t$Bu (derived from 654 mg (1.21 mmol) of Fmoc-D-Phe-L-Pro-O-$^t$Bu by Procedure 8) in 6 mL of toluene. The mixture was treated with 295 mg (2.20 mmol) of silver cyanide and stirred vigorously in an oil bath maintained at 80° C. to 85° C. After 30 minutes, the mixture was diluted with toluene (ca. 60 mL) filtered through a pad of diatomaceous earth, and the filtrate was evaporated in vacuo. Purification by Method F (25% acetone in hexane) yielded 614 mg of the protected tripeptide; HPLC, single major peak (98.1% pure) at Rt=17.34 minutes (Method I); FAB MS: 787 (M+ +H), 809 (M+ +Na); [$^1$H]-NMR (300 MHz, CDCl$_3$) consistent with structure; Elemental Analysis, Calculated: C, 70.12; H, 6.40; N, 7.12. Found: C, 69.92; H, 6.15; N, 6.88.

Procedure 2
(Acid chloride/tertiary amine base)

A 49 mg (0.1 mmol) sample of Fmoc-($N^\delta$-Cbz)-L-Piz was converted to its acid chloride (Procedure 1a). To this material was added a cold (0° C. bath) solution of H-D-Phe-L-Pro-O-$^t$Bu (derived from 60 mg (0.11 mmol) of Fmoc-D-Phe-L-Pro-O-$^t$Bu by Procedure 8) in 1.5 mL of methylene chloride, followed by 0.019 mL (0.11 mmol) of DIEA. The mixture was stirred in the cold for 2 hours, then concentrated in vacuo to a small volume and purified by Method F (33% acetone/hexanes) to yield 61 mg of a foamy solid, identical to that obtained by Procedure 1.

Procedure 3
(BOP-Cl)

A cold (0° C. bath) suspension of 49 mg (0.1 mmol) of Fmoc-($N^\delta$-Cbz)-L-Piz, 0.0175 mL (0.10 mmol) of DIEA, and 28 mg (0.11 mmol) of BOP-Cl in 1 mL of methylene chloride was stirred for 1.5 hours. The flocculant mixture was treated with H-D-Phe-L-Pro-O-$^t$Bu (derived from 60 mg (0.11 mmol) of Fmoc-D-Phe-L-Pro-O-$^t$Bu according to Procedure 8) in 1.5 mL of methylene chloride, followed by 0.0175 mL (0.10 mmol) of DIEA. The mixture was stirred in the cold for 17 hours, then concentrated in vacuo and purified by Method F (33% acetone/hexanes) to yield 51 mg of a glass, identical to that obtained by Procedure 1.

Procedure 4
(Pentafluorophenyl esters)

A solution of 776 mg (2.44 mmol) of H-D-Phe-L-Pro-O-$^t$Bu in 10 mL of ethyl acetate was treated sequentially with 0.446 mL (2.56 mmol) of DIEA and 1.33 g (2.56 mmol) of Fmoc-Asn pentafluorophenyl ester. The mixture was treated, in portions during the next hour, with 1.5 mL of DMF to aid in solubility of the reaction components. After 3.5 hours, the mixture was diluted with 20 mL of ethyl acetate and washed with sodium chloride solution (3×), then with 5% aqueous sodium bicarbonate solution (2×), 10% aqueous potassium bisulfate solution (2×), and finally with brine (3×). The solution was dried over MgSO$_4$ and concentrated to yield a solid. Recrystallization from toluene, ether, and hexanes yielded 1.16 g of a white solid: FAB MS: 655 (M+ +H); TLC, Rf=0.25 in 4% MeOH/methylene chloride, E. Merck silica gel; HPLC (Method I) major peak at Rt=17.65 minutes; [$^1$H]-NMR (300 MHz, CDCl$_3$) consistent with structure.

Procedure 5
(Pivalic Mixed Anhydrides)

A solution of 151 mg (0.19 mmol) of N-Cbz-D-Phe-L-Ile-D-Pip-L-Pip-D-Phe-OH in 0.7 mL of CHCl$_3$ was cooled in a −22° C. constant temperature bath and treated with 0.044 mL (0.040 mmol) of N-methyl morpholine. After stirring for several minutes, the solution was treated, dropwise during several minutes, with 0.023 mL (0.019 mmol) of pivaloyl chloride. The mixture was stirred for 8 hours in the cold, then to it was added, via cannula, a solution of N-methyl alanine benzyl ester (from 250 mg of the p-toluene sulfonic acid salt) in 0.5 mL of CHCl$_3$, prechilled to the same temperature. The mixture was stirred for 2 days in the cold, then was poured into 4 volumes of ether and extracted with water (2x), 10% aqueous potassium bisulfate solution, water, and brine. The solution was dried over MgSO$_4$ and concentrated to yield an oil, which was purified by Method F (5% methanol/methylene chloride) to yield 110 mg of a white foam: TLC, Rf=0.30 in 30% acetone/hexane, E. Merck silica gel; [$^1$H]-NMR (300 MHz, CDCl$_3$) consistent with structure.

Deprotection Techniques

Procedure 6
(Trifluoroacetic acid Boc Removal)

Trifluoroacetic acid (2 mL) was cooled in a −10° C. bath. This acid was transferred via cannula onto an 80 mg (0.010 mmol) sample of cyclo-[D-phenylalanyl-L-isoleucyl-D-pipecolyl-L-aspartyl ($\beta$-tert butyl ester)-D-N-methyl-phenylalany-L-proplyl], precooled in an ice/water bath. After swirling to effect dissolution of the peptide, the mixture was allowed to stand for 45 minutes in the cold. Several mL of carbon tetrachloride were added to the mixture, which was concentrated in vacuo to yield a white foam. This material was purified by Method F (eluting with 90:10:1, methylene chloride/methanol/water) to yield 38 mg of a foam: TLC, Rf=0.20 in 92:8:08, methylene chloride/methanol/water, E. Merck silica gel; HPLC (Method I) single major peak at Rt=16.17 minutes, FAB MS: 745 (M+ +H), 767 (M+ +Na); [$^1$H]-NMR (360 MHz, DMSO-d$_6$) consistent with structure; Elemental Analysis, Calculated (for 0.5 moles of water): C, 63.72, H, 7.09, N, 11.15; Found: C, 63.68, H, 7.02. N, 10.95.

Procedure 7
(Formic Acid Boc Removal)

A 38 mg (0.045 mmol) sample of cyclo-[D-Phe-L-Ile-D-($N^\delta$-Boc)-Orn-L-Pip-D-MePhe-L-Pro] was treated wit 2 mL of 98% formic acid and swirled to effect dissolution of the peptide. The mixture was allowed to stand at room temperature for 2 hours, then was concentrated and the residue taken up in toluene and again concentrated to yield a white solid. This material was purified by Method F (eluting with 90:10:1.2 methylene chloride/methanol/concentrated ammonium hydroxide) to yield 25 mg of a solid: TLC, Rf=0.33 (90:10:1, methylene chloride/methanol/concentrated ammonium hydroxide) E. Merck silica gel; HPLC (Method L) single major peak at Rt=17.00 minutes, FAB MS: 744 (M++H), 766 (M++Na); [$^1$H]-NMR (360 MHz, DMSO-$d_6$) consistent with structure; Elemental Analysis, Calculated (for 0.5 moles of ammonium hydroxide): C, 64.67; H, 7.88, N; 11.15; Found: C, 64.55; H, 7.87; N, 13.80.

Procedure 8

(Diethylamine/Acetonitrile Fmoc Removal)

A solution of 218 mg (0.204 mmol) of Fmoc-D-phenylalanyl-L-isoleucyl-D-prolyl-L-pipecolyl-D-N-methyl phenylalanyl-L-proline benzyl ester in 2 mL of acetonitrile was treated with an equal volume of diethylamine at ambient temperature. The mixture was swirled to bring all material into solution, then allowed to stand for 25 minutes. The solvents were removed in vacuo and the residue was purified (Method E) using a gradient of 0% to 7% methanol in methylene chloride as eluant. Concentration of product-containing fractions yielded 145 mg of a foam: TLC, Rf=0.46 (8% methanol/methylene chloride) E. Merck silica gel; HPLC (Method L) single major peak at Rt=16.17 minutes. [$^1$H]-NMR (300 MHz, DMSO-$d_6$) consistent with structure; Elemental Analysis, Calculated (for 0.5 moles of water): C, 68.30; H, 7.52; N, 9.96; Found: C, 68.42; H, 7.58; N, 10.05.

Procedure 9

(Removal of Cbz by Hydrogenation with Pd/C)

A solution of 28 mg (0.028 mmol) of cyclo-[D-Phe-L-Ile-D-($N^\delta$-Cbz)-Piz-L-($N^\delta$-Cbz)-Piz-D-MePhe-L-Pro] in 10 mL of 95% aqueous ethanol was flushed with argon and treated with 4 mg of 10% Pd/C. The mixture was shaken in a Parr hydrogenation apparatus under 45 psi of hydrogen for 17 hours. The mixture was filtered through diatomaceous earth and the filtrate was concentrated. The residue was purified by Method F eluting with 95:5:05, chloroform/methanol/concentrated ammonium hydroxide, to yield 16 mg of a solid: TLC, Rf=0.20 in 95:5:05, chloroform/methanol/concentrated ammonium hydroxide, E. Merck silica gel; HPLC (Method I) single major peak at Rt=17.38 minutes, FAB MS: 729 (M++H), 7.51 (M++Na); [$^1$H]-NMR (360 MHz, DMSO-$d_6$) consistent with structure; Elemental Analysis, Calculated (for 1.2 moles of methanol): C, 62.93, H, 7.46, N, 14.60; Found: C, 62.99, H, 7.34, N, 14.60.

Procedure 10

(Removal of Cbz by Hydrogenation with Pd(OH)$_2$/C

A solution of 220 mg (0.221 mmol) of Cbz-D-Phe-L-Ile-D-Pip-L-Pip-D-N-MePhe-L-Pro-benzyl ester in 20 mL of 95% aqueous ethanol was treated with 55 mg of moist 20% palladium hydroxide on carbon, and the mixture was shaken in on Parr hydrogenation apparatus under 55 psi of hydrogen for 17 hour. The mixture was filtered through diatomaceous earth and the filtrate was concentrated to yield 177 mg of an off-white solid: TLC, Rf=0.48 in 90:10:1 chloroform/methanol/water, E. Merck silica gel; HPLC (Method I) single major peak at Rt=14.27 minutes, FAB MS: 773 (M++H), 795 (M++Na); [$^1$H]-NMR (300 MHz, acetone-$d_6$) consistent with structure; Elemental Analysis, Calculated (for 0.5 moles each of water and ethanol): C, 65.27, H, 8.16, N, 10.15; Found: C, 65.54, H, 7.98, N, 9.82.

PREPARATION OF KEY INTERMEDIATES

N-1-(9-Fluorenylmethyloxycarbonyl)-N-4-benzyloxycarbonyl-L-piperazine-2-carboxylic acid Pyrazine-2-carboxylic acid (18.6 g) and potassium hydroxide (0.6 g) were dissolved in 600 mL of water and hydrogenated at 55 psi in a Parr apparatus for seven hours. The reaction mixture was filtered and the filtrate was treated with 109.41 g (3 equiv) of (1S)-(+)-10-camphorsulfonic acid (CSA). The resulting solution was concentrated to 150 mL. The solids were collected and dried to yield 46.6 g of the Pipe.CSA salt, $[\alpha]_D + 16.7°$ (C=1, H$_2$O).

A solution of 150 mL of water containing 41.69 g of the above Pipe.CSA salt was combined with 6.47 g of cupric chloride in 150 mL of water. The solution was cooled to 0° and the pH was adjusted to 9.5 using 10N sodium hydroxide. Benzylchloroformate (11.77 g) and 10N sodium hydroxide were then added simultaneously over a 20 minute period taking care that the pH of the reaction mixture remained at 9.5. After addition was complete the reaction mixture was warmed to room temperature and allowed to stir overnight. The pH of the reaction mixture was adjusted to 7.2 with dilute hydrochloric acid solution and the resulting blue precipitate was collected. The solids were dissolved in acetic acid (300 mL), diluted with water (200 mL) and warmed to 50°. Hydrogen sulfide gas was passed into the reaction mixture until no more copper sulfide precipitated. The reaction mixture was filtered through Celite and the filtrate was concentrated to afford N-4-Cbz-L-Pipe.

Trimethylsilyl chloride (18.73 g) was added to a suspension of 28.7 g or N-4-Cbz-L-Pipe in 300 mL of methylene chloride. After 1 hour, the homogeneous reaction mixture was cooled to 0° C. and Fmoc-Cl (32.05 g) and DIEA (43.2 mL) were added. The reaction mixture was stirred at room temperature overnight, filtered and concentrated. The residual solid was partitioned between ether and water and treated with 1.2N HCl solution. The organic phase was washed with water until neutral and extracted with saturated sodium bicarbonate solution. The sodium salt of the title compound precipitated and was collected. The title compound (16.8 g) was obtained in greater than 98% purity (HPLC) after acidification with 1.2N HCl in CH$_2$Cl$_2$.

3-(3-Pyridyl)-D-Alanine

Prepared according to the procedure of P. N. Rao, et. al.; *Int. J. Peptide Protein Res.* (1987) 29. 118–125.

WORKUP AND PURIFICATION METHODS

Method A

Mixed Bed Ion Exchange

The crude cyclization product (1 mmole) is dissolved in DMF (60 mL) and H$_2$O (20 mL) and treated with BioRad AG 501-X8 mixed ion exchange resin (20 mL dry volume) for 1 hour at ambient temperature. The solution is filtered and the filtrate is evaporated under reduced pressure to a glass which is lyophilized from dioxane, or dioxane/H$_2$O (50 mL).

Method B

Preparative Reverse Phase HPLC

The crude cyclization product (1 mmole) is dissolved in methanol (8 mL) and chromatographed using reverse phase preparative HPLC using the following conditions:

| | |
|---|---|
| Column = DeltaPak Prep Cartridge C18, 15μ, 300A, 5cm ID, 30 cm L. | |
| Mobile Phases | A = 0.1% TFA in H₂O |
| | B = 0.1% TFA in acetonitrile |
| Gradient | T = 0 minutes, A(95%), B(5%) |
| | T = 45 minutes, A(0%), B(100%) |
| Flow = 40 mL/minute | Temperature = 23° C. |

Method C

Preparative Reverse Phase HPLC

The crude cyclization product (1 mmole) is dissolved in methanol (10 mL) and chromatographed using reverse phase preparative HPLC using the following conditions:

| | |
|---|---|
| Column = DeltaPak Prep Cartridge C18, 15μ, 100A, 5cm ID, 30 cm L. | |
| Mobile Phases | A = 0.1% TFA in H₂O |
| | B = acetonitrile |
| Gradient | T = 0 minutes, A(100%), B(0%) |
| | T = 60 minutes, A(40%), B(60%) |
| Flow = 100 mL/minute | Temperature = 23° C. |

Method D

Preparative Reverse Phase HPLC

The crude cyclization product (1 mmole) is dissolved in methanol (10 mL) and chromatographed using reverse phase preparative HPLC using the following conditions:

| | |
|---|---|
| Column = DeltaPak Prep Cartridge C18, 15μ, 300A, 5cm ID, 30 cm L. | |
| Mobile Phases | A = 0.1% H₃PO₄ H₂O |
| | B = acetonitrile |
| Gradient | T = 0 minutes, A(100%), B(0%) |
| | T = 60 minutes, A(40%), B(60%) |
| Flow = 100 mL/minute | Temperature = 23° C. |

Method E

Flash Chromatography

The crude cyclization product (1 mmole) is dissolved in methylene chloride (5 mL) and chromatographed on silica gel (230-400 mesh, 200 mL bed volume) eluting with methylene chloride/methanol/H₂O/acetic acid (90:10:1:1, v/v). The fractions are assayed for purity (Method F) and the pure fractions are combined and evaporated under reduced pressure and lyophilized from dioxane or dioxane/H₂O (50 mL).

Method F

Preparative Thick Layer Chromatography

The crude product is dissolved in methanol or THF and chromatographed on precoated E. Merck 60F₂₅₄ silica gel plates (0.25 mm, 0.5 mm, 1.0 mm or 2 mm thickness) eluting with methylene chloride/methanol/H₂O/acetic acid (90:10:1:1, v/v), or similar solvent system. The product band is isolated and washed with methylene chloride/methanol (70:30, v/v), THF/methanol (90:10, v/v) or ethanol/water (50:50, v/v). The suspension is filtered and the filtrate is concentrated to dryness under reduced pressure.

ANALYTICAL REVERSE PHASE HPLC METHODS

Method G

| | |
|---|---|
| Column = Vydac 218TP C18, 0.21 cm ID, 15 cm L. | |
| Mobile Phases | A = 0.1% TFA in H₂O |
| | B = 0.1% TFA in acetonitrile |
| Gradient | T = 0 minutes, A(95%), B(5%) |
| | T = 15 minutes, A(0%), B(100%) |
| Flow = 2 mL/minute | Temperature = 23° C. |

Method H

| | |
|---|---|
| Column = Vydac 218TP C18, 0.21 cm ID, 15 cm L. | |
| Mobile Phases | A = 0.1% TFA in H₂O |
| | B = 0.1% TFA in acetonitrile |
| Gradient | T = 0 minutes, A(95%), B(5%) |
| | T = 45 minutes, A(5%), B(95%) |
| Flow = 1.5 mL/minute | Temperature = 23° C. |

Method I

| | |
|---|---|
| Column = Waters MicroBondapak C18, 0.39 cm ID, 30 cm L. | |
| Mobile Phases | A = 0.1% H₃PO₄ H₂O |
| | B = acetonitrile |
| Gradient | T = 0 minutes, A(95%), B(5%) |
| | T = 30 minutes, A(5%), B(95%) |
| Flow = 3.0 mL/minute | Temperature = 40° C. |

Method J

| | |
|---|---|
| Column = Vydac 218TP C18, 0.21 cm ID, 15 cm L. | |
| Mobile Phases | A = 0.1% H₃PO₄ in H₂O |
| | B = acetonitrile |
| Gradient | T = 0 minutes, A(95%), B(5%) |
| | T = 45 minutes, A(5%), B(95%) |
| Flow = 1.5 mL/minute | Temperature = 23° C. |

Method K

| | |
|---|---|
| Column = Vydac 218TP C18, 0.21 cm ID, 15 cm L. | |
| Mobile Phases | A = 0.1% TFA in H₂O |
| | B = 0.1% TFA in acetonitrile |
| Gradient (Isocratic) | A(52%): B(48%) |
| Flow = 1.5 mL/minute | Temperature = 23° C. |

Method L

| | |
|---|---|
| Column = Vydac 218TP C18, 0.21 cm ID, 15 cm L. | |
| Mobile Phases | A = 0.1% H₃PO₄ in H₂O |
| | B = acetonitrile |
| Gradient | T = 0 minutes, A(95%), B(5%) |
| | T = 15 minutes, A(5%), B(95%) |
| Flow = 1.5 mL/minute | Temperature = 23° C. |

Method M

| |
|---|
| Column = Vydac 218TP C18, 2.54 cm ID, 22 cm L. |

-continued

| | |
|---|---|
| Mobile Phases | A = 0.1% TFA in H$_2$O |
| | B = 0.1% TFA in acetonitrile |
| Gradient | T = 0 minutes, A(95%), B(5%) |
| | T = 45 minutes, A(5%), B(95%) |
| Flow = 8.0 mL/minute | Temperature = 23° C. |

Method N

| | |
|---|---|
| Column = Vydac 218TP C18, 0.21 cm ID, 15 cm L. | |
| Mobile Phases | A = 0.1% H$_3$PO$_4$ in H$_2$O |
| | B = acetonitrile |
| Gradient | T = 0 minutes, A(95%), B(5%) |
| | T = 20 minutes, A(5%), B(95%) |
| Flow = 2.0 mL/minute | Temperature = 23° C. |

EXAMPLE 1

Preparation of
Cyclo-[D-Phenylalanyl-L-isoleucyl-D-pipecolyl-L-pipecolyl-D-(N$^\alpha$-methyl)-phenylalanyl-L-prolyl]

STEP 1

Boc-L-Pro-O-(PAM)-resin→Boc-D-(N$^\alpha$Me)Phe-L-Pro-O-(PAM)-resin

Boc-L-Pro-O-(PAM)-resin (1.32 gm, 1 mmole, 0.76 meq of nitrogen/gram) was placed in a shaker flask and swelled for 2 hours by the addition of 20 ml of CH$_2$Cl$_2$. The resin was then carried through the procedure in Table 4, which includes 2 deblocking with 4N HCl/Dioxane for 15 minutes each and 2 neutralizations with 10% DIEA/DMF. Coupling was achieved by the addition of Boc-D-(N$^\alpha$Me)Phe (0.558 gm, 2 mmol) in 15 ml of 1:1 CH$_2$Cl$_2$/DMF followed by DIEA (0.350 ml, 2 mmol) and after 5 minutes of shaking, solid BOP reagent (0.884 gm, 2 mmol) was added to the flask. After shaking for 10 minutes the mixture was adjusted to pH 8 (measured with wetted E. Merck pH sticks) by the addition of 40 ul more of DIEA, and the reaction was shaken for 15 hours at ambient temperature. The resin was then washed as indicated in Table 2 with DMF, methanol and CH$_2$Cl$_2$ and used in the next coupling step as given in Table 3.

STEP 2

Boc-D-(N$^\alpha$Me)Phe-L-Pro-O-(PAM)-resin→Fmoc-L-Pip-D-(N$^\alpha$Me)Phe-L-Pro-O-(PAM)-resin

TABLE 3

| SOLVENT | VOLUME (ML) | TIME (MIN) | REPEAT (XS) | COMMENT |
|---|---|---|---|---|
| CH$_2$Cl$_2$ | 15 | 2 | 3 | |
| 4N HCl 1N Dioxane | 15 | 15 | 2 | Deprotection |
| CH$_2$Cl$_2$ | 15 | 2 | 6 | |
| Fmoc-L-Pip-Cl in CH$_2$Cl$_2$/0° C. | 15 | 2 | | Resin Mixture at 5° C.; 2 equiv. of amino acid chloride |
| DIEA | 0.522 | 15 hrs | | 3 equiv. |
| CH$_2$Cl$_2$ | 15 | 2 | 3 | |
| Methanol | 15 | 2 | 2 | CH$_2$Cl$_2$ and methanol alternating twice |
| CH$_2$Cl$_2$ | 15 | 2 | 2 | |

After two deblockings with 4N HCl in dioxane, coupling was achieved via the acid chloride of Fmoc-L-Pip the preparation of which is given below: Fmoc-L-Pip (0.712 gm, 2 mmol) was dissolved in dry CH$_2$CH$_2$ (5 ml) and cooled to 0° C. under N$_2$. Oxalyl chloride (0.350 ml, 4 mmol) was added followed by DMF (0.0155 ml, 0.2 mmol) and the reaction was stirred for 1 hour during which time gas evolution took place. The solvent was removed under reduced pressure and CH$_2$Cl$_2$ (5 ml, dry) was added and evaporated 2 times under reduced pressure to yield a foam. This material was dissolved in CH$_2$Cl$_2$ (15 mL) at 0° C. and was added to the dipeptide resin at 5° C. DIEA (0.522 ml, 3 mmol) was added and the reaction mixture was shaken for 15 hours at 5° C. The resin was washed as indicated in Table 3 with CH$_2$Cl$_2$ and methanol. Coupling of the remaining three amino acids was accomplished using the protocol in Table 4.

TABLE 2

PROCEDURE FOR 1 MMOLE SCALE

| SOLVENT | VOLUME (ML) | TIME (MIN) | REPEAT (XS) | COMMENT |
|---|---|---|---|---|
| CH$_2$Cl$_2$ | 15 | 120 | 1 | Swells resin |
| CH$_2$Cl$_2$ | 15 | 2 | 3 | |
| 4N HCl 1N Dioxane | 15 | 15 | 2 | Deprotection |
| CH$_2$Cl$_2$ | 15 | 2 | 3 | |
| DMF | 15 | 2 | 3 | |
| 10% DIEA IN DMF | 15 | 5 | 2 | Neutralization |
| DMF | 15 | 2 | 2 | |
| Boc-AA IN 1:1 DMF/CH$_2$Cl$_2$ | 15 | 5 | | 2 equivalents |
| DIEA | * | | | *3 equivalents |
| BOP reagent | * | 15 hrs | | *2 equivalents of solid added |
| DMF | 15 | 2 | 2 | |
| CH$_2$Cl$_2$ | 15 | 2 | 2 | CH$_2$Cl$_2$ and MEOH alternating twice |
| MEOH | 15 | 2 | 2 | |

STEP 3-5

Fmoc-L-Pip-D-(N$^\alpha$Me)Phe-L-Pro-O-(PAM)-resin→
Fmoc-D-Phe-L-Ile-D-Pip-L-Pip-D-(N$^\alpha$Me)Phe-L-Pro-O-(PAM)-resin

TABLE 4

| SOLVENT | VOLUME (ML) | TIME (MIN) | REPEAT (XS) | COMMENT |
|---|---|---|---|---|
| CH$_2$Cl$_2$ | 15 | 2 | 2 | |
| DMF | 15 | 2 | 3 | |
| 20% Piperidine in DMF | 15 | 2 | 1 | Deprotection of Fmoc (and DNP when present) |
| DMF | 15 | 2 | 3 | |
| CH$_2$Cl$_2$ | 15 | 2 | 3 | |
| Fmoc-AA-Cl in CH$_2$Cl$_2$/25° C. | 15 | 2 | | Addition of the acid chloride (2 equiv.) |
| DIEA | 0.348 | 15 hrs. | | Check pH for adjustment to 8 |
| CH$_2$Cl$_2$ | 15 | 2 | 4 | |
| Methanol | 15 | 2 | 2 | Alternate CH$_2$Cl$_2$ and Methanol washes |
| CH$_2$Cl$_2$ | 15 | 2 | 2 | |

The final Fmoc-D-Phe-L-Ile-D-Pip-L-Pip-D-(N$^\alpha$Me)-Phe-L-Pro-O-(PAM)-resin was deprotected at the N-terminus using 20% piperidine in DMF as shown in Table 5.

TABLE 5

| SOLVENT | VOLUME (ML) | TIME (MIN) | REPEAT (XS) | COMMENT |
|---|---|---|---|---|
| CH$_2$Cl$_2$ | 15 | 2 | 2 | |
| DMF | 15 | 2 | 3 | |
| 20% Piperidine in DMF | 15 | 2 10 | 1 | Deprotection |
| DMF | 15 | 2 | 3 | |
| CH$_2$Cl$_2$ | 15 | 2 | 4 | |
| Methanol | 15 | 2 | 2 | Alternate Methanol and CH$_2$CL$_2$ washes |
| CH$_2$Cl$_2$ | 15 | 2 | 2 | |
| CH$_2$Cl$_2$ | 15 | 2 | 3 | |

STEP 6

Fmoc-D-Phe-L-Ile-D-Pip-L-Pip-D-(N$^\alpha$Me)Phe-L-Pro-O-(PAM)-resin→H-D-Phe-L-Ile-D-Pip-L-Pip-D-(N$^\alpha$Me)Phe-L-Pro-O-(PAM)-resin

TABLE 5

| SOLVENT | VOLUME (ML) | TIME (MIN) | REPEAT (XS) | COMMENT |
|---|---|---|---|---|
| CH$_2$Cl$_2$ | 15 | 2 | 2 | |
| DMF | 15 | 2 | 3 | |
| 20% Piperidine in DMF | 15 | 2 10 | 1 1 | Deprotection |
| DMF | 15 | 2 | 3 | |
| CH$_2$Cl$_2$ | 15 | 2 | 4 | |
| Methanol | 15 | 2 | 2 | Alternate Methanol and CH$_2$Cl$_2$ washes |
| CH$_2$Cl$_2$ | 15 | 2 | 2 | |
| CH$_2$Cl$_2$ | 15 | 2 | 3 | |

STEP 7

H-D-Phe-L-Ile-D-Pip-L-Pip-D-(N$^\alpha$Me)Phe-L-Pro-O-(PAM)-resin→H-D-Phe-L-Ile-D-Pip-L-Pip-D-(N$^\alpha$Me)-Phe-L-Pro-NHNH$_2$ After the indicated washings were completed the resin was dried in vacuo for 24 hours. The dried resin (1.5 gm) had a nitrogen value of 4.97% from combustion analysis, indicating a peptide loading of 0.583 mmoles/gm. The resin was stirred with 1:1 methanol/hydrazine (60 ml) under nitrogen at room temperature for 1 hour and at 50° C. for 30 minutes. The excess hydrazine and methanol were removed under reduced pressure at 50° C., and methanol (60 ml) was added and evaporated under reduced pressure three times. The residue was then suspended in methanol and filtered. The filtrate was evaporated under reduced pressure and the resulting glass was dried in vacuo for 15 hours. The glass was dissolved in n-butanol (400 ml) and extracted three times with water (300 ml) to remove traces of hydrazine. The n-butanol layer was then evaporated under reduced pressure and methanol (60 ml) was added and evaporated under reduced pressure. The resulting hydrazide was dried in vacuo for 15 hours. The HPLC retention time of this hydrazide is 7.75 minutes using Method G.

STEP 8

H-D-Phe-L-Ile-D-Pip-L-Pip-D-(N$^\alpha$Me)Phe-L-Pro-NHNH$_2$→cyclo[D-Phe-L-Ile-D-Pip-L-Pip-D-(N$^\alpha$Me)-Phe-L-Pro]

The hydrazide (540 mg, 0.698 mmole) was dissolved in dry, degassed DMF (6 mL) and cooled under nitrogen to 15° C. To the stirred solution was added a 5-fold excess of 5N HCl/THF (0.69 ml, 3.49 mmol) and the reaction was further cooled to −25° C. Isoamylnitrite (0.103 ml, 0.768 mmol) was added in small portions over one hour, monitoring for excess isoamylnitrite by spotting aliquots on starch/KI paper. When a slight excess (positive test) was maintained for 30 minutes, addition was stopped. HPLC analysis using Method F, indicated completed conversion to the acyl azide which had a retention time of 9.29 minutes. The reaction was then diluted with DMF (dry, degassed, 150 ml) which was precooled under nitrogen to −25° C. The solution was brought to pH 8 (wetted E. Merck pH sticks) by the addition of DIEA (0.67 ml, 3.84 mmole). The reaction temperature was maintained at −20° C. for 24 hours.

A single product was detected by HPLC analysis (Method G) with a retention time of 11.16 minutes. The solution was then evaporated under reduced pressure to an oil which was purified using Method A. The final product was obtained as a white solid by lyophilization from dioxane, which gave 520 mg (70%) of the title compound.

HPLC (Method G) RT=11.14 minutes: purity 99%, NMR (CD$_3$OD) in agreement with title compound.
FAB MS: 741 (M++H).
Analysis Calc'd for C$_{42}$H$_{56}$N$_6$O$_6$: N, 11.34; C, 68.08; H, 7.62. Found: N, 11.39; C, 67.30; H, 7.55.

EXAMPLE 2

Cylco[D-alanyl-L-isoleucyl-D-pipecolyl-L-pipecolyl-D-phenylalanyl-L-prolyl]

Cyclo[D-Ala-L-Ile-D-Pip-L-Pip-D-Phe-L-Pro] was prepared form Boc-L-Pro-O-(PAM)-resin (1 mmole)

according to the solid phase procedure set forth in Example 1 with the following exceptions: Boc-D-Phe (530 mg, 2 mmol) was used in Step 1 and Fmoc-D-Ala (622 mg, 2 mmol) was used in Step 5. The final resin was cleaved with hydrazine and the hexapeptide hydrazide was cyclized as the acyl azide. Workup and purification (Method A) gave 452 mg (70%) of the title compound.

HPLC (Method G) RT=8.80 minutes: purity 99%, NMR (CD$_3$OD) in agreement with title compound. FAB MS: 651 (M+ +H).

Analysis Calc'd for C$_{35}$H$_{50}$N$_6$O$_6$: N, 12.91; C, 64.59; H, 7.74. Found: N, 12.96; C, 62.02; H. 7.79.

EXAMPLE 3

Cyclo[D-phenylalanyl-L-isoleucyl-D-pipecolyl-L-pipecolyl-D-histidyl-L-prolyl]

Cyclo[D-Phe-L-Ile-D-Pip-L-Pip-D-His-L-Pro] was prepared from Boc-L-Pro-O-(PAM)-resin (1 mmole) according to the solid phase procedure set forth in Example 1 with the following exception: Boc-D-(DNP)-His (840 mg, 2 mmol) was used in Step 1. The final resin was cleaved with hydrazine and the hexapeptide hydrazide was cyclized as the acyl azide. Workup and purification (Method B) gave 248 mg (28%) of the title compound.

HPLC (Method G) RT=7.49 minutes; purity 99%, NMR (CD$_3$OD) in agreement with title compound. FAB MS: 718 (M+ +H).

Analysis Calc'd for C$_{38}$H$_{52}$N$_8$O$_6$.1C$_2$HF$_3$O$_2$.4H$_2$O: N, 12.41; C, 53.21; H, 6.92. Found: N, 12.27; C, 53.83; H, 5.79.

EXAMPLE 4

Cyclo[D-histidyl-L-isoleucyl-D-pipecolyl-L-pipecolyl-D-(N$^\alpha$-methyl)-phenylalanyl-L-prolyl]

Cyclo[D-His-L-Ile-D-Pip-L-Pip-D-(N$^\alpha$Me)Phe-L-Pro] was prepared from Boc-L-Pro-O-(PAM)-resin (1 mmole) according to the solid phase procedure set forth in Example 1 with the following exception: Fmoc-D-(DNP)-His (1.086 gm, 2 mmol) was used in Step 5. The final resin was cleaved with hydrazine and the hexapeptide hydrazide was cyclized as the acyl azide. Workup and purification (Method B) gave 242 mg (26%) of the title compound.

HPLC (Method G) RT=7.95 minutes: purity 99%, NMR (CD$_3$OD) in agreement with title compound. FAB MS: 732 (M+ +H).

Analysis Calc'd for C$_{39}$H$_{54}$N$_8$O$_6$ 1 C$_2$HF$_3$O$_2$.4H$_2$O: N, 12.22; C, 53.70; H, 7.03. Found: N, 12.07; C, 54.35; H, 5.93.

EXAMPLE 5

Cyclo[D-phenylalanyl-L-isoleucyl-D-pipecolyl-L-pipecolyl-D-(N$^\alpha$methyl)alanyl-L-prolyl]

Cyclo[D-Phe-L-Ile-D-Pip-L-Pip-D-(N$^\alpha$Me)Ala-L-Pro] was prepared from Boc-L-Pro-O-(PAM)-resin (1 mmole) according to the solid phase procedure set forth in Example 1 with the following exception: Boc-D-(N$\alpha$Me)Ala (410 mg, 2 mmol) was used in STEP 1. The final resin was cleaved with hydrazine and the hexapeptide hydrazide was cyclized as the acyl azide. Workup and purification (Method B) gave 340 mg (44%) of the title compound.

HPLC (Method G) RT=9.41 minutes; purity 99%. NMR (CD$_3$OD) in agreement with title compound. FAB MS: 665 (M+ +H).

Analysis Calc'd for C$_{36}$H$_{52}$N$_6$O$_6$.1C$_2$HF$_3$O$_2$: N, 10.79; C, 58.60; H, 6.99. Found: N, 10.81; C, 58.60; H, 6.84.

EXAMPLE 6

Cyclo[D-phenyalanyl-L-isoleucyl-D-pipecolyl-L-(N$^\alpha$-methyl)alanyl-D-(N$^\alpha$Methyl)phenylanyl-L-prolyl]

Cyclo[D-Phe-L-Ile-D-Pip-L-(N$^\alpha$Me)Ala-D-(N$^\alpha$Me)-Phe-L-Pro] was prepared from Boc-L-Pro-O-(PAM)-resin (1 mmole) according to the solid phase procedure set forth in Example 1 with the following exception: Fmoc-D-(N$^\alpha$Me)Ala (650 mg, 2 mmol) was used in Step 2. The final resin was cleaved with hydrazine and the hexapeptide hydrazine was cyclized as the acyl azide. Workup and purification (Method A) gave 470 mg (64%) of the title compound.

HPLC (Method G) RT=10.17 minutes; purity 99%. NMR (CD$_3$OD) in agreement with title compound. FAB MS: 716 (M+ +H).

Analysis Calc'd for C$_{40}$H$_{54}$N$_6$O$_6$.1H$_2$O: N, 11.46; C, 65.55; H, 7.70. Found: N, 11.45; C, 65.41; H, 7.58.

EXAMPLE 7

Cyclo[D-phenylalanyl-L-isolelucyl-D-pipecolyl-L-propyl-D-(N$^\alpha$Methyl)phenyl-L-prolyl]

Cyclo[D-Phe-L-Ile-D-Pip-L-Pro-D-(N$^\alpha$Me)Phe-L-Pro] was prepared from Boc-L-Pro-O-(PAM)-resin (1 mmole) according to the solid phase procedure set forth in Example 1 with the following exception: Fmoc-L-Pro (674 mg, 2 mmol) was used in Step 2. The final resin was cleaved with hydrazine and the hexapeptide hydrazide was cyclized as the acyl azide. Workup and purification (Method A) gave 382 mg (39%) of the title compound.

HPLC (Method G) RT=9.98 minutes; purity 98%. NMR (CD$_3$OD) in agreement with title compound. FAB MS: 728 (M+ +H).

Analysis Calc'd for C$_{41}$H$_{54}$N$_6$O$_6$.1 H$_2$O: N, 11.28; C, 66.11; H, 7.58: Found: N, 11.33; C, 65.47; H, 7.25:

EXAMPLE 8

Cyclo[D-Phenylalanyl-L-isoleucyl-D-(N$^\alpha$methyl)alanyl-L-pipecolyl-D-(N$^\alpha$methyl)phenylanyl-L-prolyl]

Cyclo[D-Phe-L-Ile-D-(N$^\alpha$Me)-Ala-L-Pip-D-(N$^\alpha$Me)-Phe-L-Pro] was prepared from Boc-L-Pro-O-(PAM)-resin (1 mmole) according to the solid phase procedure set forth in Example 1 with the following exception: Fmoc-D-(N$^\alpha$Me)Ala (650 mg, 2 mmol) was used in step 3. The final resin was cleaved with hydrazine and the hexapeptide hydrozide was cyclized as the acyl azide. Workup and purification (Method A) gave 350 mg (48%) of the title compound.

HPLC (Method G) RT=9.95 minutes; purity 99%. NMR (CD$_3$OD) in agreement with title compound, FAB MS: 728 (M+ +H).

Analysis Calc'd for C$_{40}$H$_{54}$N$_6$O$_6$.H$_2$O: N, 10.68; C, 61.05; H, 7.94. Found: N, 10.46; C, 61.87; H, 6.87.

EXAMPLE 9

Cyclo[D-phenylalanyl-L-alanyl-D-pipecolyl-L-pipecolyl-D-(N$^\alpha$methyl)phenylalanyl-L-prolyl]

Cyclo[D-phe-L-Ala-D-Pip-D-($^\alpha$Me)Phe-L-Pro] was prepared from Boc-L-Pro-O-(PAM)-resin (1 mmole) according to the solid phase procedure set forth in Example 1 with the following exception: Fmoc-L-Ala (622 mg, 2 mmol) was used in Step 4. The final resin was cleaved with hydrazine and the hexapeptide hydrazide was cyclized as the acyl azide. Workup and purification (Method A) gave 202 mg (28%) of the title compound.

HPLC (Method G) RT=9.66 minutes; purity 98.5%. NMR (CD$_3$OD) in agreement with title compound, FAB MS: 700 (M+ +H).

Analysis Calc'd for C$_{39}$H$_{50}$N$_6$O$_6$.1 5H$_2$O: N, 11.58; C, 64.53; H, 7.36. Found: N, 11.53; C, 64.71; H, 7.06.

EXAMPLE 10

Cyclo[D-phenylalanyl-L-isoleucyl-D-pipecolyl-L-pipecolyl-DL-3

Cyclo[D-Phe-L-Ile-D-Pip-L-Pip-D,L-3-PyrAla-L-Pro]

Cyclo[D-Phe-L-Ile-D-Pip-L-Pip-D,L-3-PyrAla-L-Pro] was prepared from Boc-L-Pro-O-(PAM)-resin (1 mmole) according to the solid phase procedure set forth in Example 1 with the following exception: Boc-dl-3-PyrAla (682 mg, 2 mmol) was used in Step 1. The final resin was cleaved with hydrazine and the hexapeptide hydrazide was cyclized as the acyl azide. Workup and purification (Method B, followed by Method F) gave 31 mg (4%) of isomer 1 and 40 mg (27%) of isomer 2 of the title compound.

Isomer 1

HPLC (Method G) RT=7.54 minutes; purity 97%. NMR (CD$_3$OD) in agreement with title compound. FAB MS: 729 (M+ +H).

Analysis Calc'd for C$_{40}$H$_{53}$N$_7$O$_6$.1 C$_2$H$_4$O$_2$: N, 12.42; C, 63.94; H, 7.28. Found: N, 12.49; C, 63.17; H, 7.13.

Isomer 2

HPLC (Method G) RT=7.84 minutes; purity 96%. NMR (CD$_3$OD) in agreement with title compound. FAB MS: 729 (M+ +H).

Analysis Calc'd for C$_{40}$H$_{53}$N$_8$O$_6$.1 C$_2$H$_4$O$_2$.2H$_2$O N, 11.82; C, 60.79; H, 7.40. Found: N, 11.86; C, 61.97; H, 7.10.

EXAMPLE 11

Cyclo[D-a-naphthalalanyl-L-isoleucyl-D-pipecolyl-L-pipecolyl-D-histidyl-L-prolyl]

Cyclo[D-a-Nal-L-Ile-D-Pip-L-Pip-D-His-L-Pro] was prepared from Boc-L-Pro-O-(PAM)-resin (1 mmole) according to the solid phase procedure set forth in Example 1 with the following exceptions: Boc-D-(DNP)-His (840 mg, 2 mmol) was used in Step 1 and Fmoc-D-a-Nal (875 mg, 2 mmol) was used in Step 5. The final resin was cleaved with hydrazine and the hexapeptide hydrazide was cyclized as the acyl azide. Workup and purification (Method B) gave 142 mg (14%) of the title compound.

HPLC (Method G) RT=8.65 minutes; purity 99%. NMR (CD$_3$OD) in agreement with title compound. FAB MS: 729 (M+ +H).

Analysis Calc'd for C$_{42}$H$_{54}$N$_8$O$_6$.4H$_2$O N, 11.26; C, 55.33; H, 5.67 Found N, 11.28; C, 55.05; H, 5.72

EXAMPLE 12

Cyclo[D-2-naphthalalanyl-L-isoleucyl-D-pipecolyl-L-pipecolyl-D-histidyl-L-prolyl]

Cyclo[D-2-Nal-L-Ile-D-Pip-L-Pip-D-His-L-Pro] was prepared from Boc-L-Pro-O-(PAM)-resin (1 mmole) according to the solid phase procedure set forth in Example 1 with the following exception: Boc-D-(DNP)-His (840 mg, 2 mmol) was used in Step 1 and Fmoc-D-β-Nal (875 mg, 2 mmol) was used in Step 5.

The final resin was cleaved with hydrazine and the hexapeptide hydrazide was cyclized as the acyl azide. Workup and purification (Method B) gave 120 mg (12%) of the title compound.

HPLC (Method G) RT=8.48 minutes; purity 99%. NMR (CD$_3$OD) in agreement with title compound. FAB MS: 767 (M+ +H).

Analysis Calc'd for C$_{42}$H$_{54}$N$_8$O$_6$.4H$_2$O: N, 11.26; C, 55.53; H, 5.67. Found: N, 11.44; C, 54.80; H, 5.71.

EXAMPLE 13

Cyclo [D-phenylalanyl-L-isoleucyl-D-pipecolyl-L-histidyl-D-(NαMethyl)phenylalanyl-L-prolyl Cyclo[D-Phe-L-Ile-D-Pip-L-His-D-(N$^α$Me)Phe-L-Pro] was prepared from Boc-L-Pro-O-(PAM)-resin (1 mmole) according to the solid phase procedure set forth in Example 1 with the following exception: Fmoc-L-(DNP)His (1.086 gm, 2 mmol) was used in a modified version of Step 2. Due to the insolubility of the amino acid in CH$_2$Cl$_2$ an active ester coupling was used. The amino acid was dissolved in DMF (15 ml) and cooled to 0° C. then added to the resin at 5° C. BOP reagent (884 mg, 2 mmol) was added as the solid and the reaction was adjusted to pH 8 with DIEA (0.522 ml, 3 mmol) and the resin was shaken for 15 hours at 5° C. before proceeding to Step 3. The remaining steps proceeded as previously described. The final resin was cleaved with hydrazine and the hexapeptide hydrazide was cyclized as the acyl azide. Workup and purification (Method B) gave 42 mg (5%) of the title compound.

HPLC (Method G) RT=8.06 minutes; purity 98.5%. NMR (CD$_3$OD) in agreement with title compound. FAB MS: 768 (M+ +H).

Analysis Calc'd.for C$_{42}$H$_{54}$N$_8$O$_6$.1 C$_2$HF$_3$O$_2$.1 H$_2$O: N, 12.46; C, 58.79; H, 7.14. Found: N, 12.52; C, 58.29; H, 6.59.

EXAMPLE 14

Cyclo[D-phenylalanyl-L-isoleucyl-D-piperazyl-L-pipecolyl-D-histidyl-L-prolyl]

Cyclo[D-Phe-L-Ile-D-Piz-L-Pip-D-His-L-Pro] was prepared from Boc-L-Pro-O-(PAM)-resin (1 mmole) according to the solid phase procedure set forth in Example 1 with the following exception: Boc-D-His-(DNP) (840 mg, 2 mmol) was used in Step 1, Fmoc-D-(Cbz)Piz (4.2 gm, 10 mmole) was used in Step 3 with the addition of AgCN (300 mg) to the acid chloride coupling. The final resin was cleaved with hydrazine and the hexapeptide hydrazide was cyclized as the acyl azide. The Cbz group was removed by hydrogenation at ambient temperature and pressure with 10% Pd/C catalyst (100 mg) in Ethanol (5 ml). Workup and purification (Method B) gave 38 mg (4%) of the title compound.

HPLC (Method G) RT=7.70 minutes; purity 99%. NMR (CD$_3$OD) in agreement with title compound. FAB MS: 695 (M+ +H).

Analysis Calc'd for C$_{35}$H$_{51}$N$_9$O$_6$.2 C$_2$HF$_3$O$_2$: N, 13.67; C, 50.81; H, 6.01. Found: N, 13.94; C, 52.88; H, 5.96.

EXAMPLE 15

C-[D-(N$^\alpha$methyl)phenylalanyl-L-(N$^\alpha$methyl)isoleucyl-D-pipecolyl-L-pipecolyl-D-(N$^\alpha$methyl)phenylalanyl-L-prolyl]

Cyclo[D-Phe-L-Ile-D-Pip-L-Pip-D-(N$^\alpha$Me)Phe-L-Pro] (50 mg, 0.067 mmol) was dissolved in DMF (5 ml) at ambient temperature. NaH (50% oil dispersion) (16 mg, 0.335 mmol) and CH$_3$I (0.5 mL) were added and the reaction was stirred for 15 hours. The solvents were removed by evaporation under reduced pressure and the resulting product was purified using Method F. Lyophilization from dioxane gave 22 mg (40%) of the title compound.

HPLC (Method G) RT=11.74 minutes; purity 98%.
NMR (CD$_3$OD) in agreement with title compound
FAB MS: 770 (M+ +H).
Analysis Calc'd for C$_{44}$H$_{60}$N$_6$O$_6$. 3 H$_2$O: N, 10.21; C, 64.21; H, 8.06. Found: N, 10.11; C, 66.45; H, 7.70.

EXAMPLE 16

C-[D-(N$^\alpha$methyl)alanyl-L-(N$^\alpha$methyl)isoleucyl-D-pipecolyl-L-pipecolyl-D-(N$^\alpha$methyl)phenylalanyl-L-prolyl]

Cyclo[D-Ala-L-Ile-D-Pip-L-Pip-D-Phe-L-Pro] (50 mg, 0.077 mmol) was dissolved in DMF (5 ml) at ambient temperature. NaH (50% oil dispersion) (18 mg, 0.385 mmol) and CH$_3$I (0.5 ml) were added and the reaction was stirred for 15 hours. The solvents were removed by evaporation under reduced pressure and the resulting product was purified using Method F. Lyophilization form dioxane gave 19 mg (34%) of the title compound.

HPLC (Method G) RT=9.98 minutes; purity 98%.
NMR (CD$_3$OD) in agreement with title compound.
FAB MS: 694 (M+ +H).
Analysis Calc'd for C$_{38}$H$_{56}$N$_6$O$_6$.1.5 H$_2$O: N, 11.67; C, 63.40; H, 8.26. Found: N, 11.66; C, 63.89; H, 7.82.

EXAMPLE 17

C-[D-tryptophanyl-L-isolelucyl-D-pipecolyl-L-pipecolyl-D-histidyl-L-prolyl]

Cyclo[D-Trp-L-Ile-D-Pip-L-Pip-D-His-L-Pro] was prepared from Boc-L-Pro-O-(PAM)-resin (1 mmole) according to the solid phase procedure set forth in Example 1 with the following exception: Boc-D-(DNP)-His (840 mg, 2 mmol) was used in Step 1. Due to insolubility of the Fmoc-D-Trp in CH$_2$Cl$_2$ an active ester coupling was used in Step 5. The Fmoc-D-Trp (852 mg, 2 mmol) was dissolved in DMF at ambient temperature and added to the resin. BOP reagent (884 mg, 2 mmol) was added as the solid and the reaction was brought to pH 8 with the addition of DIEA (0.35 ml, 2 mmol). After shaking for 15 hours the resin was washed and processed as previously described. The final resin was cleaved with hydrazine and the hexapeptide hydrazide was cyclized as the acyl azide. Workup and purification Using Method E gave a product which was lyophilized from acetic acid/H$_2$O and then crystallized from methanol giving 257 mg (33%) of the title compound.

HPLC (Method G) RT=7.45 minutes; purity 99%.
NMR (CD$_3$OD) in agreement with title compound.
FAB MS: 756 (M+ +H).
Analysis Calc'd for C$_{40}$H$_{53}$N$_9$O$_6$.2 H$_2$O: N, 15.92; C, 60.67; H, 7.25. Found: N, 15.88; C, 60.84; H, 7.12.

EXAMPLE 18

Cyclo[D-tryptophanyl-L-isoleucyl-D-pipecolyl-L-pipecolyl-D-[im-(CH$_3$)$_2$]+histidyl-L-prolyl] trifluoroacetate Cyclo[D-Trp-L-Ile-D-Pip-L-Pip-D-His-L-Pro] (50 mg, 0.07 mmol) was dissolved in DMF (5 ml) at ambient temperature and treated with CH$_3$I (0.5 ml, 8 mmol) for 6 hours. The solvents were removed by evaporation under reduced pressure and the resulting product was purified using Method B. Lyophilization of homogeneous HPLC fractions containing the product yielded 30 mg (42%) of the title compound.

HPLC (Method G) RT=7.70 minutes; purity 99%.
NMR (CD$_3$OD) in agreement with title compound.
FAB MS: 898 (M+ +H).
Analysis Calc'd for C$_{44}$H$_{58}$F$_3$N$_9$O$_8$.1H$_2$O: N, 12.24; C, 53.64; H, 5.97. Found: N, 12.11; C, 53.82; H, 5.74.

EXAMPLE 19

Cyclo[D-tryptophanyl-L-isoleucyl-D-pipecolyl-L-pipecolyl-D-(N$^\alpha$methyl)histidyl-L-prolyl]

Cyclo[D-Trp-L-Ile-D-Pip-L-Pip-D-His-L-Pro] was prepared from Boc-L-Pro-O-(PAM)-resin (1 mmole) according to the solid phase procedure set forth in Example 1 with the following exceptions: Boc-D-(Tos)-(N$^\alpha$Me)-His (846 mg, 2 mmol) was used in Step 1. Due to the insolubility of the Fmoc-D-Trp in CH$_2$Cl$_2$ an active ester coupling was used in Step 5. The Fmoc-D-Trp (852 mg, 2 mmol) was dissolved in DMF at ambient temperature and was added to the resin. BOP reagent (884 mg, 2 mmol) was added and the reaction was brought to pH 8 with the addition of DIEA (0.35 ml, 2 mmol). After shaking for 15 hours the resin was washed and processed as previously described. The final resin was cleaved with hydrazine and the hexapeptide hydrazide was cyclized as the acyl azide. Workup and purification using Method B gave 110 mg (12%) of the title compound.

HPLC (Method G) RT=7.92 minutes; purity 99%.
NMR (CD$_3$OD) in agreement with title compound.
FAB MS: 771 (M+ +H).
Analysis Calc'd for C$_{41}$H$_{55}$N$_9$O$_6$.1C$_2$HF$_3$O$_2$.1H$_2$O: N, 13.51; C, 55.14; H, 6.24. Found: N, 13.51; C, 55.59; H, 6.14.

EXAMPLE 20

Cyclo[D-tryptophanyl-L-Norleucyl-D-pipecolyl-L-pipecolyl-D-histidyl-L-prolyl]

Cyclo[D-Trp-L-Nle-D-Pip-L-Pip-D-His-L-Pro] was prepared from Boc-L-Pro-O-(PAM)-resin (1 mmole) according to the solid phase procedure set forth in Example 1 with the following exceptions: Boc-D-(DNP)-His (840 mg, 2 mmol) was used in Step 1 and Fmoc-L-Nle (706 mg, 2 mmol) was used in Step 4. Due to the insolubility of the Fmoc-D-Trp in CH$_2$Cl$_2$ an active ester coupling was used in Step 5. The Fmoc-D-Trp (852 mg, 2 mmol) was dissolved in DMF at ambient temperature and added to the resin. BOP reagent (884 mg, 2 mmol) was added and the reaction was brought to pH 8 with the addition of DIEA (0.35 ml, 2 mmol). After shaking for 15 hours the resin was washed and processed as previously described. The final resin was cleaved with hydrazine and the hexapeptide hydrazide was cyclized as the acyl azide. Workup and purification using Method B gave 252 mg (29%) of the title compound.

HPLC (Method G) RT=7.76 minutes; purity 99%.
NMR (CD$_3$OD) in agreement with title compound.
FAB MS: 756 (M+ +H).
Analysis Calc'd for C$_{40}$H$_{53}$N$_9$O$_6$ 1C$_2$HF$_3$O$_2$.4H$_2$O: N, 13.38; C, 53.55; H, 6.63. Found: N, 13.43; C, 53.25; H, 5.25.

EXAMPLE 21

Cyclo[D-tryptophanyl-L-leucyl-D-pipecolyl-L-pipecolyl-D-histidyl-L-prolyl]

Cyclo[D-Trp-L-Leu-D-Pip-L-Pip-D-His-L-Pro] was prepared from Boc-L-Pro-O-(PAM)-resin (1 mmole) according to the solid phase procedure set forth in Example 1 with the following exceptions: Boc-D-(DNP)-His (840 mg, 2 mmol) was used in Step 1 and Fmoc-L-Leu (706 mg, 2 mmol) was used in Step 4. Due to the insolubility of Fmoc-D-Trp in CH$_2$Cl$_2$, an active ester coupling was used in Step 5. The Fmoc-D-Trp (852 mg, 2 mmol) was dissolved in DMF at ambient temperature and was added to the resin. BOP reagent (884 mg, 2 mmol) was added as the solid and the reaction was brought to pH 8 with the addition of DIEA (0.35 ml, 2 mmol). After shaking for 15 hours the resin was washed and processed as previously described. The final resin was cleaved with hydrazine and the hexapeptide hydrazide was cyclized as the acyl azide. Workup and purification using Method B gave 150 mg (16%) of the title compound.

HPLC (Method G) RT=7.66 minutes; purity 99%.
NMR (CD$_3$OD) in agreement with title compound.
FAB MS: 756 (M+ +H).
Analysis Calc'd for C$_{40}$H$_{53}$N$_9$O$_6$.1C$_2$HF$_3$O$_2$.4H$_2$O: N, 13.38; C, 53.55; H, 6.63. Found: N, 13.14; C, 53.69; H, 5.69.

EXAMPLE 22

Cyclo[D-Phenylalanyl-L-isoleucyl-D-pipecolyl-D-(3,4-Dehydro)-pipecolyl-D-(N$^\alpha$methyl)phenylalanyl-L-Prolyl]

Cyclo-[D-Phe-L-Ile-D-Pip-D-(3,4-dehydro)-Pip-D-(N$^\alpha$Me)Phe-L-Pro] was prepared form Boc-L-Pro-O-(PAM)-resin (1 mmole) according to the solid phase procedure set forth in Example 1 with the following exception: Racemic Fmoc-(3,4-dehydro)-Pip (698 mg, 2 mmole) was used in Step 2. The final resin was cleaved with hydrazine and the hexapeptide hydrazide was cyclized as the acyl azide. Workup and purification (Method A) gave 150 mg (20%) of the title compound.

HPLC (Method G) RT=10.76 minutes: purity 99%
NMR (CDCl$_3$) in agreement with title compound.
FAB MS: 740 (M+ +H).
Analysis Calc'd for C$_{42}$H$_{54}$N$_6$O$_6$.1H$_2$O: N, 11.10; C, 66.65; H, 7.46. Found N, 10.66; C, 66.96; H, 7.36.

EXAMPLE 23

Cyclo[D-phenylanyl-L-isoleucyl-D-pipecolyl-L-(3,4-dehydro)-pipecolyl-D-(N$^\alpha$methyl)phenylalanyl-L-prolyl]

Cyclo[D-Phe-L-Ile-D-Pip-L-(3,4-dehydro)-Pip-D-(N$^\alpha$Me)Phe-L-Pro] was prepared form Boc-L-Pro-O-(PAM)-resin (1 mmole) according to the solid phase procedure set forth in Example 1 with the following exception: Racemic Fmoc-(3,4-dehydro)-Pip (698 mg, 2 mmole) was used in Step 2. The final resin was cleaved with hydrazine and the hexapeptide hydrazide was cyclized as the acylazide. Workup and the purification (Method A) gave 520 mg (70%) of the title compound. The configuration of the 3,4-dehyropipecolic acid was determined by hydrogenation (10% Pd-C, EtOAc, 1 Atm H$_2$) which gave the saturated analog of known configuration (NMR and HPLC analysis).

HPLC (Method G) RT=10.44 minutes; purity 99%.
NMR (CDCl$_3$) in agreement with title compound.
FAB MS: 739 (M+ +H).
Analysis Calc'd for C$_{42}$H$_{54}$N$_6$O$_6$.1H$_2$O: N, 11.10; C, 66.64; H, 7.46. Found: N, 10.96; C, 66.65; H, 7.28.

EXAMPLE 24

Cyclo[D-phenylanyl-L-isoleucyl-D-(3,4-dehydro)-pipecolyl-L-pipecolyl-D-(N$^\alpha$methyl)phenyalanyl-L-prolyl]

Cyclo[D-Phe-L-Ile-D-(3,4-dehydro)-Pip-L-Pip D-(N$^\alpha$Me)Phe-L-Pro] was prepared form Boc-L-Pro-O-(PAM)-resin (1 mmole) according to the solid phase procedure set forth in Example 1 with the following exception: Racemic Fmoc-(3,4-dehydro)-Pip (698 mg, 2 mmole) was used in STEP 3. The final resin was cleaved with hydrazine and the hexapeptide hydrazide was cyclized as the acyl azide. Workup and purification (Method A) gave 320 mg (45%) of the title compound.

HPLC (Method G) RT=10.45 min.; purity 98.5%.
NMR (CDCl$_3$) in agreement with title compound.
FAB MS: 739 (M+ +H).
Analysis Calc'd for C$_{42}$H$_{54}$N$_6$O$_6$.2H$_2$O: N, 10.84; C, 65.09; H, 7.48. Found: N, 10.67; C, 64.88; H, 7.08.

EXAMPLE 25

Cyclo[D-phenylalanyl-L-isoleucyl-D-pipecolyl-L-pipecolyl-D-trytophanyl-L-prolyl]

Cyclo[D-Phe-L-Ile-D-Pip-L-Pip-D-Trp-L-Pro] was prepared from Boc-L-Pro-O-(PAM)-resin (1 mmole) according to the solid phase procedure set forth in Example 1 with the following exception: Boc-D-Trp-(608 mg, 2 mmole) was used in Step 1. The final resin was cleaved with hydrazine and the hexapeptide hydrazide was cyclized as the acyl azide. Workup and purification (Method B) gave 500 mg (65%) of the title compound.

HPLC (Method G) RT=10.26 minutes; purity 99%.
NMR (CDCl$_3$) in agreement with title compound.
FAB MS: 766 (M+ +H).
Analysis Calc'd for C$_{43}$H$_{54}$N$_7$O$_6$.1H$_2$O: N, 12.34; C, 65.74; H, 7.18. Found: N, 12.70; C, 65.41; H, 7.22.

EXAMPLE 26

Cyclo[D-phenylalanyl-L-isoleucyl-D-pipecolyl-L-pipecolyl-D-(2-chlorocarbobenzyloxy)-lysyl-L-prolyl]

Cyclo[D-Phe-L-Ile-D-Pip-L-Pip-D-(2-Cl-Cbz)-Lys-L-Pro] was prepared from Boc-L-Pro-O-(PAM)-resin (1 mmole) according to the solid phase procedure set forth in Example 1 with the following exception: Boc-D-(2-Cl-Cbz)-Lys (830 mg, 2 mmole) was used in Step 1. The final resin was cleaved with hydrazine and the hexapeptide hydrazine was cyclized as the acyl azide. Workup and purification (Method B) gave 564 mg (65%) of the title compound.

HPLC (Method G) RT=11.10 minutes; purity 797%.
NMR (CDCl$_3$) in agreement with title compound.
FAB MS: 876 (M+ +H).
Analysis Calc'd for C$_{46}$H$_{62}$N$_7$O$_8$ Cl.0.5dioxane.0.75-H$_2$O: N, 10.51; C, 61.76; H, 7.24. Found: N, 10.97; C, 61.53; H, 6.97.

EXAMPLE 27

Cyclo[D-phenylalanyl-L-isoleucyl-D-pipecolyl-L-pipecolyl-D-(carbobenzyloxy)-ornithyl-L-prolyl]

Cyclo[D-Phe-L-Ile-D-Pip-L-Pip-D-(Cbz)-Orn-L-Pro] was prepared from Boc-L-Pro-O-(PAM)-resin (1 mmole) according to the solid phase procedure set forth in Example 1 with the following exception: Boc-D-(Cbz)-Orn (830 mg, 2 mmole) was used in Step 1. The final resin was cleaved with hydrazine and the hexapeptide hydrazide was cyclized as the acyl azide. Workup and purification (Method B) gave 582 mg (70%) of the title compound.

HPLC (Method G) RT=10.41 minutes; purity >97%.

NMR (CDCl$_3$) in agreement with title compound.

FAB MS: 828 (M+ +H).

Analysis Calc'd for $C_{45}H_{61}N_7O_8.0.5$dioxane; N, 11.24; C, 64.73; H, 7.45. Found: N, 11.47; C, 64.25; H, 7.30.

EXAMPLE 28

Cyclo[D-phenylalanyl-L-isoleucyl-D-pipecolyl-L-pipecolyl-D-(N$^\alpha$methyl-O-Benzyl)-tyrosyl-L-prolyl]

Cyclo[D-Phe-L-Ile-D-Pip-L-Pip-D-(Bzl)(N$^\alpha$Me)-Tyr-L-Pro] was prepared from Boc-L-Pro-O-(PAM)-resin (1 mmole) according to the solid phase procedure set forth in Example 1 with the following exceptions: Boc-D-(Bzl)(N$^\alpha$Me)-Tyr (770 mg, 2 mmole) was used in Step 1. The final resin was cleaved with hydrazine and the hexapeptide hydrazide was cyclized as the acyl azide. Workup and purification (Method B) gave 700 mg (84%) of the title compound.

HPLC (Method G) RT=12.51 minutes; purity 98.4%.

NMR (CDCl$_3$) in agreement with title compound.

FAB MS: 848 (M+ +H).

Analysis Calc'd for $C_{49}H_{21}N_6O_8 1.H_2O$: N, 9.71; C, 67.98; H, 7.40. Found: N, 9.70; C, 68.02; H, 7.70.

EXAMPLE 29

Cyclo[D-tryptophanyl-L-isoleucyl-D-pipecolyl-L-(carbobenzloxy)lysyl-D-tryptophanyl-L-prolyl]

Cyclo[D-Trp-L-Ile-D-Pip-L-(Cbz)Lys-D-Trp-L-Pro] was prepared from Boc-L-Pro-O-(PAM)-resin (1 mmole) according to the solid phase procedure set forth in Example 1 with the following exception: Boc-L-(Cbz)Lysine (760 mg, 2 mmole) was used in a modified version of Step 2. The amino acid was dissolved in DMF (15 ml), cooled to 0° C. and added to the resin at 5° C. BOP reagent (884 mg, 2 mmole) was added as the solid and the reaction was adjusted to pH 8 with DIEA (0.522 ml, 3 mmole) and the resin was shaken for 15 hours before proceeding to Step 3. Due to the insolubility of Fmoc-D-Trp in CH$_2$Cl$_2$, an active ester coupling was used in Step 5. The Fmoc-D-Trp (852 mg, 2 mmole) was dissolved in DMF at ambient temperature and was added to the resin. BOP reagent (884 mg, 2 mmole) was added as the solid and the reaction was brought to pH 8 with the addition of DIEA (0.35 ml, 2 mmole). After shaking for 15 hours the resin was washed and processed as previously described. The final resin was cleaved with hydrazine and the hexapeptide hydrazide was cyclized as the acyl azide. Workup and purification using Method A gave a pure product which was lyophilized from dioxane to give 650 mg (67%) of the title compound.

HPLC (Method G) RT=10.43 minutes; purity 99%.

NMR (CDCl$_3$) in agreement with title compound.

FAB MS: 957 (M+ +H).

Analysis Calc'd for $C_{53}H_{65}N_9O_8.0.5$dioxane.$2H_2O$: N, 12.16; C, 63.70; H, 7.04. Found: N, 12.54; C, 63.92; H, 7.04.

EXAMPLE 30

Cyclo[D-tryptophanyl-L-isoleucyl-D-pipecolyl-L-pipecolyl-D(N$^\alpha$methyl)phenylalanyl-L-prolyl]

Cyclo[D-Trp-L-Ile-D-Pip-L-Pip-D-(N$^\alpha$Me)Phe-L-Pro] was prepared from Boc-L-Pro-O(PAM)-resin 1 (mmole) according to the solid phase procedure set forth in Example 1 with the following exception: Due to the insolubility of Fmoc-D-Trp in CH$_2$Cl$_2$, an active ester coupling was used in Step 5. The Fmoc-D-Trp (852 mg, 2 mmole) was dissolved in DMF at ambient temperature and was added to the resin. BOP reagent (884 mg, 2 mmole) was added as the solid and the reaction was brought to pH 8 with the addition of DIEA (0.35 ml, 2 mmole). After shaking for 15 hours the resin was washed and processed as previously described. The final resin was cleaved with hydrazine and the hexapeptide hydrazide was cyclized as the acyl azide. Workup and purification using Method A gave a pure product which was lyophilized from dioxane to give 400 mg (52%) of the title compound.

HPLC (Method G) RT=10.64 minutes; purity 99%.

NMR (CDCl$_3$) in agreement with title compound.

FAB MS: 780 (M+ +H).

Analysis Calc'd for $C_{44}H_{57}N_7O_6.0.66$ dioxane: N, 11.69; C, 66.77; H, 7.43. Found: N, 12.09; C, 66.44; H, 7.40.

EXAMPLE 31

Cyclo[D-Tryptophanyl-L-phenylalanyl-D-pipecolyl-L-pipecolyl-D-(N$^\alpha$-methyl)phenylalanyl-L-prolyl]

Cyclo[D-Trp-L-Phe-D-Pip-L-Pip-D-(N$^\alpha$Me)Phe-L-Pro] was prepared from Boc-L-Pro-O-(PAM)-resin (1 mmole) according to the solid phase procedure set forth in Example 1 with the following exceptions. Fmoc-L-Phe was substituted for Fmoc-L-Ile in Step 4. Due to the insolubility of the Fmoc-D-Trp in CH$_2$Cl$_2$ an active ester coupling was used in Step 5. The Fmoc-D-Trp (852 mg, 2 mmole) was dissolved in DMF at ambient temperature and added to the resin. BOP reagent (884 mg, 2 mmole) was added as the solid and the reaction was brought to pH 8 with the addition of DIEA (0.35 ml, 2 mmole). After shaking for 15 hours the resin was washed and processed as previously described. The final resin was cleaved with hydrazine and the hexapeptide hydrazide was cyclized as the acyl azide. Workup and purification using Method A gave a pure product which was lyophilized from dioxane to give 500 mg (65%) of the title compound.

HPLC (Method G) RT=11.09 minutes; purity 99%.

NMR (CDCl$_3$) in agreement with title compound.

FAB MS: 814 (M+ +H).

Analysis Calc'd for $C_{47}H_{55}N_7O_6.0.25$ dioxane. 2.5 $H_2O$: N, 11.13; C, 65.44; H, 7.09. Found: N, 11.20; C, 65.54; H, 6.53.

EXAMPLE 32

Cyclo[D-trytophanyl-L-homophenylalanyl-D-pipecolyl-L-pipecolyl-D-(N$^\alpha$methyl)phenylalanyl-L-prolyl]

Cyclo[D-Trp-L-HomoPhe-D-Pip-L-Pip-D-(N$^\alpha$Me)-Phe-L-Pro] was prepared from Boc-L-Pro-O-(PAM)-resin (1 mmole) according to the solid phase procedure set forth in Example 1 with the following exceptions: Fmoc-L-homoPhe was substituted for Fmoc-L-Ile in Step 4. Due to the insolubility of the Fmoc-D-Trp in CH$_2$Cl$_2$ an active ester coupling was used in Step 5. The Fmoc-D-Trp (852 mg, 2 mmole) was dissolved in DMF at ambient temperature and added to the resin. BOP reagent (884 mg, 2 mmole) was added as the solid and the reaction was brought to pH 8 with the addition of DIEA (0.35 ml, 2 mmole). After shaking for 15 hours the resin was cleaved with hydrazine and the hexapeptide hydrazide was cyclized as the acyl azide. Workup and purification using Method A gave a pure product which was lyophilized from dioxane to give 520 mg (63%) of the title compound.

HPLC (Method G) RT=11.26 minutes; purity 99%.
NMR (CDCl$_3$) in agreement with title compound.
FAB MS: 828 (M+ +H).
Analysis Calc'd for C$_{48}$H$_{57}$N$_7$O$_6$.2 H$_2$O: N, 11.34; C, 66.67; H, 7.06. Found: N, 11.29; C, 66.97; H, 6.56.

EXAMPLE 33

Cyclo[D-tryptophanyl-L-isoleucyl-D-pipecolyl-L-pipecolyl-D-(N$^\alpha$methyl-O-benzyl)tyrosyl-L-prolyl]

Cyclo[D-Trp-L-Ile-D-Pip-L-Pip-D-(N$^\alpha$Me-O-Bzl)-Tyr-L-Pro] was prepared from Boc-L-Pro-O-(PAM)-resin (1 mmole) according to the solid phase procedure set forth in Example 1 with the following exceptions. The amino acid Boc-D-(N$^\alpha$Me-O-Bzl)Tyr (770 mg, 2 mmole) was used in Step 1. Due to the insolubility of Fmoc-D-Trp in CH$_2$Cl$_2$ an active ester coupling was used in Step 5. The Fmoc-D-Trp (852 mg, 2 mmole) was dissolved in DMF at ambient temperature and added to the resin. BOP reagent (884 mg, 2 mmole) was added as the solid and the reaction was brought to pH 8 with the addition of DIEA (0.35 ml, 2 mmole). After shaking for 15 hours the resin was washed and processed as previously described. The final resin was cleaved with hydrazine and the hexapeptide hydrazide was cyclized as the acyl azide. Workup and purification using Method A gave the product which was lyophilized from dioxane to give 350 mg (35%) of the title compound.

HPLC (Method G) RT=12.15 minutes; purity 99%.
NMR (CDCl$_3$) in agreement with title compound.
FAB MS: 887 (M+ +H).
Analysis Calc'd for C$_{51}$H$_{64}$N$_7$O$_7$.1C$_2$HF$_3$O$_2$: N, 9.79; C, 63.52; H, 6.49. Found: N, 9.91; C, 63.54; H, 6.41.

EXAMPLE 34

Cyclo[D-trytophanyl-L-isoleucyl-D-pipecolyl-L-(carbobenzyloxy)ornithyl-D-(N$^\alpha$methyl)phenylalanyl-L-prolyl]

Cyclo[D-Trp-L-Ile-D-Pip-L-(Cbz)Orn-D-(N$^\alpha$Me)-Phe-L-Pro] was prepared from Boc-L-Pro-O-(PAM)-resin (1 mmole) according to the solid phase procedure set forth in Example 1 with the following exceptions: The amino acid Boc-D-(N$^\alpha$Me)Phe (560 mg, 2 mmole) was used in Step 1, and the amino acid Boc-L-(Cbz)Orn was used in Step 2. The final resin was cleaved with hydrazine and the hexapeptide hydrazide was cyclized as the acyl azide. Workup and purification using Method A gave a pure product which was lyophilized from dioxane to give 500 mg (54%) of the title compound.

HPLC (Method G) RT=10.22 minutes; purity 99%.
NMR (CDCl$_3$) in agreement with title compound.
FAB MS: 917 (M+ +H).
Analysis Calc'd for C$_{51}$H$_{65}$N$_8$O$_8$.0.25 dioxane: N, 11.93; C, 66.51; H, 7.19. Found: N, 11.90; C, 65.39; H, 6.95.

EXAMPLE 35

Cyclo[D-tryptophanyl-L-isoleucyl-D-pipecolyl-L-(carbobenzyloxy)lysyl-D-(N$^\alpha$Methyl)phenylalanyl-L-prolyl]

Cyclo[D-Trp-L-Ile-D-Pip-L-(Cbz)Lys-D-(N$^\alpha$Me)-Phe-L-Pro] was prepared from Boc-L-Pro-O-(PAM)-resin (1 mmole) according to the solid phase procedure set forth in Example 1 with the following exceptions. The amino acid Boc-D-(N$^\alpha$Me)Phe (560 mg, 2 mmole) was used in Step 1, and the amino acid Boc-L-(Cbz)Lys (760 mg, 2 mmole) was used in Step 2. The final resin was cleaved with hydrazine and the hexapeptide hydrazide was cyclized as the acyl azide. Workup and purification using Method A gave a pure product which was lyophilized from dioxane to give 480 mg (49%) of the title compound.

HPLC (Method G) RT=10.90 minutes; purity 99%.
NMR (CDCl$_3$) in agreement with title compound.
FAB MS: 931 (M+ +H).
Analysis Calc'd for C$_{52}$H$_{67}$N$_8$O$_8$.0.25 dioxane.0.5 H$_2$O: N, 11.65; C, 66.17; H, 7.33. Found: N, 11.67; C, 65.97; H, 7.13.

EXAMPLE 36

Cyclo[D-tryptophanyl-L-isoleucyl-D-pipecolyl-L-(carbobenzyloxy)ornithinyl-D-trytophanyl-L-prolyl]

Cyclo[D-Trp-L-Ile-D-Pip-L-(Cbz)Orn-D-Trp-L-Pro] was prepared from Boc-L-Pro-O-(PAM)-resin (1 mmole) according to the solid phase procedure set forth in Example 1 with the following exceptions: The amino acid Boc-L-(Cbz)Orn (732 mg, 2 mmole) was substituted for Boc-L-(Cbz)Lys in Step 2. The final resin was cleaved with hydrazine and the hexapeptide hydrazide was cyclized as the acyl azide. Workup and purification using Method A gave a product which was lyophilized from dioxane to give 370 mg (39%) of the title compound.

HPLC (Method G) RT=10.24 minutes; purity 99%.
NMR (CDCl$_3$) in agreement with title compound.
FAB MS: 942 (M+ +H).
Analysis Calc'd for C$_{52}$H$_{63}$N$_9$O$_8$.0.5 H$_2$O: N, 13.22; C, 64.40; H, 6.93. Found: N, 13.00; C, 64.10; H, 6.81.

EXAMPLE 37

Cyclo[D-Phenylalanyl-L-isoleucyl-D-pipecolyl-L-(carbobenzyloxy)lysyl-D-histidyl-L-prolyl]

Cyclo[D-Phe-L-Ile-D-Pip-L-(Cbz)Lys-D-His-L-Pro] was prepared from Boc-L-Pro-O-(PAM)-resin (1 mmole) according to the solid phase procedure set forth in Example 1 with the following excepations: Boc-D-His(DNP) (530 mg, 2 mmole) was used in Step 1 and Boc-L-(Cbz)Lysine (760 mg, 2 mmole) was used in a modified version of Step 2. The amino acid was dissolved in DMF (15 ml), cooled to 0° C. and then added to the resin at 5° C. BOP reagent (884 mg, 2 mmole) was added as the solid and the reaction was adjusted to pH 8 with DIEA (0.522 ml, 3 mmole). The resin was shaken for 15 hours before proceeding to Step 3. The remaining steps proceed as previously described. The final resin was cleaved with hydrazine and the hexapeptide hydrazide was cyclized as the acyl azide. Workup and purification using Method B gave a pure product which was lyophilized from dioxane to give 186 mg (11%) of the title compound as the TFA salt.

HPLC (Method G) RT=8.59 minutes; purity 99%.
NMR (CDCl$_3$) in agreement with title compound.
FAB MS: 868 (M+ +H).
Analysis Calc'd for $C_{46}H_{61}N_9O_8.1C_2HF_3O_2.1H_2O$: N, 12.61; C, 57.64; H, 6.45. Found: N, 12.37; C, 57.16; H, 6.23.

EXAMPLE 38

Cyclo[D-tryptophanyl-L-isoleucyl-D-pipecolyl-L-(carbobenzyloxy)lysyl-D-histidyl-L-prolyl]

Cyclo[D-Trp-L-Ile-D-Pip-L-(Cbz)Lys-D-His-L-Pro] was prepared from Boc-L-Pro-O-(PAM)-resin (1 mmole) according to the solid phase procedure set forth in Example 1 with the following exceptions: Boc-D-His(DNP) (530 mg, 2 mmole) was used in Step 1 and Boc-L-(Cbz)Lys (760 mg, 2 mmole) was used in a modified version of Step 2. The amino acid was dissolved in DMF (15 ml), cooled to 0° C. and added to the resin at 5° C. BOP reagent (884 mg, 2 mmole) was added as the solid and the reaction was adjusted to pH 8 with DIEA (0.522 ml, 3 mmole). The resin was shaken for 15 hours before proceeding on to Step 3. Due to the insolubility of Fmoc-D-Trp in CH$_2$Cl$_2$ an active ester coupling was used in Step 5. The Fmoc-D-Trp (852 mg, 2 mmole) was dissolved in DMF at ambient temperature and was added to the resin. BOP reagent (884 mg, 2 mmole) was added as the solid and the reaction was brought to pH 8 with the addition of DIEA (0.35 ml, 2 mmole). After shaking for 15 hours the resin was washed and processed as previously described. The final resin was cleaved with hydrazine and the hexapeptide hydrazide was cyclized as the acyl azide. Workup and purification using Method B gave a pure product which was lyophilized from dioxane to give 350 mg (30%) of the title compound.

HPLC (Method G) RT=8.35 minutes; purity 99%.
NMR (DMSO) in agreement with title compound.
FAB MS: 908 (M+ +H).
Analysis Calc'd for $C_{48}H_{62}N_{10}O_8.2C_2HF_3O_2.1H_2O$: N, 12.33; C, 54.98; H, 5.81. Found: N, 12.37; C, 55.11; H, 5.80.

EXAMPLE 39

Cyclo[D-phenylalanyl-L-isoleucyl-D-pipecolyl-L-pipecolyl-D-ornithyl-L-prolyl]

Cyclo[D-Phe-L-Ile-D-Pip-L-Pip-D-(Cbz)Orn-L-Pro] (100 mg, 0.12 mmoles) was dissolved in 25 ml of a 4% acetic acid in ethanol solution and an equal weight of catalyst (10% palladium on carbon) was added. The reaction mixture was hydrogenated at atmospheric pressure for 15 hours, then flushed with argon, filtered through celite. The filtrate solvents were evaporated under reduced pressure. Lyophilization from dioxane afforded 40 mg (38%) of the title compound as a powder.

HPLC (Method G) RT=7.73 minutes; purity 99%.
NMR (CDCl$_3$) in agreement with title compound.
FAB MS: 695 (M+ +H).
Analysis Calc'd for $C_{37}H_{55}N_7O_6.1.5C_2HF_3O_2.1H_2O$: N, 11.12; C, 54.48; H, 6.64. Found: N, 10.90; C, 54.19; H, 6.44.

EXAMPLE 40

Cyclo[D-tryptophanyl-L-isoleucyl-D-pipecolyl-L-ornithyl-D-(N$^\alpha$Methyl)phenylalanyl-L-prolyl]

Cyclo[D-Trp-L-Ile-D-Pip-L-Orn-D-(N$^\alpha$Me)Phe-L-Pro] was prepared from cyclo[D-Trp-L-Ile-D-Pip-L-(Cbz)Orn-D-(N$^\alpha$Me)Phe-L-Pro] (200 mg, 0.22 mmole) using the same procedure as described in Example 39. Workup and purification (Method B) gave a pure compound. Lyophilization from dioxane afforded 90 mg (41%) of the title compound as a white powder.

HPLC (Method G) RT=7.83 minutes; purity 99%.
NMR (CDCl$_3$) in agreement with title compound.
FAB MS: 783 (M+ +H).
Analysis Calc'd for $C_{43}H_{58}N_8O_6.2C_2HF_3O_2.2H_2O$: N, 10.70; C, 53.87; H, 6.11. Found: N, 10.78; C, 53.77; H, 5.98.

EXAMPLE 41

Cyclo[D-tryptophanyl-L-isoleucyl-D-pipecolyl-L-ornithyl-D-tryptophanyl-L-prolyl]

Cyclo[D-Trp-L-Ile-D-Pip-L-Orn-D-Trp-L-Pro] was prepared from cyclo[D-Trp-L-Ile-D-Pip-L-(Cbz)Orn-D-Trp-L-Pro] (500 mg, 0.53 mmole) using the same procedure as described in Example 39. Workup and purification (Method B) gave a homogeneous compound. Lyophilization from dioxane afforded the title compound, 350 mg (64%), as a powder.

HPLC (Method G) RT=7.60 minutes; purity 99%.
NMR (DMSO) in agreement with title compound.
FAB MS: 808 (M+ +H).
Analysis Calc'd for $C_{44}H_{57}N_9O_6.2C_2HF_3O_2.3H_2O$: N, 11.57; C, 52.87; H, 5.97. Found: N, 11.49; C, 52.81; H, 5.64.

EXAMPLE 42

Cyclo[D-tryptophanyl-L-isoleucyl-D-pipecolyl-L-lysyl-D-tryptophanyl-L-prolyl]

Cyclo[D-Trp-L-Ile-D-Pip-L-Lys-D-Trp-L-Pro] was prepared from cyclo[D-Trp-L-Ile-D-Pip-L-(Cbz)Lys-D-Trp-L-Pro] (30 mg, 0.03 mmole) using the same procedure as described in Example 39. Workup and purification (Method B) afforded 10 mg (33%) of a homogeneous compound. Lyophilization from dioxane afforded the title compound as powder.

HPLC (Method G) RT=7.63 minutes; purity 99%.
NMR (DMSO) in agreement with title compound.
FAB MS: 822.5 (M+ +H).
Analysis Calc'd for $C_{45}H_{59}N_9O_6.1.5C_2HF_3O_2.2H_2O$: N, 12.48; C, 57.03; H, 6.19. Found: N, 11.96; C, 57.31; H, 6.35.

EXAMPLE 43

Cyclo[D-phenylalanyl-L-isoleucyl-D-pipecolyl-L-pipecolyl-D-lysyl-L-prolyl]

Cyclo[D-Phe-L-Ile-D-Pip-L-Pip-D-Lys-L-Pro] was prepared from cyclo[D-Trp-L-Ile-D-Pip-L-Pip-D-(2-Cl-Cbz)Lys-L-Pro] (150 mg, 0.17 mmole) using the same procedure as described in Example 39. Workup and purification (Method B) afforded 80 mg (67%) of a homogeneous compound. Lyophilization from dioxane afforded the title compound as a white powder.

HPLC (Method G) RT=7.71 minutes; purity 99%.

NMR (CDCl₃) in agreement with title compound.
Analysis Calc'd for C₃₈H₅₇N₇O₆.0.5H₂O.0.5 dioxane: N, 12.89; C, 63.16; H, 8.16. Found: N, 13.25; C, 63.15; H, 7.85.

EXAMPLE 44

Cyclo[D-tryptophanyl-L-isoleucyl-D-pipecolyl-L-lysyl-D-histidyl-L-prolyl]

Cyclo[D-Trp-L-Ile-D-Pip-L-Lys-D-His-L-Pro] was prepared from cyclo[D-Trp-L-Ile-D-Pip-L-(Cbz)Lys-D-His-L-Pro] using the same procedure as described in Example 39. Workup and purification (Method B) afforded 350 mg (32%) of a pure compound. Lyophilization from dioxane afforded the title compound as a white powder.

HPLC (Method G) RT=6.36 minutes; purity 99%.
NMR (DMSO) in agreement with title compound.
FAB MS: 774 (M⁺ +H).
Analysis Calc'd for C₄₀H₅₆N₁₀O₆.2.5C₂HF₃O₂.1-H₂O: N, 13.02; C, 50.19; H, 5.67. Found: N, 12.78; C, 50.60; H, 5.63.

EXAMPLE 45

Cyclo[D-phenylalanyl-L-isoleucyl-D-pipecolyl-L-lysyl-D-histidyl-L-prolyl]

Cyclo[D-Phe-L-Ile-D-Pip-L-Lys-D-His-L-Pro] was prepared from cyclo[D-Phe-L-Ile-D-Pip-L-(Cbz) Lys-D-His-L-Pro] (35 mg, 0.04 mmole) using the same procedure as described in Example 39. Workup and purification (Method B) afforded 15 mg (50%) of a pure compound. Lyophilization from dioxane afforded the title compound as a white powder.

HPLC (Method G) RT=6.45 minutes; purity 97.5%.
NMR (DMSO) in agreement with title compound.
FAB MS: 741 (M⁺ +H).
Analysis Calc'd for C₃₈H₅₅N₉O₆.2C₂HF₃O₂.2H₂O: N, 13.01; C, 50.44; H, 5.68. Found: N, 13.02; C, 50.10; H, 4.90.

EXAMPLE 46

Cyclo[D-phenylalanyl-L-isoleucyl-D-pipecolyl-L-pipecolyl-D-(NᵅMethyl)tyrosyl-L-prolyl]

Cyclo[D-Phe-L-Ile-D-Pip-L-Pip-D-(NᵅMe)Tyr-L-Pro] was prepared from cyclo[D-Phe-L-Ile-D-Pip-L-Pip-D-(NᵅMe-O-Bzl)Tyr-L-Pro] (140 mg, 0.17 mmole) using the same procedure as described in Example 39. Workup and purification (Method B) afforded the title compound as a white powder after lyophilization from dioxane.

HPLC (Method G) RT=9.65 minutes; purity 97.5%.
NMR (CDCl₃) in agreement with title compound.
FAB MS: 757 (M⁺ +H).
Analysis Calc'd for C₄₂H₅₆N₆O₇.0.5 C₂HF₃O₂.0.5 H₂: N, 10.21; C, 62.52; H, 6.99. Found: N, 10.47; C, 62.70; H, 6.73.

EXAMPLE 47

Cyclo[D-phenylalanyl-L-isoleucyl-D-pipecolyl-L-pipecolyl-D(p-nitro)phenylalanyl-L-prolyl]

Cyclo[D-Phe-L-Ile-D-Pip-L-Pip-(p-nitro)-Phe-L-Pro] was prepared from Boc-L-Pro-O-(PAM)-resin (1 mmole) according to the solid phase procedure set forth in Example 1 with the following exception: Boc-D-(p-nitro)Phe (622 mg, 2 mmole) was used in Step 1. The final resin was cleaved with hydrazine and the hexapeptide hydrazide was cyclized as the acyl azide. Workup and purification (Method B) gave a homogeneous product. Lyophilization from dioxane afforded 800 mg (70%) of the title compound.

HPLC (Method G) RT=7.77 minutes; purity 98%.
NMR (CDCl₃) in agreement with title compound.
FAB MS: 772 (M⁺ +H).
Analysis Calc'd for C₄₁H₅₃N₇O₆.0.75 H₂O. 0.25 dioxane: N, 12.15; C, 62.49; H, 7.06. Found: N, 12.44; C, 62.38; H, 6.84.

EXAMPLE 48

Cyclo[D-phenylalanyl-L-isoleucyl-D-pipecolyl-L-pipecolyl-D-(p-amino)phenylalanyl-L-prolyl]

Cyclo[D-Phe-L-Ile-D-Pip-L-Pip-D-(p-amino)-Phe-L-Pro] was prepared from cyclo[D-Phe-L-Ile-D-Pip-L-Pip-D-(p-nitro)Phe-L-Pro] (150 mg, 0.19 mmole) using the same procedure as described in Example 39. Workup and purification (Method B) gave a pure compound. Lyophilization from dioxane afforded 130 mg (92%) of the title compound as a white powder.

HPLC (Method G) RT=7.84 minutes; purity 97.5%.
NMR (CDCl₃) in agreement with title compound
FAB MS: 742 (M⁺ +H).
Analysis Calc'd for C₄₁H₅₅N₇O₆.2.5 H₂O: N, 12.45; C, 62.52; H, 7.62. Found: N, 11.93; C, 62.92; H, 7.32.

EXAMPLE 49

Cyclo[D-phenylalanyl-L-isoleucyl-D-pipecolyl-L-pipecolyl-D-([N,N-dimethylglycyl]p-amino)phenylalanyl-L-prolyl]

Cyclo[D-Phe-L-Ile-D-Pip-L-Pip-D(p-amino)-Phe-L-Pro] (50 mg, 0.07 mmole) was dissolved in dry CH₂Cl₂ (2 ml). The acid chloride of (dimethylamino)glycine was prepared from the corresponding acid and oxallyl chloride described in Example 1. The acid chloride was dissolved in dry CH₂Cl₂ (1 ml) and added to the cyclic hexapeptide. DIEA (30 ul, 0.17 mmol) was added and the reaction was stirred under argon for 15 hours. The reaction mixture was diluted with CH₂Cl₂ (5 ml), extracted twice with saturated aqueous NaHCO₃ (5 ml) and brine (5 ml), then dried over NaSO₄ and evaporated under reduced pressure. Workup and purification using Method B and lyophilization from dioxane (50 ml) gave 15 mg (47%) of the title compound.

HPLC (Method G) RT=8.07 minutes; purity 99%.
NMR (CDCl₃) in agreement with title compound.
FAB MS: 827 (M⁺ +H).
Analysis Calc'd for C₄₅H₆₂N₈O₆.1 C₂HF₃O₂. 3.5 dioxane: N, 8.97; C, 58.61; H, 7.29. Found: N, 8.81; C, 58.32; H, 7.17.

EXAMPLE 50

Cyclo[D-phenylalanyl-L-isoleucyl-D-pipecolyl-L-pipecolyl-D-(Nᵅmethyl-O-2-(morpholin-4-yl)ethyl))-tyrosyl-L-prolyl]

Cyclo[D-Phe-L-Ile-D-Pip-L-Pip-D-(NᵅMe)Tyr-L-Pro] (100 mg, 0.125 mmol) was dissolved in absolute ethanol (2 ml) and 4-(2-chloroethyl)-morpholine hydrochloride (140 mg, 6 equiv.) was added followed by an excess (12 equiv.) of NaOEt in ethanol. The reaction was refluxed under Argon for 4 days. Following evaporation under reduced pressure the product was dissolved in CH₂Cl₂ (10 ml), extracted 3 times with water (10 ml), dried over Na₂SO₄, and evaporated under reduced pressure. Purification (Method B) followed by lyophilization from dioxane (10 ml) gave 20 mg (15%) of the title compound.

HPLC (Method G) RT=8.48 minutes; purity 98.6%.
NMR (CDCl₃) in agreement with title compound.
FAB MS: 870 (M+ +H).
Analysis Calc'd for $C_{47}H_{65}N_7O_8 \cdot 2C_2HF_3O_2$: N, 8.92; C, 56.80; H, 6.28. Found: N, 9.10; C, 57.35; H, 6.66.

EXAMPLE 51 c-[D-Phenylalanyl-L-isoleucyl-D-alanyl-L-alanyl-D-phenylalanyl-L-prolyl]

The title peptide was prepared in three stages: first, the linear sequence was assembled by standard solid phase methodology, as described by Erickson and Merrifield, Proteins, 3rd Ed., 2:257–527, 1976, using a Beckman Model 990B peptide synthesizer to carry out the operations (Step A); second, the linear peptide was cleaved from the solid resin support (Step B); the linear peptide was cyclized, and purified (Step C).

Step 1

D-Phenylalanyl-L-isoleucyl-D-alanyl-L-alanyl-D-phenylalanyl-L-prolyl-O-resin

The starting polymer was Boc-L-Pro esterified to 2% cross-linked polystyrene-divinylbenzene (2.5 mMol, 1.92 g). The $N^\alpha$-Boc derivatives of D-Phe, L-Ala, D-Ala, and L-Ile were coupled using diisopropylcarbodiimide with an equivalent of the additive 1-hydroxybenzotriazole hydrate. The Boc protecting group was removed with 40% trifluoroacetic acid. The operations were carried out according to the following programs:

| Step | SCHEDULE OF STEPS FOR 2.5 MMOLE RUN Solvent/Reagent | Vol. (mL) | Mix time (min) |
|---|---|---|---|
| | Coupling Program 1 | | |
| 1 | $CH_2Cl_2$ | 6 × 50 | 2 |
| 2 | 40% TFA, 0.5% ethanedithiol in $CH_2Cl_2$ | 1 × 50 | 2 |
| 3 | 40% TFA, 0.5% ethanedithiol in $CH_2Cl_2$ | 1 × 50 | 25 |
| 4 | $CH_2Cl_2$ | 3 × 50 | 2 |
| 5 | 10% TEA in DMF | 2 × 50 | 5 |
| 6 | $CH_2Cl_2$ | 3 × 50 | 2 |
| 7 | DMF | 3 × 50 | 2 |
| 8 | Boc-Amino Acid, HBT in 1:1 DMF/$CH_2Cl_2$ | 40 | 5 |
| 9 | 1.0 M DICI in $CH_2Cl_2$ | 15 | 180 |
| 10 | DMF | 1 × 50 | 2 |
| 11 | MeOH | 2 × 50 | 2 |
| 12 | $CH_2Cl_2$ | 1 × 50 | 2 |

The fully assembled resin-peptide was deblocked (removal of Boc on the D-Phe residue) following steps 1–4 in the above program. After a final washing with $CH_2Cl_2$, the resin peptide was dried.

Step 2

D-Phenylalanyl-L-isoleucyl-D-alanyl-L-alanyl-D-phenylalanyl-L-proline

The resin-peptide from A was swelled in 2 mL of anisole. The reaction vessel was immersed in a liquid nitrogen bath and the reaction vessel was evacuated to 1 Torr. Liquid HF (40 mL) was condensed into the reaction vessel which was then allowed to warm to 0° C. After stirring for 1 hour at 0° C. all volatile material was distilled into a liquid nitrogen cooled trap. The residual solids were suspended in ethyl ether and filtered. The filter cake was resuspended in an acetic acid-water mixture and filtered once more. The filtrate was diluted with water until the concentration of acetic acid was approximately 10% by volume. The resulting solution was then lyophilized. In this way, the resin-peptide from Step A yield 953 mg of the title compound.

Step 3 c-[D-Phenylalanyl-L-isoleucyl-D-alanyl-L-alanyl-D-phenylalanyl-L-prolyl]

To a solution of 200 mL of DMF containing 400 mg of peptide from step B was added 1.45 mL of DPPA and 760 mg of sodium bicarbonate at 0° C. The resulting suspension was stirred for 16 hours at 0° C. The reaction mixture was filtered and the filtrate was diluted with 50 mL of water and treated with sufficient amounts of analytical grade mixed-bed resin (Bio Rad, AG 501-X8(C), 20–50 mesh) such that its blue color persisted for 1 hour. The reaction mixture was filtered and the solvents were removed under reduced pressure. The residue was subjected to HPLC purification (Method C) to afford 112 mg of the title compound as a solvated, white solid: m.p. 304°–307° C.

HPLC (Method J) RT=19.15 minutes 99.9% pure at 210 nM.

NMR (DMSO-D₆): Confirmed structure of the title compound and the presence of solvent.

MS FAB: 647 (M+ +H), 669 (M+ +Na).

Elemental Analysis for $C_{35}H_{46}N_6O_6 \cdot 0.75H_2O$: Calculated: C, 63.66; H, 7.25; N, 12.73. Found: C, 63.69; H, 6.86; N, 12.61.

EXAMPLE 52 c-[D-Phenylalanyl-L-isoleucyl-D-prolyl-L-prolyl-N-methyl-D-phenylalanyl-L-prolyl]

The procedure of Example 51 was carried out utilizing the $N^\alpha$-Boc derivatives of D-Phe, L-Ile, D-Pro, L-Pro, and N-methyl-D-Phe to synthesize the title compound which was obtained in analytically pure form after HPLC purification (Method C).

HPLC (Method J) RT=23.82 minutes, >99% pure at 210 nM.

NMR (DMSO-D₆): Spectrum confirmed structure of the title compound and the presence of solvent.

Amino Acid Analysis: Pro 3(2.77), N-Me-Phe (0.99), Ile (0.85).

EXAMPLE 53 c-[D-Phenylalanyl-L-isoleucyl-D-prolyl-L-prolyl-D-phenylalanyl-L-prolyl]

The procedure of Example 51 was carried out utilizing the $N^\alpha$-Boc derivatives of D-Phe, L-Ile, D-Pro, and L-Pro, to synthesize the title compound which was obtained in analytically pure form after HPLC purification (Method C).

HPLC (Method J) RT=20.70 minutes, 99% pure at 210 nM.

NMR (DMSO-D₆): Spectrum confirmed structure of the title compound and the presence of solvent.

MS FAB: 699 (M+ +H), 721 (M+ +Na).

Amino Acid Analysis: Phe 2(1.00), Pro 3(1.02); Ile (0.97).

EXAMPLE 54 c-[D-Phenylalanyl-L-isoleucyl-N-methyl-D-alanyl-N-methyl-L-alanyl-D-phenylalanyl-L-prolyl]

The procedure of Example 51 was carried out utilizing the $N^\alpha$-Boc derivatives of D-Phe, L-Ile, N-methyl-D-Ala, N-methyl-L-Ala, and L-Pro to synthesize the title compound which was obtained in analytically pure form after HPLC purification (Method C).

HPLC (Method J) RT=18.46 minutes, 99% pure at 210 nM.

NMR (DMSO-$D_6$): Spectrum confirmed structure of the title compound and the presence of solvent.

MS FAB: 675 (M++H).

Amino Acid Analysis: Phe 2(1.00), Pro (1.00); Ile (0.942).

EXAMPLE 55 c-[D-Cyclohexylalanyl-L-isoleucyl-D-prolyl-D-phenylalanyl-L-prolyl]

The procedure of Example 51 was carried out utilizing the $N^{60}$-Boc derivatives of D-Phe, L-Ile, D-cyclohexyl-Ala, D-Pro, and L-Pro to synthesize the title compound which was obtained in analytically pure form after HPLC purification (Method C).

HPLC (Method J) RT=22.86 minutes, 99% pure at 210 nM.

NMR (DMSO-$D_6$): Spectrum confirmed structure of the title compound and the presence of solvent.

MS FAB: 705 (M++H), 727 (M++Na).

Amino Acid Analysis: Pro 3(1.00), Phe (1.00); Ile (0.94).

EXAMPLE 56 c-[D-Phenylalanyl-L-cyclohexylalanyl-D-prolyl-L-prolyl-D-phenylalanyl-L-prolyl]

The procedure of Example 51 was carried out utilizing the $N^\alpha$-Boc derivatives of D-Phe, L-cyclohexyl-Ala, D-Pro, and L-Pro to synthesize the title compound which was obtained in analytically pure form after HPLC purification (Method C). m.p. 80°-97° C.

HPLC (Method J) RT=24.94 minutes, 99% pure at 210 nM.

NMR (DMSO-$D_6$): Spectrum confirmed structure of the title compound and the presence of solvent.

MS FAB: 739 (M++H), 761 (M++Na).

Elemental Analysis for $C_{42}H_{54}N_6O_6.0.05$-$H_2O.0.5$TFA Calculated: C, 64.81; H, 6.91; N, 10.55. Found: C, 64.78; H, 6.84; N, 10.55.

EXAMPLE 57 c-[D-Phenylalanyl-L-isoleucyl-D-prolyl-L-prolyl-D-$\alpha$-glutaminyl-glycyl]

The procedure of Example 51 was carried out utilizing the $N^\alpha$-Boc derivatives of D-Phe, D-$\alpha$-Gln, Gly, Ile, D-Pro, and L-Pro to synthesize the title compound which was obtained in analytically pure form after HPLC purification (Method C). m.p. 305°-325° C.

HPLC (Method I) RT=11.05 minutes, 99.81% pure at 210 nM.

NMR (DMSO-$D_6$): Spectrum confirmed structure of the title compound and the presence of solvent.

MS FAB: 640 (M++H).

Elemental Analysis for $C_{32}H_{45}N_7O_7.0.25$-$H_2O.0.4$TFA: Calculated: C, 57.10; H, 6.71; N, 14.21. Found: C, 57.14; H, 6.76; N, 14.12.

EXAMPLE 58 c-[D-Phenylalanyl-L-isoleucyl-D-prolyl-L-prolyl-D-cysteinyl(Acm)-L-prolyl]

The procedure of Example 51 was carried out utilizing the $N^\alpha$-Boc derivatives of D-Phe, D-Cys(Acm), Ile, D-Pro, and L-Pro to synthesize the title compound which was obtained in analytically pure form after HPLC purification (Method C). m.p. 80°-97° C.

HPLC (Method J) RT=17.79 minutes, 99% pure at 210 nM.

NMR (DMSO-$D_6$): Spectrum confirmed structure of the title compound and the presence of solvent.

MS FAB: 726 (M+).

Elemental Analysis for $C_{36}H_{51}N_7O_7S.0.8$-$H_2O.0.1$TFA: Calculated: C, 52.58; H, 6.18; N, 11.18. Found: C, 52.60; H, 6.15; N, 11.18.

EXAMPLE 59 c-[D-Phenylalanyl-L-isoleucyl-D-prolyl-L-prolyl-D-crsteinyl(Bzl)-L-prolyl]

The procedure of Example 51 was carried out utilizing the $N^\alpha$-Boc derivatives of D-Phe, D-Cys(Bzl), Ile, D-Pro, and L-Pro to synthesize the title compound which was obtained in analytically pure form after HPLC purification (method C). m.p. 72°-88° C.

HPLC (Method J) RT=24.18 minutes, 97.5% pure at 210 nM.

NMR (DMSO-$D_6$): Spectrum confirmed structure of the title compound and the presence of solvent.

MS FAB: 745 (M++H).

Elemental Analysis for $C_{40}H_{52}N_6O_6S.1.2$-$H_2O.0.7$TFA: Calculated: C, 59.00; H, 6.54; N, 9.97. Found: C, 59.02; H, 6.58; N, 9.86.

EXAMPLE 60 c-[L-Phenylalanyl-D-isoleucyl-L-prolyl-D-prolyl-L-phenylalanyl-D-prolyl]

The procedure of Example 51 was carried out utilizing the $N^\alpha$-Boc derivatives of D-Phe, L-Ile, D-Pro, and L-Pro to synthesize the title compound which was obtained in analytically pure form after HPLC purification (Method C).

HPLC (Method J) RT=22.94 minutes, 100% pure at 210 nM.

NMR (DMSO-$D_6$): Spectrum confirmed structure of the title compound and the presence of solvent.

MS FAB: 699 (M++H).

Elemental Analysis for $C_{39}H_{59}N_6O_6.1.35$-$H_2O.0.35$TFA: Calculated: C, 62.34; H, 7.02; N, 10.99. Found: C, 62.35; H, 7.01; N, 11.14.

EXAMPLE 61 c-[D-Phenylalanyl-L-isoleucyl-D-prolyl-L-prolyl-D-threoninyl(Bzl)-L-prolyl]

The procedure of Example 51 was carried out utilizing the $N^\alpha$-Boc derivatives of D-Phe, D-Thr(Bzl), L-Ile, D-Pro, and L-Pro to synthesize the title compound which was obtained in analytically pure form after HPLC purification (Method C).

HPLC (Method I) RT=17.46 minutes 98.51% pure at 210 nM.

NMR (DMSO-$D_6$): Spectrum confirmed structure of the title compound and the presence of solvent.

MS FAB: 743 (M++H).

Elemental Analysis for $C_{41}H_{54}N_6O_7.0.4$-$H_2O.0.4$TFA: Calculated: C, 63.09; H, 6.99; N, 10.56. Found: C, 63.05; H, 6.96; N, 10.64.

EXAMPLE 62 c-[D-Phenylalanyl-L-isoleucyl-D-prolyl-L-prolyl-D-threoninyl-L-prolyl]

The procedure of Example 51 was carried out utilizing the $N^\alpha$-Boc derivatives of D-Phe, D-Thr, L-Ile, D-Pro, and L-Pro to synthesized the title compound which was obtained in analytically pure form after HPLC purification (Method C). m.p. 182°–188° C.

HPLC (Method J) RT=16.9 minutes, 99.74% pure at 210 nM.

NMR (DMSO-$D_6$): Spectrum confirmed structure of the title compound and the presence of solvent.

MS FAB: 653 (M++H), 675 (M++Na).

Elemental Analysis for $C_{34}H_{48}N_6O_7.1.35\text{-}H_2O.0.7TFA$: Calculated: C, 56.17; H, 6.84; N, 11.10. Found: C, 56.16; H, 6.81; N, 11.26.

EXAMPLE 63 c-[D-Phenylalanyl-L-phenylglycyl-D-prolyl-L-prolyl-D-phenylalanyl-L-prolyl]

The procedure of Example 51 was carried out utilizing the $N^\alpha$-Boc derivatives of D-Phe, L-Phg, L-Phe, D-Pro, and L-Pro to synthesize the title compound which was obtained in analytically pure form after HPLC purification (Method C). m.p. 135°–160° C.

HPLC (Method J) RT=20.40 minutes, 99% pure at 214 nM.

NMR (DMSO-$D_6$): Spectrum confirmed structure of the title compound and the presence of solvent.

MS FAB: 719 (M++H), 741 (M++Na).

Elemental Analysis for $C_{41}H_{46}N_6O_6.0.45\text{-}H_2O..0.7TFA$: Calculated: C, 63.12; H, 5.95; N, 10.42. Found: C, 63.13; H, 5.96; N, 10.43.

EXAMPLE 64 c-[D-Phenylalanyl-L-prolyl-D-prolyl-L-prolyl-D-phenylalanyl-L-prolyl]

The procedure of Example 51 was carried out utilizing the $N^\alpha$-Boc derivatives of D-Phe, D-Pro, and L-Pro to synthesize the title compound which was obtained in analytically pure form after HPLC purification (Method C). m.p. 70°–80° C.

HPLC (Method J) RT=19.52 minutes, 97% pure at 214 nM.

NMR (DMSO-$D_6$): Spectrum confirmed structure of the title compound and the presence of solvent.

MS FAB: 683 (M++H), 706 (M++Na).

Elemental Analysis for $C_{35}H_{46}N_6O_6.0.75H_2O$: Calculated: C, 63.66; H, 7.25; N, 12.73. Found: C, 63.69; H, 6.86; N, 12.61.

EXAMPLE 65 c-[D-Phenylalanyl-L-isoleucyl-D-cyclohexyglycyl-L-cyclohexylglycyl-D-phenylalanyl-L-prolyl The procedure of Example 51 was carried out utilizing the $N^\alpha$-Boc derivatives of D-Phe, L-Ile, D-ChGly, L-ChGly D-Pro, and L-Pro to synthesize the title compound which was obtained in analytically pure form after HPLC purification (Method C). m.p. 345°–353° C.

HPLC (Method J) RT=33.77 minutes, 96% pure at 214 nM.

NMR (DMSO-$D_6$): Spectrum confirmed structure of the title compound and the presence of solvent.

MS FAB: 783 (M++H), 805 (M++Na).

Elemental Analysis for $C_{45}H_{62}N_6O_6.0.55CHCl_3$ Calculated: C, 64.46; H, 7.43; N, 9.90. Found: C, 64.63; H, 7.32; N, 9.98.

EXAMPLE 66 c-[D-Phenylalanyl-L-isoleucyl-D-prolyl-L-prolyl-D-α-glutaminyl-glycyl]

The procedure of Example 51 was carried out utilizing the $N^\alpha$-Boc derivatives of D-Phe, L-Ile, Gly, D-α-Gln, D-Pro, and L-Pro to synthesize the title compound which was obtained in analytically pure form after HPLC purification (Method C). m.p. 168°–175° C.

HPLC (Method J) RT=9.34 minutes, 99% pure at 214 nM.

NMR (DMSO-$D_6$): Spectrum confirmed structure of the title compound and the presence of solvent.

MS FAB: 640 (M++H), 662 (M++Na).

Elemental Analysis for $C_{45}H_{62}N_6O_6.0.55CHCl_3$: Calculated: C, 55.64; H, 6.82; N, 13.93. Found: C, 55.65; H, 6.77; N, 14.06.

EXAMPLE 67 c-[D-Phenylalanyl-L-cyclohexylglycyl-D-prolyl-L-prolyl-D-phenylalanyl-L-prolyl]

The procedure of Example 51 was carried out utilizing the $N^\alpha$-Boc derivatives of D-Phe, L-ChGly, D-Pro, and L-Pro to synthesize the title compound which was obtained in analytically pure form after HPLC purification (Method C). m.p. 325°–328° C.

HPLC (Method J) RT=25.14 minutes, 99% pure at 214 nM.

NMR (DMSO-$D_6$): Spectrum confirmed structure of the title compound and the presence of solvent.

MS FAB: 725 (M++H).

Elemental Analysis for $C_{41}H_{51}N_6O_6.1.0H_2O.0.2TFA$ Calculated: C, 65.02; H, 7.01; N, 10.99. Found: C, 64.99; H, 6.98; N, 10.99.

EXAMPLE 68 c-[D-Phenylalanyl-L-isoleucyl-D-prolyl-L-prolyl-D-α-glutaminyl-L-prolyl]

The procedure of Example 51 was carried out utilizing the $N^\alpha$-Boc dericatives of D-Phe, L-Ile, α-Gln, D-Pro, and L-Pro to synthesize the title compound which was obtained in analytically pure form after HPLC purification (Method C). m.p. 127°–138° C.

HPLC (Method J) RT=15.26 minutes, 99% pure at 214 nM.

NMR (DMSO-$D_6$): Spectrum confirmed structure of the title compound and the presence of solvent.

MS FAB: 680 (M++H).

Elemental Analysis for $C_{35}H_{49}N_7O_7.2.2\text{-}H_2O.0.25TFA$ Calculated: C, 57.00; H, 7.23; N, 13.11. Found: C, 57.00; H, 7.22; N, 13.18.

EXAMPLE 69 c[D-Phenylalanyl-L-isoleucyl-D-histidinyl-L-histidinyl-D-phenylalanyl-L-prolyl]

Step 1

D-Phenylalanyl-L-isoleucyl-D-histidinyl-L-histidinyl-D-phenylalanyl-L-prolyl-O-resin The procedure of Example 51 Step A was carried out utilizing the $N^\alpha$-Boc derivatives of D-Phe, L-Ile, D-His(DNP), L-His(DNP), D-Pro, and L-Pro to synthesize the title compound. The Boc protecting group was removed as described in Step 1, Example 51. The DNP protecting group was removed from the peptide resin according to the following protocol:

| SCHEDULE OF STEPS FOR 2.5 MMOLES RUN | | | |
|---|---|---|---|
| Step | Solvent/Reagent | Vol. (mL) | Mix time (min) |
| | DNP Removal Program 2 | | |
| 1 | $CH_2Cl_2$ | 1 × 50 | 2 |
| 2 | 10% Phenylthiol in DMF | 1 × 50 | 25 |
| 3 | DMF | 1 × 50 | |
| 4 | MeOH | 2 × 50 | 2 |
| 5 | $CH_2Cl_2$ | 2 × 50 | 2 |
| 6 | MeOH | 2 × 50 | 2 |
| 7 | $CH_2Cl_2$ | 2 × 50 | 2 |

The finished resin-peptide was dried and suspended in 40 mL of dry methanol.

Step 2

D-Phenylalanyl-L-isoleucyl-D-histidinyl-L-histidinyl-D-phenylalanyl-L-proline methyl ester To the suspension prepared in Step 1 above was added 10 mL of triethylamine and the reaction mixture was stirred under a dry nitrogen atmosphere for 18 hours. The reaction mixture was filtered and the filtrate was concentrated under reduced pressure to afford the crude methyl ester which was used directly without purification in the next step.

Step 3 c-[D-Phenylalanyl-L-isoleucyl-D-histidinyl-L-histidinyl-D-phenylalanyl-L-prolyl]

The crude methyl ester was dissolved in 100 mL of a mixture of methanol-water-triethyl amine (1:1:0.5 v/v) and stirred for 18 hours. The solution was evaporated under reduced pressure and the crude product was subjected to the same cyclization and work-up conditions as described in Step 3, Example 51. The title compound was obtained in analytically pure form after HPLC purification (Method C). m.p. 250°-274° C.

HPLC (Method J) RT=13.19 minutes, 97.33% pure at 214 nM.

NMR (DMSO-$D_6$): Spectrum confirmed structure of the title compound and the presence of solvent.

MS FAB: 779 (M+ +H).

Amino Acid Analysis: Phe 2(1.00); Pro (1.01), His 2 (1.01); Ile (0.99).

EXAMPLE 70 c-[D-Phenylalanyl-L-isoleucyl-D-phenylglycinyl-L-phenylglycinyl-D-phenylalanyl-L-prolyl]

The procedure of Example 51 was carried out utilizing the $N^\alpha$-Boc derivatives of D-Phe, L-Ile, D-Phg, L-Phg, and L-Pro to synthesize the title compound which was obtained in analytically pure form after HPLC purification (Method C). m.p. 305°-310° C.

HPLC (Method J) RT=26.51 minutes, 99% pure at 214 nM.

NMR (DMSO-$D_6$): Spectrum confirmed structure of the title compound and the presence of solvent.

MS FAB: 793 (M+ +H).

Elemental Analysis for $C_{45}H_{50}N_6O_6$.0.6-$H_2O$.1.10TFA: Calculated: C, 62.49; H, 5.81; N, 9.26. Found: C, 62.52; H, 5.84; N, 9.07.

EXAMPLE 71 c-[D-Phenylalanyl-L-isoleucyl-D-prolyl-L-trans-hydroxyprolyl-D-phenylalanyl-L-prolyl]

The procedure of Example 51 was carried out utilizing the $N^\alpha$-Boc derivatives of D-Phe, L-Ile, L-trans-Hyp, D-Pro, and L-Pro to synthesize the title compound which was obtained in analytically pure form after HPLC purification (Method C). m.p. 105°-120° C.

HPLC (Method I) RT=14.11 minutes, 98% pure at 214 nM.

NMR (DMSO-$D_6$): Spectrum confirmed structure of the title compound and the presence of solvent.

MS FAB: 715 (M+ +H).

Elemental Analysis for $C_{39}H_{50}N_6O_7$.0.5$H_2O$.0.8TFA Calculated: C, 59.82; H, 6.41; N, 10.31. Found: C, 59.82; H, 6.42; N, 10.40.

EXAMPLE 72 c-[D-Phenylalanyl-L-(O-benzyl)-threoninyl-D-prolyl-L-prolyl-D-phenylalanyl-L-prolyl]

The procedure of Example 51 was carried out utilizing the $N^\alpha$-Boc derivatives of D-Phe, L-Thr-(Bzl), D-Pro, and L-Pro to synthesize the title compound which was obtained in analytically pure form after HPLC purification (Method C).

HPLC (Method I) RT=17.55 minutes, 99% pure at 214 nM.

NMR (DMSO-$D_6$): Spectrum confirmed structure of the title compound and the presence of solvent.

MS FAB: 777 (M+ +H).

Elemental Analysis for $C_{44}H_{52}N_6O_7$.0.85-$H_2O$.1.15TFA: Calculated: C, 60.22; H, 5.99; N, 9.10. Found: C, 60.23; H, 5.99; N, 9.20.

EXAMPLE 73 c-[D-Phenylalanyl-L-threoninyl-D-prolyl-L-prolyl-D-phenylalanyl-L-prolyl]

To 100 mL of absolute ethanol were added 100 mg of the protected peptide c-[D-phenylalanyl-L-(O-benzyl)-threoninyl-D-prolyl-L-prolyl-D-phenylalanyl-L-prolyl] and 2 drops of glacial acetic acid. The solutions was treated with 50 mg of 10% palladium/carbon catalyst and the resulting suspension was hydrogenated on a Parr apparatus at 55 psi for 6 hours. The reaction mixture was filtered through Celite and the filtrate was concentrated in vacuo to give the crude product which was obtained in analytically pure form after HPLC purification (Method C).

HPLC (Method I) RT=17.98 minutes 97% pure at 214 nM.

NMR (DMSO-$D_6$): Spectrum confirmed structure of the title compound and the presence of solvent.

MS FAB: 687 (M+ +H).

Elemental Analysis for $C_{37}H_{46}N_6O_7$.1.1-$H_2O$.0.75TFA Calculated: C, 58.37; H, 6.23; N, 10.61. Found: C, 58.35; H, 6.22; N, 10.68.

EXAMPLE 74 c-[D-Phenylalanyl-L-isoleucinyl-D-prolyl-L-cis-hydroxyprolyl-D-phenylalanyl-L-prolyl]

The procedure of Example 51 was carried out utilizing the $N^\alpha$-Boc derivatives of D-Phe, L-Ile, D-Pro, cis-L-Hyp, and L-Pro to synthesize the title compound which was obtained ian analytically pure form after HPLC purification (Method C). m.p. 126°-128° C.

HPLC (Method J) RT=20.80 minutes 98% pure at 214 nM.

NMR (DMSO-D$_6$): Spectrum confirmed structure of the title compound and the presence of solvent.

MS FAB: 715 (M$^+$+H), 737 (M$^+$+Na).

Elemental Analysis for C$_{39}$H$_{50}$N$_6$O$_7$.0.65-H$_2$O.0.45TFA: Calculated: C, 61.60; H, 6.71; N, 10.80. Found: C, 61.62; H, 6.66; N, 10.89.

EXAMPLE 75 c-[D-Phenylalanyl-L-isoleucinyl-D-prolyl-cis-D-hydroxyprolyl-D-phenylalanyl-L-prolyl]

The procedure of Example 51 was carried out utilizing the N$^\alpha$-Boc derivatives of D-Phe, L-Ile, D-Pro, cis-D-Hyp, and L-Pro to synthesize the title compound which was obtained in analytically pure form after HPLC purification (Method C). m.p. 130°–134° C.

HPLC (Method J) RT=21.07 minutes, 99% pure at 214 nM.

NMR (DMSO-D$_6$): Spectrum confirmed structure of the title compound and the presence of solvent.

MS FAB: 715 (M$^+$+H), 737 (M$^+$+Na).

Elemental Analysis for C$_{39}$H$_{50}$N$_6$O$_7$.0.95-H$_2$O.0.60TFA: Calculated: C, 60.32; H, 6.61; N, 10.50. Found: C, 60.30; H, 6.65; N, 10.51.

EXAMPLE 76 c-[D-Phenylalanyl-L-isoleucinyl-D-pipecolyl-D-piperazin-2-yl(4-Cbz)-D-phenylalanyl-L-prolyl]

The procedure of Example 51 was carried out utilizing the N$^\alpha$-Boc derivatives of D-Phe, L-Ile, D-Pip, D-Pipe(4-Cbz), and L-Pro to synthesize the title compound which was obtained in analytically pure form after HPLC purification (Method C). m.p. 295 (d) °C.

HPLC (Method J) RT=28.49 minutes, 97% pure at 214 nM.

NMR (DMSO-D$_6$): Spectrum confirmed structure of the title compound and the presence of solvent.

MS FAB: 863 (M$^+$+H), 885 (M$^+$+Na).

Amino Acid Analysis: Phe 2(1.023), Pro (1.00), Ile (0.984).

Elemental Analysis for C$_{48}$H$_{59}$N$_7$O$_8$.0.5-H$_2$O.1.25TFA Calculated: C, 59.84; H, 6.09; N, 9.67. Found: C, 59.85; H, 6.25; N, 9.29.

EXAMPLE 77 c-[D-Phenylalanyl-L-isoleucinyl-D-pipecolyl-L-piperazin-2-yl(4-Cbz)-D-phenylalanyl-L-prolyl]

The procedure of Example 51 was carried out utilizing the N$^\alpha$-Boc derivatives of D-Phe, L-Ile, D-Pip, L-Pipe(4-Cbz), and L-Pro to synthesize the title compound which was obtained in analytically pure form after HPLC purification (Method C). m.p. 117°–119° C.

HPLC (Method J) RT=29.17 minutes, >96% pure at 214 nM.

NMR (DMSO-D$_6$): Spectrum confirmed structure of the title compound and the presence of solvent.

MS FAB: 863 (M$^+$+H), 885 (M$^+$+Na).

Elemental Analysis for C$_{48}$H$_{59}$N$_7$O$_8$.0.5-H$_2$O.1.25TFA Calculated: C, 59.84; H, 6.09; N, 9.67. Found: C, 59.85; H, 6.25; N, 9.29.

EXAMPLE 78 c-[D-Phenylalanyl-L-isoleucinyl-D-pipecolyl-D-piperazin-2-yl-D-phenylalanyl-L-prolyl]

c-[D-Phenylalanyl-L-isoleucinyl-D-pipecolyl-D-piperazin-2-yl(4-Cbz)-D-phenylalanyl-L-prolyl] (200 mg) was dissolved in 40 mL of absolute ethanol and treated with 2 drops of glacial acetic acid and 50 mg of 10% Pd/C catalyst. The resulting suspension was hydrogenated for 7 hours in a Parr apparatus, filtered and concentrated to dryness. The residual material was obtained in analytically pure form after HPLC purification (Method C). m.p. 264°–280° C.

HPLC (Method I) RT=12.46 minutes, >99% pure at 214 nM.

NMR (DMSO-D$_6$): Spectrum confirmed structure of the title compound and the presence of solvent.

MS FAB: 728 (M$^+$+H), 750 (M$^+$+Na).

Elemental Analysis for C$_{42}$H$_{54}$N$_7$O$_8$.1.95-H$_2$O.1.05TFA: Calculated: C, 53.13; H, 5.96; N, 9.84. Found: C, 52.89; H, 5.58; N, 10.23.

EXAMPLE 79 c-[D-Phenylalanyl-L-isoleucinyl-D-piperazin-2-yl(4-Cbz)-L-piperazin-2-yl(4-Cbz)-D-phenylalanyl-L-prolyl]

The preparation of the title compound was carried out, in part, as described in Example 1, Steps 1–6, with the following minor modifications: PAM resin was replaced with Merrifield resin, BOP was replaced with DCC, D-(N$^\alpha$-Me)Phe was replaced with D-Phe, and L-and D-Pip were replaced with L-and D-Pipe(4-Cbz), respectively.

The fully assembled peptide-resin (@2 mmole) was suspended in 300 mL of dry methanol and treated with 30 mL of triethylamine. The resulting suspension was stirred for 18 hours under a nitrogen atmosphere. The reaction mixture was then filtered and the filtrate was evaporated under reduced pressure to give the methyl ester (1.93 g) which, without purification, was dissolved in 200 mL of a mixture of methanol-water-triethylamine (2:2:1, v/v) and stirred at 23°C. overnight. The reaction mixture was rotoevaporated under reduced pressure and the crude product was subjected to cyclization conditions as described in Example 51, Step 3. Employing the identical work-up and purification procedures as in Example 51, Step 3, afforded the analytical product in 10% overall yield. m.p. 135°–140° C.

HPLC (Method J) RT=29.88 minutes, >96% pure at 214 nM.

NMR (DMSO-D$_6$): Spectrum confirmed structure of the title compound and the presence of solvent.

MS FAB: 997 (M$^+$).

Elemental Analysis for C$_{55}$H$_{64}$N$_8$O$_{10}$.O.4TFA: Calculated: C, 64.27; H, 6.23; N, 10.75. Found: C, 64.36; H, 6.08; N, 10.61.

EXAMPLE 80 c-[D-Phenylalanyl-L-isoleucinyl-D-piperazin-2-yl-L-piperazin-2-yl-D-phenylalanyl-L-prolyl]

The title compound was obtained from c-[D-phenylalanyl-L-isoleucinyl-D-piperazin-2-y(4-Cbz)-L-piperazin-2-yl(4-Cbz)-D-phenylalanyl-L-prolyl] using the procedure outlined in Example 73 with the following exception: 20% palladium hydroxide on carbon catalyst was used in place of 10% palladium on carbon catalyst. The title compound was obtained in analytically pure form after HPLC purification (Method C). m.p. 225°–230° C.

HPLC (Method J) 98.49% pure at 214 nM.

NMR (DMSO-D$_6$): Spectrum confirmed structure of the title compound and the presence of solvent.

MS FAB: 729 (M+).

Elemental Analysis for $C_{39}H_{52}N_8O_{10}.2.35-H_2O.3.4TFA$: Calculated: C, 47.46; H, 5.23; N, 9.67. Found: C, 47.47; H, 5.24; N, 9.62.

EXAMPLE 81 c-[D-Phenylalanyl-L-isoleucinyl-D-pipecolyl-L-piperazin-2yl(4Cbz)-D-histidinyl-L-prolyl]

The title compound was obtained from Boc-L-Pro-(Merrifield)-resin (1 mMole) using the procedure outlined Example 1 and utilizing the Fmoc derivatives of D-(DNP)-His, L-Pipe(4-Cbz), D-Pip, L-Ile, and D-Phe. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product (retention time @45 minutes) was lyophilized and subjected to Step 8 in Example 1. The title compound was obtained in analytically pure form after HPLC purification (method D).

HPLC (Method I) 13.84 minutes, >99% pure at 214 nM.

NMR (DMSO-D$_6$): Spectrum confirmed structure of the title compound and the presence of solvent.

MS FAB: 852 (M++H), 874 (M++Na). Amino Acid Analysis: Ile (0.93), Phe (1.00), His (0.996), Pro (1.00).

Elemental Analysis for $C_{45}H_{57}N_9O_8.1.25EtOAc.0.7H_3PO_4$ Calculated: C, 58.26; H, 6.76; N, 12.23. Found: C, 58.23; H, 6.93; N, 12.24.

EXAMPLE 82 c-[D-Phenylalanyl-L-isoleucinyl-D-pipecolyl-D-piperazin-2-yl(4Cbz)-D-histidinyl-L-prolyl]

The title compound was obtained from Boc-L-Pro-(Merrifield)-resin (1 mMole) using the method outlined in Example 81 and utilizing the Fmoc derivatives of D-Pipe(4Cbz), D-(DNP)-His, D-Pip, L-Ile, and D-Phe. The title compound was obtained in analytically pure form after HPLC purification (Method D).

HPLC (Method I) 14.07 minutes, >95% pure at 214 nM.

NMR (DMSO-D$_6$): Spectrum confirmed structure of the title compound and the presence of solvent.

MS FAB: 852 (M++H), 874 (M++Na).

Elemental Analysis for $C_{45}H_{57}N_9O_8.1.0EtOAc.0.55H_3PO_4$: Calculated: C, 59.20; H, 6.76; N, 12.68. Found: C, 59.32; H, 6.62; N, 12.67.

EXAMPLE 83 c-[D-Phenylalanyl-L-isoleucinyl-D-piperazin-2-yl-(4-Cbz)-L-pipecolyl-D-phenylalanyl-L-prolyl]

The title compound was obtained from Boc-L-Pro-(Merrifield)-resin (1 mMole) using the procedure outlined in Example 81 and utilizing the Fmoc derivatives of D-Pipe(4-Cbz), L-Pip, L-Ile, L-Pro, and D-Phe. The title compound was obtained in analytically pure form after HPLC purification (Method C). m.p. 110°–127° C.

HPLC (Method I) 16.43 minutes, >95% pure at 214 nM.

NMR (DMSO-D$_6$): Spectrum confirmed structure of the title compound and the presence of solvent.

MS FAB: 862 (M++H).

Elemental Analysis for $C_{48}H_{59}N_7O_8.1.35-H_2O.1.10TFA$ Calculated: C, 59.59; H, 6.26; N, 9.69. Found: C, 59.58; H, 6.23; N, 9.96.

EXAMPLE 84 c-[D-Phenylalanyl-L-isoleucinyl-D-piperazin-2-yl-L-pipecolyl-D-phenyalanyl-L-prolyl]

The title compound was obtained using the procedure outlined in Example 73 with following exception: 20% palladium hydroxide on carbon catalyst was used in place of 10% palladium on carbon catalyst. The title compound was obtained in analytically pure form after HPLC purification (Method C). m.p. 168°–188° C.

HPLC (Method I) 12.62 minutes, >97.6% pure at 214 nM.

NMR (DMSO-D$_6$): Spectrum confirmed structure of the title compound and the presence of solvent.

MS FAB: 728 (M++H).

Elemental Analysis for $C_{40}H_{53}N_7O_6.1.55-H_2O.1.65TFA$ Calculated: C, 55.09; H, 6.17; N, 10.39. Found: C, 55.08; H, 6.08; N, 10.77.

EXAMPLE 85 c-[Phenylalanyl-L-isoleucinyl-D-piperazin-2-yl(4-Cbz)-D-piperazin-2-yl(4-Cbz)-D-($N^\alpha$-methyl)phenylalanyl-L-prolyl]

The preparation of the title compound was carried out as described in Example 79 except that Fmoc-D-Phe was replaced with Fmoc-$N^\alpha$-methyl-D-Phe, and Fmoc-L-piperazin-2-yl(4-Cbz) was replaced with Fmoc-D-piperazin-2-yl(4-Cbz). The title compound was obtained in analytically pure form after HPLC purification (Method C). The final product was lyophilized from dioxane. m.p. 65°–70° C.

HPLC (Method I) 20.21 minutes, >99% pure at 210 nM.

NMR (DMSO-D$_6$): Spectrum confirmed structure of the title compound and the presence of solvent.

MS FAB: 1012 (M++H).

Elemental Analysis for $C_{56}H_{66}N_8O_{10}.1.5C_4H_8O_2.0.75TFA$ Calculated: C, 62.06; H, 6.46; N, 9.12. Found: C, 62.04; H, 6.53; N, 9.21.

EXAMPLE 86 c-[D-Phenylalanyl-L-isoleucinyl-D-piperazin-2-yl(4-Cbz)-L-piperazin-2-yl(4-Cbz)-D-($N^\alpha$-methyl)-phenylalanyl-L-prolyl]

The preparation of the title compound was carried out as described in Example 79 except that Fmoc-D-Phe was replaced with Fmoc-$N^\alpha$-methyl-D-Phe. The title compound was obtained in analytically pure form after HPLC purification (Method C). m.p. 131°–144° C.

HPLC (Method I) 21.07 minutes, >94% pure at 210 nM.

NMR (DMSO-D$_6$): Spectrum confirmed structure of the title compound and the presence of solvent.

MS FAB: 1012 (M++H).

Elemental Analysis for $C_{56}H_{66}N_8O_{10}.1.25-H_2O.1.40TFA$ Calculated: C, 59.18; H, 5.90; N, 9.39. Found: C, 59.16; H, 5.89; N, 9.48.

EXAMPLE 87 c-[D-Tryptophanyl-L-isoleucinyl-D-pipecolyl-L-piperazin-2-yl-D-phenylalanyl-L-prolyl]

The title compound was obtained from c-[D-tryptophanyl-L-isoleucinyl-D-pipecolyl-L-piperazin-2-yl-(4-Cbz)-D-phenylalanyl-L-prolyl]using the procedure outlined in Example 73 with the following exception: 20% palladium hydroxide on carbon catalyst was used in place of 10% palladium on carbon catalyst. The title compound was obtained in analytically pure form after HPLC purification (Method C). m.p. 197°–210° C.

HPLC (Method I) 11.89 minutes, >98.5% pure at 210 nM.

NMR (DMSO-$D_6$): Spectrum confirmed structure of the title compound and the presence of solvent.

MS FAB: 767 (M+ +H).

Elemental Analysis for $C_{42}H_{54}N_8O_6$.1.9TFA Calculated: C, 55.92; H, 5.73; N, 11.39. Found: C, 55.90; H, 5.72; N, 11.43.

EXAMPLE 88 c-[D-Trytophanyl-L-isoleucinyl-D-pipecolyl-L-piperazin-2-yl-D-tryptophanyl-L-prolyl]

The title compound was obtained from c-[D-tryptophanyl-L-isoleucinyl-D-pipecolyl-L-piperazin-2 -yl(4-Cbz)-D-tryptophanyl-L-prolyl] using the procedure outlined in Example 73 with the following exception: 20% palladium hydroxide on carbon catalyst was used in place of 10% palladium on carbon catalyst. The title compound was obtained in analytically pure form after HPLC purification (Method C). m.p. 200°–220° C.

HPLC (Method I) 13.30 minutes, >97.7% pure at 210 nM.

NMR (DMSO-$D_6$): Spectrum confirmed structure of the title compound and the presence of solvent.

MS FAB: 806 (M+ +H).

Elemental Analysis for $C_{42}H_{54}N_8O_6$.2.15TFA.0.3-$H_2O$ Calculated: C, 54.90; H, 5.51; N, 11.93. Found: C, 54.90; H, 5.52; N, 11.84.

EXAMPLE 89 c-[D-Tryptophanyl-L-isoleucinyl-D-pipecolyl-L-piperazin-2-yl(4-Cbz)-D-phenylalanyl-L-prolyl]

The title compound was obtained from Boc-L-Pro-(Merrifield)-resin (1 mMole) using the procedure outlined in Example 1 and utilizing the Fmoc derivatives of D-Trp, L-Ile, D-Pip, L-(4-Cbz)-Pipe, and D-Phe. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product was collected, lyophilized, and subjected to Step 8 in Example 1. The titled compound was obtained in analytically pure form after HPLC purification (Method C). m.p. 116°–140° C.

HPLC (Method I) 17.32 minutes, >94.5% pure at 210 nM.

NMR (DMSO-$D_6$): Spectrum confirmed structure of the title compound and the presence of solvent.

MS FAB: 901 (M+ +H).

Elemental Analysis for $C_{50}H_{60}N_8O_8$.1.2TFA.1.1$H_2O$ Calculated: C, 59.50; H, 6.04; N, 10.59. Found: C, 59.52; H, 6.05; N, 10.66.

EXAMPLE 90 c-[D-Tryptophanyl-L-isoleucinyl-D-pipecolyl-D-piperazin-2-yl(4-Cbz)-D-phenylalanyl-L-prolyl]

The title compound was obtained from Boc-L-Pro-(Merrifield)-resin (1 mMole) using the procedure outlined in Example 1 and utilizing the Fmoc derivatives of D-Trp, L-Ile, D-Pip, D-(4-Cbz)-Pipe, and D-Phe. Step 7 was modified in the following manner: the fully assembled peptide-resin was suspended in a solution consisting of 10 mL of methanol and 10 mL 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product was collected, lyophilized, and subjected to Step 8 in Example 1. The title compound was obtained in analytically pure form after HPLC purification (Method C). m.p. 120°–140° C.

HPLC (Method I) 17.77 minutes, >94.7% pure at 210 nM.

NMR (DMSO-$D_6$): Spectrum confirmed structure of the title compound and the presence of solvent.

MS FAB: 901 (M+ +H).

Elemental Analysis for $C_{50}H_{60}N_8O_8$.0.85TFA.1.25-$H_2O$ Calculated: C, 60.84; H, 6.26; N, 10.98. Found: C, 60.82; H, 6.25; N, 11.00.

EXAMPLE 91 c-[D-Tryptophanyl-L-isoleucinyl-D-pipecolyl-D-piperazin-2-yl(4-Cbz)-D-($N^\alpha$-methyl)phenylalanyl-L-prolyl]

The title compound was obtained from Boc-L-Pro-(Merrifield)-resin (1 mMole) using the procedure outlined in Example 1 and utilizing the Fmoc derivatives of D-Trp, L-Ile, D-Pip, D-(4-Cbz)-Pipe, and D-($N^\alpha$-methyl)Phe. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product was collected, lyophilized, and subjected to Step 8 in Example 1. The title compound was obtained in analytically pure form after HPLC purification (Method C). m.p. 135°–196° C.

HPLC (Method K) 17.77 minutes, >98% pure at 210 nM.

NMR (DMSO-$D_6$): Spectrum confirmed structure of the title compound and the presence of solvent.

MS FAB: 915 (M+ +H), 937 (M+ +Na).

Elemental Analysis for $C_{51}H_{62}N_8O_8$.0.90TFA.0.7-$H_2O$: Calculated: C, 61.55; H, 6.29; N, 10.88. Found: C, 61.54; H, 6.26; N, 11.04.

EXAMPLE 92 c-[D-Tryptophanyl-L-isoleucinyl-D-pipecolyl-L-piperazin-2-yl-D-(N$^\alpha$-methyl)phenylalanyl-L-prolyl]

The title compound was obtained from c-[D-tryptophanyl-L-isoleucinyl-D-pipecolyl-L-piperazin-2-yl(4-Cbz)-D-(N$^\alpha$-methyl)phenylalanyl-L-prolyl] using the procedure outlined in Example 73. The title compound was obtained in analytically pure form after HPLC purification (Method C). m.p. 182°–248° C.

HPLC (Method J) 19.23 minutes, >97% pure at 210 nM.

NMR (DMSO-D$_6$): Spectrum confirmed structure of the title compound and the presence of solvent.

MS FAB: 781 (M+ +H).

Elemental Analysis for C$_{43}$H$_{56}$N$_8$O$_6$.1.6TFA.2.45-H$_2$O Calculated: C, 51.61; H, 5.70; N, 9.99. Found: C, 51.32; H, 5.70; N, 10.39.

EXAMPLE 93 c-[D-Phenylalanyl-L-isoleucinyl-D-pipecolyl-D-piperazin-2-yl(4-Cbz)-L-(BOM)histidyl-L-prolyl]

The title compound was obtained from Boc-L-Pro(-Merrifield)-resin (1 mMole) using the procedure outlined in Example 1 and the utilizing the Fmoc derivatives of D-Phe, L-Ile, D-Pip, D-(4-Cbz)-Pipe, and L-(BOM)His. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product was collected, lyophilized, and subjected to Step 8 in Example 1. The title compound was obtained in analytically pure form after HPLC purification (Method C).

HPLC (Method H) 24.18 minutes, >98% pure at 210 nM. (Sample is a 4:1 mixture, of diastereoisomers at the Pipe residue).

NMR (DMSO-D$_6$): Spectrum confirmed structure of the title compound and the presence of solvent.

MS FAB: 972 (M+ +H), 994 (M+ +Na).

Elemental Analysis for C$_{53}$H$_{65}$N$_9$O$_9$.2.3TFA.0.5H$_2$O Calculated: C, 55.63; H, 5.54; N, 10.14. Found: C, 55.62; H, 5.52; N, 10.49.

EXAMPLE 94 c-[D-Tryptophanyl-L-isoleucinyl-D-prolyl-L-histidyl-D-histidyl-L-prolyl]

The title compound was obtained from Boc-L-Pro-(Merrifield)-resin (1 mMole) using the procedure outlined in Example 1 and utilizing the Fmoc derivatives of D-Trp, L-Ile, D-Pro, D-(DNP)His, and L-(DNP)His. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (containing traces of hydrazine) was then dissolved in methanol (@10 mL) and purified according to Method C. The product was collected, lyophilized, and subjected to Step 8 in Example 1. The title compound was obtained in analytically pure form after HPLC purification (Method C). m.p. 175°–200° C.

HPLC (Method I) 8.73 minutes, 99.7% pure at 210 nM.

NMR (DMSO-D$_6$): Spectrum confirmed structure of the title compound and the presence of solvent.

MS FAB: 768 (M+ +H).

Elemental Analysis for C$_{39}$H$_{49}$N$_{11}$O$_9$.2.75TFA.1.3-H$_2$O Calculated: C, 48.37; H, 4.96; N, 13.95. Found: C, 48.36; H, 4.90; N, 14.02.

EXAMPLE 95 c-[D-Tryptophanyl-L-isoleucinyl-D-prolyl-L-ornithinyl(Cbz)-D-histidyl-L-prolyl]

The title compound was obtained from Boc-L-Pro-(Merrifield)-resin (1 mMole) using the procedure outline in Example 1 and utilizing the Fmoc derivatives of D-Trp, L-Ile, D-Pro, L-Orn(Cbz), and L-(DNP)his. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The residue was redissolved in methanol and again concentrated. The crude hydrazide product (congaining traces of hydrazine) was then dissolved in methanol (@10 mL) and purified according to Method C. The product was collected, lyophilized, and subjected to Step 8 in Example 1. The title compound was obtained in analytically pure form after HPLC purification (Methoc C). m.p. 135°–172° C.

HPLC (Method I) 13.31 minutes, 96.7% pure at 210 nM.

NMR (DMSO-D$_6$): Spectrum confirmed structure of the title compound and the presence of solvent.

MS FAB: 879 (M+ +H).

Elemental Analysis for C$_{46}$H$_{58}$N$_{10}$O$_8$.1.85TFA.0.2-H$_2$O Calculated: C, 54.58; H, 5.55; N, 12.81. Found: C, 54.56; H, 5.53; N, 13.04.

EXAMPLE 96 c-[L-prolyl-D-phenylalanyl-L-isoleucyl-D-piperazyl-L-piperazyl-D-phenylalanyl]

1. Fmoc-L-(N$^\delta$-Cbz)-piperazic acyl-D-phenylalanyl-L-prolinetert-butyl ester. 49 mg (0.1 mmol) of Fmoc-L-(N$^\delta$Cbz)-Piz was converted to its acid chloride (Procedure 1a). A 60 mg (0.11 mmol) sample of Fmoc-D-Phe-L-Pro-O-$^t$Bu was N-protected (Procedure 8) and the crude product reacted with the acid chloride (Procedure 1b). Purification (Method F), eluting with 33% acetone/hexanes, provided the product as an oil: TLC R$_f$=0.45 in 30% acetone/hexanes; HPLC (Method I) single major peak at RT=23.99 minutes, FAB MS: 787 (M+ +H), 809 (M+ +Na); NMR (300 MHz, CDCl$_3$) consistent with structure;

Elemental analysis: Calculated: C, 70.21, H, 6.40, N, 7.12. Found: C, 69.92, H, 6.15, N, 6.88.

2. Boc-D-phenylalanyl-L-isoleucyl-D-(N$^{67}$-Cbz)-piperazyl-L-(N$^\delta$-Cbz)-piperazyl-D-phenylalanyl-L-proline-tert-butyl ester. Using the amino acids Boc-D-Phe, Fmoc-L-Ile, and Fmoc-D-(N$^\delta$-Cbz)-Piz, the above tripeptide was extended on its N-terminus to yield the title hexapeptide as an oil. This material was purified by Method E, eluting with 28% acetone/hexanes. The product was obtained as a white foam; TLC, R$_f$=0.36 in 30% acetone/hexane; FAB MS: 1171 (M+ +H); NMR (360 MHz, DMSO-d$_6$) consistent with structure.

3. H-D-Phenylalanyl-L-isoleucyl-D-(N$^\delta$-Cbz)-piperazyl-L-(N$^\delta$-Cbz)-piperazyl-D-phenylalanyl-L-proline-OH. A 108 mg (0.092 mmol) sample of the above fully protected hexapeptide was deprotected according to Procedure 6 (17 hours reaction period) to give a residue. This material was triturated with 1 mL of ether and 3 mL of hexane to yield the product as a solid which was used directly in the next step after drying in vacuo.

4. c-[D-Phenylalanyl-L-isoleucyl-D-(N$^\delta$-Cbz)-piperazyl-D-phenylalanyl-L-prolyl]. A solution of 86 mg (0.076 mmol) of the above N and C-terminal deblocked hexapeptide in 38 mL of DMF was cooled in ice water and treated with 64 mg (0.78 mmol) of sodium bicarbonate followed by 0.038 mL (0.18 mmol) of DPPA. The mixture was stirred for five days at 0° C., then concentrated. The residue was taken up in methylene chloride, filtered, and concentrated. The residue was then treated with warm acetonitrile and filtered, and the filtrate was purified by Method F (8% methanol/methylene chloride eluent). Isolation of the major band yield the title compound as as solid after precipitation from methylene chloride/hexane; TLC, $R_f=0.49$ in 7.5%, methanol/methylene chloride; HPLC (Method I) major peak (89% pure) at RT=22.22 minutes, FAB MS: 997 (M$^+$+H), 1019 (M$^+$+Na); NMR (360 MHz, DMSO-d$_6$) consistent with structure.

5. c-[D-Phenylalanyl-L-isoleucyl-D-piperazyl-L-piperazyl-D-phenylalanylL-prolyl]. A solution of 28 mg (0.028 mmol) of the above cyclic hexapeptide in 10 mL of 95% aqueous ethanol was treated with 4mg of 10% palladium on charcoal. The mixture was shaken for 17 hours under 45 psi of hydrogen, then filtered, concentrated. The residue was purified by preparative thick layer silica gel chromatography, eluting with 95:5:0.5, chloroform/methanol/concentrated ammonium hydroxide. On isolation of the major product band, a colorless glass was obtained which was triturated with chloroform/hexane to yield the title compound as a white solid: TLC, $R_f=0.20$ in 95:5:05, chloroform/methanol/concentrated ammonium hydroxide; HPLC, single major peak (96% pure) at RT=17.34 minutes system A; FAB MS: 729 (M$^+$+H), 751 (M$^+$+Na); NMR (360 MHz, DMSO-d$_6$) consistent with structure; Elemental analysis (for 1.2 moles methanol solvate), Calculated: C, 62.93, H, 7.46, N, 14.60. Found: C, 62.99, H, 7.34, N, 14.60.

EXAMPLE 97 c-[D-Lysyl-L-isoleucyl-D-piperazyl-L-piperazyl-D-phenylalanyl-L-prolyl]

1. In a manner similar to Example 96, using the amino acids Boc-D-(O-Benzyl)-Tyr, Fmoc-L-Ile, Fmoc-D-(N$^{\delta\text{-}Cbz}$-Piz, Fmoc-L-(N$^\delta$-Cbz)-Piz, Boc-D-Phe, and L-Pro-O-$^t$Bu, the cyclic hexapeptide c-[D-(O-Benzyl)-tyrosyl-L-isoleucyl-D-(N$^\delta$-Cbz)-piperazyl-L-(N$^\delta$-Cbz)-piperazyl-D-phenylalanyl-L-prolyl] was synthesized and purified (Method F, methanol/methylene chloride eluant): TLC, $R_f=0.51$ in 5% methanol/methylene chloride; HPLC (Method I) single major peak (96.3% pure) at RT=21.80 minutes; FAB MS: 1103 (M$^+$+H), 1125 (M$^+$+Na); NMR (400 MHz,CDCl$_3$) consistent with structure; elemental analysis (for 0.75 moles methanol and 0.4 moles hexane), Calculated: C, 67.35, H, 6.82, N, 9.65. Found: C, 67.39, H, 6.92, N, 9.65.

2. c-[D-Tyrosyl-L-isoleucyl-D-piperazyl-L-piperazyl-D-phenylalanyl-L-prolyl]. A solution of 43 mg (0.039 mmol) of the above cyclic hexapeptide was deprotected according to Procedure 10. Filtration, concentration, and purification via Method F (95:5:5, methylene chloride/methanol/concentrated ammonium hydroxide eluant) yielded, on isolation of the product and reconcentration from methylene chloride/hexane, a white solid: TLC, $R_f=0.42$ in 8% methanol/methylene chloride; HPLC (Method I) single major peak (98.3% pure) at RT=14.99 minutes, FAB MS: 745 (M$^+$+H), 767 (M$^+$+Na); NMR (400 MHz, DMSO-d$_6$) consistent with structure; elemental analysis for (0.25 moles methylene chloride), Calculated: C, 61.53, H, 6.89, N, 14.63. Found: C, 61.70, H, 6.23, N, 14.58.

EXAMPLE 98 c-[D-Phenylalanyl-L-isoleucyl-L-threonyl-L-asparagyl-D-phenylalanyl-L-prolyl]

1. Boc-D-phenylalanyl-L-isoleucyl-L-(O-tert-butyl)-threonyl-L-asparagyl-D-phenylalanyl-L-prolinetertbutyl ester. A solution of 84 mg (0.22 mmol) of Boc-D-Phe-L-Ile-OH in 2 mL of methylene chloride was treated with 30 mg (0.22 mmol) of HBT and a small amount of DMF to assist in solubilizing solids. To this solution was added 46 mg (0.22 mmol) of dicyclohexylcarbodiimide and the solution was stirred in the cold for 1 hour. The mixture was filtered and concentrated to yield to the hydroxybenzotriazole active ester. 90 mg (0.11 mmol) of Fmoc-L-Thr-L-Asn-D-Phe-L-Pro-O-$^t$Bu (synthesized from the amino acids Fmoc-L-Thr, Fmoc-L-Asn, Boc-D-Phe, and L-Pro-O-$^t$Bu according to Procedures 1 and 3) was N-deprotected (Procedure 8). The crude product was treated with a solution of the above active ester in 1 mL of DMF at 0° C. and the mixture was stirred for 16 hours, warming slowly to ambient temperature. The reaction mixture was then concentrated and the residue partitioned between ethyl acetate and brine. The organic layer was washed with brine, saturated aqueous sodium bicarbonate (twice), water, 10% aqueous potassium bisulfate, 50% brine and brine and concentrated to a yellow oil. This material was purified by Method F using 4% methanol/methylene chloride as eluant, to yield the product as a colorless oil; TLC, $R_f=0.42$ in 7.5% methanol/methylene chloride; of NMR(300 MHz, CDCl$_3$) consistent with structure.

2. c-[D-Phenylalanyl-L-isoleucyl-L-threonyl-L-asparagyl-D-phenylalanyl-L-prolyl].

The linear hexapeptide was deblocked (Procedure 6) and cyclized with DPPA to yield, following purification by Method F (4:4:4:0.5 chloroform/hexane/methanol/water), a white solid: TLC $R_f=0.67$ (4:4:4:0.5 chloroform/hexane/methanol/water); HPLC (Method I): RT=11.23 minutes, >99% pure;

FAB MS: 720 (M$^+$+H), 742 (M$^+$+Na):

NMR (360 MHz, DMSO-d$_6$): consistent with structure.

Amino Acid analysis: Asp(1.02); Thr(0.98); Phe 2(1.01); Ile(0.97), Pro(1.02).

EXAMPLE 99 c-[D-(O-Ethyl)-tyrosyl-L-isoleucyl-D-(O-tert-butyl)-threonyl-L-asparagyl-D-phenylalanyl-L-prolyl]. The title cyclic hexapeptide was synthesized in a manner similar to Example 98 and using the amino acids, Boc-D-(O-ethyl)-Tyr, Fmoc-L-Ile, Fmoc-D-(O-tert-butyl)-Thr, Fmoc-L-Asn, Boc-D-Phe, and L-Pro-O-$^t$Bu. The crude product was purified by Method F (8:8:1.9:0.1 chloroform/hexane/methanol/water eluant); TLC, $R_f=0.68$ in 4:4:4:0.5, chloroform/hexane/methanol/- water; HPLC (Method I), single major peak (98.6% pure) at RT=13.53 minutes, FAB MS: 764 (M++H), 786 (M++Na); NMR (360 MHz, DMSO-d$_6$) consistent with structure; elemental analysis (for 1.80 moles methanol solvate): Calculated: C, 59.64, H, 7.39, N, 11.94. Found: C, 59.38, H, 7.40, N, 12.23.

EXAMPLE 100 c-[D-Phenylalanyl-L-isoleucyl-L-glutamyl-L-asparagyl-D-phenylalanyl-L-prolyl]

In a manner similar to Example 98, using the amino acids Boc-D-Phe, Fmoc-L-Ile, Fmoc-L-Gln, Fmoc-L-Asn, Boc-D-Phe, and L-Pro-O-'Bu ester, the title cyclic hexapeptide was synthesized as a white solid: TLC, R$_f$=0.63 in 4:4:4:0.5, chloroform/hexane/methanol/water; HPLC (Method I), single major peak (99.4% pure) at RT=10.97 minutes. FAB MS: 747 (M++H), 769 (M++Na); NMR (360 MHz, DMSO-d$_6$) consistent with structure; elemental analysis (for 0.25 moles trifluoroacetic acid): Calculated: C, 58.55, H, 6.45, N, 14.24. Found: C, 58.42, H, 6.33, N, 14.23.

EXAMPLE 101 c-[D-(O-Ethyl)-tyrosyl-D-isoleucyl-D-glutamyl-L-asparagyl-D-phenylalanyl-L-prolyl]

1. Boc-D-(O-Ethyl)-tyrosyl-(D,L)-isoleucyl-D-glutamyl-L-asparagyl-D-phenylalanyl-L-proline-tert-butyl ester. A solution of 336 mg (0.759 mmol) of Fmoc-D-(O-Ethyl)-Tyr-L-Ile-OH in 3 mL of methylene chloride was treated with 103 mg (0.759 mmol) of HBT and a small amount of DMF. To this solution was added 146 mg 0.759 mmol) of EDC and the solution was stirred in the cold for 2 hours. The mixture was filtered and concentrated to yield the hydroxybenzotriazole active ester. 460 mg (0.538 mmol) of Fmoc-D-Glu-L-Thr-L-Asn-D-Phe-L-Pro-O-tBu was N-deprotected (Procedure 6). The crude product was treated with a solution of the above active ester in 3 mL of DMF and the mixture was stirred for 2 hours, then the mixture was treated with 66 μL (0.60 mmol) of N-methyl morpholine and stirred for an additional 16 hours. The reaction mixture was then concentrated and the residue treated with ether, then with water, saturated NaHCO$_3$, water, and finally ether. The residual solid was recrystallized from isopropanol/ether to yield a pale yellow solid; TLC, two spots, R$_f$=0.33, 0.38 in 85:10:5 chloroform/methanol/acetic acid; NMR (300 MHz, CD$_3$OD) consistent with structure.

2. c-[D-(O-Ethyl)-tyrosyl-D-isoleucyl-D-glutamyl-L-asparagyl-D-phenylalanyl-L-prolyl]. From the linear hexapeptide the title cyclic hexapeptide was synthesized according to Example 98 to yield, following purification by Method F, (4:4:4:0.5 chloroform/hexane/methanol/water) a white solid: HPLC (Method I) single major peak (94.0% pure) at RT=14.00 minutes. FAB MS: 791 (M++H), 813 (M++Na); NMR (360 MHz, DMSO-d$_6$): consistent with structure; amino acid analysis: Asn, 0.98; Gln, 1.11; AlloIle, 0.93; Tyr, 0.95; Phe, 0.94; Pro, 0.69.

EXAMPLE 102 c-[D-Phenylalanyl-L-isoleucyl-D-glutamyl-L-asparagyl-D-penylalanyl-L-prolyl]

1. H-L-Ile-D-Gln-L-Asn-D-Phe-L-Pro-D-Phe-OMe. In a manner similar to Example 98 and using the amino acids Fmoc-L-Ile, Fmoc-D-Gln, Fmoc-L-Asn, Boc-D-Phe, Boc-L-Pro, and D-Phe-O-Me, the title compound was synthesized as a solid: TLC, R$_f$=0.59 in 4:1:1 butanol/acetic acid/water.

2. c-[D-Phenylalanyl-L-isoleucyl-D-glutamyl-L-asparagyl-D-phenylalaninyl-L-proyly]. A solution 90 mg (0.116 mmol) of the linear hexapeptide material was taken up in 300 mL of methanol and treated with 5.5 mg (0.13 mmol) of sodium hydroxide and 50 mL of water at 0° C. The mixture was stirred for 4 hours in the cold, then 0.13 mL of 1N HCl was added to bring the pH to ca. 6. The mixture was concentrated in vacuo to a white solid which was triturated with ethyl acetate and ether, then filtered and dried. Cyclization of this material according to Example 98 and purification by Method F using 35:18:2 methylene chloride/trifluoroethanol/water as eluant, gave a white solid: TLC, R$_f$=0.31 in 35:18:2 methylene chloride/trifluoroethanol/water; HPLC (Method I) single major peak (90.0% pure) at RT=12.32 minutes; FAB MS: 747 (M++H), 769 (M++Na); NMR (360 MHz, DMSO-d$_6$) consistent with structure; Elemental analysis (for 1.5 moles water): Calculated: C, 58.98, H, 6.90, N, 14.50. Found: C, 58.91, H, 6.72, N, 14.39.

EXAMPLE 103 c-[D-Phenylalanyl-L-isoleucyl-D-pipecolyl-L-pipecolyl-D-phenylalanyl-L-prolyl]

1. A 505 mg (1.43 mmol) sample of Fmoc-L-Pip was converted to its acid chloride (Procedure 1a). This compound was added to a solution of H-D-Phe-L-Pro-OBzl.HCl (576 mg, 1.58 mmol) in 15 mL of methylene chloride at 0° C., and the mixture was neutralized with 275 mL (1.58 mmol) of DIEA. The mixture was stirred for 16 hours at 0°-5° C., then washed in succession with water, 10% aqueous KHSO$_4$, water, saturated NaHCO$_3$, water, and brine. After drying over MgSO$_4$ and concentrating, the mixture was purified by Method E (25% acetone/hexanes) to yield 620 mg of a white solid: TLC, R$_f$=0.25 in 25% methanol/methylene chloride.

2. The above tripeptide was elaborated according to Example 96 using the amino acids Cbz-D-Phe, Fmoc-L-Ile, and Fmoc-D-Pip. The title cyclic hexapeptide was purified by Method F (6% methanol/methylene chloride eluent) to yield a white solid: TLC, R$_f$=0.37 in 6% methanol/methylene chloride; HPLC (Method I) 95.8% pure at RT=16.80 minutes; FAB MS: 727 (M++H), 749 (M++Na); NMR (360 MHz, DMSO-d$_6$) consistent with structure; elemental analysis (for 0.65 moles hexane and 0.6 moles water): Calculated: C, 67.94, H, 8.17, N, 10.59. Found: C, 67.81, H, 8.46, N, 10.42.

EXAMPLE 104 c-[D-Phenylalanyl-L-isoleucyl-D-pipecolyl-L-pipecolyl-D-N-methyl-phenylalanyl-L-prolyl]

In a manner similar to Example 103 the title cyclic hexapeptide was synthesized using the amino acids Cbz-D-Phe, Fmoc-L-Ile, Fmoc-D-Pip, Fmoc-L-Pip, Boc-N-Me-D-Phe, and L-Pro-benzyl ester. The crude product was purified by Method H and F (7.5% methanol/methylene chloride eluant) to yield a white solid: TLC, R$_f$=0.76 in 35% acetone/methylene chloride; HPLC (Method I) single major peak (93.8% pure) at RT=18.25 minutes, FAB MS: 741 (M++H), 763 (M++Na); NMR (400 MHz, DMSO-d$_6$) consistent with structure; Elemental analysis (for 0.5 moles acetone): Calculated: C, 67.85, H, 7.72, N, 10.91. Found: C, 67.85, H, 7.75, N, 10.85.

EXAMPLE 105 c-[D-Phenylalanyl-N-methyl-L-isoleucyl-D-pipecolyl-L-pipecolyl-N-methyl-D-phenylalanyl-L-prolyl]

Using the amino acids Cbz-D-Phe, Fmoc-L-MeIle, Fmoc-D-Pip, Fmoc-L-Pip, Boc-N-Me-D-Phe, and L-Pro-benzyl ester, the title cyclic hexapeptide was synthesized according to Example 103 and purified by Method F (7% methanol/methylene chloride) to give a solid: TLC, $R_f$=0.48 in 8% methanol/methylene chloride; HPLC, single major peak (98.4% pure) at RT=18.33 minutes (Method I); FAB MS: 755 (M++H), 777 (M++Na); NMR (400 MHz, DMSO-$d_6$) consistent with structure; Elemental analysis (for 0.30 moles methylene chloride); Calculated: C, 66.64, H, 7.57, N, 10.77. Found: C, 66.58, H, 7.53, N, 10.79.

EXAMPLE 106 c-[D-Phenylalanyl-L-(O-tert-butyl)-threonyl-D-pipecolyl-L-pipecolyl-D-N-methyl-phenylalanyl-L-prolyl]

Using the amino acids Cbz-D-Phe, Fmoc-L-(O-$^t$Bu)-Thr, Fmoc-D-Pip, Fmoc-L-Pip, Boc-N-Me-D-Phe, and L-Pro-benzyl ester, the title cyclic hexapeptide was synthesized and purified by Method F (7% methanol/methylene chloride) to give a solid: TLC $R_f$=0.55, 8:8:1.9:01 chloroform/hexane/methanol/water; HPLC (Method I) single major peak, 98.5% pure at RT=19.01 minutes; FAB MS: 785 (M++H), 807 (M++Na); NMR (400 MHz, DMSO-$d_6$) consistent with structure; Elemental analysis (for 0.4 moles methylene chloride): Calculated: C, 65.12, H, 7.48, N, 10.26. Found: C, 65.07, H, 7.31, N, 10.11.

EXAMPLE 107 c-[D-Phenylalanyl-L-isoleucyl-D-(N$^\delta$-Boc)-ornithyl-L-pipecolyl-N-methyl-D-phenylalanyl-L-prolyl]

Using the amino acids Cbz-D-Phe, Fmoc-L-Ile, Fmoc-D-(N$^\delta$-Boc)-Orn, Fmoc-L-Pip, Boc-N-Me-D-Phe, and L-Pro-benzyl ester, the title cyclic hexapeptide was synthesized according to Example 103 and purified by Method F (95:5:0.5 chloroform/methanol/water) to give a solid: TLC, $R_f$=0.40 in 95:5:0.5 chloroform/methanol/water; HPLC (Method J) single major peak 97.0% pure at RT=20.99 minutes; FAB MS: 844 (M++H); NMR (360 MHz, DMSO-$d_6$) consistent with structure; elemental analysis (for 0.8 moles water and 0.3 moles hexane): Calculated: C, 64.92, H, 8.07, N, 11.09. Found: C, 64.91, H, 7.98, N, 11.15.

EXAMPLE 108 c-[D-phenylalanyl-L-isoleucyl-D-pipecolyl-L-pipecolyl-N-methyl-D-phenylalanyl-L-pipecolyl]

1. Fmoc-L-isoleucyl-D-pipecolyl-L-pipecolyl-N-methyl-D-phenylalanyl-benzyl ester. In a manner similar to Example 103, using the amino acids Fmoc-L-Ile, Fmoc-D-Pip, Boc-L-Pip, and N-Me-D-Phe-benzyl-ester, the title tetrapeptide was obtained as a solid after purification (Method E) (24% acetone/hexane). TLC, $R_f$=0.40 in 30% acetone/hexane; HPLC (Method I) single major peak 95.2% pure at RT=24.70 minutes; FAB MS: 785 (M++H), 807 (M++Na); NMR (300 MHz, DMSO-$d_6$)consistent with structure; Elemental analysis (for 0.25 moles hexane): Calculated: C, 72.89, H, 7.31, N, 6.60. Found: C, 72.74, H, 7.51, N, 6.52.

2. Cbz-D-phenylalanyl-L-isoleucyl-D-pipecolyl-L-pipecolyl-N-methyl-D-phenylalanyl-benzyl ester. A sample of 687 mg (1.33 mmol) of L-Ile-D-Pip-L-Pip-N-Me-D-Phe-OH (from deprotection of the above tetrapeptide (Procedures 8 and 9) in 6 ml of methylene chloride was treated with 186 μL of trimethylsilyl chloride and stirred at ambient temperature for 30 minutes. The solution was treated with 244 μL of DIEA cooled in a −17° C. constant temperature bath. A solution of 479 mg (1.60 mmol) of Cbz-D-Phe and 176 μL of 4-methyl morpholine in 6 mL of ethyl acetate was cooled in a −17° C. constant temperature bath and treated with 208 μL of isobutyl chloroformate. After stirring for 2.5 minutes, this mixture was treated with the solution of the tetrapeptide trimethylsilyl ester by cannulation. The resulting mixture was stirred for 5 minutes in the cold, then removed from the cold bath and stirred for 15 minutes at ambient temperature. The reaction mixture was then diluted with 40 mL of ethyl acetate, partially concentrated to remove methylene chloride, and washed with water, 5:1 water/saturated NaHCO$_3$ solution, water, and finally with 10% KHSO$_4$. The residue was purified by Method E (methanol/methylene chloride) to yield a foam: TLC, $R_f$=0.18 in 7% methanol/methylene chloride.

3. c-[-D-Phenylalanyl-L-isoleucyl-D-pipecolyl-L-pipecolyl-N-methyl-D-phenylalanyl-L-pipecolyl]. According to Procedure 5, a 151 mg (0.19 mmol) sample of the above pentapeptide acid was condensed with L-pipecolic acid benzyl ester to yield Cbz-D-Phe-L-Ile-D-Pip-L-Pip-N-Me-D-Phe-L-Pip-benzyl ester. Elaboration of the hexapeptide according to Procedure 9 and Example 98 yielded the title cyclic hexapeptide as a solid after purification by Method F (methanol/methylene chloride). TLC, $R_f$=0.59 in 8:8:1.9:0.1 chloroform/hexane/methanol/water; HPLC (Method J) single major peak 98.3% pure at RT=21.34 minutes; FAB MS: 755 (M++H); NMR (400 MHz, DMSO-$d_6$) consistent with structure; Elemental analysis (for 0.25 moles methanol and 0.25 moles hexane): Calculated: C, 68.51, H, 8.03, N, 10.71; Found: C, 68.48, H, 8.00, N, 10.66.

EXAMPLE 109 c-[D-phenylalanyl-L-isoleucyl-D-pipecolyl-L-pipecolyl-N-methyl-D-phenylalanyl-N-methyl-L-alanyl]

In a manner similar to that described for Example 108 and using the amino acids Cbz-D-Phe, Fmoc-L-Ile, Fmoc-D-Pip, Boc-L-Pip, N-Me-D-Phe benzyl ester, and Me-L-Ala benzyl ester, the title cyclic hexapeptide was obtained as a solid after purification by Method F (95:5:0.5 chloroform/methanol/concentrated ammonium hydroxide). TLC, $R_f$=0.52 in 95:5:0.5 methylene chloride/methanol/concentrated ammonium hydroxide; HPLC (Method G), single major peak 95.1% pure at RT=8.72 minutes, FAB MS: 729 (M++H); NMR (400 MHz, DMSO-$d_6$) consistent with structure; Elemental analysis (for 1.40 moles water): Calculated: C, 65.30, H, 7.86, N, 11.14. Found: C, 65.27, H, 7.73, N, 11.44.

EXAMPLE 110 c-[D-Phenylalanyl-L-isoleucyl-D-prolyl-L-pipecolyl-N-methyl-D-phenylalanyl-L-prolyl]

In a manner similar to that described for Example 108 and using the amino acids Cbz-D-Phe, Fmoc-L-Ile, Fmoc-D-Pro, Fmoc-L-Pip, Boc-N-Me-D-Phe, and L-Pro-benzyl ester the title cyclic hexapeptide was obtained as a solid after purification by Method F (95:5:0.5 chloroform/methanol/water): TLC, $R_f$=0.55 in 95:5:0.5 chloroform/methanol/water; HPLC (Method J) single major peak (98.4% pure) at RT=21.17 minutes, FAB MS: 727 (M+ +H); NMR (400 MHz, DMSO-$d_6$) consistent with structure; Elemental analysis (for 0.1 moles chloroform): Calculated: C, 66.79, H, 7.38, N, 11.37. Found: C, 66.87, H, 7.45, N, 11.16.

EXAMPLE 111 c-[D-Phenylalanyl-L-isoleucyl-D-piperazyl-L-pipecolyl-N-methyl-D-phenylalanyl-L-prolyl]

In a manner similar to that described for Example 108 and using the amino acids Cbz-D-Phe, Fmoc-L-Ile, Fmoc-D-($N^\delta$-Cbz)-Piz, Fmoc-L-Pip, Boc-N-Me-D-Phe, and L-Pro-benzyl ester, the title cyclic hexapeptide was obtained as a solid after purification by Method F (95:5:0.5 chloroform/methanol/water) TLC, $R_f$=0.40 in 95:5:0.5 chloroform/methanol/water; HPLC (Method J) single major peak 97.0% pure at RT=28.19 minutes; FAB MS: 742 (M+ +Na); NMR (360 MHz, DMSO-$d_6$) consistent with structure; Elemental analysis (for 0.4 moles chloroform): Calculated: C, 62.97, H, 7.07, N, 12.42. Found: C, 63.08, H, 7.06, N, 12.47.

EXAMPLE 112 c-[D-Phenylalanyl-L-isoleucyl-D-$\Delta$-piperazyl-L-pipecolyl-N-methyl-D-phenylalanyl-L-prolyl]

A solution of 39 mg (0.053 mmol) of cyclo-[D-phenylalanyl-L-isoleucyl-D-piperazyl-L-pipecolyl-N-methyl-D-phenylalanyl-L-prolyl] in 0.5 mL of pyridine was cooled in an ice/water bath and to it was added, in one portion, 6.3 μL (0.053 mmol) of tert-butyl hypochlorite. The mixture was treated with additional portions of tert-butyl hypochlorite (48 μL total) during the next 4 hours. After stirring further for 1.5 hours in the cold, the volatiles were removed under a stream of argon and the residue taken up in $CH_2Cl_2$ and washed successively with water, 10% $KHSO_4$ solution, water, saturated $NaHCO_3$ solution, water, and brine. After drying over $MgSO_4$ and concentration in vacuo, the mixture was purified by Method F (95:5:0.5 chloroform/methanol/water) to yield the title compound as a solid; TLC, $R_f$=0.48 in 95:5:0.5 chloroform/methanol/water; HPLC (Method G) single major peak, (97.4% pure) at RT=10.67 minutes; FAB MS: 774 (M+ +Na); NMR (400 MHz, DMSO-$d_6$) consistent with structure; Elemental analysis (for 0.1 moles hexane and 0.2 moles methylene chloride): Calculated: C, 65.58, H, 7.22, N, 12.81. Found: C, 65.70, H, 7.02, N, 12.56.

EXAMPLE 113 c-[D-Phenylalanyl-L-isoleucyl-D-ornithyl-L-pipecolyl-N-methyl-D-phenylalanyl-L-prolyl]

A sample of 38 mg (0.045 mmol) of c-[D-phenylalanyl-L-isoleucyl-($N^\delta$-Boc)-ornithyl-L-pipecolyl-N-methyl-D-phenylalanyl-L-prolyl] was treated according to Procedure 7. The crude product was purified according to Method F (90:10:1.2 chloroform/methanol/concentrated ammonium hydroxide) to yield the title compound. TLC, $R_f$=0.33 in 90:10:1 chloroform/methanol/concentrated ammonium hydroxide; HPLC (Method J) single major peak 99.4% pure at RT=17.00 minutes; FAB MS: 744 (M+ +H), 766 (M+ +Na); NMR (360 MHz, DMSO-$d_6$) consistent with structure; Elemental analysis (for 0.5 moles ammonium hydroxide): Calculated: C, 64.67, H, 7.88, N, 13.80. Found: C, 64.55, H, 7.87, N, 14.06.

EXAMPLE 114 c-[D-Phenylalanyl-L-isoleucyl-D-prolyl-L-seryl-N-methyl-D-phenylalanyl-L-prolyl]

1. Fmoc-D-phenylalanyl-L-isoleucyl-D-prolyl-(O-$^t$Bu)-seryl-N-methyl-D-phenylalanyl-L-prolinebenzyl ester. A 1.32 g (1.80 mmol) sample of Fmoc-(D-tert-butyl)-Ser-N-Me-D-Phe-L-Pro-benzyl ester was N-deprotected according to Procedure 8. The crude product was taken up in 35 mL of acetonitrile and treated at ambient temperature with 1.04 g (1.80 mmol) of Fmoc-D-Phe-L-Ile-D-Pro-OH, and the two components were condensed with BOP as described in Procedure 3. Aqueous workup and purification via Method E, using 30% acetone/hexane as eluant, yielded a foam: TLC, $R_f$=0.72 in 50% acetone/hexane.

2. c-[D-Phenylalanyl-L-isoleucyl-D-prolyl-L-seryl-N-methyl-D-phenylalanyl-L-prolyl]. The above hexapeptide (1.58 g, 1.46 mmol) was deprotected as described in procedure 6 to yield Fmoc-D-Phe-L-Ile-D-Pro-L-Ser-N-Me-D-Phe-L-Pro-OBzl which was purified by Method E using a gradient of 35% to 55% acetone/hexane as eluant to yield a solid: TLC, $R_f$=0.53 in 50% acetone/hexane. In a manner similar to that described in Procedures 8 and 9, this linear hexapeptide was deprotected at its N and C termini and cyclized to yield the title compound which was purified by Method F (95:5:0.5 chloroform/methanol/water; TLC, $R_f$=0.22 in 95:5:0.5 chloroform/methanol/water; HPLC (Method I) single major peak, 97.8% pure at RT=14.39 minutes; FAB MS: 703 (M+ +H), 725 (M+ +Na); NMR (360 MHz, DMSO-$d_6$) consistent with structure; Elemental analysis (for 0.9 moles chloroform): Calculated: C, 57.66, H, 6.33, N, 10.37. Found: C, 57.82, H, 6.44, N, 10.45.

EXAMPLE 115 c-[D-Phenylalanyl-L-isoleucyl-D-pipecolyl(O-tert-butyl)-L-aspartyl-N-methyl-D-phenylalanyl-L-prolyl]

The title cyclic hexapeptide was synthesized in a manner similar to that described for Example 114 and using the amino acids Cbz-D-Phe, Fmoc-L-Ile, Fmoc-D-Pip, Fmoc-L-Asp-(O-$^t$Bu), Boc-N-Me-D-Phe, and L-Pro-benzyl ester. The crude product was purified by Method E (97.5:2.5:0.25 methylene chloride/methanol/concentrated ammonium hydroxide) followed by Method F (7% methanol/methylene chloride). TLC, $R_f$=0.57 in 95:5:0.5 chloroform/methanol/water; HPLC (Method I) single major peak, 94.7% pure at RT=20.30 minutes; FAB MS: 801 (M+ +H), 823 (M+ +Na); NMR (360 MHz, DMSO-$d_6$) consistent with structure; Elemental analysis (for 0.1 moles chloroform): Calculated: C, 65.98, H, 7.55, N, 10.49. Found: C, 65.95, H, 7.56, N, 10.32.

EXAMPLE 116 c-[D-Phenylalanyl-L-isoleucyl-D-pipecolyl-L-aspartyl-N-methyl-D-phenylalanyl-L-prolyl]

A 80 mg (0.010 mmol) sample of c-[D-phenylalanyl-L-isoleucyl-D-pipecolyl-(O-tert-butyl)-L-aspartyl-N-methyl-D-phenylalanyl-L-prolyl] was deprotected according to procedure 6. The product was purified by Method F using 90:10.1 methylene chloride/methanol/water as eluant, to yield the product as a solid: TLC R$_f$=0.20 in 92:8:0.8 chloroform/methanol/water; HPLC (Method I) major peak (90.4% pure) at RT=16.17 minutes; FAB MS: 745 (M++H), 767 (M++Na); NMR (400 MHz, DMSO-d$_6$) consistent with structure; Elemental analysis (for 0.5 moles water solvate): Calculated: C, 63.92, H, 7.09, N, 11.15. Found: C, 63.68, H, 7.02, N, 10.95.

EXAMPLE 117 c-[D-Phenylalanyl-L-isoleucyl-D-prolyl-dehydroalanyl-N-methyl-D-phenylalanyl-L-prolyl]

A solution of 100 mg (0.137 mmol) of c-[D-phenylalanyl-L-isoleucyl-D-prolyl-L-seryl-N-methyl-D-phenylalanyl-L-prolyl], 36 mg (0.14 mmol) of triphenylphosphine, and 20 mg (0.14 mmol) of phthalimide in 1.5 mL of THF was treated, during 1 minute, with 22 μL of diethylazodicarboxylate at ambient temperature. At 4.5 hours, the reaction was concentrated, and the residue was triturated with ether. The ether was decanted and concentrated to yield a white gum, which was purified by Method F using 95:5:0.5, chloroform/methanol/concentrated ammonium hydroxide as eluant. Further chromatographic purification, using 70:22.5:2.5, methylene chlorode/acetone/methanol gave the product as a solid: TLC, R$_f$=0.26 in 95:5:0.8 chloroform/methanol/water; HPLC (Method I), single major peak, 98.2% pure at RT=12.50 minutes; FAB MS: 685 (M++H), 707 (M++Na); NMR (400 MHz, DMSO-d$_6$) consistent with structure; Elemental analysis (for 0.5 moles water and 0.4 moles hexane: Calculated: C, 66.99, H, 7.65, N, 11.43. Found: C, 67.02, H, 7.58, N, 11.10.

EXAMPLE 118 c-[D-Phenylalanyl-L-isoleucyl-D-pipecolyl-L-asparagyl-N-methyl-D-phenylalanyl-L-prolyl]

A 15 mg (0.020 mmol) sample of c-[D-phenylalanyl-L-isoleucyl-D-pipecolyl-L-aspartyl-N-methyl-D-phenylalanyl-L-prolyl] in methylene chloride was condensed with 20 μL of concentrated ammonium hydroxide in the presence of EDC. The crude product, following aqueous workup, was purified by Method F using 8% methanol/methylene chloride as eluant, to yield the product (following lyophilization from acetonitrile/water) as a solid: TLC, R$_f$=0.37 in 95:5:0.5 methylene chloride/methanol/concentrated ammonium hydroxide; HPLC (Method L) single major peak, 94.2% pure at RT=8.94 minutes, FAB MS: 744 (M++H); NMR (300 MHz, DMSO-d$_6$) consistent with structure; elemental analysis (for 0.5 moles water): Calculated: C, 63.43, H, 7.25, N, 12.95. Found: C, 63.65, H, 7.15, N, 12.68.

EXAMPLE 119 c-[D-Phenylalanyl-L-isoleucyl-D-pipecolyl-N$^\beta$-(aminoethyl)-L-asparagyl-N-methyl-D-phenylalanyl-L-prolyl]

A 42 mg (0.052 mmol) sample of c-[D-phenylalanyl-L-isoleucyl-D-pipecolyl-L-aspartyl-N-methyl-D-phenylalanyl-L-prolyl] in methylene chloride was condensed, with 35 μL of ethylene diamine in the presence of EDC. The reaction was concentrated after 19 hours and the residue was purified by Method F using 4:4:4:0.5 chloroform/hexane/methanol/water as eluant. The resulting product was further purified by Method M to give a solid: TLC, R$_f$=0.48 in 4:4:4:0.5 chloroform/hexane/methanol/water; HPLC (Method I) single major peak (99%) at RT=17.27 minutes; FAB MS: 787 (M++H); NMR (400 MHz, DMSO-d$_6$) consistent with structure; Elemental analysis (for 1 mole water and 1.25 moles TFA): Calculated: C, 56.09, H, 6.52, N, 11.83. Found: C, 55.02, H, 6.36, N, 11.78.

EXAMPLE 120 c-[D-Phenylalanyl-L-isoleucyl-D-pipecolyl-N$^\beta$-(imidazolylethyl)-L-asparagyl-N-methyl-D-phenylalanyl-L-prolyl]

A 50 mg (0.062 mmol) sample of c-[D-phenylalanyl-L-isoleucyl-D-pipecolyl-L-aspartyl-N-methyl-D-phenylalanyl-L-prolyl] was condensed in methylene chloride with 35 mg of histamine in the presence of EDC and HBT. Following aqueous workup, the crude product was purified by Method F using 90:10:1 methylene chloride/methanol/concentrated ammonium hydroxide. The resulting product was further purified by Method M to yield a solid: TLC, R$_f$=0.45 in 2:2:2:0.1 chloroform/hexane/methanol/water; HPLC (Method I) single major peak 99.4% pure at RT=12.94 minutes; FAB MS: 838 (M++Na); NMR (400 MHz, DMSO-d$_6$) consistent with structure; Elemental analysis (for 1.5 mole water and 2.0 moles TFA): Calculated: C, 53.84, H, 5.90, N, 11.53. Found: C, 53.50, H, 5.71, N, 11.53.

EXAMPLE 121 c-[D-Phenylalanyl-L-isoleucyl-D-pipecolyl-L-2,3-diaminopropionyl-N-methyl-D-phenylalanyl-L-prolyl]

A suspension of 40 mg (0.054 mmol) of c-[D-phenylalanyl-L-isoleucyl-D-pipecolyl-L-asparagyl-N-methyl-D-phenylalanyl-L-prolyl] and 35 mg (0.81 mmol) of bis(trifluoroacetyl)iodobenzene in 1.5 mL of 33% aqueous DMF was treated with 4.3 μL of pyridine, and the mixture was stirred for 16 hours at ambient temperature. The mixture was concentrated in vacuo to a colorless glass, which was purified by Method F using 2:2:1:0.1 chloroform/hexane/methanol/water as eluant, to yield the product as a solid: TLC Rf=0.37 in 2:2:1:0.1 chloroform/hexane/methanol/water; HPLC (Method I) single major peak, 99.7% pure at RT=21.19 minutes; FAB MS: 716 (M++H), 860 (M++Na); NMR (400 MHz, DMSO-d$_6$) consistent with structure; Elemental analysis (for 0.4 moles chloroform and 0.25 moles hexane): Calculated: C, 62.56, H, 7.39, N, 12.49. Found: C, 62.31, H, 7.12, N, 12.69.

EXAMPLE 122 c-[(O-Ethyl)-D-tyrosyl-L-isoleucyl-D-pipecolyl-L-pipecolyl-N-methyl-D-phenylalanyl-L-prolyl]

Using the amino acids Boc-(O-ethyl)-D-Tyr, Fmoc-L-Ile, Fmoc-D-Pip, Fmoc-L-Pip, Boc-N-Me-D-Phe, and L-Pro benzyl ester, the hexapeptide Boc-(O-ethyl)-D-tyrosyl-L-isoleucyl-D-pipecolyl-L-pipecolyl-N-methyl-D-phenylalanyl-L-proline benzyl ester was synthesized according to Example 105. The crude product was purified by Method E (25% acetone/hexane eluant) to give a solid. Following deprotection according to procedures 7 and 10 the linear hexapeptide was cyclized according to Example 96 to give the title cyclic hexapeptide as a solid after two purifications by Method F (95:5:0.5 methylene chloride/methanol/water), followed by repurification using 7.5% methanol/methylene chloride: TLC, R$_f$=0.48 in 7.5% methanol/methylene chloride; HPLC (Method I) 93.8% pure at RT=14.47 minutes. NMR (400 MHz, DMSO-d$_6$) consistent with structure; Elemental analysis: Calculated:

C, 67.32, H, 7.70, N, 10.71. Found: C, 67.62, H, 7.87, N, 10.40.

EXAMPLE 123 c-[D-Phenylalanyl-L-isoleucyl-D-pipecolyl-L-pipecolyl-N-allyl-D-phenylalanyl-L-prolyl]

1. Boc-D-pipecolyl-L-pipecolyl-D-phenylalanyl-L-prolyl-benzyl ester. In a manner similar to that described in Example 122 and using the amino acids Boc-D-Pip, Fmoc-Pip, Boc-D-Phe, and L-Pro-benzyl ester, the title tetrapeptide was synthesized. Purification by Method E (26% acetone/hexanes eluant) gave a foamy solid: TLC, $R_f$=0.24 in 25% acetone/hexane.

2. Boc-D-pipecolyl-L-pipecolyl-N-allyl-D-phenylalanyl-L-prolyl-benzyl ester. A solution of 382 mg (0.566 mmol) of the above tetrapeptide was taken up in 1.5 mL of DMF, treated with 1.5 mL (17.2 mmol) of allyl bromide, and cooled in an ice/water bath. To this solution was added 54 mg of 60% NaH/mineral oil dispersion (1.4 mmol), resulting in formation of a precipitate. The mixture was stirred in the cold for 45 minutes, then 300 μL acetic acid was added to quench the reaction. The mixture was concentrated in vacuo, partitioned between water and ether, and the organics were separated and washed successively with water, saturated NaHCO₃, water, and brine. After drying over MgSO₄ and concentration in vacuo, an oil was obtained which was purified by Method E (20% acetone/hexanes eluant): TLC, $R_f$=0.44 in 30% acetone/hexane.

3. c-[D-Phenylalanyl-L-isoleucyl-D-pipecolyl-L-pipecolyl-N-allyl-D-phenylalanyl-L-prolyl]. Following N-terminal deprotection by Procedure 7, the N-allylated tetrapeptide was coupled sequentially with Fmoc-Ile and Fmoc-D-Phe as described in Example 96 to yield the linear, fully protected hexapeptide. Removal of the N-terminal by Procedure 8 gave a crude residue which was taken up in acetonitrile (15 mL) and washed with 4×30 mL of hexane. The acetonitrile layer was separated and concentrated to yield an oil. This oil was taken up in 0.17 mL of methanol and cooled in an ice bath. The resulting solution was treated with 0.21 mL of 1N NaOH (0.21 mmol) during which time a viscous second phase formed. The cold bath was removed and more methanol (0.15 mL in several portions) was added to give a readily stirred suspension. At 2 hours, an additional 40 μL of 1N NaOH was added. After an additional 2.5 hours, the reaction mixture was treated with 0.25 mL of 1N HCl and concentrated. The residue was suspended in acetonitrile and again concentrated (2×) and the residue was dried in vacuo. Cyclization of this crude mixture was carried out according to Example 96 with DPPA. Purification by Method A and Method F (8:8:1.9:0.1 chloroform/hexane/methanol/water) gave a solid: TLC, $R_f$=0.46, 8:8:1.9:0.1 chloroform/hexane/methanol/water; HPLC (Method I) 96.0% pure at RT=18.54 minutes, FAB MS: 767 (M++H), 807 (M++Na); NMR (400 MHz, CDCl₃) consistent with structure; Elemental analysis (for 0.25 moles hexane): Calculated: C, 69.30, H, 7.81, N, 10.66. Found: C, 69.48, H, 7.85, N, 10.49.

EXAMPLE 124 c-[D-Phenylalanyl-L-isoleucyl-D-Δ-piperazyl(N$^δ$-Boc)-L-orinthyl-N-methyl-D-δ-phenyl-alaninyl-L-prolyl]

1. Fmoc-L-isoleucyl-N$^γ$-piperazic acid. A suspension of 1.55 g (5.86 mmol) of (N$^γ$-Cbz)-D-piperazic acid in 30 mL of CH₂Cl₂ was treated with 0.82 mL (6.45 mmol) of trimethylsilyl chloride and the mixture stirred for 30 minutes at ambient temperature. The resulting clear, colorless solution was cooled in ice/water and treated with 3.05 mL (14.0 mmol) of DIEA in one portion. After several minutes, a solution of Fmoc-L-Ile acid chloride (freshly prepared from 2.69 g (7.62 mmol) of Fmoc-L-Ile as described in procedure 1a) in 10 mL of CH₂Cl₂, precooled in ice/water, was added via cannula. The flask and needle were washed with another 5 mL of CH₂Cl₂, and the resulting mixture was stirred in the cold. After stirring for 1.5 hours, the mixture was quenched by addition of ca. 5 mL of dry MeOH. The mixture was stirred for 10 minutes and then was neutralized by addition of DIEA to pH >7. The reaction mixture was evaporated, and the residue partitioned between ether and 1N HCl. The ether layer was treated with ½ volume of hexane and extracted with 5% NaHCO₃ solution until no more oily product was observed. The aqueous layers were combined and made acidic with 6N HCl to pH @1 and extracted with 3 portions of ether. These organic extracts were washed with water and brine, dried over MgSO₄, and concentrated to yield the title dipeptide as a foam: TLC, $R_f$=0.53, 2:2:1:0.1 chloroform/hexane/methanol/water; NMR (300 MHz, CDCl₃) consistent with structure.

2. Fmoc-L-isoleucyl-D-piperazic acid. A solution of 22.07 g (36.8 mmol) of the above dipeptide was taken up in 75 mL of 95% aqueous ethanol, treated with 2.0 g of 10% Pd/C and hydrogenated in a Parr shaker for 11 hours. The reaction mixture was filtered, concentrated, and the residue purified by Method E using a gradient from 8:8:1.9:0.1 to 2:2:1:0.1, chloroform/hexane/methanol/water. The desired product was obtained as a foamy solid: TLC, $R_f$=0.39, 2:2:1:0.1 chloroform/hexane/methanol/water; NMR (400 MHz, CDCl₃) consistent with structure.

3. Fmoc-L-isoleucyl-D-Δ-piperazic acid. A solution of 2.64 g (5.67 mmol) of Fmoc-L-Ile-D-Piz-OH in 20 mL of methylene chloride was treated with 0.69 mL (8.51 mmol) of pyridine followed by 0.79 mL (6.24 mmol) of trimethylsilyl chloride. The mixture was stirred for 25 minutes at ambient temperature, then the mixture was cooled in a CCl₄/CO₂ bath (−24° C.) and 2.06 mL (25.3 mmol) of pyridine was added, followed by 0.87 mL (7.3 mmol) of tert-butyl hypochlorite in two portions. The mixture was stirred for 1 hour in the cold, then was poured into 50 mL of ether and washed with 5% aqueous citric acid (4×), water, and brine. After drying and concentrating, the crude product was taken up in 15 mL of methylene chloride and added dropwise, during 20 minutes, to a well-stirred mixture of 3 g of sodium iodide, 5 g of sodium thiosulfate, and 0.25 g of tetrabutylammonium iodide dissolved in 20 mL of water/methylene chloride (1:1). After addition was complete the mixture was stirred for 1 hour at ambient temperature and poured into 50 mL of ether. The layers were separated. The organic layer was washed successively with water, 5% aqueous sodium thiosulfate, water, and brine, then dried (MgSO₄) and concentrated to a foam. This material was purified by Method E using 70:30:1, toluene/ethyl acetate/formic acid as eluant, to yield the title compound as a solid: TLC, $R_f$=0.23, 70:30:1, toluene/ethyl acetate/formic acid; NMR (400 MHz, DMSO-d₆) consistent with structure.

4. Fmoc-L-isoleucyl-D-Δ-piperazyl-(N$^δ$-Boc)-L-ornithyl-N-methyl-D-phenylalanyl-proline benzyl ester. From the amino acid derivatives Fmoc-(N$^δ$-Boc)-

L-Orn, Boc-N-Me-D-Phe, and L-Pro-OBzl, the tripeptide Fmoc-(N$^\delta$-Boc)-L-Orn-N-D-Phe-L-Pro-OBzl was synthesized in a fashion similar to Example 103 and purified by Method E (30% acetone/hexane). 1.76 g (2.20 mmol) of this tripeptide was N$^\alpha$-deprotected according to Procedure 8 and the crude product was condensed with 1.02 g (2.20 mmol) of Fmoc-L-Ile-D-Δ-Piz-OH using BOP as the coupling reagent (Procedure 3). The crude product, after aqueous workup, was purified by Method E using a gradient of 0 to 4% methanol/ethylene chloride as eluant. The product was obtained as foam: TLC, $R_f$=0.22, 0.27 in 5% methanol/methylene chloride.

5. D-phenylalanyl-L-isoleucyl-D-Δ-piperazyl-(N$^\delta$-Boc)-L-ornithyl-N-methyl-D-phenylalanyl-L-proline benzyl ester. The above pentapeptide (2.06 g, 1.98 mmol) was N$^\alpha$-deprotected according to Procedure 8 and the crude product was condensed with 919 mg (2.37 mmol) of Fmoc-D-Phe using BOP as the coupling reagent. The crude product ($R_f$=0.38, 0.42 in 7.5% methanol/methylene chloride) was again N$^\alpha$-deprotected (Procedure 8) and the resulting material was purified by Method E eluting with a gradient of 0 to 6% methanol/methylene chloride, to obtain a solid; NMR (300 MHz, CDCl$_3$) consistent with structure.

6. c-[D-Phenylalanyl-L-isoleucyl-D-Δ-piperazyl-(N$^\delta$-Boc)-L-ornithyl-N-methyl-D-phenylalanyl-L-prolyl]. A solution of above linear hexapeptide (1.73 g, 1.80 mmol) in 2.3 mL of methanol was treated with 1.0 mL of anhydrous hydrazine and the mixture was allowed to stand for 2 hours at ambient temperature. The mixture was treated with 2 mL of water, and the volatiles were removed in vacuo. The residue was taken up in 50% aqueous methanol, concentrated, and residue again concentrated from n-butanol. This material was partitioned between n-butanol and water, and the organic layer was washed with another two portions of water. Concentration of the n-butanol layer yielded an off-white foam which was used directly for the subsequent reaction. Cyclization of this material, following the Procedure of Example 1, Step 8 was carried out to yield the crude title cyclic hexapeptide which was purified by Method E using a gradient of 0 to 6% methanol/methylene chloride as eluant: TLC, $R_f$=0.19, 95:5:0.5 chloroform/methanol/water; HPLC (Method I) 98.9% pure at RT=19.22 minutes; FAB MS: 843 (M$^+$+H), 849 (M$^+$+Li), 865 (M$^+$+Na); NMR (360 MHz, DMSO-d$_6$) consistent with structure; Elemental analysis (for 0.25 moles hexane): Calculated: C, 64.60, H, 7.64, N, 12.96. Found: C, 64.57, H, 7.62, N, 12.93.

EXAMPLE 125 c-[D-Phenylalanyl-L-isoleucyl-D-Δ-piperazyl-L-ornithyl-D-(N-methyl)phenylalanyl-L-prolyl] acetate salt A 584 mg (0.693 mmol) sample of c-[D-phenylalanyl-L-isoleucyl-D-Δ-piperazyl(N$^\delta$-Boc)-L-ornithyl-N-methyl-D-phenylalanyl-L-prolyl] was N-deprotected (Procedure 7). The resulting crude product was purified first by Method E (gradient from neat methylene chloride to (2:2:2:0.1 methylene chloride/hexane/methanol/concentrated ammonium hydroxide)) and then by Method F (6% methanol/methylene chloride) to yield the free base of title compound. This material was taken up in 10% aqueous acetic acid, filtered, and the filtrate was lyophilized. The residue was relyophilized from aquous acetonitrile to yield the title compound as a solid: TLC, $R_f$=0.14, 90:10:1 chloroform/methanol/concentrated ammonium hydroxide; HPLC (Method I) 98.2% pure at RT=13.12 minutes. FAB MS: 743 (M$^+$+H), 765 (M$^+$+Na); NMR (360 MHz, DMSO-d$_6$) consistent with structure; elemental analysis (for 1.25 moles acetic acid and 2.0 moles water): Calculated: C, 59.77, H, 7.44, N, 13.12. Found: C, 59.69, H, 7.06, N, 13.30.

EXAMPLE 126 c-[D-Tryptophanyl-L-isoleucyl-D-Δ-piperazyl (N$^\delta$-Boc)-L-ornithyl-N-methyl-D-phenylalanyl-L-prolyl]

Using the amino acids Fmoc-D-Trp, Fmoc-(N$^\delta$-Boc)-L-Orn, Boc-N-Me-D-Phe, L-Pro-benzyl ester, and the dipeptide Fmoc-L-Ile-D-Δ-Piz-OH, the title cyclic hexapeptide was synthesized according to Example 124. The title compound was purified by Method F (10% methanol/methylene chloride): TLC, $R_f$=0.43 in 7.5% methanol/methylene chloride; HPLC (Method L) single major peak, 95.6% pure at RT=12.21 minutes; FAB MS: 882 (M$^+$+Na); NMR (300 MHz, CDCl$_3$) consistent with structure; Elemental analysis (for 0.4 moles chloroform): Calculated: C, 63.07, H, 7.39, N, 13.79. Found: C, 63.30, H, 7.37, N, 13.66.

EXAMPLE 127 c-[D-Tryptophanyl-L-isoleucyl-D-Δ-piperazyl-L-ornithyl-N-methyl-D-phenylalanyl L-prolyl]

A 194 mg (0.220 mmol) sample of c-[D-Trp-L-Ile-D-Δ-Piz-(N$^\delta$-Boc)-L-Orn-N-Me-D-Phe] was N-deprotected as described in Procedure 7. The resulting crude product was purified by Method F (85:15:1.5 chloroform/methanol/concentrated ammonium hydroxide) to yield the title compound as a solid: TLC, Rf=0.57, 80:20:2 methylene chloride/methanol/concentrated ammonium hydroxide; HPLC (Method L) single major peak, 94.8% pure at RT=9.23 minutes; NMR (300 MHz, DMSO-d$_6$) consistent with structure; Elemental analysis (for 1.0 moles chloroform and 1.5 moles water): Calculated: C, 55.63, H, 6.41, N, 13.58. Found: C, 55.55, H, 6.08, N, 13.62.

EXAMPLE 128 c-[D-Tryptophanyl-L-isoleucyl-D-piperazyl(N$^\delta$-Boc)-L-or nithyl-D-histidyl-L-prolyl]

Fmoc-L-isoleucyl-(N$^\gamma$-Cbz)-D-piperazyl(N$^\delta$-Boc)-L-ornithyl-D-N$^{im}$-DNP)-histidyl proline benzyl ester. In a manner similar to that described for Example 124 and using the amino acids Fmoc-D-Trp, Fmoc-Ile, Fmoc-D-(N$^\gamma$-Cbz)-piperazic acid, Fmoc-(N$^\delta$-Boc)-L-Orn, Boc-D-(N$^{im}$-DNP)-His, and L-Pro-benzyl ester, the title pentapeptide was synthesized as a mixture which was used without purification for subsequent steps: TLC, $R_f$=0.40, 0.29 (lower spot lacking His protection) in 7.5% methanol/methylene chloride.

Cbz-D-tryptophanyl-L-isoleucyl-(N$^\gamma$-Cbz)-D-piperazyl-(N$^\delta$-Boc)-L-ornithyl-D-histidyl-L-proline benzyl ester. A solution of 1.14 (0.851 mmol) of the above pentapeptide was N-deprotected (Procedure 8). A 557 mg (0.50 mmol) sample of the N-deprotected pentapeptide was coupled with 211 mg (0.625 mmol) of Cbz-D-Trp in the presence of BOP (Procedure 3). The crude product from this reaction was taken up in 2.25 mL of DMF and treated with 0.25 mL of thiophenol and 2 drops of triethylamine, and the mixture was stirred for 45 minutes at ambient temperature. Following removal of volatiles, the product was purified by Method E, eluting with a gradient from 0 to 11% methanol in methylene chloride, to yield a solid: TLC, $R_f$=0.39 in 7.5% methanol/methylene chloride.

c-[D-tryptophanyl-L-isoleucyl-D-piperazyl-($N^\delta$-Boc)-L-ornithyl-D-histidyl-L-prolyl]. Following Procedure 9 the above linear hexapeptide was deprotected and cyclized according to Example 96 with DPPA to give the title cyclic hexapeptide. Purification via Method F (4:4:4:0.5, CHCl$_3$/MeOH/hexane/H$_2$O) yielded the product as a solid: TLC, $R_f$=0.18 (4:4:4:0.5 CHCl$_3$/MeOH/hexane/H$_2$O; HPLC (Method L) single major peak 92.18% pure at RT=8.60 minutes; FAB MS: 882 (M++Na), 904 (M++2 Na); NMR (300 MHz, DMSO-d$_6$) consistent with structure; Elemental analysis (for 1.0 mole chloroform (1.0 mole water and 2.0 moles methanol): Calculated: C, 52.04, H, 6.83, N, 14.51. Found: C, 51.75, H, 6.48, N, 14.63.

EXAMPLE 129 c-[D-Tryptophanyl-L-isoleucyl-D-pipecolyl-($N^\delta$-Boc)-L-ornithyl-D-histidyl-L-prolyl] acetate salt Cbz-D-tryptophanyl-L-isoleucyl-D-pipecolyl-($N^\delta$-Boc)-L-ornithyl-D-histidyl-L-proline benzyl ester. Using the amino acids Fmoc-L-Ile, Fmoc-D-Pip, Fmoc-($N^\delta$-Boc)-L-Orn, Boc-D-($N^{im}$)-His, and L-proline benzyl ester, the pentapeptide Fmoc-L-Ile-D-Pip-($N^\delta$-Boc)-L-Orn-D-($N^{im}$-DNP) His-L-Pro-benzyl ester was synthesized in a fashion similar to that described in Example 96. Simultaneous removal of the Fmoc and $N^{im}$-DNP groups was carried out by dissolving an 814 mg (0.696 mmol) sample of the pentapeptide in 10 mL of DMF and treating the solution with 10 mL of piperidine for 1 hour at ambient temperature. The crude material obtained on removal of volatile components in vacuo was coupled with Cbz-D-Trp according to Procedure 3 to yield the title linear hexapeptide which was purified by Method E (0 to 10% methanol/methylene chloride gradient elution): TLC, $R_f$=0.77 in 4:4:4:0.5, CHCl$_3$/MeOH/hexane H$_2$O.

c-[D-Tryptophanyl-L-isoleucyl-D-pipecolyl-($N^\delta$-Boc)-L-ornithyl-D-histidyl-L-prolyl] acetate salt. Starting from the above linear hexapeptide, the title compound was synthesized in a fashion similar to Example 103. Purification via Methods A and F (4:4:4:0.5, CHCl$_3$/MeOH/benzene/H$_2$O) was followed by further purification by Method E using a gradient from neat methylene chloride to 80:20:2 methylene chloride/methanol/acetic acid to give the product as a solid: TLC, $R_f$=0.74 in 3:2:1, CHCl$_3$/MeOH/aqueous acetic acid; HPLC (Method L) single major peak, 92.2% pure at RT=9.31 minutes; FAB MS: 859 (M++H), 881 (M++Na); NMR (300 MHz, DMSO-d$_6$) consistent with structure; elemental analysis (for 0.1 mole chloroform, 0.5 mole water, and 2.5 moles acetic acid): Calculated: C, 57.25, H, 7.15, N, 13.60. Found: C, 57.15, H, 6.92, N, 13.33.

EXAMPLE 130 c-[D-Tryptophanyl-L-isoleucyl-D-piperazyl-L-ornithyl-D-histidyl-L-prolyl]trifluoroacetate A 162 mg (0.157 mmol) sample of c-[D-tryptophanyl-L-isoleucyl-D-piperazyl-($N^\delta$-Boc)-L-ornithyl-D-histidyl-L-prolyl] was N-deprotected (Procedure 7). The resulting crude product was purified by Method M to yield the title compound as a solid after lyophilization and relyophilization from aqueous dioxane: TLC, $R_f$=0.38, 3:2:1 chloroform/methanol/37% aqueous acetic acid; HPLC (Method L) single major peak, 95.6% pure at RT=7.44 minutes; FAB MS: 758 (M++H), 781 (M++Na); NMR (400 MHz, DMSO-d$_6$) consistent with structure; Elemental analysis (for 1.0 moles dioxane and 2.5 moles trifluoroacetic acid): Calculated: C, 50.92, H, 5.79, N, 12.37. Found: C, 50.68, H, 5.57, N, 12.28.

EXAMPLE 131 c-[D-phenylalanyl-L-isoleucyl-D-$\Delta$-piperazyl-L-arginyl-D-(N$\alpha$-methyl)-phenylalanyl-L-prolyl]trifluoroacetate salt An 83 mg (0.11 mmol) sample of c-[D-phenylalanyl-L-isoleucyl-D-$\Delta$-piperazyl-L-ornithyl-N-methyl-D-phenylalanyl-L-prolyl] was taken up in 1 mL of DMF and treated with 134 mg (0.67 mmol) of 3,5dimethylpyrazole-1-carboxamidine nitrate. The mixture was stirred for 1 hour at 55° C. then concentrated and the residue was partitioned between 0.1N sodium hydroxide solution and chloroform. Extraction of the aqueous phase with chloroform (2x), concentration of the organic layers and redissolution of the residue in 1 mL of DMF was followed by further treatment with 134 mg of 3,5-dimethylpyrazole-1-carboxamidine nitrate. The reaction mixture was then heated for another hour. Workup as before yielded the crude product as a viscous oil. This material was purified by Method M and lyophilized to yield a solid: HPLC (Method I) single major peak, 93.2% pure) at RT=12.94 minutes; FAB MS: 785 (M++H); NMR (300 MHz, DMSO-d$_6$) consistent with structure; Elemental analysis (for 1.0 moles water and 1.5 moles trifluoroacetic acid): Calculated: C, 53.64, H, 6.16, N, 14.38. Found: C, 53.86, H, 6.01, N, 14.41.

EXAMPLE 132 c-[D-Tryptophanyl-L-isoleucyl-D-pipecolyl-L-lysyl-D-(N-methyl)phenylalanyl-L-prolyl]

c-[D-Trp-L-Ile-D-Pip-L-(Cbz)Lys-D-N-MePhe-L-Pro] (200 mg, 0.21 mmoles) was dissolved in 10 ml of a 4% acetic acid in ethanol solution and 40 mg of catalyst (10% Palladium on carbon) was added. The reaction mixture was flushed with argon and then hydrogenated at atmospheric pressure for 15 hours. The reaction mixture was flushed with argon, filtered through celite and concentrated under reduced pressure. Lyophilization from dioxane afford 103 mg (48%) of the title compound as a white powder.

HPLC(Method G) RT=7.80 min; purity 99%.
NMR (CD$_3$OD) in agreement with title compound.
FAB MS: 796 (M++H).
Elemental Analysis for $C_{44}H_{60}N_8O_6$·2C$_2$HF$_3$O$_2$: Calculated: N, 10.94; C, 56.25; H, 6.05. Found: N, 11.31; C, 56.18; H, 6.41.

EXAMPLE 133 c-[D-Tryptophanyl-L-homophenylalanyl-D-pipecolyl-L-pipecolyl-D-(N-methyl)phenylalanyl-prolyl]

c-[D-Trp-L-HomoPhe-D-Pip-L-Pip-D-(NMe)Phe-L-Pro] was prepared from Boc-L-Pro-O-(PAM)-resin (1 mmole) according to the solid phase procedure set forth above for Example 1 with the following exceptions: Fmoc-L-HomoPhe (802 mg, 2 mmol) was used in place of the Fmoc-L-Ile in Step 4. Due to insolubility of the Fmoc-D-Trp in CH$_2$Cl$_2$, an active ester coupling was used in Step 5. The Fmoc-D-Trp (852 mg, 2 mmole) was dissolved in DMF at ambient temperature and added to the resin. Bop reagent (884 mg, 2 mmole) was added as a solid and the reaction was brought to pH 8 with the addition of DIEA (0.35 ml, 2 mmole). After shaking for 15 hours, the resin was washed. The resin was cleaved with hydrazine and the hexapeptide hydrazide was cyclized as the acyl azide. Workup and purification using Method A gave a homogeneous product which was lyophilized from dioxane to give 520 mg (63%) of the title compound.

HPLC (Method G): RT=11.26 min. 99% pure.
NMR (CDCl$_3$) in agreement with the title compound.
FAB MS: 828 (M+ +H).
Elemental Analysis for $C_{48}H_{57}N_7O_6 \cdot H_2O$: Calculated: N, 11.34; C, 66.67; H, 7.06. Found: N, 11.29; C, 66.96; H, 6.56.

EXAMPLE 134 c-[D-Tryptophanyl-L-phenylalanyl-D-pipecolyl-L-pipecolyl-D-(N-methyl)phenylalanyl-prolyl]

c-[D-Trp-L-Phe-D-Pip-L-Pip-D-(NMe)Phe-L-Pro] was prepared from Boc-L-Pro-O-(PAM)-resin (1 mmole) according to the solid phase procedure set forth above for Example 1 with the following exceptions: Fmoc-L-Phe (774 mg, 2 mmol) was used in place of the Fmoc-L-Ile in Step 4. Due to insolubility of the Fmoc-D-Trp in $CH_2Cl_2$ an active ester coupling was used in Step 5. The Fmoc-D-Trp (852 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The resin was cleaved with hydrazine and the hexapeptide hydrazide was cyclized as the acyl azide. Workup and purification using Method A gave a homogeneous product which was lyophilized from dioxane to give 611 mg (75%) of the title compound.

HPLC (Method G) RT=11.09 min.: purity 99%.
NMR (CDCl$_3$) in agreement with title compound.
FAB MS: 814 (M+ +H).
Analysis for $C_{47}H_{55}N_7O_6 \cdot 0.25$Dioxane$\cdot 2.5H_2O$: Calculated: N, 11.13; C, 65.44; H, 7.09. Found: N, 11.20; C, 65.54; H, 6.53.

EXAMPLE 135 c-[D-Phenylalanyl-L-homophenylalanyl-D-pipecolyl-L-pipecolyl-D-(N-methyl)phenylalanyl-L-prolyl]

c-[D-HomoPhe-L-Phe-D-Pip-L-Pip-D-(N-Me)Phe-L-Pro] was prepared from Boc-L-Pro-O-(PAM)-resin (1 mmole) according to the solid phase procedure set forth above for Example 1 with the following exceptions: FMOC-L-HomoPhe (802 mg, 2 mmol) was used in place of the Fmoc-L-Ile in Step 4. The final resin was cleved with hydrazine and the hexapeptide hydrazide was cyclized as the acyl azide. Workup and purification (Method A) gave 340 mg (43%) of the title compound.

HPLC(Method G) RT=11.60 min.: purity 95%.
NMR (CDCl$_3$) in agreement with title compound.
FAB MS: 789 (M+ +H).
Analysis for $C_{46}H_{56}N_6O_6 \cdot 1H_2O$: Calculated: N, 10.41; C, 68.47; H, 7.24. Found: N, 10.52; C, 68.37; H, 6.96.

EXAMPLE 136 c-[D-Phenylalanyl-L-phenylalanyl-D-pipecolyl-L-pipecolyl-D-(N-methyl)phenylalanyl-L-prolyl]

C-[D-Phe-L-Phe-D-Pip-L-Pip-N-Me-D-Phe-L-Pro] was prepared from Boc-L-Pro-O-(PAM)-resin (1 mmole) according to the solid phase procedure set forth above for Example 1 with the following exception: FMOC-L-Phe(774 mg, 2 mmol) was used in place of the Fmoc-L-Ile in Step 4. The final resin was cleaved with hydrazine and the hexapeptide hydrazide was cyclized as the acyl azide. Workup and purification (Method A) gave 348 mg (45%) of the title compound.

HPCL (Method G) RT=11.18 min.: purity 95%.
NMR (CDCl$_3$) in agreement with title compound.
FAB MS: 775 (M+ +H).
Analysis for $C_{45}H_{54}N_6O_6 \cdot 1H_2O$: Calculated: N, 10.37; C, 66.67; H, 7.16. Found: N, 10.84; C, 66.73; H, 6.83.

EXAMPLE 137 c-[D-Tryptophanyl-L-isoleucyl-D-pipecolyl-L-pipecolyl-D-(N-methyl)tyrosyl-L-prolyl]

C-[D-Trp-L-Ile-D-Pip-L-Pip-D-(N-Me-O-Bzl)-Tyr-L-Pro] (210 mg, 0.24 mmoles) was dissolved in 15 ml of a 10% acetic acid in ethanol solution and 45 mg of catalyst (10% palladium on carbon) was added. The reaction mixture was flushed with argon and then hydrogenated under atmospheric pressure for 72 hours. The reaction mixture was flushed with argon, filtered through celite and concentrated under reduced pressure. Lyophilization from dioxane afforded 180 mg (94%) of the title compound as a white powder. Further purification Method E [6% $CH_3OH$ in $CHCl_3$] followed by lyophylization from dioxane/water afforded 100 mg (53%) of the title compound as a white powder.

HPCL (Method G) RT=9.48 min.: purity 99%.
NMR (CDCl$_3$) in agreement with title compound.
FAB MS: 797 (M+ +H).
Analysis for $C_{44}H_{57}N_7O_7 \cdot 0.5$ Dioxane $\cdot 1.5$ $H_2O$: Calculated: N, 11.31; C, 63.74; H, 7.38. Found: N, 11.28; C, 63.53; H, 7.01.

EXAMPLE 138 c-[D-2-Naphthylalanyl-L-isoleucyl-D-pipecolyl-L-(N-t-butyloxycarbonyl)lysyl-D-(N-methyl)phenylalanyl-L-prolyl]

C-[D-2-Nal-L-Ile-D-Pip-L-(Boc)-Lys-D-(N-Me)Phe-L-Pro] was prepared from Boc-L-Pro-O-(PAM)-resin (1 mmole) according to the solid phase procedure set forth above for Example 1 with the following exceptions: Fmoc-L-(Boc)Lys (904 mg, 2 mmole) was used in a modified version of Step 2. The amino acid was dissolved in DMF (15 ml) and cooled to 0° C. then added to the resin at 5° C. BOP reagent (884 mg, 2 mmole) was added as a solid and the reaction was adjusted to pH 8 with DIEA (0.522 ml, 3 mmole); the resin was shaken for 15 hours before proceeding to Steps 3 and 4. An active ester coupling was used in Step 5. The Fmoc-D-2-Nal (878 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The final resin was cleaved with hydrazine and the hexapeptide hydrazide was cyclized as the acyl azide. Workup and purification using Method B gave a homogeneous product which was lyophilized from dioxane to give 300 mg (66%) of the title compound.

HPCL (Method G) RT=12.02 min.: purity 99%.
NMR (CDCl$_3$) in agreement with title compound.
FAB MS: 909 (M+ +H).
Analysis for $C_{51}H_{69}N_7O_8.0.5$ Dioxane.1.5 $H_2O$: Calculated: N, 10.53; C, 65.82; H, 7.68. Found: N, 10.91; C, 65.68; H, 7.41.

EXAMPLE 139

C-[D-1-Napthylalanyl-L-isoleucyl-D-pipecolyl-L-(N-t-butyloxycarbonyl)lysyl-D-(N-methyl)phenylalanyl-L-prolyl]

C-[D-1-Nal-L-Ile-D-Pip-L-(Boc)Lys-D-(N-Me)-Phe-L-Pro] was prepared from Boc-Pro-O-(PAM)-resin (1 mmole) according to the solid phase procedure set forth above for Example 1 with the following exceptions: Fmoc-L-(Boc)Lys (904 mg, 2 mmole) was used in a modified version of Step 2. The amino acid was dissolved in DMF (15 ml) and cooled to 0° C. than added to the resin at 5° C. BOP reagent (884 mg, 2 mmole) was added as a solid and the reaction was adjusted to pH 8 with DIEA (0.522 ml, 3 mmole); the resin was shaken for 15 hours before proceeding to Steps 3 and 4. An active ester coupling was used in Step 5. The Fmoc-D-1-Nal (878 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The final resin was cleaved with hydrazine and the hexapeptide hydrazide was cyclized as the acyl azide. Workup and purification using Method B gave a homogeneous product which was lyophilized from dioxane to give 350 mg (77%) of the title compound.

HPCL (Method G) RT=12.15 min.: purity 99%.
NMR (CDCl$_3$) in agreement with title compound.
FAB MS: 909 (M+ +H).
Analysis for $C_{51}H_{69}N_7O_8.2H_2O$: Calculated: N, 10.38; C, 64.88; H, 7.79. Found: N, 10.55; C, 64.74; H, 7.68.

EXAMPLE 140

C-[D-2-Napthylalanyl-L-isoleucyl-D-pipecolyl-L-lysyl-D-(N-methyl)phenylalanyl-L-prolyl]

C-[D-2-Nal-L-Ile-D-Pip-L-(Boc)Lys-D-(N-Me)-Phe-L-Pro] (10 mg; 0.011 mmol) was dissolved in 5 ml of a 20% solution of trifluoroacetic acid in CH$_2$Cl$_2$. After 5 minutes at room temperature the reaction mixture was concentrated under vacuum to give an oil. The oil was lyophilized from dioxane and water to yield 11 mg (98%) of the title compound.

HPCL (Method G) RT=8.93 min.: purity 99%.
NMR (CD$_3$OD) in agreement with title compound.
FAB MS: 808 (M+ +H).
Analysis for $C_{46}H_{60}N_7O_6.2C_2HF_3O_2.1H_2O$: Calculated: N, 9.30; C, 56.98; H, 6.12. Found: N, 9.64; C, 57.12; H, 6.31.

EXAMPLE 141

C-[D-2-Napthylalanyl-L-isoleucyl-D-pipecolyl-L-lysyl-D-(N-methyl)phenylalanyl-L-prolyl]

C-[D-2-Nal-L-Ile-D-Pip-L-(Boc)Lys-D-(N-Me)-Phe-L-Pro] (10 mg; 0.011 mmol) in 5 ml of a 20% solution of trifluoroacetic acid in CH$_2$Cl$_2$. After 5 minutes at room temperature the reaction mixture was concentrated under vacuum to give an oil. The oil was lyophilized from dioxane and water to yield 11 mg (98%) of the title compound.

HPCL (Method G) RT=8.88 min.: purity 99%.
NMR (CDCl$_3$) in agreement with title compound.
FAB MS: 808 (M+ +H).
Analysis for $C_{46}H_{60}N_7O_6.2C_2HF_3O_2.2H_2O$: Calculated: N, 9.14; C, 56.02; H, 6.16. Found: N, 9.46; C, 56.30; H, 6.21.

EXAMPLE 142

C-[D-(O-Benzyl)-tyrosinyl-L-isoleucyl-D-pipecolyl-L-(N-t-butyloxycarbonyl)lysyl-D-(N-methyl)phenylalanyl-L-prolyl]

C-[D-O-Bzl)-Tyr-L-Ile-D-Pip-L-(Boc)Lys-D-(N-Me)Phe-L-Pro] was prepared from Boc-L-Pro-O-(PAM)-resin (1 mmole) according to solid phase procedure set forth above for Example 1 with the following exceptions: Fmoc-L-(Boc)Lys (904 mg, 2 mmole) was used in a modified version of Step 2. The amino acid was dissolved in DMF (15 ml) and cooled to 0° C. then added to the resin at 5° C. BOP reagent (884 mg, 2 mmole) was added as a solid and the reaction was adjusted to pH 8 with DIEA (0.522 ml, 3 mmole); the resin was shaken for 15 hours before proceeding to Steps 3 and 4. An active ester coupling was used in Step 5. The Fmoc-D-(O-Bzl)Tyr (770 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The final resin was cleaved with hydrazine and the hexapeptide hydrazide was cyclized as the acyl azide. Workup and purification using Method B, gave a homogeneous product which was lyophilized from dioxane to give 700 mg (73%) of the title compound.

HPLC (Method G) RT=12.37 min.: purity 99%.
NMR (CDCl$_3$) in agreement with title compound.
FAB MS: 965 (M+ +H).
Analysis for $C_{54}H_{73}N_7O_9.2H_2O$: Calculated: N, 9.79; C, 64.80; H, 7.69. Found: N, 9.84; C, 65.17; H, 7.90.

EXAMPLE 143

C-[D,L-meta-Tyrosinyl-L-isoleucyl-D-pipecolyl-L-(N-t-butyloxycarbonyl)lysyl-D-(N-methyl)phenylalanyl-L-prolyl]

C-[D,L-meta-Tyr-L-Ile-D-Pip-L-(Boc)Lys-D-(N-Me)Phe-L-Pro] was prepared from Boc-L-Pro-O-(PAM)-resin (1 mmole) according to solid phase procedure set forth above for Example 1 with the following exceptions: Fmoc-L-(Boc)Lys (904 mg, 2 mmole) was used in a modified version of Step 2. The amino acid was dissolved in DMF (15 ml) and cooled to 0° C. then added to the resin at 5° C. BOP reagent (884 mg, 2 mmole) was added as a solid and the reaction was adjusted to pH 8 with DIEA (0.522 ml, 3 mmole); the resin was shaken for 15 hours before proceeding to Steps 3 and 4. An active ester coupling was used in Step 5. The Fmoc-D,L-meta-Tyr (773 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The final resin was cleaved with hydrazine and the hexapeptide hydrazide was cyclized as the acyl azide. Workup and purification using Method B, gave a homogeneous product which was lyophilized from dioxane to give 500 mg (57%) of the title compound.

HPCL (Method G) RT=11.29 min.: purity 99%.
NMR (CDCl$_3$) in agreement with title compound.
FAB MS: 875 (M++H).

Analysis for $C_{47}H_{67}N_7O_9.0.25C_4H_8O_2$: Calculated: N, 10.51; C, 61.81; H, 7.82. Found: N, 10.38; C, 61.36; H, 7.82.

EXAMPLE 144

C-[D-(O-t-Butyl)Tyrosiniyl-L-isoleucyl-D-pipecolyl-L(N-t-butyloxycarbonyl)lysyl-D-(N-methyl)phenylalanyl-L-prolyl]

C-[D-(O-t-Bu)-Tyr-L-Ile-D-Pip-L-(Boc)Lys-D-(N-Me)Phe-L-Pro] was prepared from Boc-L-Pro-O-(PAM)-resin (0.5 mmole) according to solid phase procedure set forth above for Example 1 with the following exceptions: Fmoc-L-(Boc)Lys (904 mg, 1 mmole) was used in a modified version of Step 2. The amino acid was dissolved in DMF (8 ml) and cooled to 0° C. then added to the resin at 5° C. BOP reagent (442 mg, 2 mmole) was added as a solid and the reaction was adjusted to pH 8 with DIEA (0.26 ml, 1.5 mmoles); the resin was shaken for 15 hours before proceeding to Steps 3 and 4. An active ester coupling was used in Step 5. The Fmoc-D-(o-t-bu)Tyr (471 mg, 1 mmole) was dissolved in DMF at ambient temperature and added to the resin. BOP reagent (442 mg, 1 mmole) was added as a solid and the reaction was brought to pH 8 with the addition of DIEA (0.18 ml, 1 mmole). After shaking for 15 hours the resin was washed. The final resin was cleaved with hydrazine and the hexapeptide hydrazide was cyclized as the acyl azide. Workup and purification using Method B, gave a homogeneous product which was lyophilized from dioxane to give 700 mg (73%) of the title compound.

HPLC (Method G) flow rate=1.5 ml min$^{-1}$ RT=13.84 min.: purity 99%.
NMR (CDCl$_3$) in agreement with title compound.
FAB MS: 930 (M++H).

Analysis for $C_{51}H_{75}N_7O_9.1.5H_2O$: Calculated: N, 10.24; C, 64.02; H, 8.15. Found: N, 10.78; C, 63.90; H, 8.00.

EXAMPLE 145

C-[D-(O-Benzyl)Tyrosyl-L-isoleucyl-D-pipecolyl-L-lysyl-D-(N-methyl)phenylalanyl-L-prolyl]

C-[D-(O-Bzl)-Tyr-L-Ile-D-Pip-L-(BOC)Lys-D-(N-Me)Phe-L-Pro] (100 mg; 0.10 mmol) was dissolved in 5 ml of a 20% solution of trifluoroacetic acid in CH$_2$Cl$_2$. After 15 minutes at room temperature the reaction mixture was washed with a saturated NaHCO$_3$ solution, dried (Na$_2$SO$_4$) and concentrated under reduced pressure. The resulting oil was lyophilized from dioxane and water to yield 90 mg (95%) of the title compound.

HPLC (Method G) RT=10.51 min.: purity 99%.
NMR (CD$_3$OD) in agreement with title compound.
FAB MS: 865 (M++H).

Analysis for $C_{49}H_{65}N_7O_7.2.5 H_2O$: Calculated: N, 10.78; C, 64.74; H, 7.69. Found: N, 10.53; C, 64.40; H, 7.28.

EXAMPLE 146

C-[D,L-meta-Tyrosyl-L-isoleucyl-D-pipecolyl-L-lysyl-D-(N-methyl)phenylalanyl-L-prolyl]

C-[D,L-meta-Tyr-L-Ile-D-Pip-L-(Boc)Lys-D-(N-Me)Phe-L-Pro] (50 mg; 0.054 mmol) and 25 mg dithiothreitol were dissolved in 5 ml of a 20% solution of trifluoroacetic acid in CH$_2$Cl$_2$. After 15 minutes at room temperature the reaction mixture was washed with a saturated NaHCO$_3$ solution, dried (Na$_2$SO$_4$) and concentrated under reduced pressure. Purification (Method E) (90:10:1:1 CHCl$_3$MeOH/H$_2$O/NH$_4$OH) afforded two components. The component with the lower Rf was isolated and lyophilized from dioxane and water containing 0.5% TFA to yield 35 mg (49%) of the title compound. The quantity of isolated higher Rf component was negligible.

HPCL (Method G) RT=7.17 min.: purity 99%.
NMR (CD$_3$OD) in agreement with title compound.
FAB MS: 775 (M++H).

Analysis for $C_{42}H_{59}N_7O_7.3C_2HO_2F_3.1 H_2O.1SiO_2$: Calculated: N, 8.18; C, 48.08; H, 5.34. Found: N, 7.88; C, 48.28; H, 5.58.

EXAMPLE 147

C-[D-Tyrosyl-L-isoleucyl-D-pipecolyl-L-lysyl-D-(N-methyl)phenylalanyl-L-prolyl]

C-[D-(O-t-Bu)Tyr-L-Ile-D-Pip-L-(Boc)Lys-D-(N-Me)Phe-L-Pro] (22 mg; 0.02 mmol) and 10 mg dithiothreitol were dissolved in 5 ml of a 20% solution of trifluoroacetic acid in CH$_2$Cl$_2$. After 5 minutes at room temperature the reaction mixture was concentrated under reduced pressure. Purification (Method M) afforded 12 mg (61%) of the title compound.

HPCL (Method G) RT=6.91 min.: purity 99%.
NMR (CD$_3$OD) in agreement with title compound.
FAB MS: 775 (M++H).

Analysis for $C_{42}H_{59}N_7O_7.1.75C_2HO_2F_3.0.5H_2O$: Calculated: N, 9.97; C, 55.57; H, 6.28. Found: N, 9.63; C, 55.66; H, 6.69.

EXAMPLE 148

C-[D-Tyrosyl-L-isoleucyl-D-pipecolyl-L-(N-t-butyloxycarbonyl)lysyl-D-(N-methyl)phenylalanyl)-L-prolyl C-[D-(O-Bzl)-Tyr-L-Ile-D-Pip-L-(Boc)Lys-D-(N-Me)Phe-L-Pro] (50 mg; 0.05 mmol) was dissolved in 15 ml of a 10% acetic acid in ethanol solution and 15 mg of catalyst (10% palladium on carbon) was added. The reaction mixture was flushed with argon and then hydrogenated under atmospheric pressure for 72 hours. The reaction mixture was flushed with argon, filtered through celite and concentrated under reduced pressure. Lyophilization from dioxane afforded 35 mg (71%) of the title compound as a white powder.

HPCL (Method G) RT=9.55 min.: purity 99%.
NMR (CD$_3$OD) in agreement with title compound.
FAB MS: 875 (M++H).

Analysis for $C_{47}H_{66}N_7O_9.1 C_2H_4O_2.1H_2O$: Calculated: N, 10.30; C, 61.84; H, 7.57. Found: N, 10.32; C, 61.52; H, 7.53.

EXAMPLE 149 c-[D-(O-Methyl)Tyrosyl-L-isoleucyl-D-pipecolyl-L-(N-t-butyloxycarbonyl)lysyl-D-(N-methyl)phenylalanyl-L-prolyl]

c-[D-Tyr-L-Ile-D-Pip-L-(Boc)Lys-D-(N-Me)-Phe-L-Pro] 35 mg, 0.04 mmol) was dissolved in 2 mL of anhydrous THF and cooled to 0° C. 1.1 Equivalents of n-BuLi [44 µl of a 1 molar solution]) was added and the reaction mixture was stirred at 0° C. for 20 minutes. The reaction mixture was then warmed to room temperature, stirred for 30 minutes and 0.4 mmol of MeI was added. The reaction was stirred for 72 hours at room temperature and the volatiles were evaporated under reduced pressure. The residue was dissolved in $CH_2Cl_2$ and washed twice with $H_2O$ and saturated NaCl, dried over $Na_2SO_4$ and evaporated under reduced pressure. Lyophilization from dioxane and $H_2O$ afforded 30 mg (85%) of the title compound as a powder.

HPLC (Method G) RT=10.72 min.: purity 95%.
NMR ($CDCl_3$) in agreement with title compound.
FAB MS: 888 (M++H).
Analysis for $C_{48}H_{68}N_7O_9 \cdot 0.5C_2H_4O_2 \cdot 1H_2O$: Calculated: N, 10.31; C, 63.23; H, 7.79. Found: N, 10.21; C, 63.21; H, 7.80.

EXAMPLE 150 c-[D-(O-Methyl)Tyrosyl-L-isoleucyl-D-pipecolyl-L-lysyl-D-(N-methyl)phenylalanyl-L-prolyl]

c-[L-(O-Me)Tyr-L-Ile-D-Pip-L-(Boc)Lys-D-(N-Me)Phe-L-Pro] (15 mg; 0.016 mmol) and 5 mg dithiothreitol were dissolved in 5 mL of a 20% solution of trifluoroacetic acid in $CH_2Cl_2$. After 5 minutes at room temperature the reaction mixture was concentrated under reduced pressure. Purification (Method M) afforded 9 mg (50%) of the title compound.

HPLC (Method G) RT=7.91 min.: purity 99%.
NMR ($CD_3OD$) in agreement with title compound.
FAB MS: 788 (M++H).
Analysis for $C_{43}H_{61}N_7O_7 \cdot 2C_2HO_2F_3 \cdot 2.5H_2O$: Calculated: N, 9.25; C, 53.21; H, 6.32 Found: N, 8.95; C, 53.13; H, 6.09.

EXAMPLE 151 c-[D-2-Napthylalanyl-L-isoleucyl-D-pipecolyl-L-[N-(1-methyl-quinuclidinium-3-yl-carbonyl)]lysyl-D-(N-methyl)phenylalanyl-L-prolyl]

c-[D-2-Nal-L-Ile-D-Pip-L-Lys-D-(N-Me)Phe-L-Pro]trifluoroacetate (20 mg, 0.0187 mmol) and 1-methyl-quinuclidinium-3-carboxylic acid chloride (12 mg, 0.017 mmol) were dissolved in 1 mL of dry, degassed DMF. To this solution was added BOP reagent (29 mg, 0.067 mmol) and DIPEA (30 µl, 0.17 mmol). The reaction was stirred for 18 hours under argon. The reaction mixture was then evaporated to dryness under reduced pressure. Purification (Method M) afforded 14 mg (48%) of the title compound.

HPLC (Method G) RT=9.23 min.: purity 99%.
NMR (DMSO-$D_6$) in agreement with title compound.
FAB MS: 960 (M++H).
Analysis for $C_{55}H_{76}N_8O_7 \cdot 4C_2HO_2F_3 \cdot 10H_2O$: Calculated: N, 6.93; C, 46.81; H, 6.25. Found: N, 6.61; C, 46.65; H, 5.59.

EXAMPLE 152 c-[D-Tryptophanyl-L-isoleucyl-D-pipecolyl-L-pipecolyl-D-histidyl-3,4-dehydroprolyl]

c-[D-Trp-L-Ile-D-Pip-L-Pip-D-His-3,4-dehydro-Pro] was prepared from Boc-D-Trp-O-(Merrifield)-resin (1 mmole) according to the solid phase procedure set forth above for Example 1 with the following exceptions: Boc-(3,4-dehydro)-Pro (400 mg, 2 mmole) was used in STEP 1. Boc-D-His(DNP) (884 mg, 2 mmole) was used in a modified version of STEP 2. The amino acid was dissolved in DMF (15 ml) and cooled to 0° C. then added to the resin at 5° C. BOP reagent (884 mg, 2 mmole) was added as a solid and the reaction was adjusted to pH 8 with DIEA (0.522 ml, 3 mmole); the resin was shaken for 15 hours before proceeding to STEP 3. Fmoc-L-Pip (1.04 g, 3 mmol) and 523 µL DIPEA was used for STEP 3. Fmoc-D-Pip (1.04 g, 3 mmol), Fmoc-L-Ile (1.04 g, 3 mmol) and 523 µl DIPEA were used for steps 4 and 5, respectively. The final resin was cleaved with hydrazine and the hexapeptide hydrazide was cyclized as the acyl azide. Workup and purification using Method E gave a homogeneous product which was lyophilized from dioxane/$H_2O$ and then crystallized from 2% methanol in ethyl acetate giving 301 mg (40%) of the title compound.

HPLC (Method G) RT=7.44 min.: purity 99%.
NMR (DMSO-$D_6$) in agreement with title compound.
FAB MS 755 (M++H).
Analysis for $C_{40}H_{51}N_9O_6 \cdot H_2O$: Calculated: N, 16.33; C, 62.23; H, 6.87. Found: N, 16.23; C, 62.00; H, 6.69.

EXAMPLE 153 c-[D,L-3-(3-(1-Methyl)indolyl)alanyl-L-isoleucyl-D-pipecolyl-L-pipecolyl-D-histidyl-L-prolyl]

c-[D,L-(1-Me)Trp-L-Ile-D-Pip-L-Pip-D-His-L-Pro] was prepared from Boc-L-Pro-O-(PAM)resin (1 mmole) according to the solid phase procedure set forth in Example 1 with the following exceptions: Boc-D-(DNP)His (840 mg, 2 mmol) was used in STEP 1. An active ester coupling was used in Step 5. The Fmoc-D,L(1-Me)-Trp (880 mg, 2 mmole) was dissolved in DMF at ambient temperature and added to the resin. BOP reagent (884 mg, 2 mmole) was added as a solid and the reaction was adjusted to pH 8 with DIEA (0.35 ml, 2 mmole). After shaking for 15 hours the resin was washed. The final resin was cleaved with hydrazine and the hexapeptide hydrazide was cyclized as the acyl azide. Workup and purification using Method B gave a mixture which wa lyophilized from dioxane/$H_2O$ giving 49.1 mg (6.3%) of the title compound. This mixture of isomers at the 2-position was separated by silica gel chromatography using 90:10:1 $CHCl_3$:MeOH:concentrated $NH_4OH$ and lyophilized to give two compounds.

Higher $R_f$ isomer:
HPLC (Method G) RT=8.15 min.: purity 100%.
NMR (DMSO-$D_6$) in agreement with title compound.
FAB MS 770 (M++H).
Analysis for $C_{40}H_{53}N_9O_6 \cdot H_2O \cdot 0.27$ dioxane: Calculated: N, 15.19; C, 59.35; H, 6.68. Found: N, 14.49; C, 59.38; H, 6.63.
TLC 90:10:1 $CHCl_3$:MeOH:concentrated $NH_4OH$ $R_f$=0.35.

Lower $R_f$ isomer:
HPLC (Method G) RT=9.63 min.: purity 99.1%.

NMR (DMSO-D$_6$) in agreement with title compound.

FAB MS 770 (M$^+$+H).

Analysis for C$_{40}$H$_{53}$N$_9$O$_6$.H$_2$O.0.27 dioxane: TLC 90:10:1 CHCl$_3$:MeOH:concentrated NH$_4$OH R$_f$=0.26.

EXAMPLE 154 c-[D,L-3-(3-(5-Methyl)indolyl)alanyl-L-isoleucyl-D-pipecolyl-L-pipecolyl-D-histidyl-L-prolyl]

c-[D,L-(5-Me)Trp-L-Ile-D-Pip-L-Pip-D-His-L-Pro] was prepared from Boc-L-Pro-O-(PAM)resin (1 mmole) according to the solid phase procedure set forth in Example 1 with the following exceptions: Boc-D-(DNP)His (840 mg, 2 mmol) was used in STEP 1. An active ester coupling was used in Step 5. The Fmoc-D,L-(5-Me)-Trp (880 mg, 2 mmol) was dissolved in DMF at ambient temperature and added to the resin. BOP reagent (884 mg, 2 mmole) was added as a solid and the reaction was adjusted to pH 8 with DIEA (0.35 ml, 2 mmole). After shaking for 15 hours the resin was washed. The final resin was cleaved with hydrazine and the hexapeptide hydrazide was cyclized as the acyl azide. Workup and purification using Method B gave a mixture which was lyophilized from dioxane/H$_2$O giving 352 mg (46%) of the title compound. This mixture of isomers at the 2-position was separated by silica gel chromatography using 90:10:1 CHCl$_3$:MeOH:concentrated NH$_4$OH and lyophilized to give two products.

HIGHER R$_f$ISOMER:

HPLC (Method G) RT=7.97 min.: purity 98%.

NMR (DMSO-D$_6$) in agreement with title compound.

FAB MS: 770 (M$^+$+H).

TLC 90:10;1 CHCl$_3$:MeOH:concentrated NH$_4$OH RF=0.25

LOWER R$_f$ISOMER:

HPLC (Method G): purity 98%.

NMR (DMSO-D$_6$) in agreement with title compound.

FAB MS: 770 (M$^+$+H).

Analysis for C$_{41}$H$_{55}$N$_9$O$_6$.dioxane: Calculated: N, 14.82; C, 62.99; H, 7.40. Found: N, 14.69; C, 58.96; H, 6.72.

TLC 90:10;1 CHCl$_3$:MeOH:concentrated NH$_4$OH RF=0.20

EXAMPLE 155

C-[D,L-3-(3-(7-Methyl)indolyl)alanyl-L-isoleucyl-D-pipecolyl-L-pipecolyl-D-histidyl-L-prolyl]

C-[D,L-(7-Me)Trp-L-Ile-D-Pip-L-Pip-D-His-L-Pro] was prepared form Boc-L-Pro-O-(PAM)-resin (1 mmole) according to the solid phase procedure set forth in Example 1 with the following exceptions: Boc-D-(DNP)His (840 mg, 2 mmol)) was used in Step 1. An active ester coupling was used in Step 5. The Fmoc-D,L-(7-Me)Trp (880 mg, 2 mmol) was dissolved in DMF at ambient temperature and added to the resin. BOP reagent (884 mg, 2 mmol) was added as a solid and the reaction was brought to pH 8 with the addition of DIEA (0.35 ml, 2 mmol). After shaking for 15 hours the resin was washed. The final resin was cleaved with hydrazine and the hexapeptide hydrazide was cyclized as the acyl azide. Workup and purification using Method B gave a mixture which was lyophilized from dioxane/H$_2$O giving 5.4 mg (0.7%) of the title compound as a mixture of isomers at the 2-position.

HPLC (Method G) RT=7.97 min.: purity 99.4%.

NMR (DMSO-D$_6$) in agreement with title compound.

FAB MS: 770 (M$^+$+H).

Analysis for C$_{41}$H$_{55}$N$_9$O$_6$.dioxane: Calculated: N, 13.64; C, 52.05; H, 5.86. Found: N, 11.65; C, 51.99; H, 5.91.

EXAMPLE 156

C-[D,L-3-(3-(5-Methoxy)indolyl)alanyl-L-isoleucyl-D-pipecolyl-L-pipecolyl-D-histidyl-L-prolyl]

C-[D,L-(5-OMe)Trp-L-Ile-D-Pip-L-Pip-D-His-L-Pro] was prepared form Boc-L-Pro-O-(PAM-resin (1 mmole) according to the solid phase procedure set forth in Example 1 with the following exceptions: Boc-D-(DNP)His (840 mg, 2 mmol) was used in Step 1. An active ester coupling was used in Step 5. The Fmoc-D,L-(5-OMe)Trp (912 mg, 2 mmol) was dissolved in DMF at ambient temperature and added to the resin. BOP reagent (884 mg, 2 mmol) was added as a solid and the reaction was brought to pH 8 with the addition of DIEA (0.35 ml, 2 mmol). After shaking for 15 hours the resin was washed. The final resin was cleaved with hydrazine and the hexapeptide hydrazide was cyclized as the acyl azide. Workup and purification using Method B gave a mixture of two isomers (2-position) which was lyophilized from dioxane/H$_2$O to give 13.8 mg (2%) of the title compound.

HPLC (Method G) RT=7.41 min.: purity 98%.2.

NMR (DMSO-D$_6$) in agreement with title compound.

FAB MS: 786 (M$^+$+H).

Analysis for C$_{41}$H$_{55}$N$_9$O$_7$.1H$_2$O.1C$_2$HF$_3$O$_2$.0.3 dioxane: Calculated: N, 13.34; C, 52.14; H, 5.86. Found: N, 13.32; C, 52.54; H, 5.76.

EXAMPLE 157 c-[D,L-3-(3-(5-Fluoro)indolyl)alanyl-L-isoleucyl-D-pipecolyl-L-pipecolyl-D-histidyl-L-prolyl]

c-[D,L-(5-F)Trp-L-Ile-D-Pip-L-Pip-D-His-L-Pro] was prepared from Boc-L-Pro-O-(PAM)-resin (1 mmole) according to the solid phase procedure set forth in Example 1 with the following exceptions: Boc-D-(DNP)His (840 mg, 2 mmol) was used in Step 1. An active ester coupling was used in Step 5. The Fmoc-D,L-(5-F)Trp (900 mg, 2 mmol) was dissolved in DMF at ambient temperature and added to the resin. BOP reagent (884 mg, 2 mmol) was added as a solid and the reaction was brought to pH 8 with the addition of DIEA (0.35 ml, 2 mmol). After shaking for 15 hours the resin was washed. The final resin was cleaved with hydrazine and the hexapeptide hydrazide was cyclized as the acyl azide. Workup and purification using Method B gave a mixture which was lyophilized from dioxane/H$_2$O giving 410 mg (53%) of the title compound. This mixture of isomers at the 2-position was separated by silica gel chromatography using 90:10:1 CHCl$_3$:MeOH:NH$_4$OH and lyophilized from dioxane to give two products.

HIGHER R$_f$ISOMER:

HPLC (Method G) RT=7.83 min.: purity 90%

NMR (DMSO-D$_6$) in agreement with title compound.

FAB MS: 774 (M$^+$+H).

Analysis for C$_{40}$H$_{52}$FN$_9$O$_6$.4 dioxane: Calculated: N, 11.15; C, 59.50; H, 7.80. Found: N, 11.10; C, 62.67; H, 6.88.

TLC 90:10:1 CHCl$_3$:MeOH;NH$_4$OH R$_f$=0.35.

LOWER R$_f$ ISOMER:

HPLC (Method G): purity 94%.

NMR (DMSO-D$_6$) in agreement with title compound.

FAB MS: 774 (M+ +H).

Analysis for C$_{40}$H$_{52}$FN$_9$O$_6$.2 dioxane.1SiO$_2$. Calculated: N, 12.48; C, 57.07; H, 6.78. Found: N, 12.10; C, 56.78; H, 6.35.

TLC 90:10:1 CHCl$_3$:MeOH:NH$_4$OH R$_f$=0.31.

EXAMPLE 158 c-[D-2-Naphthylalanyl-L-isoleucyl-D-pipecolyl-L-piperazin-2-yl-(4-carbobenzyloxy)-D-histidyl-L-prolyl]

c-[D-2-Nal-L-Ile-D-Pip-L-(Cbz)Pipe-D-His-L-Pro] was prepared from Boc-L-Pro-O-(PAM)-resin (1 mmole) according to the solid phase procedure set forth in Example 1 with the following exceptions: Boc-D-(DNP)His (530 mg, 2 mmole) was used in STEP 1. Fmoc-L-(Cbz)Pipe (974 mg, 2 mmole) was used in a modified version of STEP 2. The amino acid was dissolved in DMF (15 ml) and cooled to 0° C. then added to the resin at 5° C. BOP reagent (884 mg, 2 mmole) was added as a solid and the reaction was adjusted to pH 8 with DIEA (0.522 ml, 3 mmole); the resin was shaken for 15 hrs. before proceeding to STEP 3. An active ester coupling was used in Step 5. The Fmoc-D-2-Nal (878 mg, 2 mmole) was dissolved in DMF at ambient temperature and added to the resin. BOP reagent (884 mg, 2 mmole) was added as a solid and the reaction was brought to pH 8 with the addition of DIEA (0.35 ml, 2 mmole). After shaking for 15 hours the resin was washed. The final resin was cleaved with hydrazine and the hexapeptide hydrazide was cyclized as the acyl azide. Workup and purification using Method B gave a mixture of two isomers in a 65:35 ratio at the 5-position piperazine-2-carboxylic acid group. This mixture was lyophilized from dioxane to give 450 mg. The isomers were separated on silica gel using 100:10:1 CHCl$_3$:MeOH:NH$_4$OH as the solvent system. The major component was lyophilized from dioxane to give 236 mg (26%) of the title compound.

HPLC (Method G) RT=9.22 min.: purity 96%.

NMR (CD$_3$OD) in agreement with title compound.

FAB MS: 903 (M+ +H).

Analysis for C$_{49}$H$_{60}$N$_9$O$_8$.2.5H$_2$O: Calculated: N, 13.30; C, 62.02; H, 6.91. Found: N, 13.29; C, 61.93; H, 6.02.

EXAMPLE 159 c-[D-2-Naphthylalanyl-L-isoleucyl-D-pipecolyl-L-piperazin-2-yl-D-histidyl-L-prolyl]

c-[D-2-Nal-L-Ile-D-Pip-L-(Cbz)Pipe-D-His-L-Pro] (100 mg, 0.11 mmole) was dissolved in 25 ml of ethanol containing 4% acetic acid by volume; to this solution was added 25 mg of catalyst (10% palladium on carbon). The reaction mixture was flushed with argon and then hydrogenated at atmospheric pressure for 15 hours. The reaction mixture was flushed with argon, filtered through celite and evaporated under reduced pressure. The resulting material was purified (Method E) using 90:10:1 CHCl$_3$:MeOH:concentrated NH$_4$OH as the solvent system. Lyophilization from dioxane afforded 32 mg (38%) of the title compound as a white powder.

HPLC (Method G) RT=7.27 min.; purity 99%.

NMR (DMSO-D$_6$) in agreement with the title compound.

FAB MS: 768 (M+ +H).

Analysis for C$_{41}$H$_{54}$N$_9$O$_6$.3SiO$_2$.1NH$_4$OH: Calculated: N, 14.25; C, 51.03; H, 5.95. Found: N, 14.34; C, 51.93; H, 5.88.

EXAMPLE 160 c-[D-2-Naphthylalanyl-L-isoleucyl-D-pipecolyl-D-piperazin-2-yl-(4-carbobenzyloxy)-D-hystidyl-L-prolyl]

c-[D-2-Nal-L-Ile-D-Pip-D-(Cbz)Pipe-D-His-L-Pro] was isolated from the mixture of isomers from the systhesis of Example 159 described above. Lyophilization from dioxane gave 150 mg (16.6%) of the title compound.

HPLC (Method G) RT=9.48 min.: purity 95.5%.

NMR (CD$_3$OD) in agreement with title compound.

FAB MS: 903 (M+ +H).

Analysis for C$_{49}$H$_{60}$N$_9$O$_8$.2H$_2$O. Calculated: N, 12.27; C, 61.98; H, 7.01. Found: N, 12.58; C, 61.36; H, 6.54.

EXAMPLE 161 c-[D-2-Naphthylalanyl-L-isoleucyl-D-pipecolyl-D-piperazin-2-yl-D-histidyl-L-prolyl]

c-[D-2-Nal-L-Ile-D-Pip-D-(Cbz)Pipe-D-His-L-Pro] (120 mg, 0.13 mmol) was dissolved in 25 ml of a 4% acetic acid in ethanol solution and 20 mg of catalyst (10% Palladium on carbon) was added. The reaction mixture was flushed with argon and then hydrogenated at atmospheric pressure for 15 hours. The reaction was flushed with argon, filtered through celite and evaporated under reduced pressure. The resulting material was purified (Method E) by using 90:10:1 CHCl$_3$:MeOH:NH$_4$OH as the solvent system. Lyophilization from dioxane afforded 54 mg (53%) of the title compound as a white powder.

HPLC (Method G) RT=7.61 min.: purity 95%.

NMR (DMSO-D$_6$) in agreement with title compound.

FAB MS: 768 (M+ +H).

Analysis for C$_{41}$H$_{54}$N$_9$O$_6$.0.5dioxane.1SiO$_2$ Calculated: N, 14.44; C, 59.16; H, 6.70. Found: N, 14.69; C, 58.90; H, 6.31.

EXAMPLE 162 c-[D-Tryptophanyl-L-isoleucinyl-D-pipecolyl-L-piperazin-2-yl(4-t-butylacetyl)-D-tryptophanyl-L-prolyl]

c-[D-Tryptophanyl-L-isoleucinyl-D-pipecolyl-L-piperazin-2-yl-D-tryptophanyl-L-prolyl] (50 mg, 0.047 mmole) was added to a suspension of potassium carbonate (13.8 mg, 0.10 mmole) in 1 ml of dry DMF. To this mixture was added t-butylbromoacetate (8 µl, 0.05 mmole) in one portion at room temperature. The reaction mixture was stirred overnight, filtered and concentrated to dryness under reduced pressure. The residue was purified by Method F (95:5:0.5, CHCl$_3$:MeOH concentrated NH$_4$OH) to give the title compound in analytically pure form: m.p. 220°-230° C.

HPLC (Method H) 22.51 min, >96% pure at 210 nM.

NMR (DMSO-D$_6$): Spectrum confirmed structure of the title compound and the presence of solvent.

MS FAB: 920 (M+).

Elemental Analysis for C$_{50}$H$_{65}$N$_9$O$_8$.2.35-H$_2$O.0.7CHcl$_3$: Calculated: C, 58.21; H, 6.79; N, 12.05. Found: C, 58.14; H, 6.79; N, 12.45.

EXAMPLE 163 c-[D-Phenylalanyl-L-isoleucinyl-D-prolyl-L-piperazin-2-yl(4-Cbz)-D-phenylalanyl-L-prolyl]

The procedure for Example 51 was carried out utilizing the $N^\alpha$-Boc derivatives of D-Phe, L-Ile, D-Pip, L-Pipe(4-Cbz), D-Pro, and L-Pro to synthesize the title compound which was obtained in analytically pure form after HPLC purification (Method C): m.p. 210°–220° C. (shrinks).

HPLC (Method I) 16.27 min, 95% pure at 210 nM.

NMR (DMSO-$D_6$): Spectrum confirmed structure of the title compound and the presence of solvent.

Elemental Analysis for $C_{47}H_{57}N_7O_8 \cdot 2.5 H_2O \cdot 0.80TFA$: Calculated: C, 59.30; H, 6.43; N, 9.96. Found: C, 59.27; H, 6.06; N, 10.35.

EXAMPLE 164 c-[D-Phenylalanyl-L-isoleucinyl-D-prolyl-L-piperazin-2-yl-D-phenylalanyl-L-prolyl]

c-[D-Phenylalanyl-L-isoleucinyl-D-prolyl-L-piperazine-2-yl(4-Cbz)-D-phenylalanyl-L-prolyl] was converted to the title compound according to the procedure delineated in Example 73. The title compound was obtained in analytically pure form after purification (Method C): m.p. 210°–220° C. (shrinks at 155° C.).

HPLC (Method I) RT=11.91 min.; >97% pure at 254 nM.

NMR (DMSO-$D_6$): Spectrum confirmed structure of the title compound and the presence of solvent.

MS FAB: 714 (M+).

Elemental Analysis for $C_{41}H_{52}F_3N_7O_8 \cdot 1.65TFA$: Calculated: C, 51.59; H, 5.41; N, 9.51. Found: C, 51.58; H, 5.36; N, 9.89.

EXAMPLE 165 c-[D-Homophenylalanyl-L-isoleucyl-D-pipecolyl-L-pipecolyl-N-Me-D-phenylalanyl-L-prolyl]

In a manner similar to Example 103 the title cyclic hexapeptide was synthesized using the amino acids Cbz-D-HPhe, Fmoc-L-Ile, Fmoc-D-Pip, Fmoc-L-Pip, Boc-N-Me-D-Phe, and L-Pro benzyl ester. The crude product was purified according to Method F utilizing 7% MeOH/$CH_2Cl_2$ to give a solid:

HPLC (Method I), >95.5% pure at 210 nM, RT=20.18 minutes.

FAB MS: 755 (M++H).

NMR (300 MHz, $CDCl_3$) Spectrum confirmed structure of title compound and presence of solvent.

Elemental analysis for $C_{43}H_{58}N_6O_6$: Calculated: C, 68.45; H, 7.75; N, 11.14. Found: C, 68.69; H, 7.76; N, 10.72.

EXAMPLE 166 c-[N-Me-D-Homophenylalanyl-N-Me-L-isoleucyl-D-pipecolyl-N-Me-D-phenylalanyl-L-prolyl]

To a solution of 0.4 mL of dry DMF containing 73 mg (0.097 mMole) of c-[D-homophenylalanyl-D-isoleucyl-D-pipecolyl-L-pipecolyl-N-Me-D-phenylalanyl-L-prolyl] and 0.1 mL of iodomethane was added 12 mg of sodium hydride. After approximately 1 hour more sodium hydride and iodomethane were added and the reaction mixture was allowed to stir for 6 hours. The reaction mixture was quenched by the addition of glacial acetic acid (5 drops) and concentrated to dryness under reduced pressure. The residue was dissolved in $CH_2Cl_2$. The organic layer was washed with water, dried ($MgSO_4$) and concentrated. The crude reaction product was purified according to Method F (7% MeOH/$CH_2Cl_2$) to give the title compound in analytical form (22.5% yield):

HPLC (Method I), >97.5% pure at 215 nM.

FAB MS: 784 (M++H).

NMR (DMSO-$D_6$) Spectrum confirmed structure of title compound and presence of solvent.

Elemental analysis for $C_{45}H_{62}N_6O_6 \cdot 0.3CH_2Cl_2 \cdot 0.15hexane$: Calculated: C, 67.75; H, 7.94; N, 10.23. Found: C, 67.79; H, 7.64; N, 10.01.

EXAMPLE 167 c-[N-Me-D-Alanyl-L-isoleucyl-D-pipecolyl-L-pipecolyl-N-Me-D-phenylalanyl-L-prolyl]

In a manner similar to Example 103 the title cyclic hexapeptide was synthesized using the amino acids Fmoc-N-Me-D-Ala, Fmoc-L-Ile, Fmoc-D-Pip, Fmoc-L-Pip, Boc-N-Me-D-Phe, and L-Pro benzyl ester. The crude product was purified according to Method F utilizing 8.5% MeOH/$CH_2Cl_2$ to give a solid:

HPLC (Method I), >96.5% pure at 210 nM, RT=16.90 minutes.

FAB MS: 679 (M++H).

NMR ($CDCl_3$) Spectrum confirmed structure of title compound and presence of solvent.

Elemental analysis for $C_{37}H_{54}N_6O_6 \cdot 0.45CH_2Cl_2 \cdot 0.85hexane$: Calculated: C, 64.69; H, 8.52; N, 10.63. Found: C, 64.74; H, 8.35; N, 10.65.

EXAMPLE 168 c-[D-Tryptophanyl-L-isoleucinyl-D-Δ-piperazyl-L-piperazin-2-yl(4-Cbz)-N-Me-D-phenylalanyl-L-prolyl]

Following the experimental procedure detailed in Example 124 and employing the amino acids Fmoc-D-Trp, Fmoc-L-Ile, $N^\beta$-Cbz-D-Piz, Fmoc-($N^\gamma$-Cbz)-L-Pipe, Boc-N-Me-D-Phe, and L-Pro the title compound was obtained as a white solid after purification (Method C): HPLC (Method I), >98.4% pure at 259 nM, RT=22.29 minutes;

FAB MS: 915 (M++H).

NMR (DMSO-$D_6$) Spectrum confirmed structure of title compound and presence of solvent.

Elemental analysis for $C_{50}H_{60}N_9O_8 \cdot 0.50H_2O \cdot 0.55TFA$: Calculated: C, 61.19; H, 6.29; N, 12.78. Found: C, 62.18; H, 6.30; N, 12.42.

EXAMPLE 169 c-[D-2-Naphthylalanyl-L-isoleucinyl-D-pipecolyl-L-piperazin-2-yl(4-Cbz)-D-($N\alpha$-methyl)-phenylalanyl-L-prolyl]

The title compound was obtained from Boc-L-Pro-(Merrifield)-resin (1 mMole) using the procedure outlined in Example 1 and utilizing the Fmoc derivatives of D-($N\alpha$-Me-D-Phe, L-Pipe(4-Cbz), D-Pip, L-Ile, and D-2-Nal. Step 7 was modified in the following manner: the fully assembled peptide-resin was suspended in a solution consisting of 30 mL of methanol and 5 mL of 95% hydrazine. The resulting suspension was stirred at ambient temperature for 30 minutes, filtered and concentrated under reduced pressure. The resin was then resuspended in 30 mL of methanol and treated with 20 mL of 95% hydrazine for 1 hour. Filtration of the suspension and repetition of this cycle yielded, after concentration of the combined filtrates, 800 mg of crude product. The crude product was azeotropically dried with toluene and the resulting crude azyl hydrazide (retention time 10.00 minutes, Method G) was subjected to Step 8 in Example 1. The title compound was obtained in analytically pure form after purification (Method F, CHCl$_3$/MeOH/concentrated NH$_4$OH, 95:5:0.5 v/v) m.p. 48°–51° C.

HPLC (Method G) 14.24 min, >98% pure at 214 nM.

NMR (DMSO-D$_6$): Spectrum confirmed structure of the title compound and the presence of solvent.

MS FAB: 926 (M+).

Elemental Analysis for C$_{53}$H$_{63}$N$_7$O$_8$.2.50-H$_2$O.2.25TFA: Calculated: C, 56.25; H, 5.77; N, 7.99. Found: C, 56.23; H, 5.78; N, 7.96.

EXAMPLE 170 c-[D-Tryptophanyl-L-isoleucinyl-D-Δ-piperazyl-L-piperazin-2-yl-N$^\alpha$-Me-D-phenylalanyl-L-prolyl]

The title compound was obtained from c-[D-tryptophanyl-L-isoleucinyl-D-Δ-piperazyl-L-piperazin-2yl(4-Cbz)-N-Me-D-phenylalanyl-L-prolyl] using the procedure outlined in Example 73 with the following exception: 20% palladium hydroxide on carbon catalyst was used in place of 10% palladium on carbon catalyst. The title compound was obtained in analytically pure form after purification (Method F, CHCl$_3$/MeOH/conc.NH$_4$OH (5:5:0.5). HPLC (Method N) >96% pure, RT=11.00 minutes.

NMR (DMSO-D$_6$): Spectrum confirmed structure of the title compound and the presence of solvent.

MS FAB: 780 (M+).

Elemental Analysis for C$_{44}$H$_{58}$N$_9$O$_8$.0.90HOAc. 1.9 dioxane: Calculated: C, 60.36; H, 7.29; N, 11.87. Found: C, 60.37; H, 6.83; N, 11.86.

EXAMPLE 171 c-[D-2-Naphthylalanyl-L-isoleucinyl-D-pipecolyl-L-piperazin-2-yl-D-(N$^\alpha$-methyl)phenylalanyl-L-prolyl]

The title compound was obtained from c-[D-2-naphthylalanyl-L-isoleucinyl-D-pipecolyl-L-piperazin-2-yl(4-Cbz)-D-(N$^\alpha$methyl)phenylalanyl-L-prolyl] using the procedure outlined in Example 73 with the following exception: 20% palladium hydroxide on carbon catalyst was used in place of 10% palladium on carbon catalyst. After hydrogenating for 23.5 hours, the reaction mixture was filtered and the title compound was obtained in analytically pure form according to Method F (CHCl$_3$/MeOH/conc.NH$_4$OH, 95:5:0.5 v/v). HPLC (Method G) >97% pure, 10.78 minutes.

NMR (DMSO-D$_6$): Spectrum confirmed structure of the title compound and the presence of solvent.

MS FAB: 792 (M++H).

Elemental Analysis for C$_{45}$H$_{57}$N$_7$O$_6$.1.80MeOH.0.6CHCl$_3$: Calculated: C, 61.79; H, 7.09; N, 10.64. Found: C, 61.81; H, 7.09; N, 10.64.

EXAMPLE 172 c-[D-Tryptophanyl-L-isoleucinyl-D-pipecolyl-L-pipecolyl-D-(β-t-butyl)aspartyl-L-prolyl]

The title compound was obtained from Boc-L-Pro-(Merrifield)-resin (1 mMole) using the procedure outlined in Example 1 and utilizing the amino acid derivatives Fmoc-D-Trp, Fmoc-L-Ile, Fmoc-D-Pip, Fmoc-L-Pip, and Boc-(β-t-butyl)Asp. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The crude hydrazide product (containing traces of hydrazine) was azeotropically dried with toluene (3 cycles) and subjected to Step 8 in Example 1. The crude product was purified (Method M) to give a solid: m.p. 131°–134° C. HPLC (Method C), >95% pure at 214 nM, RT=11.98 minutes:

MS FAB: 790 (M++H), 812 (M++Na),

NMR (DMSO-D$_6$): Spectrum confirmed structure of title compound and presence of solvent.

Elemental Analysis for C$_{41}$H$_{59}$N$_7$O$_8$.0.55CH$_3$OH: Calculated: C, 56.77; H, 6.97; N, 10.93. Found: C, 56.85; H, 6.68; N, 10.64.

EXAMPLE 173

C-[D-Phenylalanyl-L-isoleucyl-D-Δ-piperazyl-L-(N$^\epsilon$-t-Butyloxycarbonyl)-Lysl-M-Me-D-phenylalanyl-L-prolyl]

Using similar amounts of reagents and identical reaction conditions to those described in Example 124 the title compound was prepared from the amino acids N$^\beta$-Cbz-Piz, Fmoc-L-Ile, N$^\epsilon$-Boc-Lys, Fmoc-D-Phe, Boc-N-Me-D-Phe, and L-Pro benzyl ester. The crude product was purified according to Method F utilizing 95:5:0.5 CHCl$_3$/MeOH/concentrated NH$_4$OH as eluant to give a solid: HPLC (Method I), >94% pure, RT=18.30 minutes;

MS FAB: 857 (M+).

NMR (DMSO-D$_6$): Spectrum confirmed structure of title compound and presence of solvent.

Elemental Analysis for C$_{46}$H$_{64}$N$_8$O$_8$.0.40toluene.1.SiO$_2$: Calculated: C, 61.43; H, 7.10; N, 11.75. Found: C, 61.49; H, 6.89; N, 11.77.

EXAMPLE 174 c-[D-Phenylalanyl-L-isoleucyl-D-Δ-piperazyl-L-Lysyl-N-Me-D-phenylalanyl-L-prolyl]

Using identical reaction conditions to those described in Example 125, c-[D-phenylalanyl-L-isoleucyl-D-Δ-piperazyl-L-lysyl-N-Me-D-phenylalanyl-L-prolyl] was converted to the title compound which was purified according to Method F utilizing 85:15:1.5 CH$_2$Cl$_2$/MeOH/concentrated NH$_4$OH; repurification (Method F) 80:20:2 CH$_2$Cl$_2$/MeOH/concentrated NH$_4$OH gave the analytical sample:

HPLC (Method I), >98% pure, RT=12.48 minutes.

FAB MS: 757 (M+).

NMR (DMSO-D$_6$): Spectrum confirmed structure of title compound and presence of solvent.

Elemental Analysis for C$_{41}$H$_{56}$N$_8$O$_6$.0.70CH$_2$Cl$_2$.0.4-0hexane: Calculated: C, 62.25; H, 7.46; N, 13.17. Found: C, 62.26; H, 7.48, N, 13.26.

EXAMPLE 175 c-[D-2-Trytophanyl-L-isoleucinyl-D-pipecolyl-L-piperazin-2-yl-(4-Cbz)-D-histidinyl(BOM)-L-prolyl]

The title compound was obtained from Boc-L-Pro-PAM-resin (1 mMole) using the procedure outlined in Example 1 and utilizing Boc-D-His(BOM) and the Fmoc derivatives of D-Trp, L-Pipe(4-Cbz), D-Pip,L-Ile. Step 7 was modified in the following manner: the fully assembled peptide-resin was suspended in a solution consisting of 30 mL of methanol and 5 mL of 95% hydrazine. The resulting suspension was stirred at ambient temperature for 30 minutes, filtered and concentrated under reduced pressure. The resin was then resuspended in 30 mL of methanol and treated with 20 mL of 95% hydrazine for 1 hour. Filtration of the suspension and repetition of this cycle yielded the crude product. The crude product was purified by Method C and the resulting azyl hydrazide was subjected to Step 8 in Example 1. The title compound was obtained in analytically pure form after purification (Method B): m.p. 145° C.

HPLC (Method G), 11.15 minutes, >96% pure at 214 nM.

NMR (DMSO-$D_6$): Spectrum confirmed structure of title compound and presence of solvent.

FAB MS: 1011 (M+ +H).

Elemental Analysis for $C_{55}H_{66}N_{10}O_9$.1.60dioxane.3.25TFA: Calculated: C, 53.64; H, 5.44; N, 9.21. Found: C, 53.58; H, 5.84, N, 9.48.

Amino Acid Analysis: His (1.00), Pro (1.04), Ile (0.95), Pip (1.14).

EXAMPLE 176 c-[D-Phenylalanyl-L-isoleucinyl-D-pipecolyl-L-piperazin-2-yl-D-histidinyl(BOM)-L-prolyl]

The title compound was obtained from c-[D-phenylalanyl-L-isoleucinyl-D-pipecolyl-L-piperazin-2-yl (4-Cbz)-D-histidinyl(BOM)-L-prolyl] using the procedure outlined in Example 73 with the following exception: 20% palladium hydroxide on carbon catalyst was used in place of 10% palladium on carbon catalyst. The title compound was obtained in analytically pure formm after chromatography (Method B): m.p. 185° C. (d).

HPLC (Method G) >96% pure, RT=8.58 minutes.

NMR (DMSO-$D_6$): Spectrum confirmed structure of title compound and presence of solvent.

FAB MS: 838 (M+).

Amino Acid Analysis: Pro (1.00), Pip (1.06), Ile (1.04), Phe (1.09), His($N^{im}$-Me) (1.09).

EXAMPLE 177 c-[D-Tryptophanyl-L-isoleucinyl-D-pipecolyl-L-piperazin-2-yl-D-histidinyl(BOM)-L-prolyl]

The title compound was obtained from c-[D-trytophanyl-L-isoleucinyl-D-pipecolyl-L-piperazin-2-yl (4-Cbz)-D-histidinyl(BOM)-L-prolyl] using the procedure outlined in Example 73 with the following exception: 20% palladium hydroxide on carbon catalyst was used in place of 10% palladium on carbon catalyst. The title compound was obtained in analytically pure form after chromatography (Method B): m.p. 185° C. (d).

HPLC (Method G) >99% pure, RT=8.96 minutes

NMR (DMSO-$D_6$): Spectrum confirmed structure of the title compound and the presence of solvent.

FAB MS: 877 (M+).

Elemental Analysis for $C_{47}H_{60}N_{10}O_7$.2.95TFA.4.55-$H_2O$: Calculated: C, 48.91; H, 5.59; N, 10.98. Found: C, 48.70; H, 5.22, N, 11.38.

EXAMPLE 178 c-[D-Phenylalany-L-isoleucinyl-D-pipecolyl-L-piperazin-2-yl-D-($N^{im}$methyl)histidinyl-L-prolyl]

The title compound was obtained from c-[D-phenylalanyl-L-isoleucinyl-D-pipecolyl-L-piperazin-2-yl-D-histidinyl (BOM)-L-proplyl] using the procedure outlined in Example 73 with the following exception: 20% palladium hydroxide on carbon catalyst was used in place of 10% palladium on carbon catalyst. The title compound was obtained in analytically pure form after chromatography (Method M):

HPLC (Method G) >97% pure, RT=8.56 minutes.

NMR (DMSO-$D_6$): Spectrum confirmed structure of the title compound and the presence of solvent.

FAB MS: 754 (M+ +H).

Elemental Analysis for $C_{38}H_{53}N_9O_6$.3.7TFA.2.0-$H_2O$: Calculated: C, 45.35; H, 5.03; N, 10.72. Found: C, 45.45; H, 5.28, N, 10.44.

Amino Acid Analysis: Pro (1.00), Pip (0.97), Ile (0.97), Phe (1.00), His(im-Me) (1.01).

EXAMPLE 179 c-[D-Phenylalanyl-L-isoleucinyl-D-pipecolyl-L-pipecolyl-D-($\beta$-t-butyl)aspartyl-L-prolyl]

The title compound was obtained from Boc-L-Pro-(Merrifield)-resin (1-mMole) using the procedure outlined in Example 1 and utilizing the amino acid derivatives Fmoc-D-Phe, Fmoc-L-Ile, Fmoc-D-Pip, Fmoc-L-Pip, and Boc-($\beta$-t-butyl) Asp. Step 7 was modified in the following manner: the fully assembled peptide-resin was suspended in a solution consisting of 10 mL of methanol and 10 mL of 95% hydrazine. The resulting suspension was stirred at ambient temperature for 2 hours, filtered and concentrated under reduced pressure. The crude hydrazide product (containing traces of hydrazine) was azeotropically dried with toluene (3 cycles) and subjected to Step 8 in Example 1. The crude product was purified (Method B) to give the title compound:

HPLC (Method C) >98% pure, at 214 nM,

FAB MS: 751 (M+ +H) 773 (M+ +Na).

NMR (DMSO-$D_6$): Spectrum confirmed structure of title compound and presence of solvent, Amino Acid Analysis: Asp (1.08), Pro (0.99), Pip (2×1.00), Phe (0.99), Ile (1.00).

EXAMPLE 180

C-[D-Tryptophanyl-L-isoleucinyl-D-pipecolyl-L-piperazin-2-yl (4-t-butylacetyl)-D-($N^\alpha$-Me)phenylalanyl-L-prolyl]

c-[D-Tryptophanyl-L-isoleucinyl-D-pipecolyl-L-piperazin-2-yl-D-($N^\alpha$-Me)phenylalanyl-L-prolyl] (50 mg, 0.064 mMole) was added to a suspension of potassium carbonate (13.8 mg, 0.10 mMole) in 1 mL of dry DMF. To this mixture was added t-butylbromoacetate (8 μL, 0.05 mMole) in one portion at room temperature,. The reaction mixture was stirred overnight, filtered and concentrated to dryness under pressure. The residue was purified by Method M to give the title compound in analytically pure form: m.p. 220° C. (d).

HPLC (Method G) 12.75 min, >98% pure, at 210 nM.

NMR (DMSO-$D_6$): Spectrum confirmed structure of title compound and presence of solvent.

MS FAB: 895 (M+).

Elemental Analysis for $C_{49}H_{66}N_8O_8$.2.50-$H_2O$.3.50TFA: Calculated: C, 52.45; H, 5.86; N, 8.74. Found: C, 52.43; H, 5.80; N, 9.04.

EXAMPLE 181 c-[D-Tryptophanyl-L-isoleucinyl-D-pipecolyl-L-piperazin-2-yl(4-carboxymethyl)-D-($N^\alpha$-Me)phenylalanyl-L-prolyl]

c-[D-Tryptophanyl-L-isoleucinyl-D-pipecolyl-L-piperazine-2-yl (4-t-butylacetyl)-D-($N^\alpha$-Me)phenylalanyl- L-prolyl] (40 mg) was dissolved in 10 mL of ethyl acetate. The solution was treated with four drops of ethanedithiol and cooled to −25° C. Hydrogen chloride gas was passed into the reaction mixture to the saturation point. The reaction mixture was allowed to warm to room temperature and was then concentrated to dryness under reduced pressure. The residual semisolid was purified according to Method M to give the title compound:

HPLC (Method G) @98% pure at 210 nM.

NMR (DMSO-$D_6$): Spectrum confirmed structure of the title compound and the presence of solvent.

MS FAB: 839 (M+).

Elemental Analysis for $C_{45}H_{58}N_8O_8$.1.00-$H_2O$.1.80TFA: Calculated: C, 54.95; H, 5.86; N, 10.55. Found: C, 54.95; H, 5.88; N, 10.33.

EXAMPLE 182 c-[D-Tryptophanyl(t-butylacetyl)-L-isoleucinyl-D-pipecolyl-L-piperazin-2-yl(4-t-butylacetyl)-D-($N^\alpha$-Me)-phenylalanyl-L-prolyl]

c-[D-Tryptophanyl-L-isoleucinyl-D-pipecolyl-L-piperazin-2-yl-D-($N^\alpha$-Me)Phenylalanyl-L-prolyl] (50 mg, 0.064 mMole) was added to a suspension of potassium carbonate (13.8 mg, 0.10 mMole) in 1 mL of dry DMF. To this mixture was added t-butylbromoacetate (8 μL, 0.05 mMole) in one portion at room temperature. The reaction mixture was stirred overnight, filtered and concentrated to dryness under reduced pressure. The residue was purified by Method M to give the title compound in analytically pure form:

HPLC (Method G) 12.75 min, >98% pure at 210 nM.

NMR (DMSO-$D_6$): Spectrum confirmed structure of the title compound and the presence of solvent.

MS FAB: 1010 (M++H).

EXAMPLE 183 c-[D-Tryptophanyl-L-isoleucinyl-D-pipecolyl-L-piperazin-2-yl(4-dibenzylphosphoramidyl)-D-($N^\alpha$-Me)-phenylalanyl-L-prolyl]

c-[D-Tryptophanyl-L-isoleucinyl-D-pipecolyl-L-piperazin-2-yl-D-($N^\alpha$-Me)phenylalanyl-L-prolyl].TFA salt (50 mg) was added to a solution of carbon tetrachloride (1.5 mL) and methylene chloride (1.0 mL) containing dibenzylphosphite, potassium carbonate (15 mg), potassium hydrogencarbonate (11.3 mg) and tetrabutylammonium bromide (0.8 mg). The reaction mixture was stirred at 20° C. for four hours with occasional cooling and then was allowed to stir at ambient temperature overnight. The reaction mixture was filtered and the filtrate was concentrated in vacuo to give a semi-solid which was purified according to Method M.

HPLC (Method G) >96% pure at 210 nM, RT=13.43 minutes.

NMR (DMSO-$D_6$): Spectrum confirmed structure of the title compound and the presence of solvent.

Elemental Analysis for $C_{57}H_{69}N_8O_9P$.0.50-$H_2O$.0.85TFA: Calculated: C, 61.46; H, 6.23; N, 9.77. Found: C, 61.46; H, 6.23; N, 9.71.

EXAMPLE 184 c-[D-Tryptophanyl-L-isoleucinyl-D-Δ-piperazyl-L-pipecolyl-D-histidyl-L-prolyl]

Following the experimental procedure set forth in Example 124 and utilizing the amino acids Boc-L-Pro-OBz, Boc-D-His(DNP), Fmoc-L-Pip, Fmoc-($N^\beta$-Cbz)-D-Piz, Fmoc-L-Ile, and Fmoc-D-Trp, the title cyclic hexapeptide was obtained as a solid after purification by Method E (methylenechloride-methanol-water-acetic acid, 90:10:2:1 v/v).

HPLC (Method I) >97% pure at 210 nM, RT = 1 59 minutes.

NMR (DMSO-$D_6$): Spectrum confirmed structure of the title compound and the presence of solvent.

FAB MS: 755 (M+).

Elemental Analysis for $C_{39}H_{50}N_{10}O_6$.1.0$H_2O$.1 0HOAc: Calculated: C, 59.12; H, 6.77; N, 16.81. Found C, 58.68; H, 6.60; N, 16.47.

EXAMPLE 185

Effect of the Compounds of Formula I on [$^3$H]OT and [$^3$H]AVP Receptor Binding The preferred compounds of Formula I are those which inhibited specific [$^3$H]OT binding in a concentration dependent manner.

Scatchard analysis of specific [$^3$H]OT receptor binding in the absence and presence of the compounds of Formula I competitively inhibited specific [$^3$H]OT receptor binding since the $K_D$ (dissociation constant) was increased without affecting the $B_{max}$ (maximum receptor number). A $K_i$ value (dissociation constant of inhibitor) of the compounds of Formula I was estimated.

Radioligand binding assays

The high affinity binding of [$^3$H]OT ([tyrosyl, 3,5-$^3$H]OT; 30–60 Ci/mmol; New England Nuclear, Boston, Mass.) to uterine OT receptors was based on an assay using a crude membrane preparation of uteri taken from diethylstilbestrol dipropionate (DES)-treated (0.3 mg/kg, ip; 18–24 hours) rats. Competition studies were conducted at equilibrium (60 minutes; 22° C.) using 1 nM [$^3$H]OT in the following assay buffer: 50 mM Tris-HCl, 5 mM $MgCl_2$, and 0.1% BSA, pH 7.4. Nonspecific binding (10% of the total binding) was determined using 1 μM unlabeled OT, and the binding reaction was terminated by filtration through glass fiber filters using a cell harvester (model 7019, Skatron, Inc., Sterling, Va.).

The measurement of [$^3$H]AVP ([phenylalanyl-3,4,5-$^3$H]AVP; 80–90 Ci/mmol; New England Nuclear) binding to a crude membrane preparation of male rat liver (AVP-$V_1$ sites) or kidney medulla (AVP-$V_2$ sites) was determined according to the method of Butlen et. al. [Butlen, D.; Guillon, G., Rajerson, R., Jard, S., Sawyer, W., Manning, M. Mol. Pharmacol. 14, 1006 (1978)]. Competition assays were conducted at equilibrium (30 minutes at 30° C.) using 1 nM [$^3$H]AVP (liver) or 2 nM [$^3$H]AVP (kidney) in the following assay buffer: 100 mM Tris-HCl, 5 mM $MgCl_2$, 0.1% BSA, 50 μM phenylmethylsulfonylfluoride, and 50 μg/ml bacitracin, pH 8.0. Nonspecific binding (5–10% of the total binding) was determined using 10 μM unlabeled AVP, and the binding reaction was terminated by filtration as described above for the [$^3$H]OT binding assay.

$K_i$ values were obtained for each compound from three to six separate determinations of the $IC_{50}$ values ($K_i = IC_{50}/1 + c/K_d$ using the $K_d$ values obtained from saturation binding assays: [$^3$H]OT (uterus), 0.7 nM; [$^3$H]AVP (liver), 0.4 nM; [$^3$H]AVP (kidney), 1.4 nM.

Functional assays in vitro

Antagonism of the contractile response of the isolated rat uterus to OT. Uterine horns removed from Sprague-Dawley rats treated 18 hours earlier with DES (0.25 mg/kg, ip) were mounted longitudinally in standard tissue baths (30° C.) containing a buffer solution (NaCl, 152 mM; KCl, 5.6 mM; CaCl$_2$, 0.4 mM; NaHCO$_3$ 6 mM; dextrose, 2.8 mM) and aerated continuously (95% O$_2$-5% CO$_2$). Tissues were connected to isometric force displacement transducers model UC-3 Gould Stattan, Inc, Oxnard, Calif. and placed under a tension of 1 g. Contraction of the longitudinal muscle layer was amplified and recorded on a polygraph (Hewlett-Packard 8805B amplifiers and 7758B recorder, Palo Alto, Calif.). A cumulative concentration-response curve was obtained using a 4-minute exposure at each concentration of OT. Once the maximum contraction (E$_{max}$) was attained, the tissues were washed repeatedly for 75 minutes, at which time antagonist or vehicle was added, and 45 minutes later a second concentration-response curve to OT was constructed. The concentration of OT producing 50% of E$_{max}$ before and after treatment was determined by regression analysis. Dose ratios (EC$_{50}$ after treatment/EC$_{50}$ before) were corrected, if indicated, by a factor derived from concurrent vehicle-treated tissues. The results were analyzed for competitiveness, and the apparent dissociation constant (K$_B$) was determined on a tissue by tissue basic using the equation: K$_B$=[antagonist]/(dose ratio−1).

Inhibition of AVP-V$_1$-stimulated phosphatidylinositol (P1) turnover and AVP-V$_2$-stimulated adenylate cyclase. Stimulation of P1 turnover in hepatocytes by AVP was estimated by measuring the accumulation of [$^3$H]inositol phosphates generated from [$^3$H]inositol. Hepatocytes were prepared from a male rat and incubated (90 minutes; 37° C.) in Krebs-Ringer bicarbonate (pH 7.4) containing about 0.6 μM [$^3$H]inositol ([2-N-$^3$H]myoinositol; 10–20 Ci/mmol; New England Nuclear). The labeled cells were preincubated (10 minutes; 37° C.) in Krebs-Ringer bicarbonate buffer-10 mM LiCl and then exposed (10 minutes; 37° C.) to a submaximal concentration (EC$_{70}$~10 nM) of AVP. Total [$^3$H]inositol phosphates were isolated by anion exchange chromatography. The basal rate of [$^3$H]inositol phosphate accumulation (~1300 cpm/10 minutes.8 mg dry wt) was stimulated a maximal 100–200% by AVP.

AVP-stimulated adenylate cyclase activity was measured using a crude membrane preparation of kidney medulla from male rats. The reaction was initiated by the addition of tissue to the following reaction mixture (final conditions): 50 mM Tris-HCl, 5 mM MgCl$_2$, 0.2 mM EGTA, 20 mM phosphocreatine, 40 U/ml creatine phosphokinase, 1 U/ml adenosine deaminase, 2 mM isobutylmethylxanthine, 0.1% BSA, and 250 μM/1 μCi [$^3$H]ATP (New England Nuclear). After 30-minutes incubation (37° C.), the newly formed [$^3$H]cAMP was purified and collected by HPLC. Basal adenylate cyclase activity (~20 pmol/minutes mg protein) was stimulated a maximal 200–300% by AVP (EC$_{70}$~2 nM).

The data of Table 6 were obtained for compounds of Formula I.

TABLE 6

| Compound of Example | Receptor Binding Results IC$_{50}$ (nM) | | |
|---|---|---|---|
| | [$^3$H]OT | [$^3$H]-AVP-V$_1$ | [$^3$H]-AVP-V$_2$ |
| 1 | 240 | 3,200 | 3,800 |
| 2 | >>10,000 | >>10,000 | >>10,000 |
| 3 | 88 | 7,300 | 19,000 |
| 4 | >10,000 | >10,000 | >>10,000 |
| 5 | 930 | >10,000 | >10,000 |
| 6 | 1,800 | >10,000 | >10,000 |
| 7 | 350 | >10,000 | >10,000 |
| 8 | 850 | >10,000 | >10,000 |
| 9 | >10,000 | >10,000 | >10,000 |
| 10 | | | |
| (isomer 1) | 1,000 | >>10,000 | >10,000 |
| (isomer 2) | 1,000 | >10,000 | 10,000 |
| 11 | 39% @ 10+ | >1,000 | >1,000 |
| 12 | 1.2 | >1,000 | >1,000 |
| 13 | 150 | >1,000 | >1,000 |
| 14 | 38 | 10,000 | >10,000 |
| 15 | >10,000 | >10,000 | >10,000 |
| 16 | 650 | >10,000 | >10,000 |
| 17 | 14 | 8,200 | 5,400 |
| 18 | 450 | >1,000 | >10,000 |
| 19 | 18 | 13,700 | 4,330 |
| 20 | 72 | >1,000 | >1,000 |
| 21 | 190 | 10,000 | >10,000 |
| 22 | 2,400 | >10,000 | >10,000 |
| 23 | 625 | >10,000 | >10,000 |
| 24 | 640 | >10,000 | 10,000 |
| 25 | 120 | 3,000 | 3,900 |
| 26 | 86% @ 1,000 | 10,000 | 10,000 |
| 27 | 79% @ 1,000 | 10,000 | 10,000 |
| 28 | 28% @ 100 | >10,000 | 10,000 |
| 29 | 32% @ 100 | >10,000 | >10,000 |
| 30 | 20 | 12,000 | 747 |
| 31 | 100 | >10,000 | >1,000 |
| 32 | >1,000 | >10,000 | >10,000 |
| 33 | 100 | >10,000 | >10,000 |
| 34 | 100 | >1,000 | 10,000 |
| 35 | >100 | 10,000 | 10,000 |
| 36 | >100 | >10,000 | 10,000 |
| 37 | >100 | 10,000 | >10,000 |
| 38 | 60% @ 100 | >1,000 | 10,000 |
| 39 | 28% @ 100 | >1,000 | >10,000 |
| 40 | 59% @ 100 | >1,000 | >1,000 |
| 41 | 100 | >1,000 | >1,000 |

TABLE 6-continued

| Compound of Example | Receptor Binding Results IC$_{50}$ (nM) | | |
|---|---|---|---|
| | [$^3$H]OT | [$^3$H]-AVP-V$_1$ | [$^3$H]-AVP-V$_2$ |
| 42 | 100 | >1,000 | >1,000 |
| 43 | 410 | >1,000 | >10,000 |
| 44 | 100 | 10,000 | 10,000 |
| 45 | 120 | >1,000 | 10,000 |
| 46 | 60% @ 100 | 10,000 | >1,000 |
| 47 | 620 | >1,000 | 10,000 |
| 48 | 250 | 10,000 | >10,000 |
| 49 | 320 | 10,000 | 10,000 |
| 50 | 310 | >10,000 | >1,000 |
| 51 | >10,000 | ND | ND |
| 52 | 3,400 | ND | ND |
| 53 | 2,600 | ND | ND |
| 54 | 3,000 | ND | ND |
| 55 | 2,500 | ND | ND |
| 56 | >10,000 | ND | ND |
| 57 | >10,000 | ND | ND |
| 58 | >10,000 | ND | ND |
| 59 | >1,000 | ND | ND |
| 60 | >10,000 | ND | ND |
| 61 | >10,000 | ND | ND |
| 62 | >1,000 | ND | ND |
| 63 | >10,000 | ND | ND |
| 64 | >10,000 | ND | ND |
| 65 | >10,000 | ND | ND |
| 66 | >10,000 | ND | ND |
| 67 | 10,000 | >10,000 | >10,000 |
| 68 | >>10,000 | ND | ND |
| 69 | 10,000 | ND | ND |
| 70 | >10,000 | ND | ND |
| 71 | >10,000 | ND | ND |
| 72 | >10,000 | ND | ND |
| 73 | >>10,000 | ND | ND |
| 74 | 4,400 | 10,000 | >10,000 |
| 75 | >10,000 | ND | ND |
| 76 | 460 | 9,300 | 10,600 |
| 77 | 240 | 10,000 | 12,300 |
| 78 | 300 | 7,900 | >10,000 |
| 79 | 1,700 | >10,000 | 10,000 |
| 80 | 10,000 | >10,000 | >>10,000 |
| 81 | 77 | >1,000 | >1,000 |
| 82 | 73 | 10,000 | 10,000 |
| 83 | 940 | 10,000 | 10,000 |
| 84 | >1,000 | 10,000 | >10,000 |
| 85 | 1,000 | >10,000 | 10,000 |
| 86 | 58% @ 1,000 | >10,000 | >10,000 |
| 87 | 62 | >10,000 | >1,000 |
| 88 | 18 | 5,780 | 1,000 |
| 89 | 35% @ 100 | >10,000 | >1,000 |
| 90 | 59% @ 100 | >10,000 | >10,000 |
| 91 | 93 | >10,000 | >1,000 |
| 92 | 7.7 | >10,000 | 750 |
| 93 | 42% @ 1,000 | >10,000 | >10,000 |
| 94 | 64% @ 1,000 | 10,000 | >10,000 |
| 95 | 36% @ 100 | >10,000 | >10,000 |
| 96 | 245 | 2,900 | ND |
| 97 | >10,000 | ND | ND |
| 98 | 7,700 | >10,000 | >10,000 |
| 99 | >10,000 | >>10,000 | >>10,000 |
| 100 | 5,080 | ND | ND |
| 101 | >10,000 | ND | ND |
| 102 | >10,000 | >10,000 | >>10,000 |
| 103 | 370 | 5,690 | >10,000 |
| 104 | 204 | 3,200 | 3,800 |
| 105 | >10,000 | >10,000 | >10,000 |
| 106 | 1,900 | >10,000 | >10,000 |
| 107 | >10,000 | ND | ND |
| 108 | 655 | 10,000 | 10,000 |
| 109 | 933 | >10,000 | >10,000 |
| 110 | 500 | >10,000 | >10,000 |
| 111 | 111 | 4,200 | 3,500 |
| 112 | 14.7 | 3,450 | 1,170 |
| 113 | >10,000 | 10,000 | >10,000 |
| 114 | 675 | >10,000 | >10,000 |
| 115 | 460 | >10,000 | 10,000 |
| 116 | 1,450 | >>10,000 | >10,000 |
| 117 | >10,000 | >10,000 | >10,000 |
| 118 | 345 | >10,000 | 10,000 |
| 119 | 260 | 7,300 | 3,100 |
| 120 | 120 | 10,000 | 10,000 |
| 121 | 270 | 10,000 | 10,000 |

TABLE 6-continued

| Compound of Example | Receptor Binding Results IC$_{50}$ (nM) | | |
|---|---|---|---|
| | [$^3$H]OT | [$^3$H]-AVP-V$_1$ | [$^3$H]-AVP-V$_2$ |
| 122 | 130 | >10,000 | 695 |
| 123 | 185 | 10,000 | 10,000 |
| 124 | 17.5 | 2,700 | 3,600 |
| 125 | 16 | 810 | 1,600 |
| 126 | 15 | >1,000 | 1,000 |
| 127 | 22 | 1,600 | 330 |
| 128 | 118 | 10,000 | 10,000 |
| 129 | 100 | 10,000 | 10,000 |
| 130 | 120 | >1,000 | >1,000 |
| 131 | 7.2 | 400 | 500 |
| 132 | 65 | >10,000 | 10,000 |
| 133 | 3,600 | 10,000 | 10,000 |
| 134 | 110 | >10,000 | 8,000 |
| 135 | 3,400 | 8,800 | 5,000 |
| 136 | 410 | >10,000 | 8,000 |
| 137 | 7.9 | 9,300 | 245 |
| 138 | 50% @ 100 | 10,000 | 42% @ 1,000 |
| 139 | 24% @ 100 | 8,000 | 8,000 |
| 140 | 13 | 9,000 | 84% @ 1,000 |
| 141 | 45 | 48% @ 1,000 | 78% @ 1,000 |
| 142 | 12% @ 1,000 | >10,000 | >10,000 |
| 143 | 68% @ 1,000 | >10,000 | >10,000 |
| 144 | 67% @ 1,000 | >10,000 | 10,000 |
| 145 | 9% @ 1,000 | >10,000 | 10,000 |
| 146 | 300 | 16,000 | 11,000 |
| 147 | 860 | 10,000 | 10,000 |
| 148 | 50% @ 1,000 | >10,000 | >10,000 |
| 149 | 53% @ 100 | >10,000 | 10,000 |
| 150 | 44 | 10,000 | 62% @ 1,000 |
| 151 | 10 | 390 | 82 |
| 152 | 130 | 10,000 | 10,000 |
| 153 | 48% @ 10 | 10,000 | 35% @ 1,000 |
| | lower R$_f$ 42 | 70% @ 10,000 | 73% @ 10,000 |
| | higher R$_f$ 10 | 77% @ 10,000 | >1,000 |
| 154 | 680 | 13,000 | 7,300 |
| 155 | 48% @ 100 | 10,000 | 30% @ 1,000 |
| 156 | 1,100 | >30,000 | >30,000 |
| 157 | lower R$_f$ 6% @ 1,000 | 13,000 | 26,000 |
| | higher R$_f$ 590 | 10,000 | >10,000 |
| 158 | 60% @ 10 | >1,000 | 68% @ 1,000 |
| 159 | 1.8 | 4,650 | 690 |
| 160 | 53% @ 10 | >1,000 | 66% @ 1,000 |
| 161 | 6.7 | N.D. | N.D. |
| 162 | 54% @ 100 | >10,000 | 10,000 |
| 163 | 49% @ 1,000 | >10,000 | >1,000 |
| 164 | 1,300 | 10,000 | >10,000 |
| 165 | 150 | 6,600 | 2,600 |
| 166 | 23,000 | >3,000 | >3,000 |
| 167 | 5% @ 1,000 | >>10,000 | >>10,000 |
| 168 | 34 | 10,000 | 54% @ 1,000 |
| 169 | 74% @ 10 | >10,000 | 10,000 |
| 170 | 3.1 | 6,850 | 175 |
| 171 | 3.9 | 15,000 | 335 |
| 172 | 20% @ 100 | >10,000 | >10,000 |
| 173 | 71 | 1,500 | 2,800 |
| 174 | 21 | 610 | 570 |
| 175 | 79% @ 1,000 | 54% @ 10,000 | 81% @ 10,000 |
| 176 | 80% @ 1,000 | 10,000 | 81% @ 10,000 |
| 177 | 76 | 16,000 | 12,000 |
| 178 | 77% @ 1,000 | >10,000 | >10,000 |
| 179 | 63% @ 1,000 | >10,000 | >10,000 |
| 180 | 150 | 44% @ 10,000 | 79% @ 10,000 |
| 181 | 100 | >10,000 | 73% @ 10,000 |
| 182 | 56% @ 1,000 | >>10,000 | >10,000 |
| 183 | 58% @ 100 | >>10,000 | 71% @ 10,000 |
| 184 | 6.0 | 3,980 | 1,050 |

ND = Not determined.
+Defined as the percent inhibition of radioligand at the given concentration.

What is claimed is:
1. A compound having the formula:

123

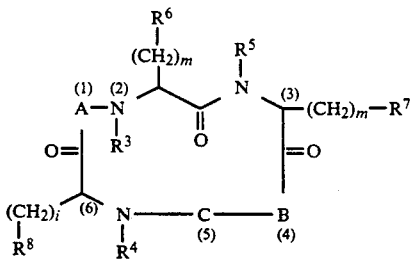

wherein:

A is glycine, N-methylglycine, alanine, N-methylalanine, serine,

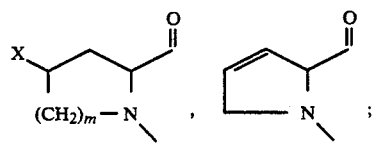

with the proviso that if X=NH$_2$ or OH, then m≠0;

B is

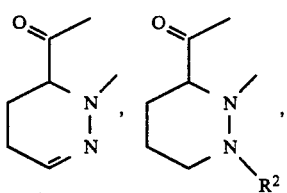

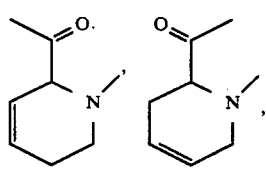

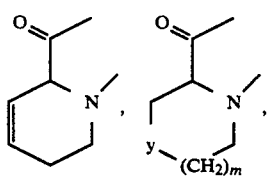

alanine, N-methylalanine, proline, serine, threonine, trans-4-hydroxyproline, cis-4-hydroxyproline, asparagine, aspartic acid, glutamic acid, glutamine, lysine, arginine, histidine, ornithine, cyclohexylalanine, ornithine-δ-tert-butyloxycarbonyl;

C is

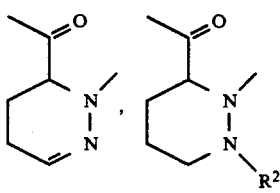

124

-continued

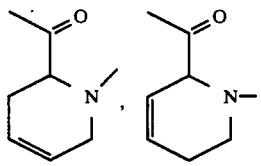

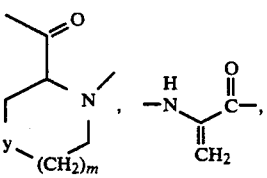

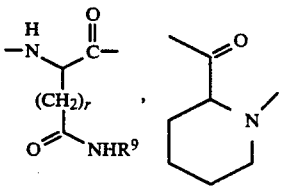

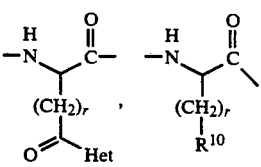

alanine, N-methylalanine, proline, threonine, trans-4-hydroxyproline, cis-4-hydroxyproline, histidine, cyclohexylalanine, ornithine-δ-tert-butyloxycarbonyl, wherein Het is an unsubstituted or mono- or disubstituted 1-pyrrolidinyl, 1-piperidinyl, 4-morpholinyl, 2-, 3-, and 4-pyridyl, and 1- and 4-piperazinyl, and the substituent(s) is (are) independently selected from the group consisting of hydroxyl, C1-C6-alkyl, CF$_3$, C1-C4-alkoxy, halo, amino, mono- or di-C1-C4-alkylamino, CO$_2$H, CO$_2$-C1-C4-alkyl;

R$^1$ is hydrogen, glycyl, trifluoromethylsulfonyl, methanesulfonyl, acetyl, benzyl;

R$^2$ is hydrogen, methyl, carboxymethyl, benzyloxycarbonyl;

R$^3$, R$^4$ and R$^5$ are the same or different and are independently selected from the group consisting of: hydrogen, methyl, ethyl, propyl, allyl, dihydroxypropyl, carboxymethyl;

R$^6$ is hydrogen, phenyl, styryl, aminopropyl, 2-pyridyl, 3-pyridyl, 4-pyridyl, 4-aminophenyl, 4-imidazolyl, 3-indolyl, 2-benzothienyl, 3-benzothienyl, mono or disubstituted phenyl where the substitutents is (are) independently chosen from the group consisting of: C$_1$-C$_4$-alkyl, fluoro, chloro, bromo, iodo, C$_1$-C$_4$-alkoxy, hydroxyl, benzyloxy, phenyl, phenoxy, amino, mono- or di-C$_1$-C$_4$-alkylamino, nitro, cyano, aminomethyl, mono- or di-C$_1$-C$_4$-alkylaminomethyl, or methylenedioxy; 1-naphthyl, 2-naphthyl, substituted 1- or 2-naphthyl where the substituent(s) is (are) selected from the group consisting of: fluoro, chloro, bromo, iodo, C$_1$-C$_4$-alkyl, hydroxyl, C$_1$-C$_4$-alkoxy, benzyloxy, phenyl, phenoxy, nitro, or cyano; substituted 3-indolyl where the substituent when connected to carbon is selected from the group consisting of: C$_1$-C$_4$-alkyl, C$_1$-C$_4$-alkoxy, fluoro, chloro, boromo, iodo, hydroxyl, cyano, nitro, and when connected to nitrogen the substituent is selected from the group consisting of: formyl, acetyl, benzoyl, benzyl, or $C_1$-$C_4$ alkyl;

$R^7$ is hydrogen, 2-propyl, 2-butyl, 1-butyl, 1-propyl, cyclohexyl, cyclopentyl, phenyl, 4-benzyloxyphenyl, 4-hydroxyphenyl, 4-tert-butyloxy-carbonyloxy-phenyl, 4-tert-butyloxyphenyl, 1-benzyloxy-ethyl, 1-tert-butyloxyethyl, 1-hydroxyethyl, hydroxymethyl;

$R^8$ is hydrogen, hydroxyl, sulfhydryl, 3-indolyl, 4-imidazolyl, phenyl, naphthyl, aminopropyl, N-(benzyloxycarbonyl)aminopropyl, N-(2-chlorobenzyloxycarbonyl)aminopropyl guanidylethyl, guanidylpropyl 2-pyridyl, 3-pyridyl, 4-pyridyl, 1-methyl-4-imidazolyl, 1-benzyloxymethyl-4-imidazolyl, 1-methyl-5-imidazolyl, (1,3-dimethyl-5-imidazolyl)$^+$Z$^-$-S-benzyl

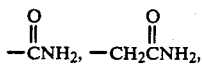

—$CO_2R^9$, —$CH_2CO_2R^9$; mono- or disubstituted phenyl where the substitutent(s) is (are) selected from the group consisting of: $C_1$-$C_4$ alkyl, hydroxyl, $C_1$-$C_4$-alkoxy, benzyloxy, nitro, amino, mono-or di- $C_1$-$C_4$-alkylamino, 1-pyrrolidinyl, cyano, aminomethyl, mono- or di-$C_1$-$C_4$-alkylamino, (N,N-dimethylglycl)amino, fluoro, chloro, bromo, iodo, 2-(4-morpholinyl)ethoxy;

$R^9$ is hydrogen, $(CH_2)_qNH_2$,

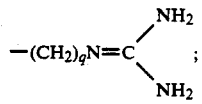

—$(CH_2)_q$—$NH(C_1$-$C_5$ alkyl), —$(CH_2)_q$—$N(C_1$-$C_5$ alkyl)$_2$, —$(CH_2)_q$-Het
(where Het is as defined above),

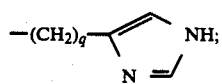

$R^{10}$ is amino, NH-t-butyloxycarbonyl, NH-benzyloxycarbonyl, NH-fluorenyloxycarbonyl, NH($C_1$-$C_5$)alkyl, N($C_1$-$C_5$alkyl)$_2$, N$^+$($C_1$-$C_5$alkyl)$_3$ Z$^-$, guanidyl, N-1-methylquinuclidinium-3-carbonyl Z-, Het (where Het is defined as 1-pyrrolidinyl, 1-piperidinyl, 4-morpholinyl, 2-, 3-, and 4-pyridyl, 1-piperazinyl, 4-($C_1$-$C_5$-alkyl) piperazinyl,

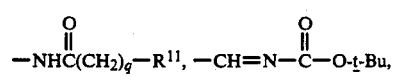

—$CO_2H$, —OH, —SH,

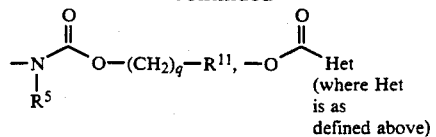

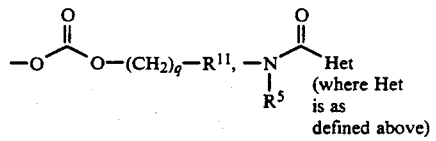

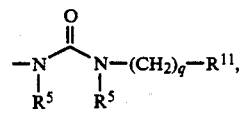

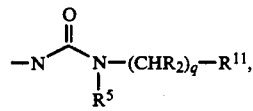

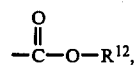

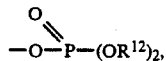

—$OSO_3H$,

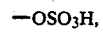

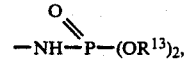

$R^{11}$ is carboxyl, amino, ($C_1$-$C_5$)alkylamino, di($C_1$-$C_5$)alkylamino, tri($C_1$-$C_5$)alkylamino Z, guanidyl;
$R^{12}$ is hydrogen, ($C_1$-$C_5$)alkyl, benzyl, phenyl
$R^{13}$ is ($C_1$C-$C_5$)alkyl, benzyl, phenyl
X is hydrogen, NHR$^1$, OR$^1$;
Y is $CH_2$, NR$^2$; S, SO, $SO_2$,

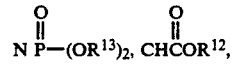

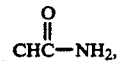

CH—$(CH_2)_r$—$NH_2$,

CH—$(CH_2)_r$—NH ,
  |
  ($C_1$-$C_5$alkyl)

CH—$(CH_2)_i$; —N ,
  |
  ($C_1$-$C_5$alkyl)$_2$

CH—$(CH_2)_r$-Het(where Het is as defined above)

Z is chloride, bromide, sulfate, sulfamate, phosphate, nitrate, and the like; acetate, propionate, succinate, glycolate, sterate, lactate, malate, tartrate, citrate, ascorbate, pamote, maleate, hydroxymaleate, phenyl acetate, glutamate, benzoate, salicylate, sulfanilate, 2-acetoxybenzoate, fumarate, toluenesulfonate, methanesulfonate, trifluoromethanesulfonate, ethane disulfonate, oxalate, isethionate, and the like;

i is 1 or 2;
m is 0, 1, or 2;
q is 2 or 3;
r is 1 to 5;
with the proviso that C and B cannot be simultaneously

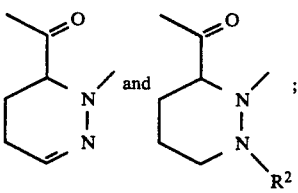

and the pharmaceutically acceptable salts thereof.

2. A compound of claim 1 wherein:
A is glycine, alanine, N-methylalanine, serine,

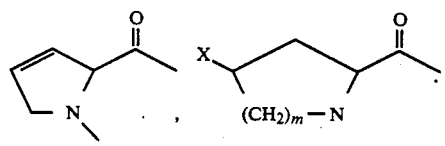

with the proviso that if X=NH$_2$ or OH, then m≠0;
B is

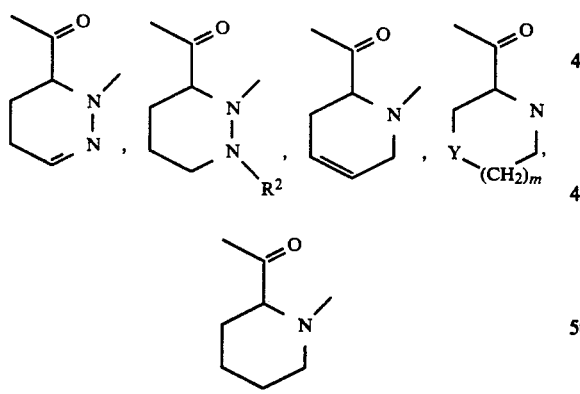

alanine, N-methylalanine, proline, serine, trans-4-hydroxyproline, c is -4-hydroxyproline, asparagine, glutamine, histidine, ornithine, cyclohexylalanine, ornithine -α-tert-butyloxycarbonyl;
C is

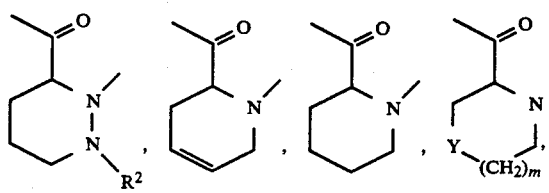

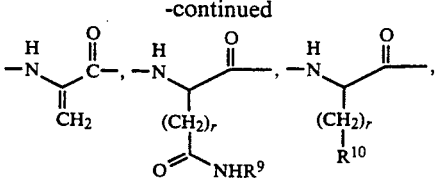

alanine, N-methylalanine, proline, serine, threonine, trans-4-hydroxyproline, cis-4-hydroxyproline, histidine, ornithine, cyclohexylalanine, -α-tert-butyloxycarbonyl;

R$^1$ is hydrogen, N-benzyloxycarbonylglycyl, methanesulfonyl, acetyl, benzyl;

R$^2$ is hydrogen, benzyloxycarbonyl;

R$^3$, R$^4$, and R$^5$ are the same or different and are independently selected from the group consisting of hydrogen, methyl, allyl;

R$^6$ is hydrogen, phenyl, 3-pyridyl, 4-imidazolyl, 3-indolyl, monosubstituted phenyl where the substituent is chosen from the group consisting of: hydroxyl, benzyloxy, methoxy, ethyloxy; 1-naphthyl, 2-naphthyl; substituted 3-indolyl where the substituent when connected to nitrogen is methyl and when connected to carbon is selected from the group consisting of methyl, methoxy, fluoro;

R$^7$ is hydrogen, 2-propyl, 2-butyl, cyclohexyl, phenyl, 4-benzyloxyphenyl, 4-hydroxyphenol;

R$^8$ is hydrogen, hydroxyl, 3-indolyl, 4-imidazolyl, phenyl, aminopropyl, N-(benzyloxycarbonyl)aminopropyl, N-(2-chlorobenzyloxycarbonyl)aminopropyl, 3-pyridyl, 1-methyl-4-imidazolyl, 1-benzyloxymethyl-4-imidazolyl, 1-methyl-5-imidazolyl, (1,3-dimethyl-5-imidazolyl)+Z-,

—S-benzyl,

—CO$_2$R$^9$, monosubstituted phenyl where the substituent is selected from the group consisting of: hydroxyl, benzyloxy, nitro, amino, (N,N-dimethylglycyl)amino, 2-(4-morpholinyl)ethoxy;

R$^9$ is hydrogen, (CH$_2$)$_q$NH$_2$,

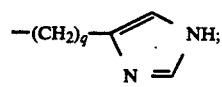

R$^{10}$ is amino, guanidyl, NH-t-butyloxycabonyl, NH-benzyloxycarbonyl, NH-(1-methylquinuclidinim-3-carbonyl)+Z-, —CH=N-t-butyloxycarbonyl, —CO$_2$R$^{12}$;

R$^{12}$ is hydrogen, t-butyl;
R$^{13}$ is benzyl;
X is hydrogen, NHR$^1$, OR$^1$;
Y is CH$_2$, NR$^2$,

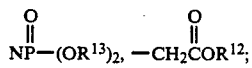

Z is chloride, citrate, maleate, trifluoromethanesulfonate, acetate;
i is 1 or 2
m is 0, 1, or 2;
q is 2 or 3;
and the pharmaceutically accepted salts thereof.
3. A compound of claim 2 wherein:
A is

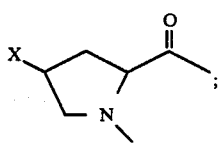

B is

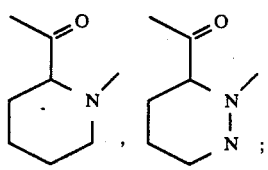

C is

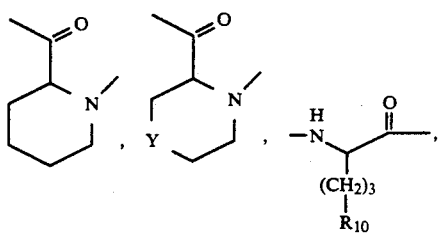

R² is hydrogen;
R³ and R⁵ is hydrogen
R⁴ is methyl
R⁶ is phenyl, 3-indolyl, 2-naphthyl;
R⁷ is 2-butyl;
R⁸ is 4-imidazolyl, phenyl;
R¹⁰ is amino, guanidyl;
X is hydrogen;
Y is NR²;
and the pharmaceutically accepted salts thereof.
4. The compounds of claim 2 which are:
Cyclo-[D-Phenylalanyl-L-isoleucyl-D-pipecolyl-L-pipecolyl-D-(Nα-methyl)-phenylalanyl-L-prolyl];
Cyclo[D-alanyl-L-isoleucyl-D-pipecolyl-L-pipecolyl-D-phenylalanyl-L-prolyl];
Cyclo[D-phenylalanyl-L-isoleucyl-D-pipecolyl-L-pipecolyl-D-histidyl-L-prolyl];
Cyclo[D-histidyl-L-isoleucyl-D-pipecolyl-L-pipecolyl-D-(Nα-methyl)-phenylalanyl-L-prolyl];
Cyclo[D-phenyalanyl-L-isoleucyl-D-pipecolyl-L-pipecolyl-D-(Nαmethyl)alanyl-L-prolyl];
Cyclo[D-phenyalanyl-L-isoleucyl-D-pipecolyl-L-(Nα-methyl)alanyl-D-(NαMethyl)phenylanyl-L-prolyl];
Cyclo[D-phenylalanyl-L-isolelucyl-D-pipecolyl-L-propyl-D-(NαMethyl)phenylanyl-L-prolyl];
Cyclo[D-Phenylalanyl-L-isoleucyl-D-(Nαmethyl)alanyl-L-pipecolyl-D-(Nαmethyl)phenylanyl-L-prolyl];
Cyclo[D-phenylalanyl-L-alanyl-D-pipecolyl-L-pipecolyl-D(Nαmethyl)phenylalanyl-L-prolyl];
Cyclo[D-phenylalanyl-L-isoleucyl-D-pipecolyl-L-pipecolyl-DL-3-pyridylalanyl-L-prolyl];
Cyclo[D-a-naphthalalanyl-L-isoleucyl-D-pipecolyl-L-pipecolyl-D-histidyl-L-prolyl];
Cyclo[D-2-naphthalalanyl-L-isoleucyl-D-pipecolyl-L-pipecolyl-D-histidyl-L-prolyl];
Cyclo[D-phenylalanyl-L-isoleucyl-D-pipecolyl-L-histidyl-D-(NαMethyl)phenylalanyl-L-prolyl];
Cyclo[D-phenylalanyl-L-isoleucyl-D-piperazyl-L-pipecolyl-D-histidyl-L-prolyl];
C-[D-(Nαmethyl)phenylalanyl-L-(Nαmethyl)isoleucyl-D-pipecolyl-L-pipecolyl-D-(Nαmethyl)phenylalanyl-L-prolyl];
C-[D-(Nαmethyl)alanyl-L-(Nαmethyl)isoleucyly-D-pipecolyl-L-pipecolyl-D-(Nαmethyl)phenylalanyl-L-prolyl];
C-[D-tryptophanyl-L-isolelucyl-D-pipecolyl-L-pipecolyl-D-histidyl-L-prolyl];
Cyclo[D-tryptophanyl-L-isoleucyl-D-pipecolyl-L-pipecolyl-D-[im-(CH₃)₂]⁺histidyl-L-prolyl]trifluoroacetate;
Cyclo[D-tryptophanyl-L-isoleucyl-D-pipecolyl-L-pipecolyl-D-(Nαmethyl)histidyl-L-prolyl];
Cyclo[D-tryptophanyl-L-Norleucyl-D-pipecolyl-L-pipecolyl-D-histidyl-L-prolyl];
Cyclo[D-tryptophanyl-L-leucyl-D-pipecolyl-L-pipecolyl-D-histidyl-L-prolyl];
Cyclo[D-Phenylalanyl-L-isoleucyl-D-pipecolyl-D-(3,4-Dehydro)-pipecolyl-D-(Nαmethyl)phenylalanyl-L-Prolyl];
Cyclo[D-phenylanyl-L-isoleucyl-D-pipecolyl-L-(3,4-dehydro)-pipecolyl-D-(Nαmethyl)phenylanyl-L-prolyl];
Cyclo[D-phenylanyl-L-isoleucyl-D-(3,4-dehydro)-pipecolyl-L-pipecolyl-D-(Nαmethyl)phenylanyl-L-prolyl];
Cyclo[D-phenylalanyl-L-isoleucyl-D-pipecolyl-L-pipecolyl-D-trytophanyl-L-prolyl];
Cyclo[D-phenylalanyl-L-isoleucyl-D-pipecolyl-L-pipecolyl-D-(2-chlorocarbobenzyloxy)-lysyl-L-prolyl];
Cyclo[D-phenylalanyl-L-isoleucyl-D-pipecolyl-L-pipecolyl-D-(carbobenzyloxy)-ornithyl-L-prolyl];
Cyclo[D-phenylalanyl-L-isoleucyl-D-pipecolyl-L-pipecolyl-D-(Nαmethyl-O-Benzyl)-tyrosyl-L-prolyl];
Cyclo[D-tryptophanyl-L-isoleucyl-D-pipecolyl-L-(carbobenzyloxy)lysyl-D-tryptophanyl-L-prolyl];
Cyclo[D-tryptophanyl-L-isoleucyl-D-pipecolyl-L-pipecolyl-D(Nαmethyl)phenylalanyl-L-prolyl];
Cyclo[D-Tryptophanyl-L-phenylalanyl-D-pipecolyl-L-pipecolyl-D-(Nα-methyl)phenylalanyl-L-prolyl];
Cyclo[D-trytophanyl-L-homophenylalanyl-D-pipecolyl-L-pipecolyl-D-(Nαmethyl)phenylalanyl-L-prolyl];
Cyclo[D-tryptophanyl-L-isoleucyl-D-pipecolyl-L-pipecolyl-D-(Nαmethyl-O-benzyl)tyrosyl-L-prolyl];
Cyclo[D-trytophanyl-L-isoleucyl-D-pipecolyl-L-(carbobenzyloxy)ornithyl-D-(Nαmethyl)phenylalanyl-L-prolyl];
Cyclo[D-tryptophanyl-L-isoleucyl-D-pipecolyl-L-(carbobenzyloxy)lysy--D-(NαMethyl)phenylalanyl-L-prolyl];

Cyclo[D-tryptophanyl-L-isoleucyl-D-pipecolyl-L-(carbobenzyloxy)ornithinyl-D-trytophanyl-L-prolyl];
Cyclo[D-Phenylalanyl-L-isoleucyl-D-pipecolyl-L-(carbobenzyloxy)lysyl-D-histidyl-L-prolyl];
Cyclo[D-tryptophanyl-L-isoleucyl-D-pipecolyl-L-(carbobenzyloxy)lysyl-D-histidyl-L-prolyl];
Cyclo[D-phenylalanyl-L-isoleucyl-D-pipecolyl-L-pipecolyl-D-ornithyl-L-prolyl];
Cyclo[D-tryptophanyl-L-isoleucyl-D-pipecolyl-L-ornithyl-D-(N$^\alpha$Methyl)phenylalanyl-L-prolyl];
Cyclo[D-tryptophanyl-L-isoleucyl-D-pipecolyl-L-ornithyl-D-tryptophanyl-L-prolyl];
Cyclo[D-tryptophanyl-L-isoleucyl-D-pipecolyl-L-lysyl-D-tryptophanyl-L-prolyl];
Cyclo[D-phenylalanyl-L-isoleucyl-D-pipecolyl-L-pipecolyl-D-lysyl-L-prolyl];
Cyclo[D-tryptophanyl-L-isoleucyl-D-pipecolyl-L-lysyl-D-histidyl-L-prolyl];
Cyclo[D-phenylalanyl-L-isoleucyl-D-pipecolyl-L-lysyl-D-histidyl-L-prolyl];
Cyclo[D-phenylalanyl-L-isoleucyl-D-pipecolyl-L-pipecolyl-D-(N$^\alpha$Methyl)tyrosyl-L-prolyl];
Cyclo[D-phenylalanyl-L-isoleucyl-D-pipecolyl-L-pipecolyl-D(p-nitro)phenylalanyl-L-prolyl];
Cyclo[D-phenylalanyl-L-isoleucyl-D-pipecolyl-L-pipecolyl-D-(p-amino)phenylalanyl-L-prolyl];
Cyclo[D-phenylalanyl-L-isoleucyl-D-pipecolyl-L-pipecolyl-D-([N,N-dimethylglycyl]p-amino)-phenylalanyl-L-prolyl];
Cyclo[D-phenylalanyl-L-isoleucyl-D-pipecolyl-L-pipecolyl-D-(N$^\alpha$methyl-O-2-(morpholin-4-yl)ethyl))-tyrosyl-L-prolyl];
c-[D-Phenylalanyl-L-isoleucyl-D-alanyl-L-alanyl-D-phenylalanyl-L-prolyl];
c-[D-Phenylalanyl-L-isoleucyl-D-prolyl-L-prolyl-N-methyl-D-phenylalanyl-L-prolyl];
c-[D-Phenylalanyl-L-isoleucyl-D-prolyl-L-prolyl-D-phenylalanyl-L-prolyl];
c-[D-Phenylalanyl-L-isoleucyl-N-methyl-D-alanyl-N-methyl-L-alanyl-D-phenylalanyl-L-prolyl];
c-[D-Cyclohexylalanyl-L-isoleucyl-D-prolyl-D-phenylalanyl-L-prolyl];
c-[D-Phenylalanyl-L-cyclohexylalanyl-D-prolyl-L-prolyl-D-phenylalanyl-L-prolyl];
c-[D-Phenylalanyl-L-isoleucyl-D-prolyl-L-prolyl-D-$\alpha$-glutaminyl-glycyl];
c-[D-Phenylalanyl-L-isoleucyl-D-prolyl-L-prolyl-D-cysteinyl(Acm)-L-prolyl];
c-[D-Phenylalanyl-L-isoleucyl-D-prolyl-L-prolyl-D-cysteinyl(Bzl)-L-prolyl];
c-[L-Phenylalanyl-D-isoleucyl-L-prolyl-D-prolyl-L-phenylalanyl-D-prolyl];
c-[D-Phenylalanyl-L-isoleucyl-D-prolyl-L-prolyl-D-threoninyl(Bzl)-L-prolyl];
c-[D-Phenylalanyl-L-isoleucyl-D-prolyl-L-prolyl-D-threoninyl-L-prolyl];
c-[D-Phenylalanyl-L-phenylglycyl-D-prolyl-L-prolyl-D-phenylalanyl-L-prolyl];
c-[D-Phenylalanyl-L-prolyl-D-prolyl-L-prolyl-D-phenylalanyl-L-prolyl];
c-[D-Phenylalanyl-L-isoleucyl-D-cyclohexyglycyl-L-cyclohexylglycyl-D-phenylalanyl-L-prolyl];
c-[D-Phenylalanyl-L-isoleucyl-D-prolyl-L-prolyl-D-$\alpha$-glutaminyl-glycyl];
c-[D-Phenylalanyl-L-cyclohexylglycyl-D-prolyl-L-prolyl-D-phenylalanyl-L-prolyl];
c-[D-Phenylalanyl-L-isoleucyl-D-prolyl-L-prolyl-D-$\alpha$-glutaminyl-L-prolyl];
c[D-Phenylalanyl-L-isoleucyl-D-histidinyl-L-histidinyl-D-phenylalanyl-L-prolyl];
c-[D-Phenylalanyl-L-isoleucyl-D-phenylglycinyl-L-phenylglycinyl-D-phenylalanyl-L-prolyl];
c-[D-Phenylalanyl-L-isoleucyl-D-prolyl-L-transhydroxyprolyl-D-phenylalanyl-L-prolyl];
c-[D-Phenylalanyl-L-(O-benzyl)-threoninyl-D-prolyl-L-prolyl-D-phenylalanyl-L-prolyl];
c-[D-Phenylalanyl-L-threoninyl-D-prolyl-L-prolyl-D-phenylalanyl-L-prolyl];
c-[D-Phenylalanyl-L-isoleucinyl-D-prolyl-L-cis-hydroxyprolyl-D-phenylalanyl-L-prolyl];
c-[D-Phenylalanyl-L-isoleucinyl-D-prolyl-cis-D-hydroxyprolyl-D-phenylalanyl-L-prolyl];
c-[D-Phenylalanyl-L-isoleucinyl-D-pipecolyl-D-piperazin-2-yl(4-Cbz)-D-phenylalanyl-L-prolyl];
c-[D-Phenylalanyl-L-isoleucinyl-D-pipecolyl-L-piperazin-2-yl(4-Cbz)-D-phenylalanyl-L-prolyl];
c-[D-Phenylalanyl-L-isoleucinyl-D-pipecolyl-D-piperazin-2-yl-D-phenylalanyl-L-prolyl];
c-[D-Phenylalanyl-L-isoleucinyl-D-piperazin-2-yl(4-Cbz)-L-piperazin-2-yl(4-Cbz)-D-phenylalanyl-L-prolyl];
c-[D-Phenylalanyl-L-isoleucinyl-D-piperazin-2-yl-L-piperazin-2-yl-D-phenylalanyl-L-prolyl];
c-[D-Phenylalanyl-L-isoleucinyl-D-pipecolyl-L-piperazin-2-yl(4-Cbz)-D-histidinyl-L-prolyl];
c-[D-Phenylalanyl-L-isoleucinyl-D-pipecolyl-L-piperazin-2-yl(4-Cbz)-D-histidinyl-L-prolyl];
c-[D-Phenylalanyl-L-isoleucinyl-D-piperazin-2-yl-(4-Cbz)-L-pipecolyl-D-phenylalanyl-L-prolyl];
c-[D-Phenylalanyl-L-isoleucinyl-D-piperazin-2-yl-L-pipecolyl-D-phenylalanyl-L-prolyl];
c-[Phenylalanyl-L-isoleucinyl-D-piperazin-2-yl(4-Cbz)-D-piperazin-2-yl(4-Cbz)-D-(N$^\alpha$-methyl)phenylalanyl-L-prolyl];
c-[D-Phenylalanyl-L-isoleucinyl-D-piperazin-2-yl-(4-Cbz)-L-piperazin-2-yl(4-Cbz)-D-(N$^\alpha$-methyl)-phenylalanyl-L-prolyl];
c-[D-Tryptophanyl-L-isoleucinyl-D-pipecolyl-L-piperazin-2-yl-D-phenylalanyl-L-prolyl];
c-[D-Tryptophanyl-L-isoleucinyl-D-pipecolyl-L-piperazin-2-yl-D-tryptophanyl-L-prolyl];
c-[D-Tryptophanyl-L-isoleucinyl-D-pipecolyl-L-piperazin-2-yl(4-Cbz)-D-phenylalanyl-L-prolyl];
c-[D-Tryptophanyl-L-isoleucinyl-D-pipecolyl-D-piperazin-2-yl(4-Cbz)-D-phenylalanyl-L-prolyl];
c-[D-Tryptophanyl-L-isoleucinyl-D-pipecolyl-D-piperazin-2-yl(4-Cbz)-D-(N$^\alpha$-methyl)phenylalanyl-L-prolyl];
c-[D-Tryptophanyl-L-isoleucinyl-D-pipecolyl-L-piperazin-2-yl-D-(N$^\alpha$-methyl)phenylalanyl-L-prolyl];
c-[D-Phenylalanyl-L-isoleucinyl-D-pipecolyl-D-piperazin-2-yl(4-Cbz)-L-(BOM)histidyl-L-prolyl];
c-[D-Tryptophanyl-L-isoleucinyl-D-prolyl-L-histidyl-D-histidyl-L-prolyl];
c-[D-Tryptophanyl-L-isoleucinyl-D-prolyl-L-ornithinyl-(Cbz)-D-histidyl-L-prolyl];
c-[L-prolyl-D-phenylalanyl-L-isoleucyl-D-piperazyl-L-piperazyl-D-phenylalanyl];
c-[D-Lysyl-L-isoleucyl-D-piperazyl-L-piperazyl-D-phenylalanyl-L-prolyl];
c-[D-Phenylalanyl-L-isoleucyl-L-threonyl-L-asparagyl-D-phenylalanyl-L-prolyl];
c-[D-(O-Ethyl)-tyrosyl-L-isoleucyl-D-(O-tert-butyl)-threonyl-L-asparagyl-D-phenylalanyl-L-prolyl];
c-[D-Phenylalanyl-L-isoleucyl-L-glutamyl-L-asparagyl-D-phenylalanyl-L-prolyl];

c-[D-(O-Ethyl)-tyrosyl-D-isoleucyl-D-glutamyl-L-asparagyl-D-phenylalanyl-L-prolyl];
c-[D-Phenylalanyl-L-isoleucyl-D-glutamyl-L-asparagyl-D-phenylalanyl-L-prolyl];
c-[D-Phenylalanyl-L-isoleucyl-D-pipecolyl-L-pipecolyl-D-phenylalanyl-L-prolyl];
c-[D-Phenylalanyl-L-isoleucyl-D-pipecolyl-L-pipecolyl-D-N-methyl-phenylalanyl-L-prolyl];
c-[D-Phenylalanyl-N-methyl-L-isoleucyl-D-pipecolyl-L-pipecolyl-N-methyl-D-phenylalanyl-L-prolyl];
c-[D-Phenylalanyl-L-(O-tert-butyl)-threonyl-D-pipecolyl-L-pipecolyl-D-N-methyl-phenylalanyl-L-prolyl];
c-[D-Phenylalanyl-L-isoleucyl-D-(N$^\delta$-Boc)-ornithyl-L-pipecolyl-N-methyl-D-phenylalanyl-L-prolyl];
c-[D-phenylalanyl-L-isoleucyl-D-pipecolyl-L-pipecolyl-N-methyl-D-phenylalanyl-L-pipecolyl];
c-[D-phenylalanyl-L-isoleucyl-D-pipecolyl-L-pipecolyl-N-methyl-D-phenylalanyl-N-methyl-L-alanyl];
c-[D-Phenylalanyl-L-isoleucyl-D-prolyl-L-pipecolyl-N-methyl-D-phenylalanyl-L-prolyl];
c-[D-Phenylalanyl-L-isoleucyl-D-piperazyl-L-pipecolyl-N-methyl-D-phenylalanyl-L-prolyl];
c-[D-Phenylalanyl-L-isoleucyl-D-$\Delta$-piperazyl-L-pipecolyl-N-methyl-D-phenylalanyl-L-prolyl];
c-[D-Phenylalanyl-L-isoleucyl-D-ornithyl-L-pipecolyl-N-methyl-D-phenylalanyl-L-prolyl];
c-[D-Phenylalanyl-L-isoleucyl-D-prolyl-L-seryl-N-methyl-D-phenylalanyl-L-prolyl];
c-[D-Phenylalanyl-L-isoleucyl-D-pipecolyl(O-tert-butyl)-L-aspartyl-N-methyl-D-phenylalanyl-L-prolyl];
c-[D-Phenylalanyl-L-isoleucyl-D-pipecolyl-L-aspartyl-N-methyl-D-phenylalanyl-L-prolyl];
c-[D-Phenylalanyl-L-isoleucyl-D-prolyl-dehydroalanyl-N-methyl-D-phenylalanyl-L-prolyl];
c-[D-Phenylalanyl-L-isoleucyl-D-pipecolyl-L-asparagyl-N-methyl-D-phenylalanyl-L-prolyl];
c-[D-Phenylalanyl-L-isoleucyl-D-pipecolyl-N$^\beta$-(aminoethyl)-L-asparagyl-N-methyl-D-phenylalanyl-L-prolyl];
c-[D-Phenylalanyl-L-isoleucyl-D-pipecolyl-N$^\beta$-(imidazolylethyl)-L-asparagyl-N-methyl-D-phenylalanyl-L-prolyl];
c-[D-Phenylalanyl-L-isoleucyl-D-pipecolyl-L-2,3-diaminopropionyl-N-methyl-D-phenylalanyl-L-prolyl];
c-[(O-Ethyl)-D-tyrosyl-L-isoleucyl-D-pipecolyl-L-pipecolyl-N-methyl-D-phenylalanyl-L-prolyl];
c-[D-Phenylalanyl-L-isoleucyl-D-pipecolyl-L-pipecolyl-N-allyl-D-phenylalanyl-L-prolyl];
c-[D-Phenylalanyl-L-isoleucyl-D-$\Delta$-piperazyl(N$^\delta$-Boc)-L-ornithyl-N-methyl-D-$\delta$-phenyl-alaninyl-L-prolyl];
c-[D-Phenylalanyl-L-isoleucyl-D-$\Delta$-piperazyl-L-ornithyl-D-(N-methyl)phenylalanyl-L-prolyl] acetate salt;
c-[D-Tryptophanyl-L-isoleucyl-D-$\Delta$-piperazyl(N$^\delta$-Boc)-L-ornithyl-N-methyl-D-phenylalanyl-L-prolyl];
c-[D-Tryptophanyl-L-isoleucyl-D-$\Delta$-piperazyl-L-ornithyl-N-methyl-D-phenylalanyl L-prolyl];
c-[D-Tryptophanyl-L-isoleucyl-D-piperazyl(N$^\delta$-Boc)-L-ornithyl-D-histidyl-L-prolyl];
c-[D-Tryptophanyl-L-isoleucyl-D-pipecolyl-(N$^\delta$-Boc)-L-ornithyl-D-histidyl-L-prolyl] acetate salt;
c-[D-Tryptophanyl-L-isoleucyl-D-piperazyl-L-ornithyl-D-histidyl-L-prolyl]trifluoroacetate;

c-[D-phenylalanyl-L-isoleucyl-D-$\Delta$-piperazyl-L-arginyl-D-(N$\alpha$-methyl)-phenylalanyl-L-prolyl]trifluoroacetate salt;
c-[D-Tryptophanyl-L-isoleucyl-D-pipecolyl-L-lysyl-D-(N-methyl)phenylalanyl-L-prolyl];
c-[D-Tryptophanyl-L-homophenylalanyl-D-pipecolyl-L-pipecolyl-D-(N-methyl)phenylalanyl-prolyl];
c-[D-Tryptophanyl-L-phenylalanyl-D-pipecolyl-L-pipecolyl-D-(N-methyl)phenylalanyl-prolyl];
c-[D-Phenylalanyl-L-homophenylalanyl-D-pipecolyl-L-pipecolyl-D-(N-methyl)phenylalanyl-L-prolyl];
c-[D-Phenylalanyl-L-phenylalanyl-D-pipecolyl-L-pipecolyl-D-(N-methyl)phenylalanyl-L-prolyl];
c-[D-Tryptophanyl-L-isoleucyl-D-pipecolyl-L-pipecolyl-D-(N-methyl)tyrosyl-L-prolyl];
c-[D-2-Napthylalanyl-L-isoleucyl-D-pipecolyl-L-(N-t-butyloxycarbonyl)lysyl-D-(N-methyl)phenylalanyl-L-prolyl];
C-[D-1-Napthylalanyl-L-isoleucyl-D-pipecolyl-L-(N-t-butyloxycarbonyl)lysyl-D-(N-methyl)phenylalanyl-L-prolyl];
C-[D-2-Napthylalanyl-L-isoleucyl-D-pipecolyl-L-lysyl-D-(N-methyl)phenylalanyl-L-prolyl];
C-[D-2-Napthylalanyl-L-isoleucyl-D-pipecolyl-L-lysyl-D-(N-methyl)phenylalanyl-L-prolyl];
C-[D-(O-Benzyl)-tyrosinyl-L-isoleucyl-D-pipecolyl-L-(N-t-butyloxycarbonyl)lysyl-D-(N-methyl)-phenylalanyl-L-prolyl];
C-[D,L-meta-Tyrosinyl-L-isoleucyl-D-pipecolyl-L-(N-t-butyloxycarbonyl)lysyl-D-(N-methyl)phenylalanyl-L-prolyl];
C-[D-(O-t-Butyl)Tyrosiniyl-L-isoleucyl-D-pipecolyl-L(N-t-butyloxycarbonyl)lysyl-D-(N-methyl)-phenylalanyl-L-prolyl];
C-[D-(O-Benzyl)Tyrosyl-L-isoleucyl-D-pipecolyl-L-lysyl-D-(N-methyl)phenylalanyl-L-prolyl];
C-[D,L-meta-Tyrosyl-L-isoleucyl-D-pipecolyl-L-lysyl-D-(N-methyl)phenylalanyl-L-prolyl];
C-[D-Tyrosyl-L-isoleucyl-D-pipecolyl-L-lysyl-D-(N-methyl)phenylalanyl-L-prolyl];
C-[D-Tyrosyl-L-isoleucyl-D-pipecolyl-L-(N-t-butyloxycarbonyl)lysyl-D-(N-methyl)phenylalanyl)-L-prolyl];
c-[D-(O-Methyl)Tyrosyl-L-isoleucyl-D-pipecolyl-L-(N-t-butyloxycarbonyl)lysyl-D-(N-methyl)-phenylalanyl-L-prolyl];
c-[D-(O-Methyl)Tyrosyl-L-isoleucyl-D-pipecolyl-L-lysyl-D-(N-methyl)phenylalanyl-L-prolyl];
c-[D-2-Napthylalanyl-L-isoleucyl-D-pipecolyl-L-[N-(1-methyl-quinuclidinium-3-yl-carbonyl)]lysyl-D-(N-methyl)phenylalanyl-L-prolyl];
c-[D-Tryptophanyl-L-isoleucyl-D-pipecolyl-L-pipecolyl-D-histidyl-3,4-dehydroprolyl];
c-[D,L-3-(3-(1-Methyl)indolyl)alanyl-L-isoleucyl-D-pipecolyl-L-pipecolyl-D-histidyl-L-prolyl];
c-[D,L-3-(3-(5-Methyl)indolyl)alanyl-L-isoleucyl-D-pipecolyl-L-pipecolyl-D-histidyl-L-prolyl];
C-[D,L-3-(3-(7-Methyl)indolyl)alanyl-L-isoleucyl-D-pipecolyl-L-pipecolyl-D-histidyl-L-prolyl];
C-[D,L-3-(3-(5-Methoxy)indolyl)alanyl-L-isoleucyl-D-pipecolyl-L-pipecolyl-D-histidyl-L-prolyl];
c-[D,L-3-(3-(5-Fluoro)indolyl)alanyl-L-isoleucyl-D-pipecolyl-L-pipecolyl-D-histidyl-L-prolyl];
c-[D-2-Napthylalanyl-L-isoleucyl-D-pipecolyl-L-piperazin-2-yl-(4-carbobenzyloxy)-D-hystidyl-L-prolyl];
c-[D-2-Naphthylalanyl-L-isoleucyl-D-pipecolyl-L-piperazin-2-yl-D-histidyl-L-prolyl];

c-[D-2-Naphthylalanyl-L-isoleucyl-D-pipecolyl-D-piperazin-2-yl-(4-carbobenzyloxy)-D-hystidyl-L-prolyl];
c-[D-2-Naphthylalanyl-L-isoleucyl-D-pipecolyl-D-piperazin-2-yl-D-histidyl-L-prolyl];
c-[D-Tryptophanyl-L-isoleucinyl-D-pipecolyl-L-piperazin-2-yl(4-t-butylacetyl)-D-tryptophanyl-L-prolyl];
c-[D-Phenylalanyl-L-isoleucinyl-D-prolyl-L-piperazin-2-yl(4-Cbz)-D-phenylalanyl-L-prolyl];
c-[D-Phenylalanyl-L-isoleucinyl-D-prolyl-L-piperazin-2-yl-D-phenylalanyl-L-prolyl];
c-[D-Homophenylalanyl-L-isoleucyl-D-pipecolyl-L-pipecolyl-N-Me-D-phenylalanyl-L-prolyl];
c-[N-Me-D-Homophenylalanyl-N-Me-L-isoleucyl-D-pipecolyl-N-Me-D-phenylalanyl-L-prolyl];
c-[N-Me-D-Alanyl-L-isoleucyl-D-pipecolyl-L-pipecolyl-N-Me-D-phenylalanyl-L-prolyl];
c-[D-Tryptophanyl-L-isoleucinyl-D-Δ-piperazyl-L-piperazin-2-yl(4-Cbz)-N-Me-D-phenylalanyl-L-prolyl];
c-[D-2-Naphthylalanyl-L-isoleucinyl-D-pipecolyl-L-piperazin-2-yl (4-Cbz)-D-(Nα-methyl)-phenylalanyl-L-prolyl];
c-[D-Tryptophanyl-L-isoleucinyl-D-Δ-piperazyl-L-piperazin-2-yl-N$^\alpha$-Me-D-phenylalanyl-L-prolyl];
c-[D-2-Naphthylalanyl-L-isoleucinyl-D-pipecolyl-L-piperazin-2-yl-D-(N$^\alpha$-methyl)phenylalanyl-L-prolyl];
c-[D-Tryptophanyl-L-isoleucinyl-D-pipecolyl-L-pipecolyl-D-(β-t-butyl)aspartyl-L-prolyl];
C-[D-Phenylalanyl-L-isoleucyl-D-Δ-piperazyl-L-(N$^E$-t-Butyloxycarbonyl)-Lysl-M-Me-D-phenylalanyl-L-prolyl];
c-[D-Phenylalanyl-L-isoleucyl-D-Δ-piperazyl-L-Lysyl-N-Me-D-phenylalanyl-L-prolyl];
c-[D-2-Trytophanyl-L-isoleucinyl-D-pipecolyl-L-piperazin-2-yl-(4-Cbz)-D-histidinyl(BOM)-L-prolyl];
c-[D-Phenylalanyl-L-isoleucinyl-D-pipecolyl-L-piperazin-2-yl-D-histidinyl(BOM)-L-prolyl];
c-[D-Tryptophanyl-L-isoleucinyl-D-pipecolyl-L-piperazin-2-yl-D-histidinyl (BOM)-L-prolyl];
c-[D-Phenylalany-L-isoleucinyl-D-pipecolyl-L-piperazin-2-yl-D-(N$^{im}$-methyl)histidinyl-L-prolyl];
c-[D-Phenylalanyl-L-isoleucinyl-D-pipecolyl-L-pipecolyl-D-(β-t-butyl)aspartyl-L-prolyl];
C-[D-Tryptophanyl-L-isoleucinyl-D-pipecolyl-L-piperazin-2-yl(4-t-butylacetyl)-D-(N$^\alpha$-Me)phenylalanyl-L-prolyl];
c-[D-Tryptophanyl-L-isoleucinyl-D-pipecolyl-L-piperazin-2-yl(4-carboxymethyl)-D-(N$^\alpha$-Me)phenylalanyl-L-prolyl];
c-[D-Tryptophanyl(t-butylacetyl)-L-isoleucinyl-D-pipecolyl-L-piperazin-2-yl(4-t-butylacetyl)-D-(N$^\alpha$-Me)phenylalanyl-L-prolyl];
c-[D-Tryptophanyl-L-isoleucinyl-D-pipecolyl-L-piperazin-2-yl(4-dibenzylphosphoramidyl)-D-(N$^\alpha$-Me)-phenylalanyl-L-prolyl];
c-[D-Tryptophanyl-L-isoleucinyl-D-Δ-piperazyl-L-pipecolyl-D-histidyl-L-prolyl];

Effect of the Compounds of Formula I on [$^3$H]OT and [$^3$H] AVP Receptor Binding.

5. The compounds of claim 4 which are:
c-[D-Tryptophanyl-L-isoleucyl-D-Δ-piperazyl-L-pipecolyl-D-histidyl-L-prolyl];
c-[D-Tryptophanyl-L-isoleucyl-D-pipecolyl-L-pipecolyl-D-histidyl-L-prolyl];
c-[D-2-Naphtylalanyl-L-isoleueyl-D-pipecolyl-L-pipecolyl-D-histidyl-L-prolyl];
c-[D-Tryptophanyl-L-isoleucyl-D-pipecolyl-L-piperazin-2-yl-D-(Nα-methyl)phenylalanyl-L-prolyl];
c-[D-Phenylalanyl-L-isoleucyl-D-Δ-piperazyl-L-ornithyl-D-(Nα-methyl)phenylalanyl-L-prolyl];
c-[D-Phenylalanyl-L-isoleucyl-D-Δ-piperazyl-L-arginyl-D-(Na-methyl)phenylalanyl-L-prolyl];
c[D-2-Naphthylalanyl-L-isoleucyl-D-pipecolyl-L-piperazin-2-yl-D-histidyl-L-prolyl].

* * * * *